US008338450B2

(12) United States Patent
Arora et al.

(10) Patent No.: US 8,338,450 B2
(45) Date of Patent: Dec. 25, 2012

(54) COMPOUNDS AS DIPEPTIDYL PEPTIDASE IV (DPP IV) INHIBITORS

(75) Inventors: Sudershan Arora, Pune (IN); Neelima Sinha, Pune (IN); Prathap Nair, Pune (IN); Sai Kumar Chakka, Pune (IN); Anil Hajare, Pune (IN); Azmi Reddy, Pune (IN); Pravin Patil, Pune (IN); Majid Sayyed, Pune (IN); Rajender Kumar Kamboj, Pune (IN); K. H. Sreedhara Swamy, Pune (IN); Rajan Goel, Pune (IN)

(73) Assignee: Lupin Limited, Mumbai, Maharashtra (IN)

( * ) Notice: Subject to any disclaimer, the term of this patent is extended or adjusted under 35 U.S.C. 154(b) by 333 days.

(21) Appl. No.: 12/679,443

(22) PCT Filed: Sep. 19, 2008

(86) PCT No.: PCT/IN2008/000600
§ 371 (c)(1),
(2), (4) Date: Mar. 22, 2010

(87) PCT Pub. No.: WO2009/037719
PCT Pub. Date: Mar. 26, 2009

(65) Prior Publication Data
US 2010/0291020 A1   Nov. 18, 2010

(30) Foreign Application Priority Data
Sep. 21, 2007   (IN) .............. 1318/KOL/2007

(51) Int. Cl.
*A61K 31/44* (2006.01)
*C07D 221/02* (2006.01)
(52) U.S. Cl. .................... 514/299; 546/112
(58) Field of Classification Search ........... 546/112; 514/299
See application file for complete search history.

(56) References Cited

U.S. PATENT DOCUMENTS

| 4,277,472 A | 7/1981 | Amschler |
| 5,939,560 A | 8/1999 | Jenkins et al. |
| 6,011,155 A | 1/2000 | Villhauer |
| 6,166,063 A | 12/2000 | Villhauer |
| 6,395,767 B2 | 5/2002 | Robl et al. |
| 6,432,969 B1 | 8/2002 | Villhauer |
| 6,617,340 B1 | 9/2003 | Villhauer |
| 6,710,040 B1 | 3/2004 | Hulin et al. |
| 6,849,622 B2 | 2/2005 | Yasuda et al. |
| 6,861,440 B2 | 3/2005 | Boehringer et al. |
| 6,911,467 B2 | 6/2005 | Evans |
| 7,026,316 B2 | 4/2006 | Aston et al. |
| 7,109,347 B2 | 9/2006 | von Hoersten et al. |
| 7,132,443 B2 | 11/2006 | Haffner et al. |
| 7,138,397 B2 | 11/2006 | Yasuda et al. |
| 7,183,290 B2 | 2/2007 | Haffner et al. |
| 7,186,731 B2 | 3/2007 | Shima et al. |
| 7,268,150 B2 | 9/2007 | Hayakawa et al. |
| 7,332,487 B2 | 2/2008 | Yasuda et al. |
| 2002/0019411 A1 | 2/2002 | Robl et al. |
| 2004/0110817 A1 | 6/2004 | Hulin |
| 2004/0180925 A1 | 9/2004 | Matsuno et al. |
| 2005/0038020 A1 | 2/2005 | Hamann et al. |
| 2005/0070719 A1 | 3/2005 | Belyakov et al. |
| 2005/0090539 A1 | 4/2005 | Vu et al. |
| 2005/0130981 A1 | 6/2005 | Aranyl et al. |
| 2005/0192324 A1 | 9/2005 | Thomas et al. |
| 2005/0215784 A1 | 9/2005 | Madar et al. |
| 2005/0234065 A1 | 10/2005 | Hulin et al. |
| 2005/0261501 A1 | 11/2005 | De Nanteuil et al. |
| 2006/0035954 A1 | 2/2006 | Sharma et al. |
| 2006/0205711 A1 | 9/2006 | Himmelsbach et al. |
| 2006/0258621 A1 | 11/2006 | Campbell et al. |
| 2006/0276487 A1 | 12/2006 | Aranyi et al. |
| 2006/0281727 A1 | 12/2006 | Ashton et al. |
| 2006/0281796 A1 | 12/2006 | Edmondson et al. |
| 2007/0021477 A1 | 1/2007 | Edmondson et al. |
| 2007/0093492 A1 | 4/2007 | Jiaang et al. |
| 2007/0112205 A1 | 5/2007 | Fukushima et al. |
| 2007/0167501 A1 | 7/2007 | Fukuda et al. |
| 2007/0238753 A1 | 10/2007 | Madar et al. |
| 2007/0265320 A1 | 11/2007 | Fukuda et al. |
| 2008/0015146 A1 | 1/2008 | Edwards et al. |
| 2012/0082635 A1* | 4/2012 | Sinha et al. ........ 424/78.16 |

FOREIGN PATENT DOCUMENTS

| EP | 1 541 551 A1 | 6/2005 |
| EP | 1 560 811 | 8/2005 |
| WO | WO 98/19998 | 5/1998 |
| WO | WO 03/002553 A2 | 1/2003 |
| WO | WO 2004/026822 A2 | 4/2004 |
| WO | WO 2004/041795 A1 | 5/2004 |
| WO | WO 2004/052850 A2 | 6/2004 |
| WO | WO 2005/033099 A2 | 4/2005 |
| WO | WO 2005/037828 A1 | 4/2005 |

(Continued)

OTHER PUBLICATIONS

White et al., Clinical diabetes, vol. 26(2), (2008), pp. 53-57.*
Gloanec et al., "Synthesis of benzyl (6S)-1,3-dichloro-4-oxo-4,6,7,8-tetrahydro-pyrrolo[1,2-α]pyrazine-6-carboxylic ester, a new confonnationally constrained peptidomimetic derivative," *Tetrahedron Letters* (2002) 43:.3499-3501.
Caldwell et al., "Fluropyrrolidine amides as dipeptidyl peptidase IV inhibitors," *Bioorganic & Medicinal Chemistry Letters* (2004) 14: 1265-1268.
August et al., "Stereospecific synthesis of (2S,4R)-[5,5,5-$^2$H$_3$]leucine," *J. Chem. Soc., Perkins Trans.* 1 (1996) 1: 507-514.

(Continued)

*Primary Examiner* — D M Seaman
*Assistant Examiner* — Niloofar Rahmani
(74) *Attorney, Agent, or Firm* — Merchant & Gould P.C.

(57) ABSTRACT

The present invention is related to novel compounds of the general formula A, their tautomeric forms, their stereoisomers, their pharmaceutically acceptable salts, pharmaceutical compositions containing them, methods of making of the above compounds, and their use as Dipeptidyl Peptidase-IV (DPP-IV) Inhibitors, which are useful in the treatment or prevention of diseases particularly Type II diabetes, other complications related to diabetes and other pathogenic conditions in which DPP IV enzyme is involved.

23 Claims, No Drawings

FOREIGN PATENT DOCUMENTS

| WO | WO 2005/095339 A1 | 10/2005 |
|---|---|---|
| WO | WO 2006/011035 A1 | 2/2006 |
| WO | WO 2006/012395 A2 | 2/2006 |
| WO | WO 2006/012441 A1 | 2/2006 |
| WO | WO 2006/040625 A1 | 4/2006 |
| WO | WO 2006/090244 A1 | 8/2006 |
| WO | WO 2006/116157 A2 | 11/2006 |
| WO | WO 2007/029086 A2 | 3/2007 |
| WO | WO 2007/071738 A1 | 6/2007 |
| WO | WO 2007/099385 A1 | 9/2007 |
| WO | WO 2007/113226 A1 | 10/2007 |
| WO | WO 2007/113634 A1 | 10/2007 |
| WO | WO 2007/115821 A2 | 10/2007 |

OTHER PUBLICATIONS

Madar et al., "Discovery of 2-[4-{{(2-(2S,5R)-2-Cyano-5-ethynyl-1-pyrrolidinyl]-2-oxoethyl]amino]-4-methyl-1-piperidinyl]-4-pyridinecarboxylic Acid (ABT-279): A very potent, selective, effective, and well-tolerated inhibitor o dipeptidyl peptidase-IV, useful for the treatment of diabetes," *J. Med. Chem.* (2006) 49: 6416-6420.

Halab et al., "Improved synthesis of (2S,5S)-5-*tert*-butylproline," *Tetrahedron* (2001) 57: 6439-6446.

Ratner et al., "The action of formaldehyde upon cysteine," *J. Am. Chem. Soc.* (1937) 59: 200-206.

Gaertner, V.R., "Cyclization of 1-Alkylamino-3-halo-2-alkanols to 1-alkyl-3-azetidinols," *J. Org. Chem.* (1967) 32 (10): 2972-2976.

Hunig et al., "Nucleophile acylierung mit verkappten acylanionen: III. Synthese von α-hydroxyketonen," *Synthesis* (1975) 391-392.

Willstätter, R., "Zur Kenntnias von tropinon and Nortropinon," *Ber.* (1896): 1575-1584.

Gorrell, M.D., "Dipeptidyl peptidase IV and related enzymes in cell biology and liver disorders," *Clinical Science* (2005) 108: 277-292.

Green et al., "Inhibition of dipeptidyl peptidase IV activity as a therapy of Type 2 diabetes," *Expert Opin. Emerging Drugs* (2006) 11 (3): 525-539.

McIntosh et al., "Applications of dipeptidyl peptidase IV inhibitors in diabetes mellitus," *The international Journal of Biochemistry & Cell Biology* (2006) 38: 860-872.

Berge et al., "Pharmaceutical salts," *Journal of Pharmaceutical Sciences* (1977) 66 (1): 1-19.

Skyler, J.S., "Diabetes mellitus: Pathogenes and treatment strategies," *J. Med. Chem.* (2004) 47: 4113-4117.

Stahl et al., "Handbook of pharmaceutical salts—Properties, selection and use," *Wiley-VCH* (2002).

Willstätter, R., "Ueber ein Isomeres des Cocains," *Ber.* (1896): 2216-2227.

Drucker, D.J., "The biology of incretin hormones," *Cell Metabolism* (2006) 3: 153-165.

Frias et al., "Incretins and their role in the management of diabetes," *Curr. Opin. Endocrinol. Diabetes Obes.* (2007) 14: 269-276.

Idris et al., "Dipeptidyl peptidase-IV inhibitors: a major new class of oral antidiabetic drug," *Diabetes, Obesity and Metabolism* (2007) 9: 153-165.

Deacon, C.F., "Therapeutic strategies based on glucagon-like peptide 1," *Diabetes* (2004) 53: 2181-2189.

Lankas et al., "Dipeptidyl peptidase IV inhibition for the treatment of Type 2 Diabetes," *Diabetes* (2005) 54: 2988-2994.

Drucker, D.J., "Dipetidyl peptidase-4 inhibition and the treatment of Type 2 Diabetes," *Diabetes Care* (2007) 30 (6): 1335-1343.

Drucker, D.J., "The role of gut hormones in glucose homeostasis," *The Journal of Clinical Investigation* (2007) 117 (1): 24-32.

Matthaei et al., "Pathophysiology and pharmacological treatment of insulin resistance," *Endocrine Reviews* (2000) 21 (6): 585-618.

Yach et al., "Epidemiologic and economic consequences of the global epidemics of obesity and diabetes," *Nature Medicine* (2006) 12 (1): 62- 66.

Brubaker, P.L., "Incretin-based therapies: mimetics versus protease inhibitors," *TRENDS in Endocrinology and Metabolism* (2007) 18 (6): 240-245.

Ashworth et al., "2-Cyanopyrrolidides as potent, stable inhibitors of dipeptidyl peptidase IV," *Bioorganic & Medicinal Chemistry Letters* (1996) 6 (10): 1163-1166.

Kato et al., "New 5-HT3 (Serotonin-3) receptor antagonists. IV. Synthesis and structure-activity relationships of azabicycloalkaneacetamide derivatives," *Chem. Pharm. Bull.* (1995) 43 (8): 1351-1357.

Estermann et al., "194. Diastereoslektive alkylierung von-3-Aminobutansäure in der 2-stellung," *Helevtica Chimica Acta* (1988) 71: 1824-1839. (With English Abstract).

Olivo et al., "Syntheses of new open-ring and homo-epibatidine analogues from tropinone," *J. Org. Chem.* (1999) 64: 4966-4968.

Zirkle et al., "3-substituted tropane derivatives. I. The synthesis and stereochemistry of the tropane-3-carboxylic acids and their esters. A comparison of positional isomers in the tropane series," *J. Org. Chem.* (1962) 27: 1269-1279.

Ashby et al., "A greatly improved procedure for ruthenium tetraoxide catalyzed oxidations of organic compounds," *J. Org. Chem.* (1981) 46: 3936-3938.

Barton et al., "The invention of radical reactions. 32. Radical deoxygenations, dehalogenations, and deaminations with dialkyl phosphites and hypophosphorous acid as hydrogen sources," *J. Org. Chem.* (1993) 58: 6838-6842.

Sebokova et al., "Dipeptidyl peptidase IV inhibitors: The next generation of new promising therapies for the management of Type 2 Diabetes," *Current Topics in Medicinal Chemistry* (2007) 7: 547-555.

Barton et al., "Tris(trimethylsilyl)silane and diphenylsilane in the radical chain dideoxygenation of 1,6-anhydro-d-glucose: A comparative study," *Tetrahedron Letters* (1992) 33 (44): 6629-6632.

Barton et al., "Radical deoxygenations and dehaolgenations with dialkyl phosphites as hydrogen atom source," *Tetrahedron Letters* (1992) 33 (17): 2311-2314.

Wild et al., "Global prevalence of diabetes," *Diabetes Care* (2004) 27 (5): 1047-1053.

Form PCT/IPEA/409 for International Application PCT/IN2008/000600.

Form PCT/ISA/220 for International Application PCT/IN2008/000600.

Form PCT/ISA/237 for International Application PCT/IN2008/000600.

Hünig et al., "Nucleophilic Acylation with blocked acyl anions; III. Synthesis of α-Hydroxyketones", *Sythesis*, 1975, pp. 391-392. (English translation provided.).

Willstäter, "Understanding Tropinone and Nortropinone", *Chem. Ber. 29*, 1896, pp. 1575-1584. (English translation provided.).

Willstäter, "An isomer of Cocaine", *Chem Ber. 29*, 1896, pp. 2216-2227. (English translation provided.).

\* cited by examiner

COMPOUNDS AS DIPEPTIDYL PEPTIDASE IV (DPP IV) INHIBITORS

This application is a National Stage Application of PCT/IN2008/000600, filed Sep. 19, 2008, which claims benefit of Serial No. 1318/KOL/2007, filed Sep. 21, 2007 in India and which applications are incorporated herein by reference. To the extent appropriate, a claim of priority is made to each of the above disclosed applications.

FIELD OF THE INVENTION

The present invention is related to novel compounds of the general formula A, their stereoisomers, their racemates, their pharmaceutically acceptable salts, pharmaceutical compositions containing them, methods of making the above compounds, and their use as Dipeptidyl Peptidase IV (DPP IV) Inhibitors, which are useful in the treatment or prevention of diseases in which DPP IV enzyme is known to be involved in the pathogenesis. These diseases include mainly type II diabetes and related diseases, such as, syndrome X which includes insulin resistance, hypertension, obesity, dyslipidemia, hyperglycemia, atherosclerosis as well as for the prevention or treatment for other pathogenic conditions in which DPP IV is involved.

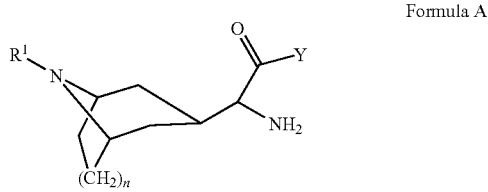

Formula A

BACKGROUND OF THE INVENTION

Diabetes mellitus is a major, growing health problem worldwide (Yach, D., et al. *Nat. Med.* 12, 62-66, 2006). Type 2 diabetes mellitus (hereafter referred as type 2 diabetes, also known as non-insulin-dependent diabetes mellitus, NIDDM) is a heterogeneous disorder, with both genetic and environmental factors contributing to its development. The pathogenesis of type 2 diabetes involves multiple mechanisms leading to hyperglycemia, most notably increased hepatic glucose production, impaired insulin secretion by pancreatic β cells and reduced glucose uptake by skeletal muscle and adipose tissue (peripheral insulin resistance). Type 2 diabetic patients are at substantially increased risks of macrovascular disease including coronary heart disease and stroke and microvascular disease including retinopathy, nephropathy and neuropathy.

Type 2 diabetes is a therapeutic area with huge market potential. The number of diabetic patients is projected to increase from 170-175 million in 2000 to over 350 million by 2030 (Wild, S., et al. *Diab. Care* 27, 1047-1053, 2004; Yach, D., et al. *Nat. Med.* 12, 62-66, 2006). The major part of this numerical increase is expected to occur in developing countries and India will have the distinction of having the largest number of diabetic patients in the world by 2030.

The treatment approaches for type 2 diabetes include diet, exercise, and a variety of pharmacological agents. Clinically established therapies for type 2 diabetes include insulin and its analogs and various oral hypoglycemic agents: sulfonylureas, metformin, α-glucosidase inhibitors (acarbose, miglitol), non-sulfonylurea insulin secretagogues (repaglinide, nateglinide) and thiazolidinedione (TZD) derivatives (rosiglitazone, pioglitazone) acting via PPARγ agonism (Matthaei, S., et al. *Endocrine Rev.* 21, 585-618, 2000; Skyler, J. S. *J. Med. Chem.* 47, 4113-4117, 2004). These agents act by different mechanisms to normalize blood glucose levels, but are limited in their abilities, either alone or in combination, to prevent the onset of diabetic complications. Further, each of the above oral agents suffers either from generally inadequate efficacy or number of adverse effects. For example, sulfonylureas, which have been the mainstay of oral treatment for over 5 decades, are known to be associated with a high rate of secondary failure and hypoglycemia. The TZD class of antidiabetic agents (glitazones) improves glucose utilization without stimulating insulin release, but their use is associated with undesirable effects (e.g. risk of myocardial infarction, cardiac hypertrophy, liver toxicity, weight gain).

Considering together the facts that about 90% of all diabetic cases account for NIDDM and the inadequacy of the currently available treatment, the clinical need and market potential for new oral antidiabetic drugs, which maintain tight glycemic control and prevent diabetic diabetic complications are very high.

The recent introduction of incretin-based therapies, which include incretin mimetics (e.g. exenatide) and incretin enhancers (e.g. sitagliptin, vildagliptin) is gaining clinical importance, as novel strategies for the treatment of type 2 diabetes. The incretin concept was first developed based on observations that insulin release was enhanced after oral ingestion of glucose, as compared with an equivalent glucose challenge given intravenously. This led to a hypothesis that in response to nutrient ingestion the gastrointestinal tract released one or more hormones ("incretins") that augmented insulin secretion. This hypothesis was validated with the identification of two key hormones, physiological incretin mimetics, glucagon-like peptide-1 (GLP-1) and glucose-dependent insulinotropic polypeptide (GIP) (Frias, J. and S. V. Edelman. *Curr. Opin. Endocrinol. Diab. Obes.* 14, 269-276, 2007; Drucker, D. J., *J. Clin. Invest.* 117, 24-32, 2007). GLP-1 is released from the enteroendocrine L-cells of the small intestine and GIP is released from duodenal K-cells. These hormones account for about 50% of the total insulin response, following a meal. The discovery of these incretin hormones has stimulated tremendous interest in their therapeutic potential for type 2 diabetes patients.

The incretins, chiefly GLP-1, lower blood glucose levels through multiple mechanisms. GLP-1 potentiates glucose-dependent insulin secretion from islet β-cells by activating specific G-protein-coupled receptors (Drucker, D. J., *Cell Metab.* 3, 153-165, 2006). In addition to enhancing insulin secretion, GLP-1 also inhibits glucagon secretion and gastric emptying and induces a feeling of satiety leading to weight loss in diabetic patients. More importantly, GLP-1 has the potential to reverse β-cell dysfunction by inhibiting β-cell apoptosis, stimulating β-cell growth and differentiation and promoting β-cell turnover. The incretins also enhance target tissue insulin sensitivity. Incretin-based therapies offer low risk of hypoglycemia, as the activation of incretin receptors is coupled to stimulation of insulin secretion in the presence of elevated blood glucose.

Although GLP-1 is very beneficial in maintaining glycemic control in diabetic patients, the peptide is metabolically unstable, as it is rapidly degraded by the ubiquitous serine protease dipeptidyl peptidase IV (DPP-IV), with an extremely short half-life in vivo, approximately 2 min, thus making it unattractive from the therapeutic standpoint. One approach to circumvent this stability problem has been the development of long-acting degradation-resistant peptides that can be administered parenterally (Deacon, C. F., *Diabetes*, 53, 2181-2189, 2004). This has resulted in the development of exenatide (Byetta, Amylin Pharmaceuticals), a peptidic GLP-1 receptor agonist, that was approved by the FDA for the treatment of type 2 diabetes. Several other long-acting DPP-IV resistant GLP-1 analogs are in clinical development (P. L. Brubaker, *Trends Endocrinol. Metab.* 18, 240-245, 2007). An alternative therapeutic strategy has focused on the inhibition of proteolytic activity of DPP-IV, to prevent the degradation of GLP-1 (and other incretin hormone GIP) and extend its plasma half-life (Green, B. D., et al. *Expert Opin. Emerging Drugs* 11, 525-539, 2006; Sebokova, E., et al. *Curr. Top. Med. Chem.* 7, 547-555, 2007)

Dipeptidyl peptidase IV (DPP-IV, EC 3.4.14.5; also known as CD26), a multifunctional transmembrane glycoprotein, is a serine protease that cleaves N-terminal dipeptides from polypeptides with L-proline or L-alanine at the penultimate position. It is present both in circulation (plasma) and on the surface of several cell types, including epithelial, endothelial and lymphoid cells. It is identical to the T cell activation antigen CD26 and the adenosine deaminase-binding protein. The endogenous substrates of DPP-IV include a wide variety of proline-containing peptides such as growth factors, chemokines, neuropeptides and vasoactive peptides (Gorrell, M., *Clin. Sci.* 108, 277-292, 2005; McIntosh, C. H. S., et al. *Int. J. Biochem. Cell Biol.* 38, 860-872, 2006)

Preclinical studies in laboratory animals, both genetic and pharmacological, have amply demonstrated the essential role for DPP-IV in the control of glucose homeostasis. Mice with a targeted inactivation of DPP-IV gene or Fischer344/CRJ rats with a spontaneous inactivating DPP-IV mutation have increased GLP-1 levels and show improved glucose homeostasis. Furthermore, pharmacological DPP-IV blockade was found to improve glucose tolerance in animal models of impaired glucose tolerance and diabetes (I. Idris and R. Donnelly, *Diab. Obes. Metab.* 9, 153-165, 2007; D. J. Drucker, *Diab. Care* 30, 1335-1343, 2007).

The selectivity of DPP-IV inhibitors against other closely-related proline-specific dipeptidyl peptidases, particularly DPP-8 and DPP-9, has been one of the key issues in the selection of compounds for development, as there is potential for adverse events associated with non-selective DPP-IV inhibitors. The inhibition of DPP-8 and DPP-9 has been found to be associated with toxicities in rat and dog (Lankas, G. R., et al. *Diabetes* 54, 2988-2994, 2005). Therefore, it is important to demonstrate that DPP-IV inhibitors do not appreciably inhibit these closely related enzymes. Consequently, the degree of DPP-8/DPP-9 selectivity has become an important criterion in the selection and development of DPP-IV inhibitors.

Clinically, DPP-IV inhibitors have been found to be very effective in providing glycemic control in diabetic subjects. These molecules are orally bioavailable, prevent degradation of GLP-1 leading to increased circulating levels of hormone and also stabilize other incretins. However, circulating insulin levels are not increased during DPP-IV inhibitor treatment. These inhibitors also improve fasting and postprandial blood glucose levels, as well as effectively lower HbA1c in diabetic patients. They are found to have good tolerability and safety profile during clinical trials and posed low risk of hypoglycemia. Currently, two DPP-IV inhibitors (sitagliptin and vildagliptin) are in clinical use, both as monotherapy and in combination with other antidiabetic agents, such as metformin or thiazolidinediones. Several DPP-IV inhibitors are in advanced stages of clinical development (e.g. alogliptin, saxagliptin, BI-1356, dutogliptin). Several other DPP IV inhibitors are also reported in literature but are different from the compounds of the present invention to be discussed later. Some of such compounds in the prior art are given below:

Earlier development in the filed of DPP IV inhibitors relates to various 2-cyanopyrrolidine derivatives as provided below.

U.S. Pat. No. 5,939,560 and *Bioorganic & Medicinal Chemistry Letters*, 6(10), 1163-1166 (1996), disclose several compounds of general formula (1) including possessing Dipeptidyl Peptidase IV inhibiting activity and postulated to have therapeutic potential in a number of disease states such as inflammation, graft versus host disease (GVHD), cancer and AIDS. The said research article in *Bioorganic & Medicinal Chemistry Letters* along with the DPP IV inhibitory activity also describes manufacturing methods for 2-cyanopyrrolidides.

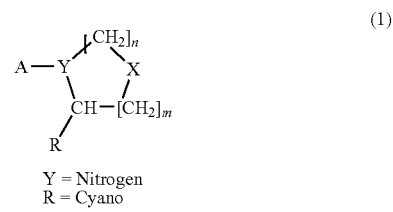

Y = Nitrogen
R = Cyano

Majority of DPP IV inhibitors in the recent inventions pertaining to the class of pyrrolidine derivatives have a common structural feature as provided below:

Figure A: Backbone of majority of DPP IV inhibitors

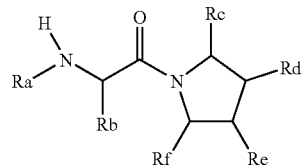

Novartis A G in U.S. Pat. Nos. 6,011,155; 6,166,063; 6,617,340; 6,432,969 and WO 98/19998 describe the compounds wherein Ra (of figure A) is substituted or unsubstituted alkyl, cycloalkyl, phenoxy, heterocyclic system, heteroaromatic system, [2.2.1] and [3.1.1]bicyclo moity or adamantly.

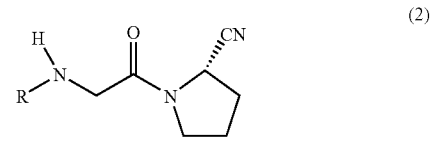

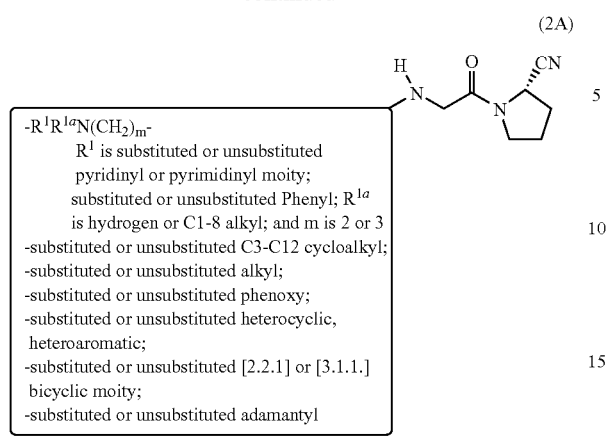

(2A)

U.S. Pat. Nos. 7,138,397; 7,332,487 & 6,849,622 describes various DPP IV inhibitors wherein Ra is a substituted six membered ring as shown below.

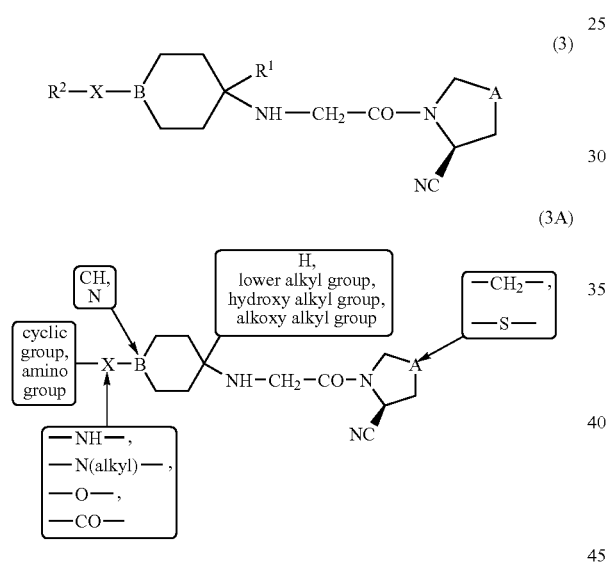

(3)

(3A)

U.S. Pat. No. 7,183,290 describes various fluoropyrrolidines of formulae 4 to 9 as dipeptidyl peptidase inhibitors wherein Re of Figure 'A' is fluoro and of the same figure Ra is selected from various cycles like substituted piperidinyl, pyrrolidinyl, cyclohexanyl, tropanyl, azetidinyl as provided in the compounds 4 to 9.

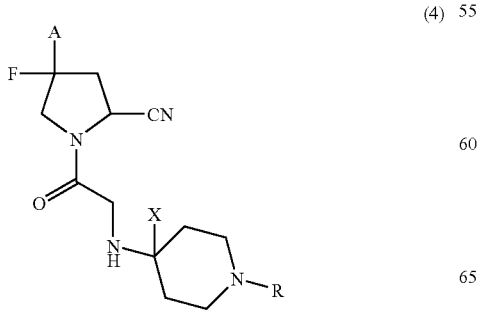

(4)

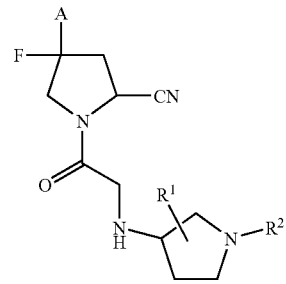

(5)

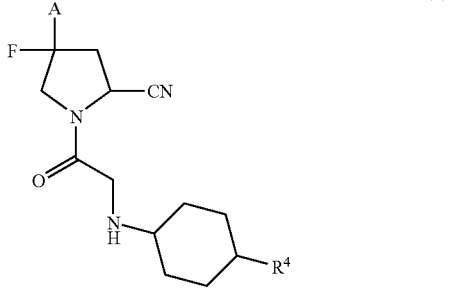

(6)

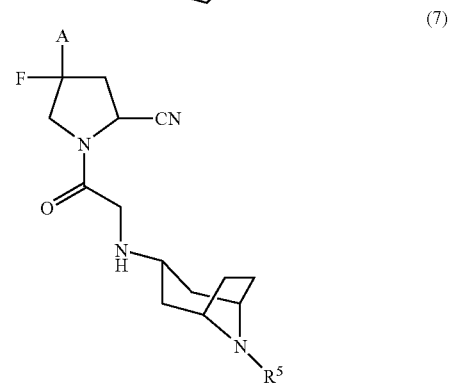

(7)

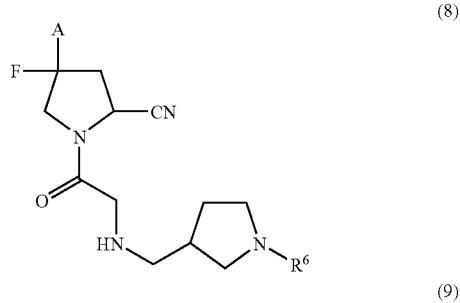

(8)

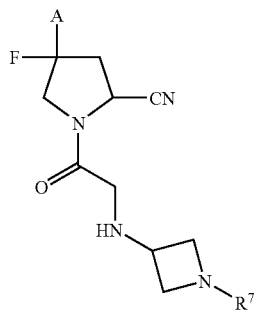

(9)

Following literature on DPP IV inhibitors also provide various substituents at Ra (of Figure A).

U.S. Pat. No. 6,861,440 relates to compounds of formula (10) and pharmaceutically acceptable salts thereof. The compounds are useful for the treatment and/or prophylaxis of diseases that are associated with DPP IV, such as diabetes, particularly non-insulin dependent diabetes mellitus, and impaired glucose tolerance.

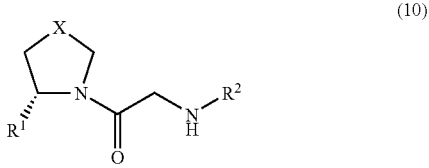

(10)

wherein $R^1$ is CN, $R^2$ is $-C(R^3,R^4)-(CH_2)_n-R^5$, $R^3$ is hydrogen, lower-alkyl, benzyl, or hydroxybenzyl, $R^4$ is hydrogen or lower-alkyl, $R^5$ is oxazolyl or imidazolyl which can be unsubstituted or substituted with 1 to 3 substituents independently selected from the group consisting of lower-alkyl, lower-alkoxy, halogen, CN, $CF_3$, trifluoroacetyl, pyridinyl and phenyl, which pyridinyl can be unsubstituted or substituted with 1 to 3 substituents independently selected from the group consisting of lower-alkyl, lower-alkoxy, halogen, and $CF_3$, and which phenyl can be unsubstituted or substituted with 1 to 3 substituents independently selected from the aroup consisting of lower-alkyl, lower-alkoxy, benzyloxy, halogen, $CF_3$, $CF_3$—O, CN and NH—CO-lower-alkyl, X is $C(R^8,R^9)$, $R^8$ and $R^9$ independently from each other are H or lower-alkyl, n is 0, 1 or 2, or a pharmaceutically acceptable salt thereof.

US 20050130981 describes a compound having the formula 11 as potent DPP-IV enzyme inhibitor.

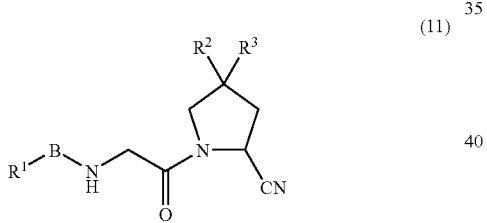

(11)

wherein $R^1$ represents a nitrogen-containing aromatic moiety consisting of one or two aromatic rings; which is optionally mono- or disubstituted by a substituent independently selected from the group consisting of C1-4 alkyl, C1-4 alkoxy, halogen, trihalogenomethyl, methylthio, nitro, cyano, amino, and phenyl group; or $R^1$ represents a thienyl, furyl or benzyl group; or $R^1$ represents a p-toluenesulfonyl group; or $R^1$ represents an acyl group of formula $R_{1a}$—CO, wherein $R_{1a}$ represents a C1-4 alkyl, phenyl, piperidin-1-yl, 4-methylpiperazin-1-yl, pyrrolidin-1-yl; or phenyl, pyridyl or phenylethenyl substituted with one or more groups selected from an alkyl, alkoxy, nitro, or halogen atom; or a phenylethenyl or phenylethyl substituted with alkylene-dioxy; B represents a group having the formula:

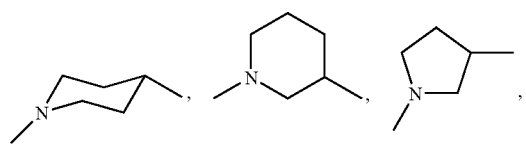

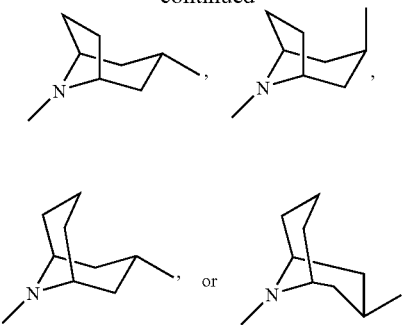

$R^2$ represents a hydrogen atom or a fluorine atom; $R^3$ represents a fluorine atom; or a salt, isomer, tautomer, solvate, or hydrate thereof.

U.S. Pat. No. 7,268,150 discloses a 2-cyano-4-fluoropyrrolidine derivatives of formula 12 having dipeptidyl peptidase IV-inhibiting activity, and a remedy based on the activity for insulin-dependent diabetes (type 1 diabetes), especially for non insulin-dependent diabetes (type 2 diabetes), insulin-resistant disorders, and obesity.

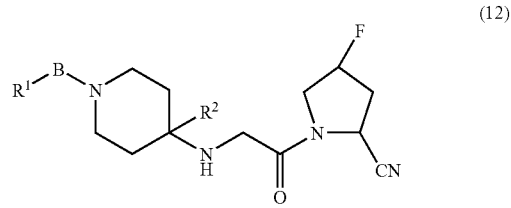

(12)

wherein, $R^1$—B represents methanesulfonyl, formyl or acetyl which may be substituted by a group selected from the group consisting of —OH and fluoro; $R^2$ represents —H, methyl or ethyl; or a pharmaceutically acceptable salt thereof.

US 20050215784 and US 20070238753 disclose compounds of formula (13) that inhibit dipeptidyl peptidase IV (DPP-IV) and are useful for the prevention or treatment of diabetes, especially type II diabetes, as well as hyperglycemia, Syndrome. X, hyperinsulinemia, obesity, atherosclerosis, and various immunomodulatory diseases.

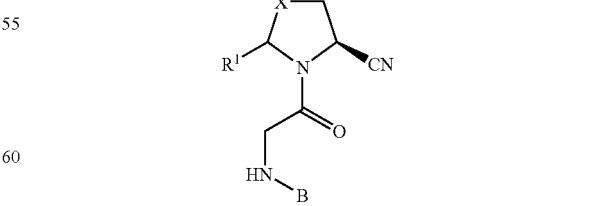

(13)

US20050192324 WO 2006040625, WO 2006011035 and WO 2007099385 describe compound of formula (14) as DPP-IV inhibitors having utility in the treatment of metabolic disorders.

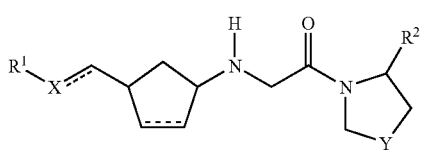
(14)

US20070265320 and US20070167501 describe bicyclo derivatives of formula (15) as DPP-IV inhibitors and claimed to be useful in the prevention and/or treatment of diabetes and associated complications and prevention and/or treatment of other diseases involving DPP-IV.

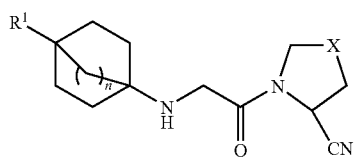
(15)

WO 2005095339 provides compound of formula (16) as DPP IV inhibitors. The compounds were claimed to be useful in the treatment of diabetic complications including diabetic neuropathy, diabetic microangiopathy, and the like.

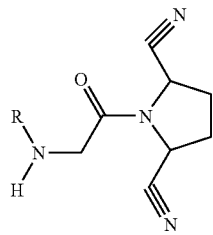
(16)

US20060276487 relates to the novel compounds of the general formula (17) possessing dipeptidyl peptidase IV enzyme inhibitory activity

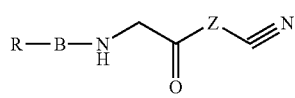
(17)

wherein B is selected from following groups

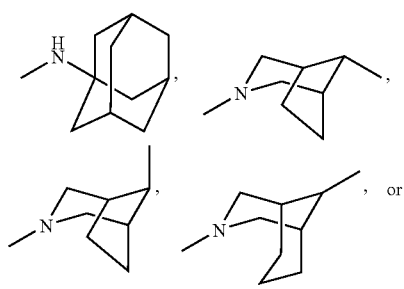

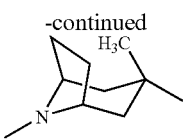

and Z is selected from the groups of formula:

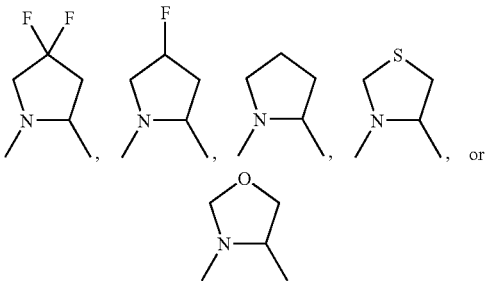

US 20060258621 is directed to pyrrolidinylaminoacetyl pyrrolidine boronic acid compounds of formula (18) that display selective, potent dipeptidyl peptidase IV (DPP-IV) inhibitory activity. These compounds are claimed to be useful for the treatment of disorders that can be regulated or normalized via inhibition of DPP-IV including those characterized by impaired glycemic control such as Diabetes Mellitus and related conditions.

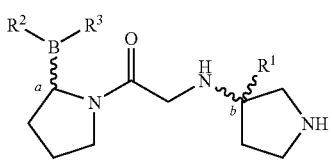
(18)

WO 2006090244 relates to DPP IV inhibitors of formula (19) claimed to be useful in treatment of disorders mediated by DPP IV inhibition such as diabetes.

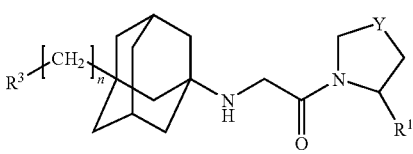
(19)

The second important point of substitution in the backbone provided in figure 'A' is Rb. Substituents at Rb tried by various inventors are summarized hereinbelow.

Invention described in U.S. Pat. No. 7,026,316 is directed to a compound of formula (20), which are inhibitors of the dipeptidyl peptidase-IV enzyme ("DP-IV inhibitors") and which are useful in the treatment or prevention of diseases in which the dipeptidyl peptidase-IV enzyme is involved, such as diabetes and particularly type 2 diabetes. The invention is also directed to pharmaceutical compositions comprising these compounds and the use of these compounds and compositions in the prevention or treatment of such diseases in which the dipeptidyl peptidase-IV enzyme is involved.

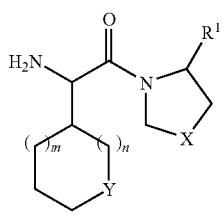

(20)

U.S. Pat. No. 7,132,443 discloses fluoropyrrolidines (compounds of formula 21 and 22, wherein Re of figure 'A' is fluoro) as dipeptidyl peptidase IV inhibitors, their use for inhibiting serine proteases, such as dipeptidyl peptidases, such as DPP-IV and to methods for their production and their therapeutic utility. The inventors specifically claim compound of formula 22.

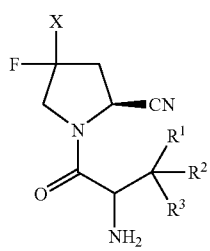

(21)

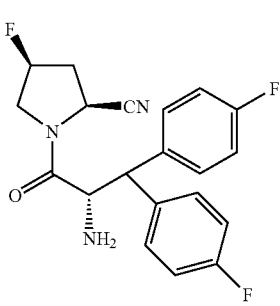

(22)

US 20060281796 provide DPP-IV inhibitors wherein Rb (of Figure A) is fused indole derivative as shown in the formula (23). The compounds were claimed to be useful in the treatment or prevention of diseases in which the dipeptidyl peptidase-IV enzyme is involved, such as diabetes and particularly type 2 diabetes. The invention is also directed to pharmaceutical compositions comprising these compounds and the use of these compounds and compositions in the prevention or treatment of such diseases in which the dipeptidyl peptidase-IV enzyme is involved.

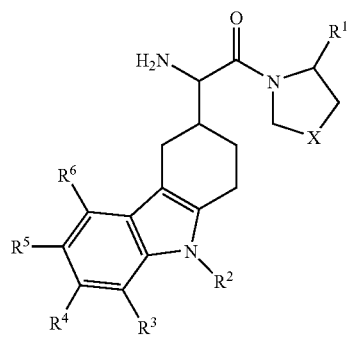

(23)

US 20070021477 is directed to DPP IV inhibitors wherein Rb (of Figure A) is fused cyclohexyl group as provided in the formula (24) and are claimed to be useful in the treatment or prevention of diseases in which the dipeptidyl peptidase-IV enzyme is involved, such as diabetes and particularly type 2 diabetes. The invention is also directed to pharmaceutical compositions comprising these compounds and the use of these compounds and compositions in the prevention or treatment of such diseases in which the dipeptidyl peptidase-IV enzyme is involved.

(24)

US 20050234065 provides compounds wherein Rb (of Figure A) is substituted cyclohexyl as shown in the formula (25) as DPP IV inhibitors. The inventors claims the compounds would have utility in the treatment of Type 1 and 2 diabetes, and related diseases.

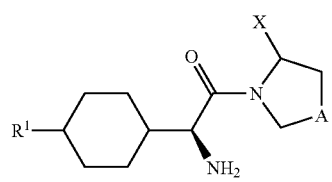

(25)

Some inventors have reported compounds wherein Ra and Rb of the basic backbone provided in figure A both were substituted with various substituents as follows.

U.S. Pat. No. 6,911,467 describes various 1-(2'-aminoacyl)-2-cyanopyrrolidine derivatives of general formula (26) with DP-IV inhibitory activity for treatment of impaired glucode tolerance or type 2 diabetes.

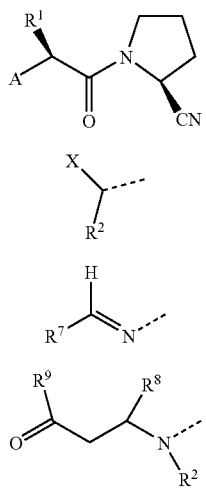

(26)

(27)

(28)

(29)

Wherein A is selected from groups (27, 28 and 29); X is selected from aminoacyl groups corresponding to the natural amino acids, acyl groups ($R^3$—CO), $R^4COOC(R^5)(R^6)OCO$, methoxycarbonyl, ethoxycarbonyl and benzyloxycarbonyl; $R^1$ is selected from H, $C_1$-$C_6$ alkyl residues, $(CH_2)_a NHW^1$, $(CH_2)_b COW^2$, $(CH_2)_c OW^3$, $CH(Me)OW^4$, $(CH_2)_d$—$C_6H_4$—$W^5$ and $(CH_2)_e SW^6$, where a is 2-5, b is 1-4, c is 1-2, d is 1-2, e is 1-3, $W^1$ is $COW^6$, $CO_2W^6$ or $SO_2W^6$, $W^2$ is OH, $NH_2$, $OW^6$ or $NHW^6$, $W^3$ is H or $W^6$, $W^4$ is H or $W^6$, $W^5$ is H, OH or OMe, and $W^6$ is $C_1$-$C_6$ alkyl, optionally substituted phenyl, optionally substituted heteroaryl or benzyl and $R_2$ is selected from H and $(CH_2)_n$—$C_5H_3N$—Y, where n is 2-4 and Y is H, F, Cl, $NO_2$ or CN, or $R^1$ and $R^2$ together are —$(CH_2)_p$— where p is 3 or 4; R.sup.3 is selected from H, $C_1$-$C_6$ alkyl and phenyl; $R^4$ is selected from H, $C_1$-$C_6$ alkyl, benzyl and optionally substituted phenyl; $R^5$ and $R^6$ are each independently selected from H and $C_1$-$C_6$ alkyl or together are —$(CH_2)_m$—, where m is 4-6; $R^7$ is selected from pyridyl and optionally substituted phenyl; $R^8$ is selected from H and $C_1$-$C_3$ alkyl; and $R^9$ is selected from H, $C_1$-$C_6$ alkyl, $C_1$-$C_6$ alkoxy and phenyl.

EP 1 560 811 discloses a compound of formula (30) which inhibit dipeptidyl peptidase IV (DPP-IV) and claims to be useful in the prevention or treatment of diabetes, especially type II diabetes, as well as hyperglycemia, Syndrome X, hyperinsulinemia, obesity, atherosclerosis, and various immunimodulatory diseases.

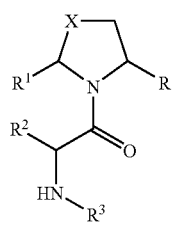

(30)

Literature providing DPP-IV inhibitors wherein, Ra and Rb of the basic backbone provided in figure A become part of a ring is summarized below.

US 20050070719 discloses a compound of Formula 31 and pharmaceutically acceptable derivatives thereof as inhibitors of DPP IV. The compounds were claimed to be useful in the treatment of neurological disorders, diabetes, inflammatory disorders such as arthritis, obesity, osteoporosis, and of such other enumerated conditions as can be treated with inhibitors of DPP IV,

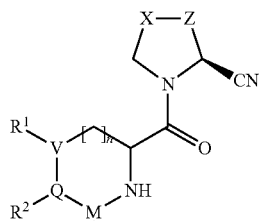

(31)

wherein the pyrrolidine ring formed by X, Z, N, and the carbon atoms to which they are attached, is saturated, or optionally contains one double bond; X is selected from the group consisting of $CH_2$, CH, S, O, NH, N, C=O, $CF_2$, CF, CH—Y, and C—Y; Z is selected from the group consisting of $CH_2$, CH, $CF_2$, CF, C—Y and CH—Y; wherein Y is halogen, hydroxy, or $C_1$-$C_3$ alkyloxy; and wherein one of X or Z must be $CH_2$; or CH if said pyrrolidine ring contains one double bond; M, Q, and V represent carbon atoms; n is 0 or 1; and where either $R^1$ and $R^2$, taken together with V and Q, or $R^2$ and $R^3$, taken together with Q and M, form a 3-6 membered, saturated carbocyclic or heterocyclic ring which may contain one or two heteroatoms selected from the group consisting of O, S, and N.

U.S. Pat. No. 7,186,731 discloses compound of formula (32) having DPP IV inhibiting activity and claimed to be useful in the treatment of conditions mediated by DPP-IV, such as non insulin dependent diabetes mellitus.

(32)

wherein X1 and X2 each is independently lower alkylene; X3 is +CH2, +CHF or +CF2; R1 is a substituent as described in the patent specification, R2 and R3 each is independently H or lower alkyl; n is 0, 1, 2, 3 or 4.

Pyrrolidine ring expansion, substitution at ring nodes and substitution at rest of the places in the backbone were also tried by various inventors to provide alternative DPP-IV inhibitors.

WO 2004041795 discloses compound of formula (33) as dipeptidyl peptidase IV (DPP-IV) inhibitors, its pharmaceutical compositions and method of treating medical conditions using compound of formula (33). The inventors claim the usefulness of these compounds in the treatment of neurological disorders, diabetes, inflammatory disorders such as arthritis, obesity, osteoporosis, and of such other enumerated conditions as can be treated with inhibitors of DPP-IV.

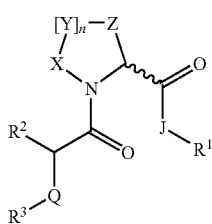

(33)

US 20050090539, US 20050038020 provide adamantylglycine-based inhibitors of dipeptidyl peptidase IV of Formula (34) or a pharmaceutically acceptable salt thereof for the treatment of diabetes and related diseases.

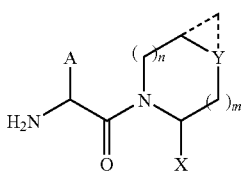

(34)

wherein: n is 0, 1 or 2; m is 0, 1 or 2; the dashed bonds forming a cyclopropyl ring when Y is CH; X is hydrogen or CN; Y is CH, CH$_2$, CHF, CF$_2$, O, S, SO, or SO$_2$A is substituted or unsubstituted; R$^1$ and R$^2$ are each independently selected from hydrogen, alkyl, alkenyl, alkynyl, aryl and heteroaryl; including pharmaceutically acceptable salts thereof, and prodrug esters thereof, and all stereoisomers thereof.

US 20060281727 describes phenylalanine derivatives of formula (35) which are inhibitors of the DPP-IV enzyme and are claimed to having utility in the treatment or prevention of diseases in with the said enzyme is involved, such as diabetes and particularly type 2 diabetes.

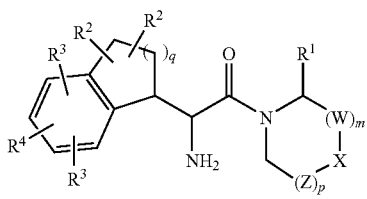

(35)

WO 2007029086 relates to 3-azabicyclo[3,1,0]hexane derivatives of formula (36) as DPP-IV inhibitors.

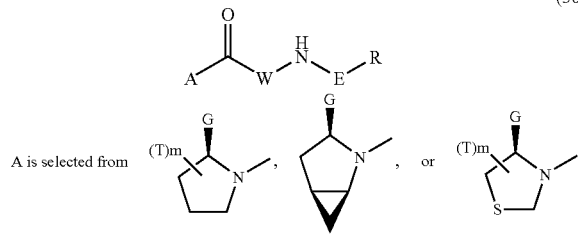

(36)

E is substituted or unsubstituted 3-azabicyclo[3.1.0]hexane.

In the recent past certain developments pertaining to the class of five membered ring systems like pyrrolidine, thiazolidine, oxothiazolidine and six membered ring systems like piperidine as DDP-IV inhibitors are summarized below.

WO 2006116157, filed by Alantos pharmaceuticals Inc., relates to pyrrolidine and thiazolidine DPP-IV inhibitors claimed to be having utility in the treatment of DPP IV mediated diseases, in particular Type-2 diabetes.

US 20070112205 discloses cyanopyrrolidine derivatives represented formula (37) or a salt thereof

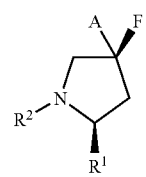

(37)

wherein A is a hydrogen atom or a fluorine atom, R$^1$ is —CONH$_2$ or —CN and R$^2$ is a hydrogen atom, a tert-butoxycarbonyl group, a trityl group, an o-nitrobenzenesulfenyl group, a benzyloxycarbonyl group, a fluorenyloxycarbonyl group, an allyloxycarbonyl group or —C(=O)—CH$_2$—Rc wherein Rc is a halogen atom, a methanesulfonyloxy group, a p-toluenesulfonyloxy group or a hydroxyl group.

US 20040180925 describes various dipeptidylpeptidase-IV inhibitors represented by general formula A-B-D, wherein A represents a substituted or unsubstituted 1-pyrrolidinyl group, a substituted or unsubstituted 3-thiazolidinyl group, a substituted or unsubstituted 1-oxo-3-thiazolidinyl group, or the like; B represents a) a group represented by —(C(R$^1$)(R$^2$))$_k$CO— (wherein k represents an integer of from 1 to 6, R$^1$ and R$^2$ may be the same or different and each represents a hydrogen atom, a hydroxyl group, a halogen atom, or the like) or the like; D represents —U—V [wherein U represents a substituted or unsubstituted piperazinediyl group or the like, V represents -E-R$^7$ (wherein E represents a single bond, —CO—, —(C=O)O—, or —SO$_2$—; R$^7$ represents a hydrogen atom, a substituted or unsubstituted alkyl group, or the like)] or a pharmacologically acceptable salt thereof.

US 20040110817 discloses inhibitors (compounds of formula 38) of the enzyme dipeptidyl peptidase-IV, pharmaceutical compositions comprising the compounds and the use of such compounds for treating diseases that are associated with proteins that are subject to processing by DPP-IV, such as Type 2 diabetes mellitus, hyperglycemia, impaired glucose tolerance, metabolic syndrome (Syndrome X or insulin resistance syndrome), glucosuria, metabolic acidosis, cataracts, diabetic neuropathy, diabetic nephropathy, diabetic retinopathy, diabetic cardiomyopathy, Type 1 diabetes, obesity, conditions exacerbated by obesity, hypertension, hyperlipidemia, atherosclerosis, osteoporosis, osteopenia, frailty, bone loss, bone fracture, acute coronary syndrome, infertility due to polycystic ovary syndrome, short bowel syndrome, anxiety, depression, insomnia, chronic fatigue, epilepsy, eating disorders, chronic pain, alcohol addiction, diseases associated with intestinal motility, ulcers, irritable bowel syndrome, inflammatory bowel syndrome and to prevent disease progression in Type 2 diabetes. The invention also relates to a method of identifying an insulin secretagogue agent for diabetes.

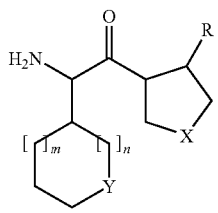

(38)

WO 2005037828 describes pyrrolidine-based compounds of formula (39) having DPP-IV inhibitory activity. The specification also describes the methods of preparing the said compounds and pharmaceutical compositions containing them.

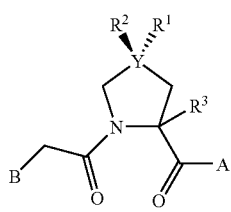

(39)

U.S. Pat. No. 7,109,347 relates to method of treating breast cancer comprising administration of the therapeutically effective amount of an atleast one inhibitor of DPP IV, wherein the said inhibitor is an amino acid linked to a thiazolidine or a pyrrrolidine group by a peptide bond.

US 20050261501 discloses compounds of formula (40) useful as DPP-IV inhibitors.

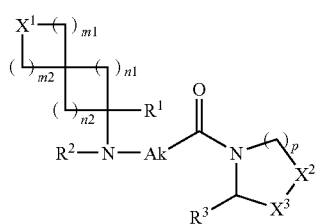

(40)

wherein: $X_1$ represents an atom or group selected from $CR^{4a}R^{4b}$, O, $S(O)_{q1}$ and $NR^5$, wherein $R^{4a}$, $R^{4b}$, $q_1$ and $R^5$ are as defined in the specification, $m_1$ represents zero or an integer from 1 to 4 inclusive, $m_2$ represents an integer from 1 to 4 inclusive, $n_1$ and $n_2$, which may be identical or different, each represent an integer from 1 to 3 inclusive, $R^1$ represents hydrogen or a group selected from carboxy, alkoxycarbonyl, optionally substituted carbamoyl and optionally substituted alkyl, $R^2$ represents hydrogen or alkyl, Ak represents an optionally substituted alkylene chain, p represents zero, 1 or 2, $R^3$ represents hydrogen or cyano, $X^2$ and $X^3$, which may be identical or different, each represent either $S(O)_{q2}$, or $CR^{6a}R^{6b}$, wherein $q_2$, $R^{6a}$ and $R^{6b}$ are as defined in the description, its optical isomers, where they exist, and its addition salts with a pharmaceutically acceptable acid.

US 20070093492 describes pyrrolidine compounds of the formula (41) and methods for using them to inhibit dipeptidyl peptidase IV or treat Type II diabetes. The compounds were claimed to have usefulness in the treatment of type 2 diabetes.

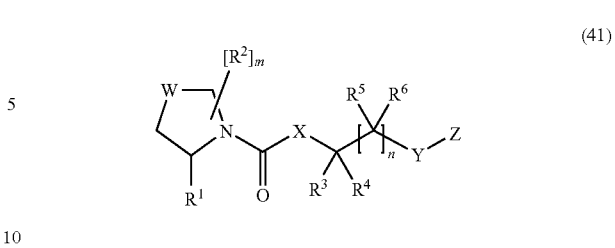

(41)

WO 2007113634 describes compounds represented by formula (42) as DPP IV inhibitors having usefulness in the treatment of type II diabetes and diabetic complications thereof and also in the treatment of dislipidemia, hypercholesterolemia, obesity and hyperglycemia.

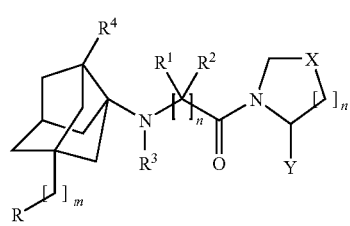

(42)

US 20080015146 describes compound of formula (43) as DPP IV inhibitors and claimed to have utility in the treatment of non-insulin-dependent diabetes mellitus.

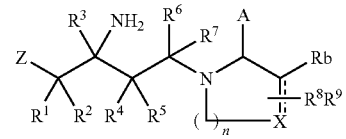

(43)

WO 2005033099 relates to DPP-IV inhibitors of the formula (44), and their analogs, isomers, pharmaceutical compositions and therapeutic uses. Such novel compounds are claimed to be potent and selective inhibitors of DPP-IV, and are effective in treating conditions that may be regulated or normalized via inhibition of DPP-IV. The invention also concerns pharmaceutical compositions comprising the novel compounds of formula (44), methods of inhibiting DPP-IV comprising administering to a subject in need thereof a therapeutically effective amount of said compound and processes for their preparation.

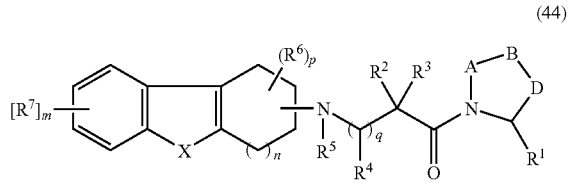

(44)

U.S. Pat. No. 6,395,767 discloses compounds of formula (45) as dipeptidyl peptidase IV (DP 4) inhibitors.

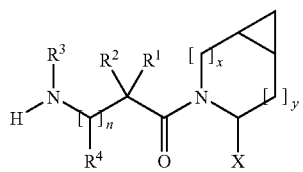

(45)

where x is 0 or 1 and y is 0 or 1 (provided that x=1 when y=0 and x=0 when y=1); n is 0 or 1; X is H or CN. A method is also provided for treating diabetes and related diseases, especially Type II diabetes, and other diseases; employing such DP 4 inhibitor or a combination of such DP 4 inhibitor and one or more of another antidiabetic agent such as metformin, glyburide, troglitazone, pioglitazone, rosiglitazone and/or insulin and/or one or more of a hypolipidemic agent and/or anti-obesity agent and/or other therapeutic agent.

Various Xanthine type molecules were also found to have DPP-IV inhibitory activity as evident from following literature.

US 20060205711 relates to substituted xanthines of general formula (46) wherein $R^1$ to $R^4$ are defined as in the specification, which have an inhibiting effect on the activity of the enzyme dipeptidylpeptidase-IV (DPP-IV).

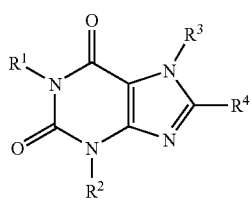

(46)

WO 2007071738 describes deazaxanthine and deazahypoxanthine compounds, of formula (47), wherein X is —CH= and Y is =N—; or X is —C(O)— and Y is —NR³)—; The compounds may be useful in the therapy of diseases and conditions in wich dipeptidylpeptidase-IV (DPP-IV) is implicated. The compounds were disclosed to have DPP IV inhibitory activity and claimed to have utility in the treatment of diabetes.

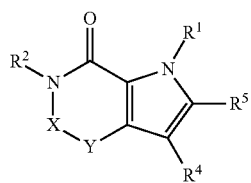

(47)

Compounds from other chemical class shown to have DPP-IV inhibitory activity are provided below.

U.S. Pat. No. 6,710,040 relates to dipeptidyl peptidase-IV inhibitors of formula (48), pharmaceutical compositions comprising the compounds and the use of such compounds for treating diseases that are associated with proteins that are subject to processing by DPP-IV.

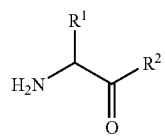

(48)

wherein: $R^1$ is 3-fluoroazetidin-1-yl, 3,3-difluoroazetidin-1-yl, 3,4-difluoropyrrolidin-1-yl, 3,3,4-trifluoropyrrolidin-1-yl, 3,3,4,4-tetrafluoropyrrolidin-1-yl, 3-fluoropiperidin-1-yl, 4-fluoropiperidin-1-yl, 3,4-difluoropiperidin-1-yl, 3,5-difluoropiperidin-1-yl, 3,3-difluoropiperidin-1-yl, 4,4-difluoropiperidin-1-yl, 3,4,5-trifluoropiperidin-1-yl, 3,3,4-trifluoropiperidin-1-yl, 3,3,5-trifluoropiperidin-1-yl, 3,4,4-trifluoropiperidin-1-yl, 3,3,4,5-tetrafluoropiperidin-1-yl, 3,4,4,5-tetrafluoropiperidin-1-yl, 3,3,4,4-tetrafluoropiperidin-1-yl, 3,3,5,5-tetrafluoropiperidin-1-yl, 3,3,4,5,5-pentafluoropiperidin-1-yl, 3,3,4,4,5-pentafluoropiperidin-1-yl or 3,3,4,4,5,5-hexafluoropiperidin-1-yl; and $R^2$ is $(C_1-C_8)$ alkyl or $(C_3-C_8)$cycloalkyl.

WO 2006012395 and WO 2006012441 relate to a series of compounds having the general formula (49) as DPP IV inhibitors and claimed to be useful in treatment of diabetes.

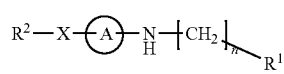

(49)

Wherein X is $NR^3$ or O; n is 1 or 2; A is a bicyclic carbocycle and $R^1$ and $R^2$ is as described in the specification.

WO 2007113226 describes compounds of formula (50) for the treatment of non-insuline-dependent diabetes mellitus.

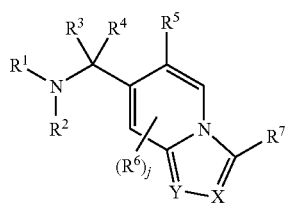

(50)

WO 2007115821 discloses the compounds of formula (51) and their use as DPP IV inhibitors. The compounds were claimed to have utility in the treatment of diabetes and metabolic disorders.

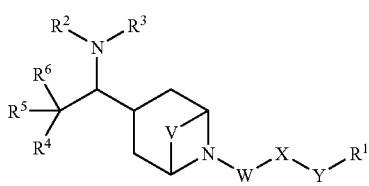

(51)

However there still remains need to provide new compounds having inhibitory activity against DPP IV

OBJECTIVE OF THE INVENTION

The main objective of the present invention is therefore to provide novel compounds of the general formula A, their tautomeric forms, their stereoisomers, their racemates, their pharmaceutically acceptable salts, pharmaceutical compositions containing them, process and intermediates for the preparation of the compounds given in Formula A which have inhibitory activity against DPP IV Another objective of the present invention to develop novel compounds which are effective and useful to lower increased levels of glucose, lipids, to improve insulin resistance, to decrease body weight, for the treatment and/or prophylaxis of metabolic disorders such as type II diabetis, obesity, hyperlipidemia, with better efficacy and lower toxicity.

SUMMARY OF THE INVENTION

Acccording to one aspect of the present invention there is provided novel organic compounds represented by the general formula (A), their stereoisomers, their racemates, their pharmaceutically acceptable salts, and pharmaceutical compositions containing them or mixture thereof.

In yet another aspect, the present invention provides a process for the preparation of novel organic compounds of the general formula (A), their stereoisomers, their pharmaceutically acceptable salts, pharmaceutical compositions containing them.

A further aspect of the present invention is to provide novel intermediates, a process for their preparation and their use in methods of making compounds of the general formula (A).

DETAILED DESCRIPTION OF THE INVENTION

The novel organic compounds of present invention represented by the general formula (A) is useful for reducing blood glucose, lowering lipid levels, cholestrol and reducing body weight and also have some excellent effects in the treatment and/or prophylaxis of diseases caused by insulin resistance such as type II diabetes, hyperlipidemia, obesity, impaired glucose tolerance, diabetic complications with better efficacy, potency, without or reduced toxicity. The present invention is related to the compounds of the general formula A in exo configuration,

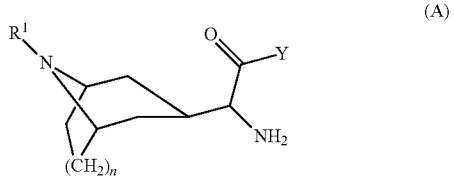

(A)

their optical isomers and pharmaceutically acceptable salts thereof, wherein, n=1, 2

Y is selected from the groups

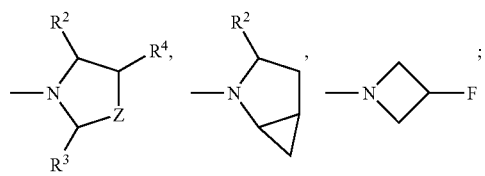

wherein, Z represents $CH_2$, —S—, CHF;

$R^1$ is selected from groups consisting of
i) Hydrogen;
ii) $C_1$-$C_8$alkyl (straight or branched) substituted with 1 to 3 substituents selected from halogens, such as pentyl, trifluoropropyl;
iii) cycloalkyl or cycloalkenyl having 3-10 carbon atoms such as cyclohexyl or cyclohex-2-enyl;
iv) cycloalkylmethyl having 4-10 carbon atoms such as cyclohexyl methyl;
v) Bridged polycycloalkyl methyl having 5 to 12 carbon atoms such as adamantyl methyl;
vi) phenyl which is unsubstituted or substituted with 1-3 substituents each independently selected from cyano or methanesulfonyl;
vii) aralkyl group such as benzyl which is unsubstituted or substituted with 1 to 3 substituents selected from halogens;
viii) heteroaryl group such as pyridyl unsubstituted or substituted with cyano;
ix) heteroaralkyl group such as pyridyl methyl;
x) aralkoxyalkyl group such as benzyloxy ethyl;
xi) $SO_2R^5$; where $R^5$ is methyl, thiophenyl, or phenyl unsubstituted or substituted with 1 to 3 fluoro;
xii) —$CONHR^6$ or —$CSNHR^6$ or —$CONHSO_2R^6$; where $R^6$ is phenyl unsubstituted or substituted with 1 to 3 substituents each independently selected from chloro, fluoro, trifluoromethyl and methoxy;
xiii) $R^7CO$—, wherein $R^7$ is selected from
  a. phenyl unsubstituted or substituted with 1 to 3 substituents selected from halogen, trifluoromethyl, cyano;
  b. benzo[1,3]dioxolyl;
  c. adamantyl;
  d. heteroaryl such as thiophenyl; furyl; pyrazinyl; pyridyl unsubstituted or substituted with a substituent selected from halogen, cyano, methyl, benzyloxy;
  e. N-acetylpiperidinyl;
  f. Cyclohexyl;
  g. Pyridine methyl;

$R^2$ is selected from hydrogen, CN, COOH, or isosteres of COOH, wherein said isosteres of COOH are selected from the groups consisting of esters, tetrazole, acid anhydrides, $CH_2OH$, $CH_2OBn$, CONHOH, $CONH_2$;

$R^3$ is selected from hydrogen, —CN, $C_2$-$C_5$alkynyl;

$R^4$ is selected from hydrogen or fluoro.

A compound its stereoisomers, racemates, pharmaceutically acceptable salts thereof as described herein above wherein the compound of the general formula (A) is selected from:

(2S)-1-{(2S)-2-Amino-2-[8-(2,4,5-trifluorobenzoyl)-8-aza-bicyclo[3.2.1]oct-3-yl]-exo-ethanoyl}-pyrrolidin-2-carbonitrile trifluoroacetic acid salt (Compound No. 1)

(2S)-1-{(2S)-2-Amino-2-[8-(4-trifluoromethylbenzoyl)-8-aza-bicyclo[3.2.1]oct-3-yl]-exo-ethanoyl}-pyrrolidin-2-carbonitrile trifluoroacetic acid salt (Compound No. 2)

(2S)-1-{(2S)-2-Amino-2-[8-(adamantane-1-carbonyl)-8-aza-bicyclo[3.2.1]oct-3-yl]-exo-ethanoyl}-pyrrolidin-2-carbonitrile trifluoroacetic acid salt (Compound No. 3)

(2S)-1-{(2S)-2-Amino-2-[8-(pyridine-4-carbonyl)-8-aza-bicyclo[3.2.1]oct-3-yl]-exo-ethanoyl}-pyrrolidin-2-carbonitrile trifluoroacetic acid salt (Compound No. 4)

(2S)-1-{(2S)-2-Amino-2-[8-(4-cyano-benzoyl)-8-aza-bicyclo[3.2.1]oct-3-yl]-exo-ethanoyl}-pyrrolidin-2-carbonitrile trifluoroacetic acid salt (Compound No. 5)

(2S)-1-{(2S)-2-Amino-2-[8-(2,5-difluorobenzoyl)-8-aza-bicyclo[3.2.1]oct-3-yl]-exo-ethanoyl}-pyrrolidin-2-carbonitrile trifluoroacetic acid salt (Compound No. 6)

(2S)-1-{(2S)-2-Amino-2-[8-(2-fluoro-pyridine-4-carbonyl)-8-aza-bicyclo[3.2.1]oct-3-yl]-exo-ethanoyl}-pyrrolidin-2-carbonitrile trifluoroacetic acid salt (Compound No. 7)

(2S)-1-[(2S)-2-Amino-2-(8-aza-bicyclo[3.2.1]oct-3-yl)-exo-ethanoyl]-pyrrolidin-2-carbonitrile trifluoroacetic acid salt (Compound No. 8)

(2S)-1-{(2S)-2-Amino-2-[8-(2,4,5-trifluorobenzyl)-8-aza-bicyclo[3.2.1]oct-3-yl]-exo-ethanoyl}-pyrrolidin-2-carbonitrile trifluoroacetic acid salt (Compound No. 9)

Methyl-(2S)-1-{(2S)-2-amino-2-[8-(4-trifluoromethyl-benzoyl)-8-aza-bicyclo[3.2.1]-oct-3-yl]-exo-ethanoyl}-pyrrolidin-2-carboxylate trifluoroacetic acid salt (Compound No. 10)

(2S)-1-{(2S)-2-amino-2-[8-(4-trifluoromethyl-benzoyl)-8-aza-bicyclo[3.2.1]-oct-3-yl]-exo-ethanoyl}-pyrrolidin-2-carboxylic acid trifluoroacetic acid salt (Compound No. 11)

(2S)-1-{(2S)-2-amino-2-[8-(4-trifluoromethyl-benzoyl)-8-aza-bicyclo[3.2.1]-oct-3-yl]-exo-ethanoyl}-pyrrolidin-2-carboxamide trifluoroacetic acid salt (Compound No. 12)

(2S)-1-{(2S)-2-Amino-2-[8-(4-trifluoromethyl-benzoyl)-8-aza-bicyclo[3.2.1]-oct-3-yl]-exo-ethanoyl}-2-(2H-tetrazol-5-yl)pyrrolidine hydrochloride (Compound No. 13)

(2S)-{(2S)-1-[(2S)-2-Amino-2-(8-(benzo[1,3]dioxole-5-carbonyl)-8-aza-bicyclo[3.2.1]-oct-3-yl)-exo-acetyl]-pyrrolidin-2-yl}methanol trifluoroacetic acid salt (Compound No. 14)

(2S,4S)-1-{(2S)-2-Amino-2-[8-(4-trifluoromethylbenzoyl)-8-aza-bicyclo[3.2.1]oct-3-yl]-exo-ethanoyl}-4-fluoro-pyrrolidin-2-carbonitrile hydrochloride salt (Compound No. 15)

(2S,4S)-1-{(2S)-2-Amino-2-[8-(2,4,5-trifluorobenzoyl)-8-aza-bicyclo[3.2.1]oct-3-yl]-exo-ethanoyl}-4-fluoro-pyrrolidin-2-carbonitrile trifluoroacetic acid salt (Compound No. 16)

(2S,4S)-1-{(2S)-2-Amino-2-[8-(2,5-difluorobenzoyl)-8-aza-bicyclo[3.2.1]oct-3-yl]-exo-ethanoyl}-4-fluoro-pyrrolidin-2-carbonitrile trifluoroacetic acid salt (Compound No. 17)

Benzyl-(2S,5R)-1-{(2S)-2-amino-2-[8-(4-trifluoromethyl-benzoyl)-8-aza-bicyclo[3.2.1]-oct-3-yl]-exo-ethanoyl}-5-cyano pyrrolidin-2-carboxylate trifluoroacetic acid salt (Compound No. 18)

(2S,4S)-1-{(2S)-2-Amino-2-[8-(2,4,5-trifluorobenzyl)-8-aza-bicyclo[3.2.1]oct-3-yl]-exo-ethanoyl}-4-fluoro-pyrrolidin-2-carbonitrile trifluoroacetic acid salt (Compound No. 19)

(4S)-3-{(2S)-2-Amino-2-[8-(4-trifluoromethylbenzoyl)-8-aza-bicyclo[3.2.1]oct-3-yl]-exo-ethanoyl}-thiazolidine-4-carbonitrile trifluoroacetic acid salt (Compound No. 20)

3-{(2S)-2-Amino-2-[8-(4-trifluoromethylbenzoyl)-8-aza-bicyclo[3.2.1]oct-3-yl]-exo-ethanoyl}-1,3-thiazolidine trifluoroacetic acid salt (Compound No. 21)

(2S)-1-{(2S)-2-Amino-2-[8-(4-trifluoromethyl phenyl carbamoyl)-8-aza-bicyclo[3.2.1]oct-3-yl]-exo-ethanoyl}-pyrrolidin-2-carbonitrile trifluoroacetic acid salt (Compound No. 22)

(1S,3S,5S)-2-{(2S)-2-Amino-2-[8-(2,4,5-trifluorobenzoyl)-8-aza-bicyclo[3.2.1]oct-3-yl]-exo-ethanoyl}-2-azabicyclo[3.1.0]hexane-3-carbonitrile trifluoroacetic acid salt (Compound No. 23)

(1S,3S,5S)-2-{(2S)-2-Amino-2-[8-(4-cyanobenzoyl)-8-aza-bicyclo[3.2.1]oct-3-yl]-exo-ethanoyl}-2-azabicyclo[3.1.0]hexane-3-carbonitrile trifluoroacetic acid salt (Compound No. 24)

(1S,3S,5S)-2-{(2S)-2-Amino-2-[8-(pyridine-4-carbonyl)-8-aza-bicyclo[3.2.1]oct-3-yl]-exo-ethanoyl}-2-azabicyclo[3.1.0]hexane-3-carbonitrile trifluoroacetic acid salt (Compound No. 25)

(1S,3S,5S)-2-{(2S)-2-Amino-2-[8-(4-trifluoromethylbenzoyl)-8-aza-bicyclo[3.2.1]oct-3-yl]-exo-ethanoyl}-2-azabicyclo[3.1.0]hexane-3-carbonitrile trifluoroacetic acid salt (Compound No. 26)

(1S,3S,5S)-2-{(2S)-2-Amino-2-[8-(2,5-difluorobenzoyl)-8-aza-bicyclo[3.2.1]oct-3-yl]-exo-ethanoyl}-2-azabicyclo[3.1.0]hexane-3-carbonitrile trifluoroacetic acid salt (Compound No. 27)

(1S,3S,5S)-2-{(2S)-2-Amino-2-[8-(2-fluoropyridine-4-carbonyl)-8-aza-bicyclo[3.2.1]oct-3-yl]-exo-ethanoyl}-2-azabicyclo[3.1.0]hexane-3-carbonitrile trifluoroacetic acid salt (Compound No. 28)

(1R,3R,5R)-2-{(2S)-2-Amino-2-[8-(2-fluoropyridine-4-carbonyl)-8-aza-bicyclo[3.2.1]oct-3-yl]-exo-ethanoyl}-2-azabicyclo[3.1.0]hexane-3-carbonitrile trifluoroacetic acid salt (Compound No. 29)

(1R,3R,5R)-2-{(2R)-2-Amino-2-[8-(2-fluoropyridine-4-carbonyl)-8-aza-bicyclo[3.2.1]oct-3-yl]-exo-ethanoyl}-2-azabicyclo[3.1.0]hexane-3-carbonitrile trifluoroacetic acid salt (Compound No. 30)

(1S,3S,5S)-2-{(2R)-2-Amino-2-[8-(2-fluoropyridine-4-carbonyl)-8-aza-bicyclo[3.2.1]oct-3-yl]-exo-ethanoyl}-2-azabicyclo[3.1.0]hexane-3-carbonitrile trifluoroacetic acid salt (Compound No. 31)

(1S,3S,5S)-2-{(2S)-2-Amino-2-[8-(2-fluoropyridine-3-carbonyl)-8-aza-bicyclo[3.2.1]oct-3-yl]-exo-ethanoyl}-2-azabicyclo[3.1.0]hexane-3-carbonitrile trifluoroacetic acid salt (Compound No. 32)

(1S,3S,5S)-2-{(2S)-2-Amino-2-[8-(pyridine-3-carbonyl)-8-aza-bicyclo[3.2.1]oct-3-yl]-exo-ethanoyl}-2-azabicyclo[3.1.0]hexane-3-carbonitrile trifluoroacetic acid salt (Compound No. 33)

(1S,3S,5S)-2-{(2S)-2-Amino-2-[8-(thiophene-2-carbonyl)-8-aza-bicyclo[3.2.1]oct-3-yl]-exo-ethanoyl}-2-azabicyclo[3.1.0]hexane-3-carbonitrile trifluoroacetic acid salt (Compound No. 34)

(1S,3S,5S)-2-{(2S)-2-Amino-2-[8-(pyrazine-2-carbonyl)-8-aza-bicyclo[3.2.1]oct-3-yl]-exo-ethanoyl}-2-azabicyclo[3.1.0]hexane-3-carbonitrile trifluoroacetic acid salt (Compound No. 35)

(1S,3S,5S)-2-{(2R)-2-Amino-2-[8-(pyrazine-2-carbonyl)-8-aza-bicyclo[3.2.1]oct-3-yl]-exo-ethanoyl}-2-azabicyclo[3.1.0]hexane-3-carbonitrile trifluoroacetic acid salt (Compound No. 36)

(1R,3R,5R)-2-{(2S)-2-Amino-2-[8-(pyrazine-2-carbonyl)-8-aza-bicyclo[3.2.1]oct-3-yl]-exo-ethanoyl}-2-azabicyclo[3.1.0]hexane-3-carbonitrile trifluoroacetic acid salt (Compound No. 37)

(1R,3R,5R)-2-{(2R)-2-Amino-2-[8-(pyrazine-2-carbonyl)-8-aza-bicyclo[3.2.1]oct-3-yl]-exo-ethanoyl}-2-azabicyclo[3.1.0]hexane-3-carbonitrile trifluoroacetic acid salt (Compound No. 38)

(1S,3S,5S)-2-{(2S)-2-Amino-2-[8-(pyridine-2-carbonyl)-8-aza-bicyclo[3.2.1]oct-3-yl]-exo-ethanoyl}-2-azabicyclo[3.1.0]hexane-3-carbonitrile trifluoroacetic acid salt (Compound No. 39)

(1S,3S,5S)-2-{(2S)-2-Amino-2-[8-(furan-2-carbonyl)-8-aza-bicyclo[3.2.1]oct-3-yl]-exo-ethanoyl}-2-azabicyclo[3.1.0]hexane-3-carbonitrile trifluoroacetic acid salt (Compound No. 40)

(1S,3S,5S)-2-{(2S)-2-Amino-2-[8-(3-fluoropyridine-4-carbonyl)-8-aza-bicyclo[3.2.1]oct-3-yl]-exo-ethanoyl}-2-azabicyclo[3.1.0]hexane-3-carbonitrile trifluoroacetic acid salt (Compound No. 41)

(1S,3S,5S)-2-{(2S)-2-Amino-2-[8-(3,5-difluorobenzene sulfonyl)-8-aza-bicyclo[3.2.1]oct-3-yl]-exo-ethanoyl}-2- azabicyclo[3.1.0]hexane-3-carbonitrile trifluoroacetic acid salt (Compound No. 42)

(1S,3S,5S)-2-{(2S)-2-Amino-2-[8-(adamantane-1-carbonyl)-8-aza-bicyclo[3.2.1]oct-3-yl]-exo-ethanoyl}-2-azabicyclo[3.1.0]hexane-3-carbonitrile trifluoroacetic acid salt (Compound No. 43)

(1S,3S,5S)-2-{(2S)-2-Amino-2-[8-(benzo[1,3]dioxole-5-carbonyl)-8-aza-bicyclo[3.2.1]oct-3-yl]-exo-ethanoyl}-2-azabicyclo[3.1.0]-hexane-3-carbonitrile trifluoroacetic acid salt (Compound No. 44)

(1S,3S,5S)-2-{(2S)-2-Amino-2-[8-(benzo[1,3]-dioxole-5-carbonyl)-8-aza-bicyclo[3.2.1]oct-3-yl]-exo-ethanoyl}-2-azabicyclo[3.1.0]-hexane-3-carboxamide trifluoroacetic acid salt (Compound No. 45)

(1S,3S,5S)-2-{(2S)-2-Amino-2-[8-(benzo[1,3]-dioxole-5-carbonyl)-8-aza-bicyclo[3.2.1]oct-3-yl]-exo-ethanoyl}-2-azabicyclo[3.1.0]-hexane-3-carboxylic acid hydrochloride (Compound No. 46)

(1S,3S,5S)-2-{(2S)-2-Amino-2-[8-(3,3,3-trifluoro propyl)-8-aza-bicyclo[3.2.1]oct-3-yl]-exo-ethanoyl}-2-azabicyclo[3.1.0]hexane-3-carbonitrile trifluoroacetic acid salt (Compound No. 47)

(1S,3S,5S)-2-{(2S)-2-Amino-2-[8-(cyclohexyl methyl)-8-aza-bicyclo[3.2.1]oct-3-yl]-exo-ethanoyl}-2-azabicyclo[3.1.0]hexane-3-carbonitrile trifluoroacetic acid salt (Compound No. 48)

(1S,3S,5S)-2-{(2S)-2-Amino-2-[8-(adamantan-1-yl methyl)-8-aza-bicyclo[3.2.1]oct-3-yl]-exo-ethanoyl}-2-azabicyclo[3.1.0]hexane-3-carbonitrile trifluoroacetic acid salt (Compound No. 49)

(1S,3S,5S)-2-{(2S)-2-Amino-2-[8-(benzyloxy-ethyl)-8-aza-bicyclo[3.2.1]oct-3-yl]-exo-ethanoyl}-2-azabicyclo[3.1.0]hexane-3-carbonitrile trifluoroacetic acid salt (Compound No. 50)

(1S,3S,5S)-2-{(2S)-2-Amino-2-[8-(5-cyanopyridine-2-yl)-8-aza-bicyclo[3.2.1]oct-3-yl]-exo-ethanoyl}-2-azabicyclo[3.1.0]hexane-3-carbonitrile trifluoroacetic acid salt (Compound No. 51)

(1S,3S,5S)-2-{(2S)-2-Amino-2-[8-(4-cyano-phenyl)-8-aza-bicyclo[3.2.1]oct-3-yl]-exo-ethanoyl}-2-azabicyclo[3.1.0]hexane-3-carbonitrile trifluoro acetic acid salt (Compound No. 52)

(1S,3S,5S)-2-{(2S)-2-Amino-2-[8-(4-methanesulfonyl phenyl)-8-aza-bicyclo[3.2.1]oct-3-yl]-exo-ethanoyl}-2-azabicyclo[3.1.0]hexane-3-carbonitrile trifluoroacetic acid salt (Compound No. 53)

(1S,3S,5S)-2-{(2S)-2-Amino-2-[8-(2-pyridin-4-yl-acetyl)-8-aza-bicyclo[3.2.1]oct-3-yl]-exo-ethanoyl}-2-azabicyclo[3.1.0]hexane-3-carbonitrile trifluoroacetic acid salt (Compound No. 54)

(1S,3S,5S)-2-{(2S)-2-Amino-2-[8-(pyridine-4-ylmethyl)-8-aza-bicyclo[3.2.1]oct-3-yl]-exo-ethanoyl}-2-azabicyclo[3.1.0]hexane-3-carbonitrile trifluoroacetic acid salt (Compound No. 55)

(1S,3S,5S)-2-{(2S)-2-Amino-2-[8-(methanesulfonyl)-8-aza-bicyclo[3.2.1]oct-3-yl]-exo-ethanoyl}-2-azabicyclo[3.1.0]hexane-3-carbonitrile trifluoroacetic acid salt (Compound No. 56)

(1S,3S,5S)-2-{(2S)-2-Amino-2-[8-(thiophene-2-sulfonyl)-8-aza-bicyclo[3.2.1]oct-3-yl]-exo-ethanoyl}-2-azabicyclo[3.1.0]hexane-3-carbonitrile trifluoroacetic acid salt (Compound No. 57)

(1S,3S,5S)-2-{(2S)-2-Amino-2-[8-(cyclohexane-carbonyl)-8-aza-bicyclo[3.2.1]oct-3-yl]-exo-ethanoyl}-2-azabicyclo[3.1.0]hexane-3-carbonitrile trifluoroacetic acid salt (Compound No. 58)

(1S,3S,5S)-2-{(2S)-2-Amino-2-[8-(1-ethyl-propyl)-8-azabicyclo[3.2.1]oct-3-yl]-exo-ethanoyl}-2-azabicyclo[3.1.0]hexane-3-carbonitrile trifluoroacetic acid salt (Compound No. 59)

(1S,3S,5S)-2-{(2S)-2-Amino-2-(8-cyclohexyl-8-aza-bicyclo[3.2.1]oct-3-yl)-exo-ethanoyl}-2-azabicyclo[3.1.0]hexane-3-carbonitrile trifluoroacetic acid salt (Compound No. 60)

(1S,3S,5S)-2-{(2S)-2-Amino-2-[8-(4-chlorophenylsulfonyl-carbamoyl)-8-aza-bicyclo[3.2.1]oct-3-yl]exo-ethanoyl}-2-azabicyclo[3.1.0]hexane-3-carbonitrile trifluoroacetic acid salt (Compound No. 61)

{(2S)-2-Amino-2-[8-(3-fluoro-pyridine-4-carbonyl)-8-aza-bicyclo[3.2.1]oct-3-yl]-exo-ethanoyl}-3-fluoro-azetidine trifluoroacetic acid salt (Compound No. 62)

(2S,5R)-1-{(2S)-2-Amino-2-[8-(4-trifluoromethyl-benzoyl)-8-aza-bicyclo[3.2.1]oct-3-yl]-exo-ethanoyl}-5-ethynyl-pyrrolidin-2-carbonitrile trifluoro acetic acid salt (Compound No. 63)

(2S,5R)-1-{(2S)-2-Amino-2-[8-(pyridin-4-carbonyl)-8-aza-bicyclo[3.2.1]oct-3-yl]-exo-ethanoyl}-5-ethynyl-pyrrolidin-2-carbonitrile trifluoroacetic acid salt (Compound No. 64)

(2S,5R)-1-{(2S)-2-Amino-2-[8-(3-fluoropyridin-4-carbonyl)-8-aza-bicyclo[3.2.1]oct-3-yl]-exd-ethanoyl}-5-ethynyl-pyrrolidin-2-carbonitrile trifluoroacetic acid salt (Compound No. 65)

(2S,5R)-1-{(2S)-2-Amino-2-[8-(2-fluoropyridin-4-carbonyl)-8-aza-bicyclo[3.2.1]-oct-3-yl]-exo-ethanoyl}-5-ethynyl-pyrrolidin-2-carbonitrile trifluoroacetic acid salt (Compound No. 66)

(2S,5R)-1-{(2S)-2-Amino-2-[8-(benzo[1,3]dioxole-5-carbonyl)-8-aza-bicyclo[3.2.1]oct-3-yl]-exo-ethanoyl}-5-ethynyl-pyrrolidin-2-carbonitrile trifluoroacetic acid salt (Compound No. 67)

(1S,3S,5S)-2-{(2S)-2-Amino-2-[8-(2-methoxyphenylthiocarbamoyl)-8-aza-bicyclo[3.2.1]oct-3-yl]-exo-ethanoyl}-2-azabicyclo[3.1.0]hexane-3-carbonitrile trifluoroacetic acid salt (Compound No. 68)

(1S,3S,5S)-2-{(2S)-2-Amino-2-[8-(1-acetyl-piperidine-4-carbonyl)-8-aza-bicyclo[3.2.1]oct-3-yl]-exo-ethanoyl}-2-azabicyclo[3.1.0]hexane-3-carbonitrile trifluoroacetic acid salt (Compound No. 69)

(2S)-1-{2-Amino-2-[9-(4-trifluoromethyl-benzoyl)-9-azabiacyclo[3.3.1]non-3-yl]-exo-ethanoyl}-pyrrolidin-2-carbonitrile trifluoro acetic acid salt (Compound No. 70A & B)

The compounds of the invention were prepared as outlined below according to the methods described herein. However, the invention is not limited to these methods, the compounds may also be prepared as described for structurally related compounds in the literature.

Scheme 1

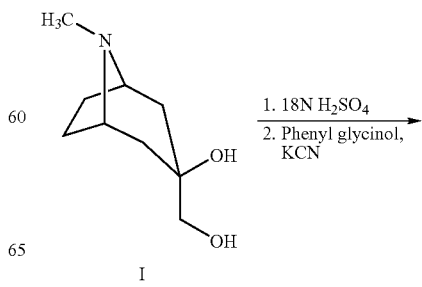

-continued

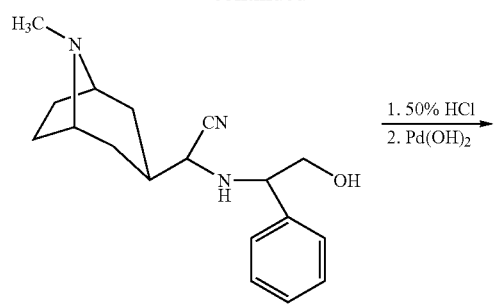

II

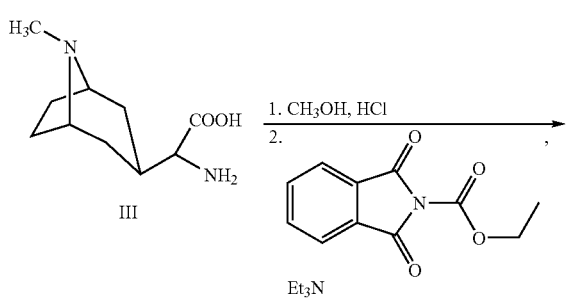

III

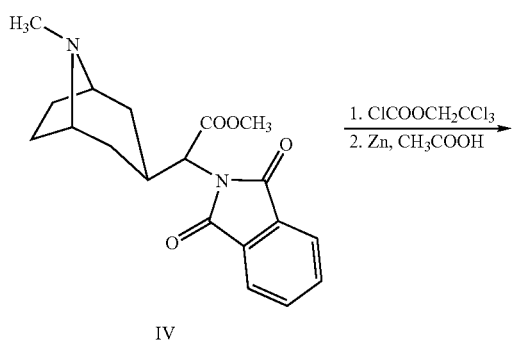

IV

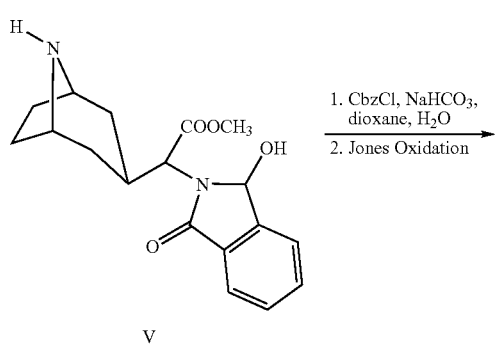

V

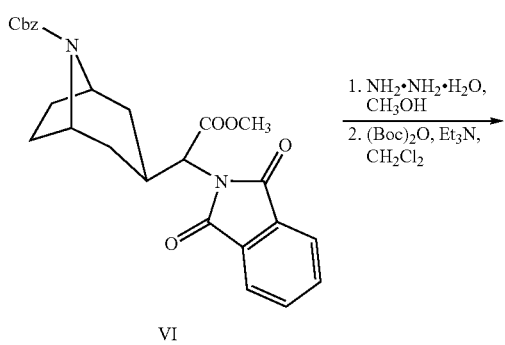

VI

-continued

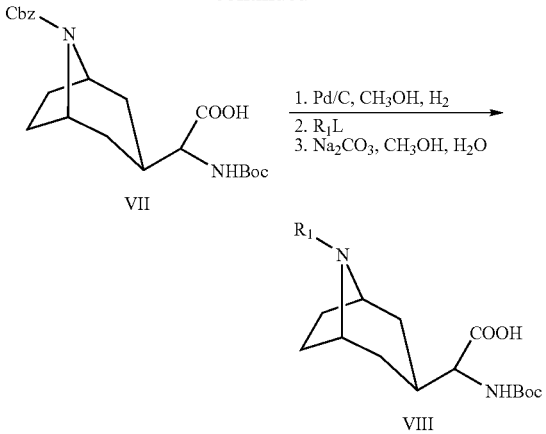

VII

VIII

The compound of formula-I can be obtained by methods described in literature. Such as Ber. 29,1575,2216, (1896) and J. org. chem. 27, 1269-1279, (1962). The compound of formula I was converted to the compound of the formula II by refluxing with 18N $H_2SO_4$ and subsequent reaction of aldehyde formed in situ at pH 6 (as a result of neutralization with a saturated aqueous solution of $K_2CO_3$) with R, S or RS phenyl glycinol in presence of sodium bisulphate and potassium cyanide under nitrogen atmosphere. This well known Strecker reaction is conducted at a temperature such as 0° C. to 30° C. for a suitable time such as 18-20 hours. The reaction forms two diastereomers of compound of formula II with exo and endo configuration if pure stereoisomer of phenyl glycinol is used as a reactant. Single diastereomer with Exo configuration was isolated by column chromatography, which was further confirmed by single crystal X-ray diffraction analysis.

The nitrile group of the compound of formula II was converted to carboxylic acid with 50% HCl (6N) and the reaction is carried out at 0-25° C. for a suitable time such as 20-25 hours. The product so obtained is subjected to hydrogenation in a parr apparatus under suitable pressure such as at 80-100 psi in the presence of the catalyst such as Pd $(OH)_2$ at 25-30° C. temperature for 12-15 hours to provide the compound of formula III. Compound of formula III was further converted to compound of formula IV by refluxing amino acid III in a solvent such as methanol under HCl gas purging for 12-15 hours. Further, the resulting amino ester is protected with a phthalimido group, optionally in the presence of the suitable base such as triethyl amine or diisopropyl ethylamine and in a solvent such as THF for 2-3 hours.

N-demethylation of the compound of formula IV was achieved by two-step process as shown in the scheme-I. In this two step process, the compound of the formula IV was subjected to react with trichloroethyl chloroformate and anhydrous $K_2CO_3$ in a hydrocarbon solvent such as toluene and refluxing under nitrogen atmosphere for a suitable time, such as 2-3 hours followed by the reaction with Zn, acetic acid, $H_2O$ at a temperature, such as 10-30° C. temperature for a suitable time 16 hours to provide the compound of formula V.

The compound of the formula V was protected with a suitable protecting group such as benzyloxy carbonyl (CBZ), so that later in the synthesis it could be removed easily while keeping other protecting groups such as tert-butoxycarbonyl intact. Protection with CBZ was readily accomplished by treatment of compound of formula V with benzyl chloroformate in a solvent such as dioxane-$H_2O$ in presence of a base such as NaHCO$_3$ at 0-30° C. temperature for a suitable time such as 2 hours. The hydroxy group of resultant compound was oxidized to a compound of formula VI by suitable oxidation method such as Jones oxidation, Dess Martin, NaOCl-TEMPO, PDC etc. The method chosen for this transformation must be compatible with the CBZ protecting group. One such approach is the oxidation of alcohol with Jones reagent in a solvent such as acetone at 0° C.-30° C. temperature for 1-2 hours.

The phthalimido group of the compound of formula VI was removed with hydrazine hydrate in solvent such as methanol at a temperature such as 0° C.-30° C. for suitable time such as 35-40 hours. Free amino group thus formed was protected with tert-butoxycarbonyl in solvent such as dichloromethane or THF, in presence of a base such as triethylamine or diisopropyl ethyl amine at a temperature 0° C.-30° C. and for suitable time 15-20 hours to provide the compound of formula VII. The benzyloxy-carbonyl of compound of formula VII was deprotected by hydrogenation in a parr apparatus in presence of 5% Pd/C in methanol at about 50 psi for about 3-4 hours.

The amine thus formed was reacted with either R$^1$L, wherein L is a leaving group such as halogen or hydroxy, R$^1$ is selected from it's definitions 'ii' to 'xi' and 'xiii' for compound of formula 'A'; or with R$^6$N═C═O or R$^6$N═C═S or R$^6$SO$_2$N═C═O in case of R$^1$ is selected from definition 'xii' for compound of formula 'A', wherein R$^6$ is selected from phenyl unsubstituted or substituted with chloro, fluoro, trifluoromethyl or methoxy; in presence of solvents such as haloganted hydrocarbon such as chloroform and dichloromethane, an aromatic hydrocarbon such as benzene and toluene an ether type solvent such as N,N'-dimethyl formamide N ethyl pyrrolidine and dimethyl sulfoxide, acetonitrile, using suitable coupling agents like EDCI, dicyclohexyl carbodiimide in presence of base such as triethyl amine or diisopropyl ethyl amine. The reaction temperature may be in range between 0° C. to 100° C. The duration of the reaction may range from 1-30 hours. The inert atmosphere may be employed by using inert gases such as nitrogen, argon, or helium. The ester group of resultant compound can be hydrolyzed using standard procedures known to a skilled artisan or by other procedures described in the literature such as in presence of a base such as K$_2$CO$_3$, Na$_2$CO$_3$, LiOH in solvent such as methanol and H$_2$O at temperature such as 0° C.—room temperature for a suitable time 15-20 hours to provide the compound of formula VIII. Wherein, if R$^1$ is cyclohex-2-enyl group, then such group is converted to cyclohexyl by catalytic hydrogenation; if R$^1$ is adamantane carbonyl, then such group is converted to adamantane.

Scheme 2

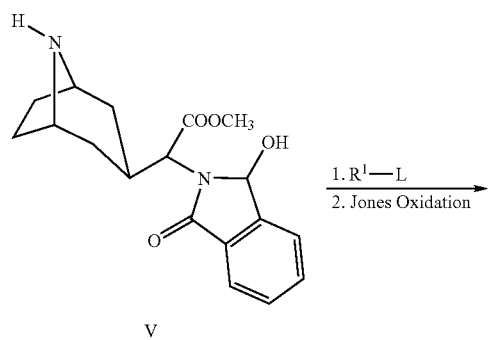

V

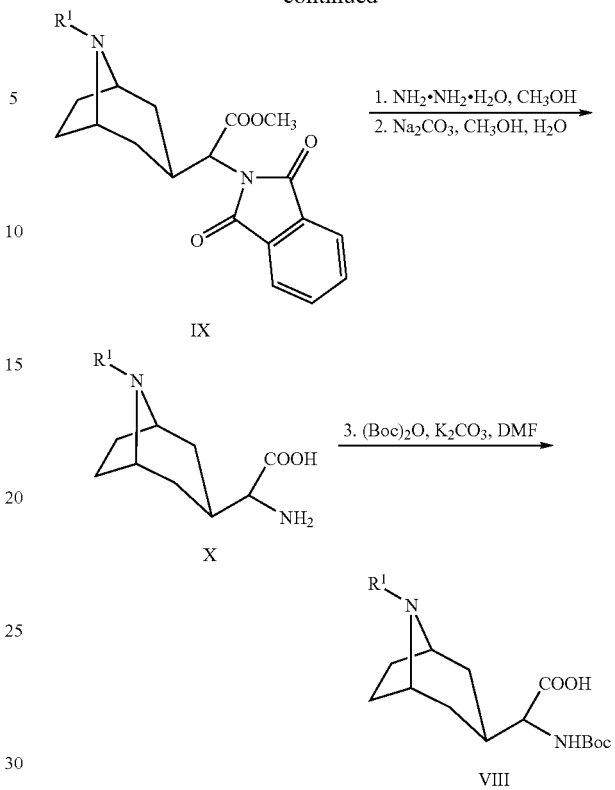

Alternatively compound of formula VIII can be synthesized from compound of formula V as per scheme 2, which involves treatment of a compound of formula V with R$^1$-L or R$^6$—N═C═O or R$^6$—N═C═S or R$^6$SO$_2$—N═C═O; wherein, R$^1$ is defined as under definition (v), (vi), (viii), (xi) and (xiii) for compound of formula 'A'; L is any suitable leaving group, more specifically hydroxy or halogen; R$^6$ is as defined herein above. The reaction can be carried out in the presence of solvents such as halogenated hydrocarbon like chloroform and dichloromethane, an aromatic hydrocarbon like benzene and toluene, an ether type solvent like diethyl ether, tetrahydrofuran and 1-4-dioxane, an aprotic polar solvent like N,N'-dimethylformamide N-methylpyrrolidine and dimethyl sulfoxide, acetonitrile using suitable coupling agents like 1-ethyl-3-[3-(dimethyl amino)propyl]carbodiimide (EDCI), diclohexyl carbodiimide in presence of base such as triethyl amine, diisopropylethyl amine and the like. The reaction may also be carried out in the presence of hydroxybenzotriol (HOBT), 2,2'-bis(diphenylphosphine)-1,1'-binaphthyl (BINAP), cesium carbonate and palladium acetate. The reaction temperature may be range between 0° C. to 100° C., the duration of reaction may range from 1-30 hours. The inert atmosphere may be employed by using inert gases such at nitrogen argon or helium. The resulting product was then oxidized to a compound of formula IX by Jones oxidation. The oxidation can also be achieved by other suitable methods known to those skilled in art, such as Dess martin, NaOCl-TEMPO, PDC etc. The Jone's oxidation is carried out in a solvent such acetone at a temperature, such as 0° C.-30° C. for 0.5-2 hours.

The Phthalimido group of the compound of formula IX was then removed by hydrazine hydrate in a solvent such as methanol at a temperature such as 0° C.-30° C. and for suitable time 35-40 hours. The ester group of the resultant compound can be hydrolyzed using any standard procedures known to a skilled artisan or by other procedures known in the literature such as in presence of a base such as K₂CO₃, Na₂CO₃, LiOH in a solvent such as methanol and H₂O at temperature such as 0° C.-30° C. for a suitable time 15-20 hours to obtain the compound of formula X. The amino group of compound of formula X was protected with tert-butoxycarbonyl in a solvent such as N,N-dimethylformamide and in presence of a base such as K₂CO₃ at temperature 0° C.-30° C. for a suitable time 15-20 hours to obtain the compound of formula VIII.

Scheme 3

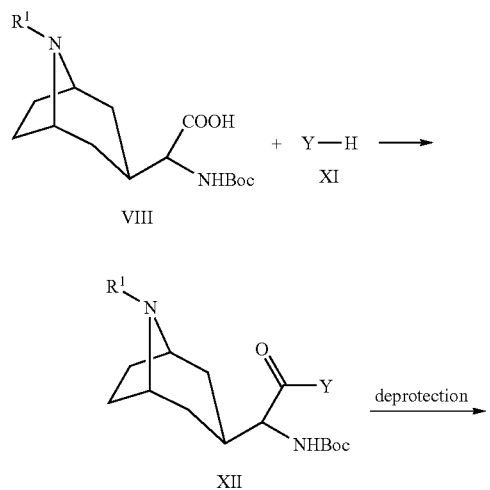

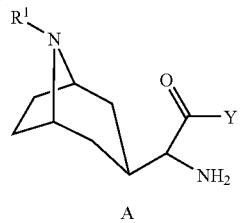

Compound of formula VIII obtained by practicing scheme 1 or 2 can be further converted to compound of the formula A as per synthetic Scheme-3. Compound of formula VIII was converted to compound of formula XII by condensation with compound of formula XI under standard peptide coupling conditions, for example, using EDCI, dicyclohexylcarbodiimide in presence of base such as triethyl amine, diisopropylethylamine and the like. The reaction may also be carried out in the presence of HOBT. The reaction temperature may be in the range between 0-35° C., the duration of reaction may range from 15-30 hours. If $R^2$ is —CONH₂, then —CONH₂ group is converted to —CN by treatment of dehydrating agent such as POCl₃; if $R^2$ is —COOH, then such group is converted to —CN by converting it to —CONH₂ and then treating the said amide with dehydrating agent such as POCl₃; if $R^2$ is —CN, then —CN group is converted to tetrazole by treatment with sodium azide or organic azides. The compound of formula XII was further deprotected using common methods known in the art such as using trifluoroacetic acid, in a solvent such as dichloromethane at a temperature 0-30° C. for 30 minutes to one hours to give the compounds of general formula (A). Wherein, if $R^1$ is tert-butoxycarbonyl, then it was hydrolyzed to get hydrogen at $R^1$ position Compound of general formula A, wherein n=2 was synthesized as per scheme 4.

Scheme 4

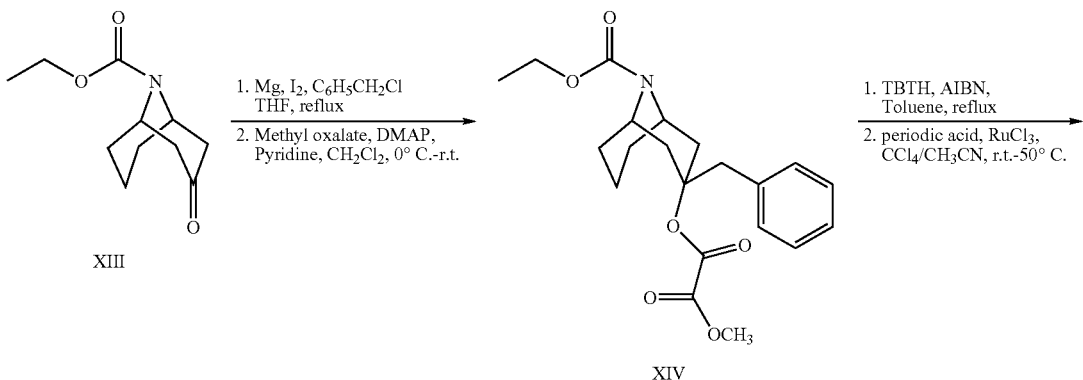

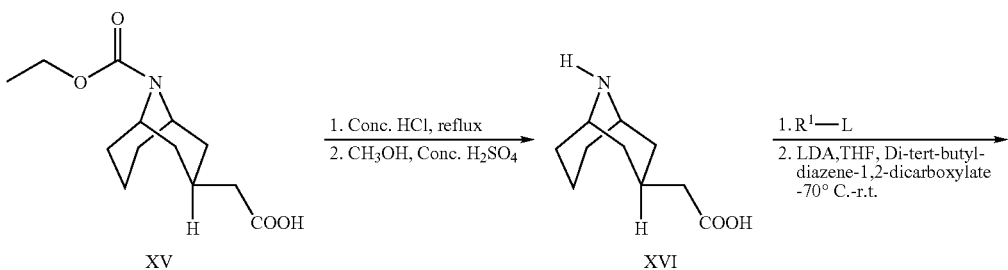

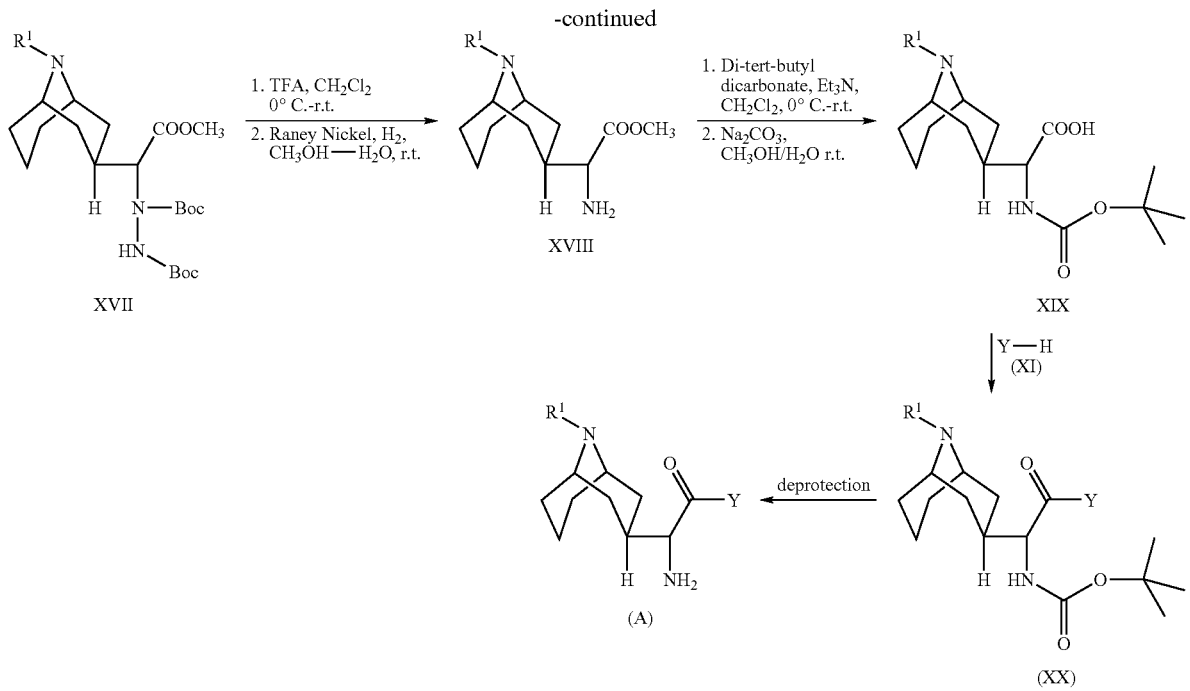

The compounds of the formula XIII can be obtained by methods described in U.S. Pat. No. 4,277,472I. The compound of the formula XIII is allowed to react with benzyl magnesium halide under Grignard conditions such as refluxing in a solvent like tetrahydrofuran and in presence of iodine for 16-18 hours to yield endo alcohol exclusively. Deoxygenation of tertiary alcohol of the intermediate can be accomplished using the Dolan-Mac Millan methodology [J. org. chem. 64, 4966-1968 (1999)]. Thus, the alcohol is subjected to react with methyl oxalate in a solvent such as dichloromethane and in presence of bases such as pyridine or 2,6-lutidine and 4-dimethylaminopyridine (DMAP) at a temperature 0° C.-30° C. and for a suitable time 18-20 hours to provide the compound of formula XIV.

The oxalate ester of the compound of formula XIV can be removed with tri butyl tin hydride (TBTH) and 2,2' azo bis (2-methyl propionitrile) (AIBN) in a hydrocarbon solvent such as toluene at a reflux temperature for a suitable time 12-14 hours. The deoxygenation can also be carried out using other reagents such as tris (trimethyl silyl) silane and 2,2-azobisisobutyronitrile (AIBN) in a hydrocarbon solvent such as toluene at a reflux temperature or refluxing with dialkyl phosphite and a radical initiator such as benzoyl peroxide in a hydrocarbon solvent such as toluene [J. Org. Chem. 58, 6838-6842 (1993); Tet. Let. 33, 2311-2314 (1992); Tet. Let. 33, 6629-6632 (1992)]. The phenyl ring of the deoxygenated product is oxidised with ruthenium trichloride and periodic acid in a solvent combination such as carbon tetrachloride and acetonitrile at a temperature 30° C.-50° C. for a suitable time 2-3 hours to provide the compound of formula XV [J. Org. Chem., 46, 3936-3938 (1981)].

The ethyl carbamate of the compound of formula XV can be removed with conc. HCl at a temperature 100° C. for a suitable time 8-10 hours. The carboxylic acid of the resultant intermediate is then converted to its methyl ester, (intermediate XVI) by refluxing in a solvent such as methanol using catalytic amount of conc. $H_2SO_4$ for a suitable time 15-20 hours. The major exo product was isolated by column chromatography. The exo stereochemistry of the intermediate XVI was assigned by comparing $^1$H NMR data as per Chem. Pharm Bull. Volume 43(8), page 1351 to 1357 (1995).

The intermediate XVI is then reacted with either $R^1L$, wherein L is a leaving group such as halogen or hydroxy, $R^1$ is selected from it's definitions 'ii' to 'vi', viii, x and 'xiii' for compound of formula 'A'; or with $R^6N=C=O$ or $R^6SO_2N=C=O$ in case of $R^1$ is selected from definition 'xii' of compound of formula 'A', wherein $R^6$ is selected from phenyl unsubstituted or substituted with chloro, fluoro, trifluoromethyl or methoxy. The reaction can be carried out in the presence of solvents such as halogenated hydrocarbon such as chloroform and dichloromethane, an aromatic hydrocarbon such as benzene and toluene, an ether type solvent such as diethyl ether, tetrahydrofuran and 1,4-dioxane, an aprotic polar solvent such as N-methylpyrrolidine, dimethyl sulfoxide, acetonitrile using suitable coupling agents such as EDCI. The reaction may be carried out in the presence of triethylamine, cesium carbonate, DMAP, HOBT, BINAP and palladium acetate. The reaction temperature may be in the range between 0° C.-100° C. The duration of the reaction may range from 1-30 hours. The inter atmosphere may be employed by using inert gases such as nitrogen, argon or helium. The resulting product is then treated with a base such as lithium diisopropylamide (LDA) and di-tert-butyl-diazene-1,2-dicarboxylate in a solvent such as tetrahydrofuran at a temperature −70° C.-30° C. for 14-16 hours to obtain the compound of formula XVII.

The tert-butoxy carbonyl groups of intermediate XVII can be deprotected using trifluoro acetic acid in a suitable solvent such as dichloromethane at a temperature 0° C.-30° C. for 4-6 hours. The resultant hydrazide is subjected to hydrogenation in an autoclave in a solvent such as methanol and water under suitable pressure such as 500-600 psi in the presence of a catalyst such as Raney Nickel at 25-30° C. for a suitable time 14-16 hours to obtain the compound of formula XVIII [Helv. chim. Acta 71, 1824-1839 (1988)].

The amino group of compound of formula XVIII is protected with tert-butoxy carbonyl in a solvent such as dichloromethane and in presence of a base such as triethyl amine at temperature 0° C.-30° C. for a suitable time 15-20 hours. The ester group of the resultant compound can be hydrolyzed using any standard procedures known to any skilled in the art or by other procedures known in the literature such as in presence of a base such as potassium carbonate, sodium carbonate, lithium hydroxide in a solvent such as methanol and water at temperature such as 0° C.-30° C. for a suitable time 15-20 hours to obtain the compound of formula XIX. Wherein, if $R^1$ is cyclohex-2-enyl group, then such group is converted to cyclohexyl by catalytic hydrogenation; if $R^1$ is adamantane carbonyl, then such group is converted to adamantane.

Compound of formula XIX obtained was further converted to compound of the formula XX by condensation with compound of formula XI under standard peptide coupling conditions, for example, using EDCI, dicyclohexylcarbodiimide. The reaction may also be carried out in the presence of HOBT. The reaction temperature may be range between 0-35° C., the duration of reaction may range from 15-30 hours. If $R^2$ is —$CONH_2$, then —$CONH_2$ group is converted to —CN by treatment of dehydrating agent such as $POCl_3$; if $R^2$ is —COOH, then such group is converted to —CN by converting it to —$CONH_2$ and then treating the said amide with dehydrating agent such as $POCl_3$; if $R^2$ is —CN, then —CN group is converted to tetrazole by treatment with sodium azide or organic azides. The compound of formula XX was further deprotected using common methods known in the art such as using trifluoroacetic acid, in a solvent such as dichloromethane at a temperature 0-30° C. for 30 minutes to one hours to give the compounds of general formula (A). Wherein, if $R^1$ is tert-butoxycarbonyl, then it was hydrolyzed to get hydrogen at $R^1$ position.

The intermediates and the compounds of the present invention are obtained in pure form in a manner known per se, for example by distilling off the solvent in vacuum and re crystallizing the residue obtained from a suitable solvent, such as pentane, diethyl ether, isopropyl ether, chloroform, dichloromethane, ethyl acetate, acetone or their combinations or subjecting it to one of the purification methods, such as column chromatography on a suitable support material such as alumina or silica gel using eluent such as dichloromethane, ethyl acetate, hexane, methanol, acetone and their combinations.

Salts are obtained by dissolving the free compound in a suitable solvent, for example in a chlorinated hydrocarbon, such as methyl chloride or chloroform or a low molecular weight aliphatic alcohol, for example, ethanol or isopropanol, which contains the desired acid or base or two which the desired acid or base is then added as described in, Berge S. M. et al. "Pharmaceutical Salts, a review article in Journal of Pharmaceutical sciences volume 66, page 1-19 (1977)" and in handbook of pharmaceutical salts properties, selection, and use by P. H. Einrich Stahland Camille G. wermuth, wiley-VCH (2002).

The stereoisomers of the compounds of 8-aza-bicyclo [3.2.1]octane series of the present invention may be prepared by the Strecker reaction or according to the methods given in literature such as resolution of the achiral amino acids using an optically active amine or acid and separating the diastereomeric salt by fractional crystallization by column chromatography.

The present invention also provides pharmaceutical compositions containing compounds of general formula A as defined above, their tautomeric forms, their stereoisomers, their enantiomers, their diastereomers, their racemates, their pharmaceutically acceptable salts or their pharmaceutically acceptable solvates in combination with the usual pharmaceutically employed carrier, diluents and the like.

The presence of one or more asymmetric centers in the compounds of general formula A can give rise to stereoisomers and each case the invention is to be understood to extend to all such stereoisomers, including enantiomers and disteriomers and their mixtures, including recemic mixtures and E & Z geometrical isomers single or mixture of both isomers wherever possible in the compounds of general formula A.

The following examples are provide to further illustrate the present invention and therefore should not be construed to limit the scope of the invention. All $^1$HNMR spectra were determined in the solvents indicated and chemical shifts are reported in 5 units downfield from the internal standard tetramethylsilane (TMS) and interproton coupling constants are reported in Hertz (Hz).

Intermediate 1

(2S)-2-(tert-Butoxycarbonyl)-amino-2-[8-(2,4,5-trifluoro-benzoyl)-8-aza-bicyclo[3.2.1]-oct-3-yl]-exo-ethanoic acid

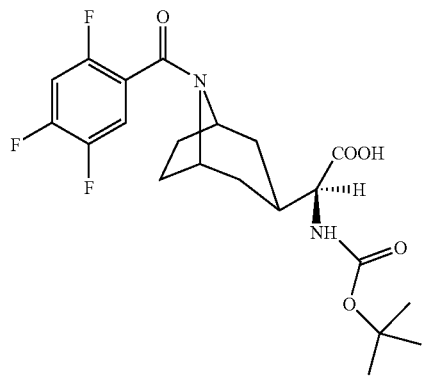

Step 1: 1-(2-Hydroxy-1-(1R)-phenylethyl amino)-1-(8-methyl-8-aza-bicyclo[3.2.1]-oct-3-yl)-exo-methane-1-(1S)-carbonitrile

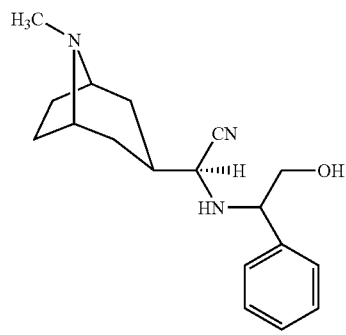

3-Hydroxymethyl-8-methyl-8-aza-bicyclo[3.2.1]octane-3-ol (prepared by the same procedure as described in Ber., 29, 1575, 2216, (1896) and J. Org. Chem. 27, 1269-1279 (1962), 36.8 g, 0.22 mol) was dissolved in $H_2SO_4$ (18 N, 110 ml) at room temperature and the reaction mixture was refluxed for 5.0 h. It was then cooled to 0° C. and neutralized to pH 6 using a saturated $K_2CO_3$ solution. The reaction mixture was diluted with water (35.0 ml) and subsequently added $NaHSO_3$ (22.37 g, 0.22 mol), KCN (15.4 g, 0.24 mol) and (R)-(−)-2-phenylglycinol (29.5 g, 0.22 mol) at 0° C. The reaction mixture was brought to room temperature immediately and stirred for 18 hours. It was then extracted with ethyl acetate (3×500 ml). The combined organic layer was washed with brine (100 ml), dried over anhydrous $Na_2SO_4$ and evaporated under reduced pressure to give a crude product, which was purified over neutral $Al_2O_3$ (Brockman III) using 20-40% ethyl acetate in hexane as an eluent to obtain the title compound (17.0 g, 26%).

mp: 121-123° C.
MS: m/z 300 (M+1)
$^1$H NMR (CDCl$_3$, 400 MHz): δ 1.52-1.63 (m, 4H), 1.66-1.83 (m, 3H), 1.91-2.09 (m, 3H), 2.28 (s, 3H), 2.32 (s, 1H), 3.06 (dd, J$_1$=7.2 Hz, J$_2$=12.8 Hz 1H), 3.17-3.27 (m, 2H), 3.54 (t, J=10 Hz, 1H), 3.73-3.78 (m, 1H), 4.04-4.08 (m, 1H), 7.26-7.36 (m, 5H).

Step 2: 1-(2-Hydroxy-1-(1R)-phenylethyl amino)-1-(8-methyl-8-aza-bicyclo[3.2.1]-oct-3-yl)-exo-methane-1-(1S)-carboxylic acid dihydrochloride

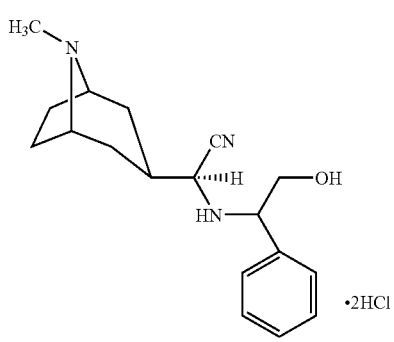

To a stirred solution of conc. HCl (266 ml) was added 1-(2-hydroxy-1-(1R)-phenyl ethyl lamino)-1-(8-methyl-8-aza-bicyclo[3.2.1]oct-3-yl)-exo-methane-1-(1S)-carbonitrile (Step 1, 13.3 g, 0.044 mol) in small portions at 0° C. After the addition was completed, the reaction mixture was brought to room temperature in 30 minutes and stirred at the same temperature for 20 hours. The solvent was completely removed at 45° C. under reduced pressure, added THF (150 ml) and again evaporated all the solvent. It was then dried under high vacuum to yield the title compound quantitatively, which was subjected to next step as such without purification.

MS: m/z 319 (M+1).

Step 3: (2S)-2-Amino-(8-methyl-8-aza-bicyclo[3.2.1]oct-3-yl)-exo-acetic acid dihydrochloride

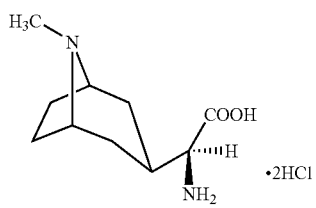

A solution of 1-(2-hydroxy-1-(1R)-phenylethylamino)-1-(8-methyl-8-aza-bicyclo[3.2.1]oct-3-yl)-exo-methane-1-(1S)-carboxylic acid dihydrochloride (step 2, 20.0 g, 51.2 mmol) in methanol (600 ml) and glacial acetic acid (120 ml) was hydrogenated at room temperature in a pressure of 100 psi in the presence of Pd (OH)$_2$ (10.0 g) for 12 hours. The catalyst was filtered through a Buchner funnel and filtrate was evaporated to obtain a pale green colored product. The sticky solid was triturated with dichloromethane (2×200 ml) and decanted in order to remove less polar impurities. It was then dried under high vacuum to obtain the title compound in quantitative yield and subjected to next reaction without purification.

MS: m/z 199 (M+1).

Step 4: Methyl (2S)-2-amino-2-(8-methyl-8-aza-bicyclo[3.2.1]-oct-3-yl)-exo-acetate

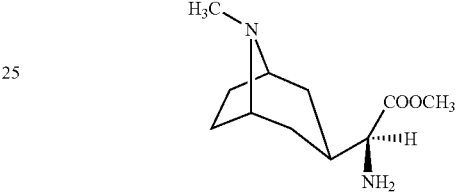

To a stirred suspension of (2S)-2-amino (8-methyl-8-aza-bicyclo[3.2.1]oct-3-yl)-exo-acetic acid dihydrochloride (step 3, 16.0 g, 58.9 mmol) in methanol (240 ml) was purged HCl gas under reflux condition for 12 hours. The solvent was evaporated under reduced pressure and the residue was stirred in chloroform (100 ml), cooled to 0° C. and basified with NH$_3$ in chloroform and stirred for 2 hours. It was then filtered through a Buchner funnel washed with chloroform (2×200 ml). The combined organic layer was evaporated to yield the title compound (10.01 g, 80%)

MS: m/z 213 (M+1)
$^1$H NMR (D$_2$O, 200 MHz): δ 1.2-1.75 (m, 5H), 1.8-2.05 (m, 4H), 2.22 (s, 3H), 3.01-3.2 (m, 3H), 3.7 (s, 3H).

Step 5: Methyl (2S)-2-(1,3-dioxo-1,3-dihydroisoindol-2-yl)-2-(8-methyl-8-aza-bicyclo[3.2.1]-oct-3-yl)-exo-acetate

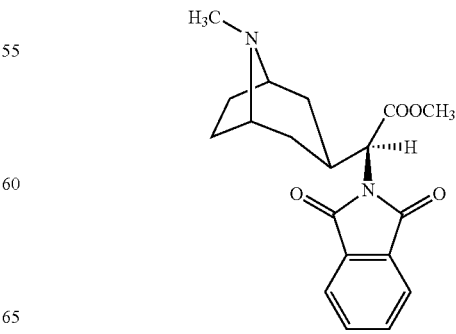

To a stirred solution of methyl (2S)-2-amino-2-(8-methyl-8-aza-bicyclo[3.2.1]oct-3-yl)-exo-acetate (step 4, 4.75 g, 0.022 mol) in dry THF (44 ml) was added, 1,3 dioxo-1,3-dihydro-iso indol-2-carboxylic acid ethyl ester (4.9 g, 0.022 mol) and triethyl amine (3.16 g, 4.4 ml, 0.0312 mol), and heated at 80° C. for 2 hours. The reaction mixture was brought to room temperature and the solvent was evaporated under reduced pressure and dried under high vacuum to obtain a crude product, which was purified by column chromatography over silica gel (100-200 mesh) using methanol:ammonia in chloroform:dichloromethane in the ratio of 3:10:87 as an eluent, to yield the title compound (3.90 g, 51%).

MS: m/z 343 (M+1)

$^1$H NMR (CDCl$_3$, 400 MHz): δ 1.55-1.65 (m, 1H), 1.82-1.95 (m, 2H), 1.98-2.08 (m, 2H), 2.10-2.25 (m, 3H), 2.54 (s, 3H), 2.82-2.92 (m, 1H), 3.45-3.6 (m, 2H), 3.69 (s, 3H), 4.72 (d, J=7.6 Hz, 1H), 7.72-7.78 (m, 2H), 7.84-7.88 (m, 2H).

Step 6: Methyl-(2S)-2-(1,3-dioxo-1,3-dihydroisoindol-2-yl)-2-[8-(2,2,2-trichloro-ethyloxy carbonyl)-8-aza-bicyclo[3.2.1]-oct-3-yl]-exo-acetate

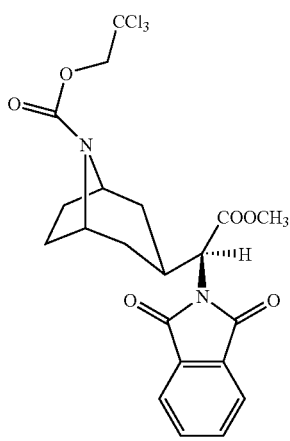

To a stirred solution of methyl (2S)-2-(1,3-dioxo-1,3-dihydro-isoindol-2-yl)-2-(8-methyl-8-aza-bicyclo[3.2.1]oct-3-yl)-exo-acetate (step 5, 3.88 g, 11.3 mmol) in dry toluene (50 ml) was added anhydrous K$_2$CO$_3$ (0.235 g, 1.7 mmol) and refluxed under N$_2$ atmosphere for 5 minutes. To this mixture was added a solution of 2,2,2-trichloro ethylchloroformate (3.6 g, 2.4 ml, 17 mmol) in dry toluene (10 ml) dropwise under N$_2$ atmosphere and refluxing was continued for 2 hours. The solvent was evaporated under reduced pressure and dried under high vacuum to get the crude product, which was purified by neutral Al$_2$O$_3$ (Brockman III) using dichloromethane as an eluent to yield the title coumpound (3.5 g, 61%).

MS: m/z 505 (M+2)

$^1$H NMR (CDCl$_3$, 200 MHz): δ 1.35-1.55 (m, 2H), 1.60-1.70 (m, 1H), 1.71-2.18 (m, 5H), 2.9-3.17 (m, 1H), 3.7 (s, 3H), 4.2-4.45 (m, 2H), 4.5-4.65 (m, 2H), 4.7-4.85 (m, 1H), 7.65-7.9 (m, 4H).

Step 7: Methyl-(2S)-2-(1-hydroxy-3-oxo-1,3-dihydroisoindol-2-yl)-2-[8-aza-bicyclo[3.2.1]-oct-3-yl]-exo-acetate

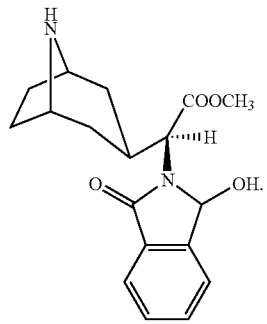

To a stirred suspension of activated Zn (4.5 g, 0.07 mol) in acetic acid (26 ml) and water (6.3 ml) at 10° C. was added a solution of methyl (2S)-2-(1,3-dioxo-1,3-dihydro-isoindol-2-yl)-2-[8-(2,2,2-trichloro-ethyloxycarbonyl)-8-aza-bicyclo [3.2.1]oct-3-yl]-exo-acetate (step 6, 3.5 g, 0.007 mol) in glacial acetic acid (30.7 ml). Cooling bath was removed after 1 hour. and reaction mixture was stirred for further 15 hours at room temperature. The solvent was evaporated under reduced pressure and dried under high vacuum to remove traces of acetic acid. To this reaction mass was added dichloromethane (20 ml), cooled to 0° C. and neutralized with ammonia in chloroform. This reaction mixture was stirred at 0° C. for 2 hours. and filtered through a Buchner funnel. The filtrate was concentrated under reduced pressure and dried under high vacuum to yield the title compound quantitatively.

MS: m/z 331 (M+1).

Step 8: Methyl-(2S)-2-(1-hydroxy-3-oxo-1,3-dihydroisoindol-2-yl)-2-[8-(2,4,5-trifluorobenzoyl)-8-aza-bicyclo[3.2.1]-oct-3-yl]-exo-acetate

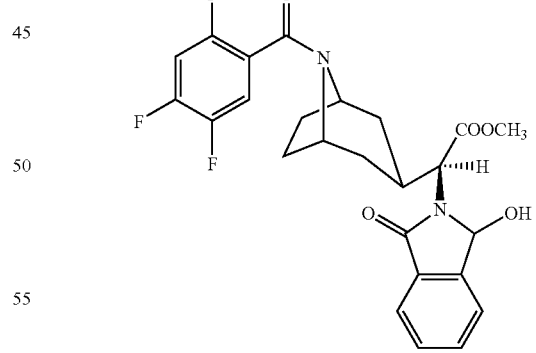

To a stirred solution of methyl (2S)-2-(1-hydroxy-3-oxo-1,3-dihydro-isoindol-2-yl)-2-[8-aza-bicyclo[3.2.1]oct-3-yl]-exo-acetate (step 7, 2.5 g, 7.57 mmol) in dry THF (90 ml) was added 2,4,5-trifluorobenzoic acid (1.33 g, 7.57 mmol) and 1-hydroxybenzotriazole (HOBT, 1.02 g, 7.57 mmol). The reaction mixture was cooled to 0° C. and added 1-(3-dimethylaminopropyl)-3-ethyl carbodimide hydrochloride (EDC, 1.6 g, 8.3 ml) in portions. The resulting mixture was stirred at 0° C. for 5 minutes and then at room temperature for 15 hours.

The solvent was removed under reduced pressure. To this was added dichloromethane (60 ml) and washed with a saturated aqueous NaHCO$_3$ solution (1×25 ml). The organic layer was dried over an anhydrous Na$_2$SO$_4$, filtered and filtrate was evaporated under reduced pressure to get the crude product, which was purified by column chromatography over silica gel (200-400 mesh) using 2% methanol in dichloromethane as an eluent to yield the title compound (2.25 g, 60%).

MS: m/z 511 (M+23).

Step 9: Methyl-(2S)-2-(1,3-dioxo-1,3-dihydroisoindol-2-yl)-2-[8-(2,4,5-trifluorobenzoyl)-8-aza-bicyclo[3.2.1]-oct-3-yl]-exo-acetate

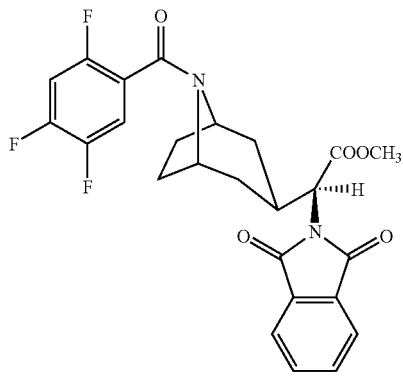

To a stirred solution of methyl (2S)-2-(1-hydroxy-3-oxo-1,3-dihydro-isoindol-2-yl)-2-[8-(2,4,5-trifluorobenzoyl)-8-aza-bicyclo[3.2.1]oct-3-yl]-exo-acetate (step 8, 2.2 g, 4.5 mmol) in acetone (75 ml) at 0° C. was added Jone's reagent dropwise and the completion of reaction was monitored by TLC. After 30 minutes, the solvent was evaporated under reduced pressure at room temperature and added dichloromethane (100 ml). The organic layer was washed with water (50 ml), brine (20 ml) and dried over anhydrous Na$_2$SO$_4$. The solvent was evaporated to yield the crude product, which was purified by column chromatography over the silica gel (100-200 mesh) using 1.2% methanol in dichloromethane as an eluent to yield the title compound (2.0 g, 91%).

MS: m/z 487 (M+1).

$^1$HNMR (CDCl$_3$, 400 MHz): δ 1.25-1.55 (m, 2H), 1.65-1.82 (m, 2H), 1.83-2.08 (m, 3H), 2.09-2.20 (m, 1H), 3.02-3.14 (m, 1H), 3.65-3.72 (m, 3H), 3.73-3.90 (m, 1H), 4.55-4.65 (m, 1H), 4.75-4.86 (m, 1H), 6.86-7.00 (m, 1H), 7.18-7.32 (m, 1H), 7.73-7.80 (m, 2H), 7.84-7.92 (m, 2H).

Analogously, by practicing the chemistry of step 1 to 9 with appropriate change in the reactants, following compounds were prepared.

Methyl-(2S)-2-(1,3-dioxo-1,3-dihydroisoindol-2-yl)-2-[8-(4-trifluoromethylbenzoyl)-8-aza-bicyclo[3.2.1]-oct-3-yl]-exo-acetate
MS: m/z 501 (M+1)

Methyl-(2S)-2-(1,3-dioxo-1,3-dihydroisoindol-2-yl)-2-[8-(adamantane-1-carbonyl)-8-aza-bicyclo[3.2.1]-oct-3-yl]-exo-acetate
MS: m/z 491 (M+1)

Methyl-(2S)-2-(1,3-dioxo-1,3-dihydroisoindol-2-yl)-2-[8-(4-trifluoromethyl-phenyl carbamoyl)-8-aza-bicyclo[3.2.1]-oct-3-yl]-exo-acetate
MS: m/z 516 (M+1)

Step 10: Methyl (2S)-2-amino-2-[8-(2,4,5-trifluorobenzoyl)-8-aza-bicyclo[3.2.1]oct-3-yl]-exo-acetate

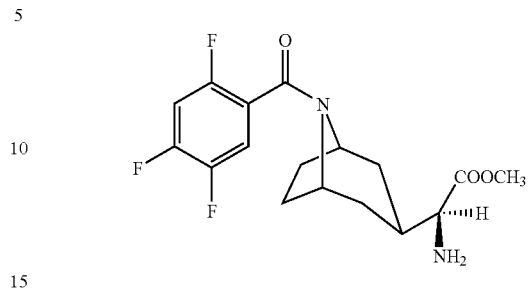

To a stirred solution of methyl (2S)-2-(1,3-dioxo-1,3-dihydro-isoindol-2-yl)-2-[8-(2,4,5-trifluorobenzoyl)-8-aza-bicyclo[3.2.1]oct-3-yl]-exo-acetate (step 9, 2.0 g, 4.1 mmol) in methanol (20 ml) was added a solution of hydrazine (1.03 g, 1.00 ml, 20.6 mmol) in methanol (22 ml) dropwise at 0° C. Ice bath was removed after 2 hours. and the reaction mixture was stirred for 20 hours at room temperature. The solvent was removed under reduced pressure at room temperature and the residue was taken in dichloromethane (100 ml) and stirred at room temperature for 15 minutes. The reaction mixture was filtered through a buchner funnel and the filtrate was concentrated to yield a crude product, which was purified by column chromatography over silica gel (100-200 mesh) using methanol:NH$_3$ in chloroform:dichloromethne in the ratio of 2:10:88 as an eluent to obtain the title compound (0.64 g, 44%)

MS: m/z 357 (M+1).

$^1$HNMR (CDCl$_3$, 200 MHz): δ 1.4-2.15 (m, 8H), 2.7-2.9 (m, 1H), 3.75-4.15 (m, 5H), 4.75-4.9 (m, 1H), 6.85-7.1 (m, 1H), 7.4-7.65 (m, 1H), 8.7-8.9 (m, 2H, exchangeable with D$_2$O).

Step 11: (2S)-2-Amino-2-[8-(2,4,5-trifluorobenzoyl)-8-aza-bicyclo[3.2.1]-oct-3-yl]-exo-ethanoic acid

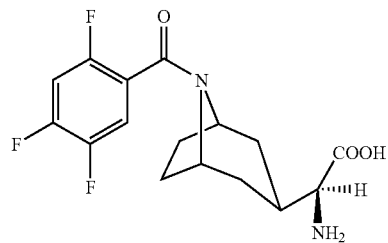

Methyl (2S)-2-amino-2-[8-(2,4,5-trifluorobenzoyl)-8-aza-bicyclo[3.2.1]oct-3-yl]-exo-acetate (step 10, 0.63 g, 1.76 mmol) was dissolved in methanol (45 ml) and added water (13 ml). The reaction mixture was cooled to 0° C. and added an aqueous solution of Na$_2$CO$_3$ (0.94 g, 8.85 mmol) in water (12 ml), dropwise under stirring. Ice bath was removed after 5 minutes and the reaction mixture was stirred at room temperature for 15 hours. The solvent was removed under reduced pressure at 35° C. and added water (10 ml). The reaction mixture was cooled to 0° C. and pH of the reaction mixture was converted to 3 with 1M HCl. The solvent was removed under reduced pressure at 35° C. and dried under high vacuum. The solid so obtained was stirred with 10% methanol in dichloromethane (50 ml) at room temperature for 30 minutes and filtered through a Buchner funnel. The filtrate was concentrated to obtain the title compound (0.54 g, 89%), which was subjected to next step without purification.

MS: m/z 343 (M+1)

$^1$HNMR (CDCl$_3$+CD$_3$OD, 200 MHz): δ 1.35-1.90 (m, 7H), 1.95-2.12 (m, 2H), 3.55-3.7 (m, 1H), 3.8-3.9 (m, 1H), 4.65-4.8 (m, 1H), 6.85-7.06 (m, 1H), 7.20-7.45 (m, 1H).

Analogously, by practicing the chemistry of step 10 and 11 with appropriate change in the reactants, following compounds were prepared.

(2S)-2-Amino-2-[8-(4-trifluoromethylbenzoyl)-8-aza-bicyclo[3.2.1]-oct-3-yl]-exo-ethanoic acid
MS: m/z 357 (M+1)

(2S)-2-Amino-2-[8-(adamantane-1-carbonyl)-8-aza-bicyclo[3.2.1]-oct-3-yl]-exo-ethanoic acid
MS: m/z 347 (M+1)

(2S)-2-Amino-2-[8-(4-trifluoromethyl-phenyl carbamoyl)-8-aza-bicyclo[3.2.1]-oct-3-yl]-exo-ethanoic acid
MS: m/z 372 (M+1)

Step 12: (2S)-2-(tert-Butoxycarbonyl)amino-2-[8-(2,4,5-trifluoro-benzoyl)-8-aza-bicyclo[3.2.1]oct-3-yl]-exo ethanoic acid

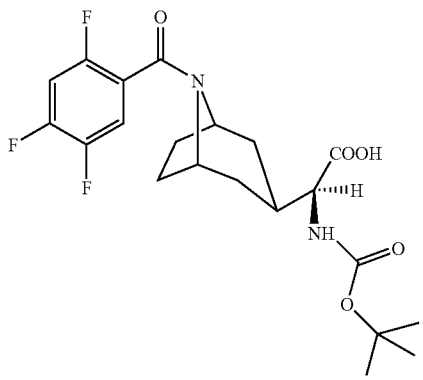

To a stirred solution of (2S)-2-amino-2-[8-(2,4,5-trifluorobenzoyl)-8-aza-bicyclo[3.2.1]oct-3-yl]-exo-ethanoic acid (step 11, 0.52 g, 1.52 mmol) in dry DMF (10 ml) was added anhydrous K$_2$CO$_3$ (0.63 g, 4.56 mmol). The reaction mixture was cooled to 0° C. and added di-tert-butyl dicarbonate (0.331 g, 0.35 ml, 1.51 mmol). After the addition, the reaction mixture was brought to room temperature and stirred for 15 hours. The solvent was removed under reduced pressure at 30° C., added THF (15 ml) and water (15 ml). It was then cooled to 0° C. and neutralised with 1M HCl to pH 6. The reaction mixture was concentrated to dryness and the solid so obtained was stirred with dichloromethane (60 ml), at room temperature and filtered through a buchner funnel and the filtrate was concentrated to yield the title compound (0.67 g, 99%).

MS: m/z 465 (M+23)

$^1$HNMR (CDCl$_3$+D$_2$O, 400 MHz): δ 1.35-1.65 (m, 12H), 1.65-1.85 (m, 3H), 1.92-2.10 (m, 2H), 2.35-2.60 (m, 1H), 3.8-3.9 (s, 1H), 4.20-4.35 (m, 1H), 4.75-4.90 (m, 1H), 6.92-7.02 (m, 1H), 7.18-7.35 (m, 1H).

Analogously, by practicing the chemistry of step 12 with appropriate change in the reactants, following compounds were prepared.

(2S)-2-(tert-Butoxycarbonyl)-amino-2-[8-(4-trifluoromethylbenzoyl)-8-aza-bicyclo[3.2.1]-oct-3-yl]-exo-ethanoic acid
MS: m/z 455 (M−1)

(2S)-2-(tert-Butoxycarbonyl)-amino-2-[8-(adamantane-1-carbonyl)-8-aza-bicyclo[3.2.1]-oct-3-yl]-exo-ethanoic acid
MS: m/z 447 (M+1)

(2S)-2-(tert-Butoxycarbonyl)-amino-2-[8-(4-trifluoromethyl-phenyl carbamoyl)-8-aza-bicyclo[3.2.1]-oct-3-yl]-exo-ethanoic acid MS: m/z 470 (M−1)

Intermediate 2

(2S)-2-(tert-Butoxycarbonyl)amino-2-[8-(2-fluoropyridine-4-carbonyl)-8-aza-bicyclo[3.2.1]-oct-3-yl]-exo-ethanoic-acid

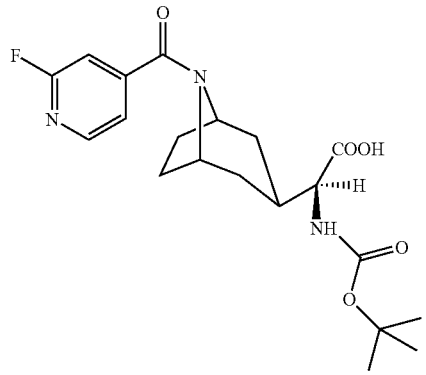

Step 1: Methyl-(2S)-2-(1-hydroxy-3-oxo-1,3-dihydroisoindol-2-yl)-2-[8-(carbobenzyl oxy)-8-aza-bicyclo[3.2.1]-oct-3-yl]-exo-acetate

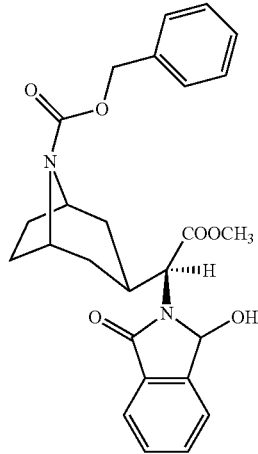

To a stirred solution of Methyl (2S)-2-(1-hydroxy-3-oxo-1,3-dihydroisoindol-2-yl)-2-[8-aza-bicyclo[3.2.1]-oct-3-yl]-exo-acetate (step 7 of intermediate 1, 42.9 g, 0.13 mol) in 1,4-dioxane was added a solution of sodium bicarbonate (43.68 g, 0.52 mol) in water (450 ml) at room temperature and then cooled to 0° C. To this solution was added-benzyloxy carbonyl chloride (66.5 g, 65.3 ml, 0.39 mol) in a drop wise manner at 0° C. in 20 minutes and resulting mixture was stirred at 0° C. for one hour and further at room temperature for one hour. The reaction mixture was extracted with ethyl acetate (4×500 ml) and the combined organic layer was washed with brine (500 ml), dried over anhydrous $Na_2SO_4$. The solvent was evaporated under reduced pressure to obtain a crude a crude product, which was purified by column chromatography over silica gel (100-200 mesh) using 3% methanol in dichloromethane as an eluent to yield the title compound (49.0 g, 81%).

MS: m/z 463 (M−1)

$^1$HNMR ($CDCl_3+D_2O$, 400 MHz): δ 1.32-1.80 (m, 6H), 1.85-2.0 (m, 2H), 2.78-3.0 (m, 1H), 3.68 (m, 3H), 4.2-4.35 (m, 2H), 4.48-4.65 (m, 1H), 5.0-5.18 (m, 2H), 5.88-6.1 (m, 1H), 7.26-7.36 (m, 5H), 7.46-7.54 (m, 1H) 7.55-7.62 (m, 2H) 7.75-7.8 (m, 1H).

Step 2: Methyl (2S)-2-(1,3-dioxo-1,3-dihydroisoindol-2-yl)-2-[8-(carbobenzyloxy)-8-aza-bicyclo[3.2.1]-oct-3-yl]-exo-acetate

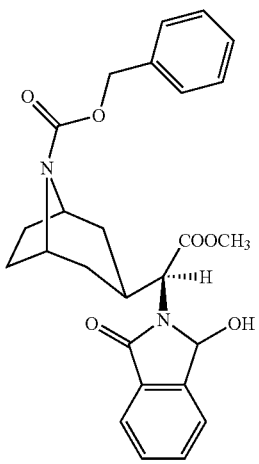

To stirred a solution of methyl-(2S)-2-(1-hydroxy-3-oxo-1,3-dihydroisoindol-2-yl)-2-[8-(carbobenzyloxy)-8-aza-bicyclo[3.2.1]-oct-3-yl]-exo-acetate (49.0 g, 0.11 mol) in acetone (1 L) at 0° C. was added Jone's reagent drop wise and the progress of reaction was monitored by TLC. After 50 minutes, the solvent was evaporated under reduced pressure at 0-5° C. and added dichloromethane (900 ml). The organic layer was washed with water (300 ml) brine (200 ml) and dried over anhydrous $Na_2SO_4$. The solvent was evaporated to yield the crude product, which was purified by column chromatography over silica gel (100-200 mesh) using 2% methanol in dichloromethane as an eluent to yield the title compound (40.8 g, 84%).

MS: m/z 463 (M+1)

$^1$HNMR ($CDCl_3$, 400 MHz): δ 1.38-1.83 (5H), 1.86-2.02 (m, 2H), 2.03-2.1 (m, 1H), 2.96-3.1 (m, 1H), 3.68 (s, 3H), 4.2-4.4 (m, 2H), 4.5-4.6 (m, 1H), 5.04-5.15 (m, 2H), 7.26-7.37 (m, 5H), 7.73-7.78 (m, 2H), 7.83-7.89 (m, 2H)

Step 3: Methyl-(2S)-2-amino-2-[8-(carbobenzyloxy)-8-aza-bicyclo[3.2.1]-oct-3-yl]-exo-acetate

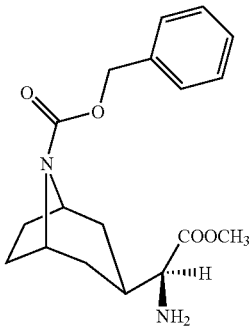

To a stirred solution of methyl (2S)-2-(1,3-dioxo-1,3-dihydroisoindol-2-yl)-2-[8-(carbobenzyloxy)-8-aza-bicyclo[3.2.1]-oct-3-yl]-exo-acetate (40.8 g, 0.088 mol) in methanol (800 ml) was added a solution of hydrazine hydrate (80%, 26.5 g, 26 ml, 0.42 mol) in methanol (800 ml) drop wise at 0° C. in two hours and stirred at 0° C. for another three hours. Then the reaction mixture was stirred at room temperature for 40 hours. The solvent was removed under reduced pressure at room temperature. The residue so obtained was taken in dichloromethane (600 ml) and stirred at room temperature for 10 minutes. The reaction mixture was filtered through a Buchner funnel and the residue was washed with dichloromethane (4×100 ml). The filtrate was concentrated to yield the crude product, which was purified by column chromatography over silica gel (100-200 mesh) using methanol:$NH_3$ in chloroform:dichloromethane in the ratio 2:10:88 as an eluent to obtain the title compound (23.9 g, 82.0%).

MS: m/z 333 (M+1)

$^1$HNMR ($CDCl_3+D_2O$, 200 MHz): δ 1.3-1.7 (m, 6H), 1.72-2.3 (m, 3H), 3.18 (d, J=6 Hz, 1H), 3.68 (s, 3H), 4.23-4.4 (m, 2H), 5.12 (s, 2H), 7.25-7.4 (m, 5H).

Step 4: Methyl-(2S)-2-(tert-butoxycarbonyl)-amino-2-[8-(carbobenzyloxy)-8-aza-bicyclo[3.2.1]-oct-3-yl]-exo-acetate

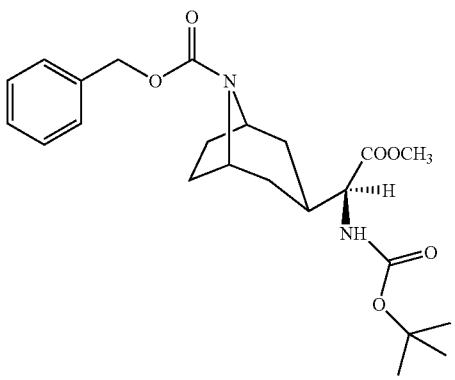

Methyl-(2S)-2-amino-2-[8-(carbobenzyloxy)-8-aza-bicyclo[3.2.1]-oct-3-yl]-exo-acetate (23.9 g, 0.072 mol) was dissolved in dichloromethane (800 ml) and added triethylamine (12.0 ml, 8.72 g, 0.086 mmol) at 0° C. followed by the addition of solution of di-tert-butyl dicarbonate (17.26 g, 0.079 mol) in dichloromethane (150 ml) under stirring. After the completion of addition, reaction mixture was stirred at room temperature for 16 hours The solvent was removed under reduced pressure at room temperature to get a crude product, which was purified by column chromatography over silica gel (100-20 mesh) using 1.5% methanol in dichloromethane as an eluent to yield the title compound (25.0 g, 80%).

MS: m/z 431 (M−1)

$^1$HNMR (CDCl$_3$, 400 MHz): δ 1.34-1.7 (m, 15H), 1.9-2.02 (m, 2H), 2.25-2.38 (m, 1H), 3.73 (s, 3H), 4.15-4.24 (m, 1H), 4.27-4.40 (m, 2H), 4.93-5.03 (m, 1H), 5.07-5.18 (m, 2H), 7.26-7.42 (m, 5H).

Step 5: Methyl-(2S)-2-(tert-butoxycarbonyl)-amino-2-[−8-aza-bicyclo[3.2.1]-oct-3-yl]-exo-acetate

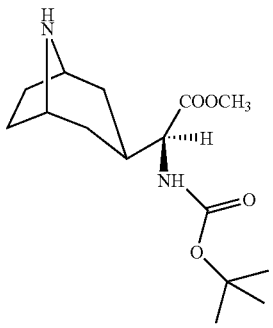

To a solution of methyl-(2S)-2-(tert-butoxycarbonyl)-amino-2-[8-(carbobenzyloxy)-8-aza-bicyclo[3.2.1]-oct-3-yl]-exo-acetate (12.5 g, 0.029 mol) in methanol (200 ml) was added 5% Pd—C as a paste in water (5.0 g in 3.0 ml. water) and the solution was hydrogenated (50 psi of H$_2$) on Parr apparatus for 3.5 hours. After completion, reaction mixture was filtered through a celite bed and the residue was washed with methanol (4×50 ml). The filterate was concentrated under reduced pressure to get a thick liquid, which was re-dissolved in dichloromethane (250 ml) and filtered through a Buchner funnel. The filtrate was concentrated to yield the title compound (8.53 g, 99%).

MS: m/z 299 (M+1)

$^1$HNMR (CDCl$_3$+D$_2$O, 400 MHz): δ 1.3-1.5 (m, 13H), 1.56-1.68 (m, 2H), 1.72-1.85 (m, 2H), 2.1-2.22 (m, 1H), 3.5-3.55 (m, 2H), 3.72 (s, 3H), 4.16-4.22 (m, 1H).

Step 6: Methyl-(2S)-2-(tert-butoxycarbonyl)-amino-2-[8-(2-fluoropyridine-4-carbonyl)-8-aza-bicyclo[3.2.1]-oct-3-yl]-exo-acetate

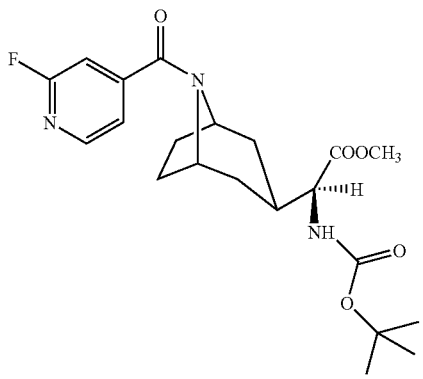

To a stirred solution of methyl-(2S)-2-(tert-butoxycarbonyl)-amino-2-[8-aza-bicyclo[3.2.1]-oct-3-yl]-exo-acetate (8.3 g, 27.85 mmol) in THF (165 ml) was added 2-fluoro-pyridine-4-carboxylic acid (3.93 g, 27.85 mmol) and 1-hydroxybenzotriazole (HOBT, 3.76 g, 27.85 mmol) The reaction mixture was cooled to 0° C. and 1-(3-dimethyl aminopropyl)-3-ethyl carbodimide hydrochloride (5.87 g, 30.64 mmol) was added in portions followed by water (8.0 ml) to get a clear solution. The reaction mixture was stirred at room temperature for 15 hours. The solvent was removed under reduced pressure, diluted with dichloromethane (250 ml), washed with a saturated NaHCO$_3$ solution (1×25 ml), followed by water (1×25 ml). The organic layer was dried over anhydrous Na$_2$SO$_4$ and the solvent was concentrated under reduced pressure to get a crude product, which was purified by column chromatography over silica gel (100-200 mesh) using 1.5% methanol in dichloromethane as an eluent to yield the title compound (8.9 g, 75%)

mp: 84-86° C.

MS: m/z 420 (M−1)

$^1$HNMR (CDCl$_3$+D$_2$O, 200 MHz): δ 1.38-1.60 (m, 11H), 1.62-1.82 (m, 3H), 1.83-2.10 (m, 2H), 2.2-2.50 (m, 1H), 3.75 (s, 3H), 3.9-4.0 (m, 1H), 4.18-4.38 (m, 1H), 4.80-4.92 (m, 1H), 4.93-5.2 (m, 1H), 6.9-7.0 (m, 1H), 7.12-7.28 (m, 1H), 8.20-8.32 (m, 1H).

Step 7: (2S)-2-(tert-Butoxycarbonyl)-amino-2-[8-(2-fluoropyridine-4-carbonyl)-8-aza-bicyclo[3.2.1]-oct-3-yl]-exo-ethanoic-acid

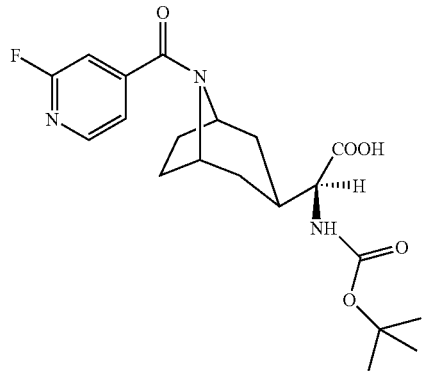

To a stirred and cooled (0° C.) solution of methyl-(2S)-2-(tert-butoxycarbonyl)-amino-2-[8-(2-fluoropyridine-4-carbonyl)-8-aza-bicyclo[3.2.1]-oct-3-yl]exo-acetate (8.9 g, 21.14 mmol) in methanol (200 ml) was added a solution of Na$_2$CO$_3$ (11.2 g, 105.7 mmol) in water (100 ml) in a drop wise manner. After the addition was completed, the turbid solution was stirred at room temperature and added more methanol (250 ml) followed by water (25 ml) until the solution become clear. This mixture was stirred at room temperature for 16 hours. After completion of reaction, the reaction mixture was concentrated under reduced pressure to dryness. To this was added water (10 ml), cooled to 0° C. and pH of the reaction mixture was adjusted to 6.5 with aqueous 20% HCl. The solvent was then removed under reduced pressure to yield a solid, which was stirred with 15% methanol in dichloromethane (100 ml) at room temperature for 30 minutes. The reaction mixture was filtered through a Buchner funnel and the filtrate was dried over anhydrous Na$_2$SO$_4$. The solvent was evaporated to yield the title compound (8.6 g., 99%), which was subjected to next step without purification.

MS: m/z 406 (M−1)

¹HNMR (CDCl₃, 400 MHz): δ 1.2-2.0 (m, 17H), 2.12-2.55 (m, 1H), 3.80-3.95 (m, 2H) 4.57-4.74 (m, 1H), 5.85-6.10 (m, 1H), 6.90-7.05 (m, 1H) 7.18-7.28 (m, 1H), 8.22-8.3 (m, 1H).

Analogously by practicing the chemistry described in steps 1 to 7 with appropriate change in the reactants, following compounds were prepared.

(2S)-2-(tert-Butoxycarbonyl)-amino-2-[8-(pyridine-4-carbonyl)-8-aza-bicyclo[3.2.1]-oct-3-yl]-exo-ethanoic acid
MS: m/z 390 (M+1)

(2S)-2-(tert-Butoxycarbonyl)-amino-2-[8-(4-cyano-benzoyl)-8-aza-bicyclo[3.2.1]-oct-3-yl]-exo-ethanoic acid
MS: m/z 414 (M+1)

(2S)-2-(tert-Butoxycarbonyl)-amino-2-[8-(2,5-difluorobenzoyl)-8-aza-bicyclo[3.2.1]-oct-3-yl]-exo-ethanoic acid
MS: m/z 447 (M+23)

(2R)-2-(tert-Butoxycarbonyl)-amino-2-[8-(2-fluoropyridin-4-carbonyl)-8-aza-bicyclo[3.2.1]-oct-3-yl]-exo-ethanoic acid
MS: m/z 430 (M+23)

(2S)-2-(tert-Butoxycarbonyl)-amino-2-[8-(2-fluoropyridine-3-carbonyl)-8-aza-bicyclo[3.2.1]-oct-3-yl]-exo-ethanoic acid
MS: m/z 406 (M−1)

(2S)-2-(tert-Butoxycarbonyl)-amino-2-[8-(pyridine-3-carbonyl)-8-aza-bicyclo[3.2.1]-oct-3-yl]-exo-ethanoic acid
MS: m/z 412 (M+23)

(2S)-2-(tert-Butoxycarbonyl)-amino-2-[8-(thiophene-2-carbonyl)-8-aza-bicyclo[3.2.1]-oct-3-yl]-exo-ethanoic acid
MS: m/z 417 (M+23)

(2S)-2-(tert-Butoxycarbonyl)-amino-2-[8-(pyrazine-2-carbonyl)-8-aza-bicyclo[3.2.1]-oct-3-yl]-exo-ethanoic acid
MS: m/z 389 (M−1)

(2R)-2-(tert-Butoxycarbonyl)-amino-2-[8-(pyrazine-2-carbonyl)-8-aza-bicyclo[3.2.1]-oct-3-yl]-exo-ethanoic acid
MS: m/z 413 (M+23)

(2S)-2-(tert-Butoxycarbonyl)-amino-2-[8-(pyridine-2-carbonyl)-8-aza-bicyclo[3.2.1]-oct-3-yl]-exo-ethanoic acid
MS: m/z 390 (M+1)

(2S)-2-(tert-Butoxycarbonyl)-amino-2-[8-(furan-2-carbonyl)-8-aza-bicyclo[3.2.1]-oct-3-yl]-exo-ethanoic acid
MS: m/z 401 (M+23)

(2S)-2-(tert-Butoxycarbonyl)-amino-2-[8-(3-fluoropyridine-4-carbonyl)-8-aza-bicyclo[3.2.1]-oct-3-yl]exo-ethanoic acid
MS: m/z 430 (M+23)

(2S)-2-(tert-Butoxycarbonyl)-amino-2-[8-(benzo[1,3]dioxole-5-carbonyl)-8-aza-bicyclo[3.2.1]-oct-3-yl]-exo-ethanoic acid
MS: m/z 433 (M+1)

(2S)-2-(tert-Butoxycarbonyl)-amino-2-[8-(2-pyridin-4-yl-acetyl)-8-aza-bicyclo[3.2.1]-oct-3-yl]-exo-ethanoic acid
MS: m/z 404 (M+1)

(2S)-2-(tert-Butoxycarbonyl)-amino-2-[8-(1-acetyl-piperidine-4-carbonyl)-8-aza-bicyclo[3.2.1]-oct-3-yl]-exo-ethanoic acid
MS: m/z 438 (M+1)

Intermediate 3

Methyl-(2S)-2-(tert-butoxycarbonyl)-amino-2-[8-(2,4,5-trifluorobenzyl)-8-aza-bicyclo[3.2.1]-oct-3-yl]-exo-acetate

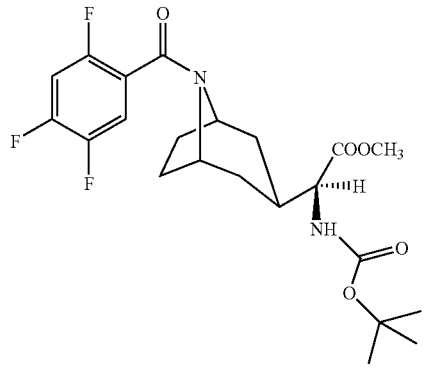

Step 1: Methyl-(2S)-2-(tent-butoxycarbonyl)-amino-2-[8-aza-bicyclo[3.2.1]-oct-3-yl]-exo-acetate (step-5 of intermediate 2, 2.1 g, 7.04 mmol) was dissolved in dichloromethane (70 ml). The reaction mixture was cooled to 0° C. and added triethylamine (1.06 g, 1.4 ml, 10.6 mmol) followed by the addition of a solution of 2,4,5-trifluorobenzyl bromide (1.58 g, 7.04 mmol) in dichloromethane (14 ml). The reaction mixture was then stirred at room temperature for 3 hours. The solvent was removed under reduced pressure to yield the crude product, which was purified by column chromatography over silica gel (100-200 mesh.) using 1% methanol as an eluent to yield the title compound (2.2 g, 71%).

MS: m/z 443 (M+1)
¹HNMR (CDCl₃+D₂O, 400 MHz): δ 1.42-1.47 (m, 9H), 1.5-1.66 (m, 6H), 1.9-2.05 (m, 3H), 3.16 (s, 2H), 3.73 (s, 3H), 4.1-4.3 (m, 2H), 5.0-5.1 (m, 1H), 6.8-6.9 (m, 1H), 7.4-7.46 (m, 1H).

Intermediate 4

Methyl-(2S)-2-(tert-butoxycarbonyl)-amino-2-[8-(4-methanesulphonylphenyl)-8-aza-bicyclo[3.2.1]-oct-3-yl]-exo-acetate

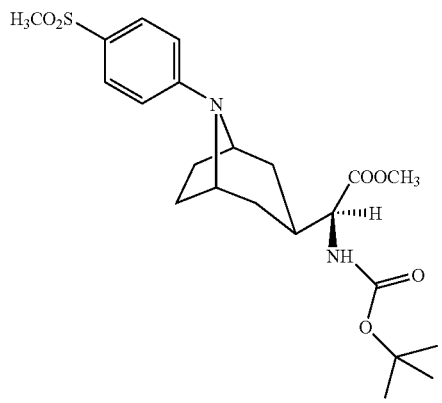

Step 1: To a stirred solution of methyl (2S)-2-(tert-butoxycarbonyl)-amino-2-[8-aza-bicyclo[3.2.1]-oct-3-yl]-exo-acetate (step 5 of intermediate 2, 1.0 g, 3.35 mmol) in dry toluene (30 ml) was added 1-bromo-4-methanesulphonyl benzene (0.787 g, 3.35 mmol), BINAP (0.312 g, 0.5 mmol), palladium acetate (0.074 g, 0.33 m mol) and $CS_2CO_3$ (1.52 g, 4.67 mmol) under $N_2$ atmosphere. The reaction mixture was then heated at 90° C. for 17 hours. The reaction mixture was allowed to come at room temperature. The solvent was removed under reduced pressure and added dichloromethane (50 ml). The organic layer was washed with water (25 ml) and dried over anhydrous $Na_2SO_4$. The solvent was concentrated under reduced pressure to get a crude product, which was purified by column chromatography over silica gel (100-200 mesh) using 30% ethyl acetate in hexane as an eluent to yield the title compound (0.52 g, 34%).

mp: 102-104° C.

MS: m/z 451 (M−1)

$^1$HNMR (CDCl$_3$, 200 MHz): δ 1.37 (s, 9H), 1.4-1.5 (m, 1H), 1.55-1.9 (m, 5H), 2.05-2.2 (m, 2H), 2.3-2.55 (m, 1H), 3.03 (s, 3H), 3.66 (s, 3H), 4.0-4.2 (m, 1H), 4.3-4.4 (m, 2H), 4.86-5.0 (m, 1H), 6.75 (d, J=8.9 Hz, 2H), 7.73 (d, J=8.9 Hz, 2H)

Intermediate 5

Methyl-(2S)-2-(tert-butoxycarbonyl)-amino-2-[8-(3,5-difluorobenzenesulphonyl)-8-aza-bicyclo[3.2.1]-oct-3-yl]-exo-acetate

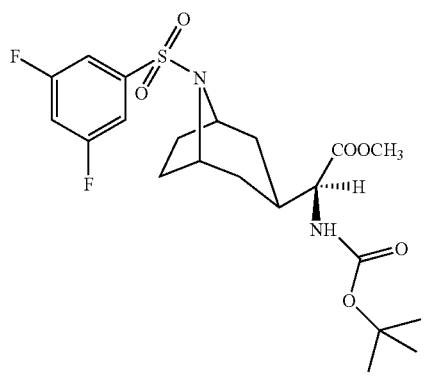

Step 1: To a stirred solution of methyl-(2S)-2-(tent-butoxycarbonyl)-amino-2-[8-aza-bicyclo[3.2.1]-oct-3-yl]-exo-acetate (step 5 of intermediate 2, 1.0 g, 3.36 mmol) in dichloromethane (20 ml) at 0° C. was added triethylamine (0.7 ml, 0.51 g, 5.03 mmol) and 3,5-difluorobenzene sulphonyl chloride (0.785 g, 3.69 mmol). The reaction mixture was then stirred at room temperature for one hour. The completion of reaction was monitored by TLC. The reaction mixture was diluted with dichloromethane (20 ml), washed with water (2×10 ml) and dried over anhydrous $Na_2SO_4$. The solvent was evaporated to yield the crude product, which was purified by column chromatography over silica gel (100-200 mesh) using 1% methanol in dichloromethane as an eluent to yield the title compound (1.0 g, 62%).

mp: 55-57° C.

MS: m/z 473 (M−1)

$^1$HNMR (CDCl$_3$, 200 MHz): δ 1.43 (s, 9H), 1.50-1.78 (m, 8H), 2.08-2.38 (m, 1H), 3.73 (s, 3H), 4.13-4.31 (m, 3H), 4.93-5.08 (m, 1H), 6.90-7.08 (m, 1H), 7.3-7.45 (m, 2H).

Intermediate 6

Methyl-(2S)-2-(tert-butoxycarbonyl)-amino-2-[8-(cyclohexyl)-8-aza-bicyclo[3.2.1]-oct-3-yl]-exo-acetate

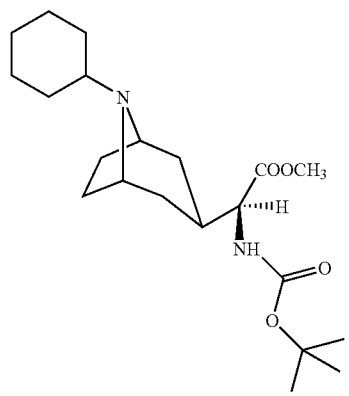

Step 1: Methyl-(2S)-2-(tert-butoxycarbonyl)-amino-2-[8-(cyclohex-2-enyl)-8-aza-bicyclo[3.2.1]-oct-3-yl]-exo-acetate

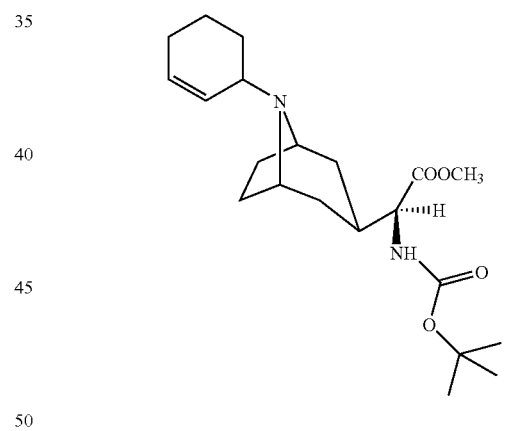

To a stirred solution of methyl-(2S)-2-(tert-butoxycarbonyl)-amino-2-[−8-aza-bicyclo[3.2.1]-oct-3-yl]-exo-acetate (step 5 of intermediate 2, 0.5 g, 1.68 mmol) in acetonitrile (20 ml) at room temperature was added anhydrous potassium carbonate (0.7 g, 5.03 mmol) and stirred for 10 minutes. To this solution was added 3-bromo cyclohexene (0.3 g, 0.22 ml, 1.84 mmol) followed by potassium iodide (0.014 g, 0.08 mmol) and heated at 45° C. for six hours. Completion of reaction was monitored by TLC. The solvent was evaporated under reduced pressure, added dichloromethane (10 ml) and washed with water (10 ml) The organic solvent was dried over anhydrous $Na_2SO_4$ and the solvent was evaporated at reduced pressure to yield the crude product, which was purified by column chromatography over silica gel (100-200 mesh) using 4% methanol in dichloromethane to get the title compound (0.55 g, 87%).

MS: m/z 379 (M+1)

¹HNMR (CDCl₃+D₂O, 400 MHz): δ 1.15-1.34 (m, 3H), 1.43 (s, 9H), 1.44-1.78 (m, 5H), 1.8-2.1 (m, 6H), 2.11-2.23 (m, 1H), 3.04-3.15 (m, 1H), 3.53-3.64 (m, 2H), 3.72 (s, 3H), 4.14-4.21 (m, 1H), 5.66-5.72 (m, 1H), 5.78-5.85 (m, 1H).

Step 2: Methyl-(2S)-2-(tert-butoxycarbonyl)-amino-2-[8-(cyclohexyl)-8-aza-bicyclo[3.2.1]oct-3-yl]-exo-acetate

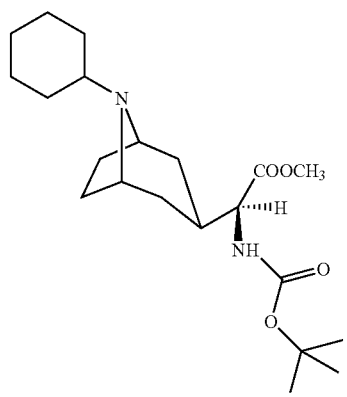

To a solution of methyl-(2S)-2-(tert-butoxycarbonyl)-amino-2-[8-(cyclohex-2-enyl)-8-aza-bicyclo[3.2.1]-oct-3-yl]-exo-acetate (0.5 g, 1.32 mmol) in methanol (20 ml) was added 5% Pd—C (0.5 g) and the solution was hydrogenated (60 psi of H₂) on Parr apparatus for 8 hours. The reaction mixture was filtered through a small celite bed and washed with 50% methanol in dichloromethane (2×20 ml) the filtrate was evaporated under reduced pressure to get the title compound quantitatively (0.48 g).

MS: m/z 381 (M+1)

¹HNMR (CDCl₃, 200 MHz): δ 1.05-2.3 (m, 28H), 2.5-2.7 (m, 1H), 3.65-3.82 (m, 5H), 4.1-4.30 (m, 1H), 5.25-5.5 (m, 1H).

Intermediate 7

Methyl-(2S)-2-(tert-butoxycarbonyl)-amino-2-[8-(cyclohexane carbonyl)-8-aza-bicyclo[3.2.1]-oct-3-yl]-exo-acetate

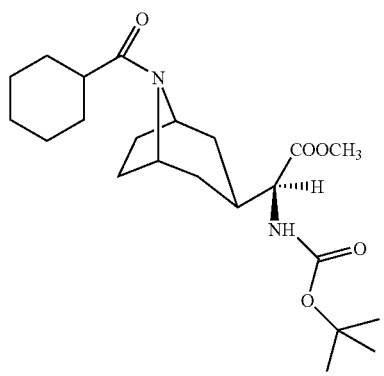

Step 1: To stirred solution of methyl-(2S)-2-(tert-butoxycarbonyl)-amino-2-[8-aza-bicyclo[3.2.1]-oct-3-yl]-exo-acetate (step 5 of intermediate 2, 1.0 g, 3.35 mmol) in dichloromethane (30 ml) at 0° C. was added cyclohexane carbonyl chloride (0.45 g, 0.42 ml, 3.35 mmol) and triethyl amine (0.676 g, 0.93 ml, 6.7 mmol). The reaction mixture was then stirred at room temperature for one hour. The reaction mixture was diluted with dichloromethane (30 ml) and washed with water (2×25 ml). The organic layer was dried over anhydrous Na₂SO₄ and the solvent was evaporated to yield the crude product, which was purified by column chromatography over silica gel (100-200 mesh) using 2.5% methanol in dichloromethane as an eluent to yield the title compound (1.25 g, 91%)

mp: 69-71° C.

MS: m/z 409 (M+1)

¹HNMR (CDCl₃+D₂O, 400 MHz): δ 1.15-1.35 (m, 5H), 1.4-1.45 (m, 9H), 1.46-1.8 (m, 10H), 1.83-2.06 (m, 2H), 2.25-2.36 (m, 2H), 3.73 (s, 3H), 4.2-4.3 (m, 2H), 4.65-4.73 (m, 1H), 4.98-5.08 (m, 1H).

Intermediate 8

Methyl-(2S)-2-(tert-butoxycarbonyl)-amino-2-[8-(4-chlorophenyl sulfonyl carbamoyl)-8-aza-bicyclo[3.2.1]-oct-3-yl]-exo-acetate

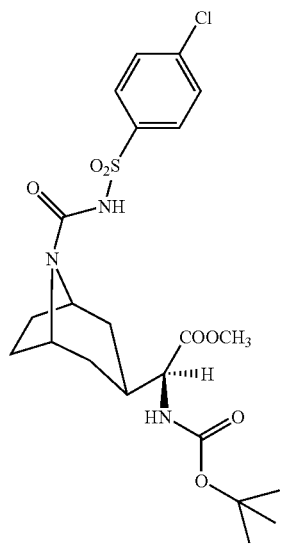

To a stirred solution of methyl-(2S)-2-(tert-butoxycarbonyl)-amino-2-[8-aza-bicyclo[3.2.1]-oct-3-yl]-exo-acetate (Step 5 of intermediate 2, 0.95 g., 3.18 mmol) in dry dichloromethane (25 ml) was added 4-chlorobenzene sulfonyl isocyanate (0.69 g, 3.18 mmol) followed by the addition of N-ethyl diisopropyl amine (0.45 g, 0.6 ml., 3.49 mmol) at 0° C. After the addition was completed, reaction mixture was stirred at room temperature for 30 minutes. The completion of reaction was monitored by TLC. The reaction mixture was diluted with dichloromethane (25 ml) and washed with water (2×25 ml). The organic layer was dried over anhydrous Na₂SO₄ and the solvent was evaporated at reduced pressure to yield the crude product, which was purified by column chromatography over silica gel (100-200 mesh) using 2% methanol in dichloromethane as an eluent to yield the title compound (1.22 g, 74%).

MS: m/z 514 (M−1)

¹HNMR (CDCl₃+D₂O, 400 MHz): δ 1.42 (s, 1H), 1.45-1.80 (m, 4H), 1.82-2.40 (m, 4H), 3.71 (s, 3H), 4.04-4.40 (m, 3H), 5.00-5.21 (m, 1H), 7.87 (d, J=8.8 Hz, 2H), 7.98 (d, J=8.8 Hz, 2H)

Intermediate 9

Methyl-(2S)-2-(tert-butoxycarbonyl)-amino-2-[8-(3,3,3-trifluoropropyl)-8-aza-bicyclo[3.2.1]-oct-3-yl]-exo-acetate

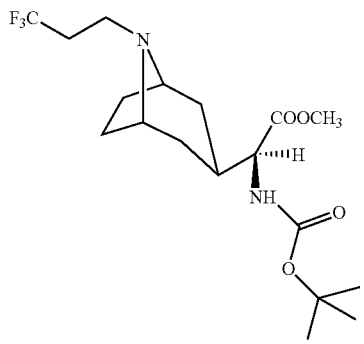

Step 1: To stirred a solution of methyl-(2S)-2-(tert-butoxycarbonyl)-amino-2-[8-aza-bicyclo[3.2.1]-oct-3-yl]-exo-acetate (step 5 of intermediate 2, 1.0 g, 3.36 mmol) in acetonitrile (20 ml) at room temperature was added anhydrous K₂CO₃ (1.39 g, 10.07 mmol) stirred for 10 minutes. To this reaction mixture was then added 3,3,3-trifluoropropyl iodide (0.827 g, 0.43 ml, 3.69 mmol) and heated at 50° C. for 6 hours under stirring. The solvent was removed under reduced pressure and added ethyl acetate (50 ml). The organic layer was washed with water (2×20 ml), bromine (10 ml) and dried over anhydrous Na₂SO₄. The solvent was evaporated to yield the crude product, which was purified by column chromatography over silica gel (100-200 mesh) using 1.3% methanol in dichloromethane as an eluent to yield the title compound (0.775 g, 58%).

MS: m/z 395 (M+1)

¹HNMR (CDCl₃, 200 MHz): δ 1.17-1.60 (m, 15H), 1.82-2.40 (m, 5H), 2.5-2.63 (m, 2H), 3.14-3.28 (m, 2H) 3.73 (s, 3H) 4.10-4.30 (m, 1H), 4.97-5.10 (m, 1H).

Intermediate 10

Methyl-(2S)-2-(tert-butoxycarbonyl)-amino-2-[8-(5-cyanopyridin-2-yl)-8-aza-bicyclo[3.2.1]-oct-3-yl]-exo-acetate

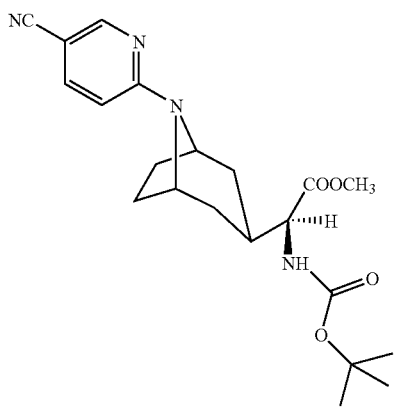

Step 1: To a stirred solution of methyl-(2S)-2-(tert-butoxycarbonyl)-amino-2-[8-aza-bicyclo[3.2.1]-oct-3-yl]-exo-acetate (step 5 of intermediate 2, 0.8 g, 2.68 mmol) in dry DMF (10 ml) was added 6-chloro-nicotinontrile (0.407 g, 2.94 mmol) and triethylamine (0.54 g, 0.75 ml, 5.36 mmol) at room temperature. The reaction mixture was then heated at 80° C. for 2 hours under stirring. The reaction mixture was allowed to come at room temperature. It was then diluted with water (80 ml) and extracted with ethyl acetate (2×40 ml) The combined organic layer was washed with water (2×30 ml) and dried over anhydrous Na₂SO₄. The solvent was removed under reduced pressure and the crude product so obtained was purified by column chromatography over silica gel (100-200 mesh) using 40% ethyl acetate in hexane as an eluent to yield the title compound (0.835 g, 62%).

mp: 65-67° C.

MS: m/z 401 (M+1)

¹HNMR (CDCl₃, 200 MHz): δ 1.38 (s, 9H), 1.4-1.65 (m, 4H), 1.72-1.9 (m, 2H), 2.0-2.2 (m, 2H), 2.28-2.5 (m, 1H) 3.7 (s, 3H) 4.01-4.2 (m, 1H), 4.5-4.7 (m, 2H) 4.88-5.0 (m, 1H), 6.46 (d, J=8.9 Hz, 1H) 7.5-7.62 (m, 1H), 8.34-8.42 (m, 1H)

Intermediate 11

Methyl (2S)-2-(tert-butoxy carbonyl)-amino-2-{8-(adamantan-1-yl-methyl)-8-aza-bicyclo[3.2.1]oct-3-yl}-exo-acetate

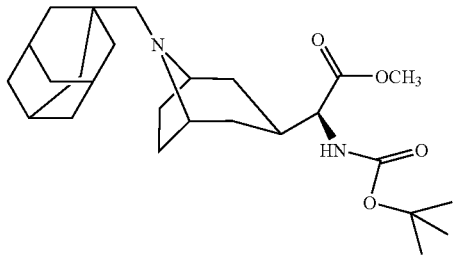

To a stirred solution of methyl (2S)-2-(tert-butoxy carbonyl)amino-2-{8-(adamantan-1-carbonyl)-8-aza-bicyclo[3.2.1]oct-3-yl}-exo-acetate (prepared by following the similar procedure as described in step 6 of intermediate 2, 1.0 g, 2.17 mmol) in dry tetrahydrofuran (30 ml) was added borane dimethyl sulfide complex (0.41 ml, 0.328 g, 4.35 m mol) drop wise at 0° C. The reaction mixture was allowed to come at room temperature and stirred for 4 h at same temperature. The progress of reaction was monitored by TLC. The reaction mixture was cooled to 0° C. and acidified to pH 5 with 10% aquous HCl. The reaction mixture was evaporated under reduced pressure to dryness and the residue was stirred with ethyl acetate (10 ml). It was then cooled to 0° C. and basified with a saturated aqueous sodium carbonate solution to pH 9. The organic layer was separated and the aqueous layer was extracted with ethyl acetate (3×25 ml). The combined organic layer was dried over anhydrous sodium sulphate and the solvent was evaporated to obtain a crude product, which was purified by column chromatography over silica gel (100-200 mesh) using 2% methanol in dichloromethane as an eluent to yield the title compound (0.82 g, 85%).

SMB/372/149
MS: m/z 447 (M+1)
¹HNMR (CDCl₃, 400 MHz): δ 1.4-1.53 (m, 19H), 1.54-1.64 (m, 12H), 1.65-1.72 (m, 4H), 1.76-1.84 (m, 4H), 1.9-1.95 (m, 5H), 2.95-3.02 (m, 2H), 3.71 (S, 3H), 4.06-4.14 (m, 1H), 4.98 (d, J=9.2 Hz, 1H)

For making the final compounds, all the Intermediates from 3-11 were converted to their corresponding acids listed below by using similar procedure as described for Intermediate 2 process.

(2S)-2-(tert-Butoxycarbonyl)-amino-2-[8-(2,4,5-trifluorobenzyl)-8-aza-bicyclo[3.2.1]-oct-3-yl]-exo-ethanoic acid
MS: m/z 429 (M+1)

(2S)-2-(tert-Butoxycarbonyl)-amino-2-[8-(4-methanesulfonyl phenyl)-8-aza-bicyclo[3.2.1]-oct-3-yl]exo-ethanoic acid
MS: m/z 437 (M−1)

(2S)-2-(tert-Butoxycarbonyl)-amino-2-[8-(3,5-difluorobenzene sulfonyl)-8-aza-bicyclo[3.2.1]-oct-3-yl]-exo-ethanoic acid
MS: m/z 459 (M−1)

(2S)-2-(tert-Butoxycarbonyl)-amino-2-[8-(cyclohexyl)8-aza-bicyclo[3.2.1]-oct-3-yl]-exo-ethanoic acid
MS: m/z 367 (M+1)

(2S)-2-(tert-Butoxycarbonyl)-amino-2-[8-(cyclohexane-carbonyl)-8-aza-bicyclo[3.2.1]-oct-3-yl]-exo-ethanoic acid
MS: m/z 395 (M+1)

(2S)-2-(tert-Butoxycarbonyl)-amino-2-[8-(4-chlorophenyl-sulfonyl-carbamoyl)-8-aza-bicyclo[3.2.1]-oct-3-yl]-exo-ethanoic acid
MS: m/z 524 (M+23)

(2S)-2-(tert-Butoxycarbonyl)-amino-2-[8-(3,3,3-trifluoro propyl)-8-aza-bicyclo[3.2.1]-oct-3-yl]-exo-ethanoic acid
MS: m/z 381 (M+1)

(2S)-2-(tert-Butoxycarbonyl)-amino-2-[8-(5-cyanopyridin-2-yl)-8-aza-bicyclo[3.2.1]-oct-3-yl]-exo-ethanoic acid.
MS: m/z 387 (M+1)

(2S)-2-(tert-Butoxycarbonyl)-amino-2-[8-(adamantan-1-yl-methyl)-8-aza-bicyclo[3.2.1]-oct-3-yl]-exo-ethanoic acid.
MS: m/z 433 (M+1)

Analogously, by practicing appropriate process seletcted from the chemistry described hereinabove for Intermediates 3 to 11, with appropriate variations in reactants and reaction conditions followed by standard ester hydrolysis following intermediates were prepared:

(2S)-2-(tert-Butoxycarbonyl)-amino-2-[8-(pyridin-4-yl-methyl)-8-aza-bicyclo[3.2.1]-oct-3-yl]-exo-ethanoic acid
MS: m/z 376 (M+1)

(2S)-2-(tert-Butoxycarbonyl)-amino-2-[8-(4-cyano-phenyl)-8-aza-bicyclo[3.2.1]-oct-3-yl]-exo-ethanoic acid
MS: m/z 386 (M+1)

(2S)-2-(tert-Butoxycarbonyl)-amino-2-[8-(methanesulfonyl)-8-aza-bicyclo[3.2.1]-oct-3-yl]-exo-ethanoic acid
MS: m/z 361 (M−1)

(2S)-2-(tert-Butoxycarbonyl)-amino-2-[8-(thiophene-2-sulfonyl)-8-aza-bicyclo[3.2.1]-oct-3-yl]-exo-ethanoic acid
MS: m/z 453 (M+23)

(2S)-2-(tert-Butoxycarbonyl)-amino-2-[8-(2-methoxyphenyl-thio-carbamoyl)-8-aza-bicyclo[3.2.1]-oct-3-yl]-exo-ethanoic acid
MS: m/z 450 (M+1)

(2S)-2-(tert-Butoxycarbonyl)-amino-2-[8-(cyclohexylmethyl)-8-aza-bicyclo[3.2.1]-oct-3-yl]-exo-ethanoic acid
MS: m/z 381 (M+1)

(2S)-2-(tert-Butoxycarbonyl)-amino-2-[8-(benzyloxyethyl)-8-aza-bicyclo[3.2.1]-oct-3-yl]-exo-ethanoic acid
MS: m/z 419 (M+1)

(2S)-2-(tert-Butoxycarbonyl)-amino-2-[8-(1-ethyl-propyl)-8-aza-bicyclo[3.2.1]-oct-3-yl]-exo-ethanoic acid
MS: m/z 355 (M+1)

Intermediate 12

(2S)-2-(tert-Butoxy carbonyl)-amino-2-{8-(tert-butoxy carbonyl)-8-aza-bicyclo[3.2.1]oct-3-yl}-exo-ethanoic acid

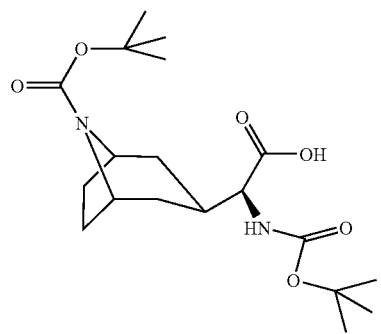

Step 1: (2S)-2-(tert-Butoxy carbonyl)-amino-2-{8-(tert-butoxy carbonyl)-8-aza-bicyclo[3.2.1]oct-3-yl}-exo-acetate

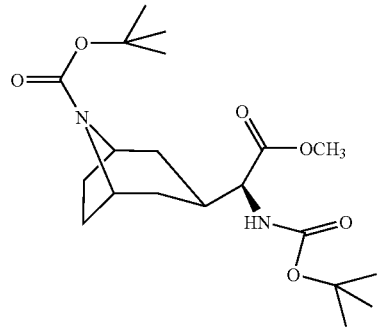

To a stirred solution of methyl-(2S)-2-(tert-butoxy carbonyl)-amino-2-(8-azabicyclo[3.2.1]-oct 3yl]exo acetate (step 5 of Intermediate 2, 0.8 g, 2.68 m mol) in dichloromethane (16 ml) at 0° C. was added triethyl amine (1.04 g, 3.22 m mol, 1.4 ml). The reaction mixture was stirred at same temperature for 15 minutes and di-tert-butyl dicarbonate (0.64 g, 0.67 ml, 2.95 m mol) was added. The reaction mixture was then stirred at room temperature for 20 hours. The solvent was removed under reduced pressure to get a crude product, which was purified by column chromatography over silica gel (100-200 mesh) using 1.5% methanol in dichloromethane as an eluent to yield the title compound (1.0 g, 93%)

MS: m/z 399 (M+1)

¹HNMR (CDCL₃+D₂O, 200 MHz): δ 1.42 (s, 9H), 1.45 (s, 9H), 1.45-1.82 (m, 6H), 1.84-2.10 (m, 2H), 3.72 (s, 2H), 4.05-4.32 (m, 3H), 4.92-5.10 (m, 1H)

Step 2: (2S)-2-(tert-Butoxy carbonyl)-amino-2-{8-(tert-butoxy carbonyl)-8-aza-bicyclo[3.2.1]oct-3-yl}-exo-ethanoic acid

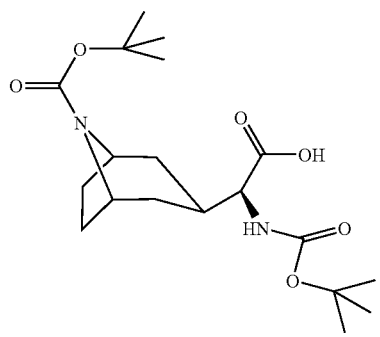

To a stirred and cooled (0° C.) solution of (1.0 g, 2.51 mmol) in methanol (50 ml) was added a solution of Na₂CO₃ (1.33 g, 12.6 mmol) in water (25 ml) in a drop wise manner. After the addition is completed, the turbid solution was stirred at room temperature for 14 hours. After completion of reaction, the reaction mixture was concentrated under reduced pressure to dryness. To this was added water (10 ml) cooled to 0° C. and pH of the reaction mixture was adjusted to 6.5 with aqueous 20% HCl. The solvent was removed under reduced pressure to yield a solid, which was stirred with ethyl acetate (75 ml) at room temperature for 30 minutes. The reaction mixture was filtered through Buchner funnel and filtrate was dried over anhydrous Na₂SO₄. The solvent was evaporated to yield the title compound (0.88 g, 91%), which was subjected to next step without purification.

MS: m/z 407 (M+23)

¹HNMR (CDCL₃, 200 MHz): δ 1.25-1.74 (m, 24H), 1.83-2.02 (m, 2H), 2.15-2.34 (m, 1H), 3.85 (s, 2H exchanges with D₂O), 4.06-4.16 (m, 3H).

Intermediate 13

2-(tert-Butoxycarbonyl)-amino-2-{9-(4-trifluoromethyl benzoyl)-9-aza-bicyclo[3.3.1]-non-3-yl}-exo-ethanoic-acid

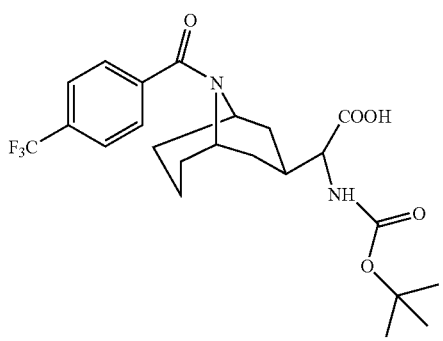

Step 1: 3-Benzyl-3-hydroxy-9-aza-bicyclo[3.3.1]nonane-9-carboxylic acid ethyl ester

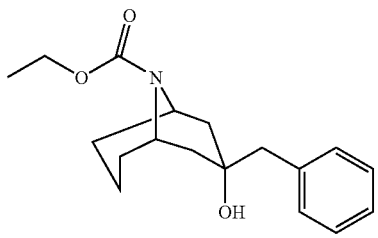

To a stirred suspension of magnesium turning (7.16 g, 0.3 mol) and iodine (5.0 mg, 0.04 mmol) in anhydrous THF (250 ml) at 65° C. temperature was added a solution of benzyl chloride (44 g, 0.35 mol) in THF (100 ml) under nitrogen atmosphere. The mixture was refluxed for 2 hours and a solution of 3-oxo-9-aza-bicyclo[3.3.1]nonane-9-carboxylic acid ethyl ester (prepared by following the procedure given in U.S. Pat. No. 4,277,472, 21.0 g, 0.1 mol) in THF (100 ml) was added at 65° C. The reaction was stirred at same temperature for 14 hours. The progress of reaction was monitored by ¹HNMR spectrum of the crude product. The reaction mixture was cooled to 0° C. and acidify to pH 4 with 1N aqueous HCl. The reaction mixture was concentrated and the residue was taken up in CH₂Cl₂ (500 ml). The organic layer was washed with water (100 ml), dried over anhydrous sodium sulphate and filtered. The solvent was evaporated to obtain a crude product, which was purified by a filter column over silica gel (100-200 mesh) using 1% methanol in dichloromethane as an eluent to yield an inseparable mixture of un reacted starting material and product (28.1 g).

The mixture so obtained was taken in ethanol (300 ml) and to this was added sodium borohydride in portionwise (7.0 g) under stirring at 0° C. After the addition was completed, the reaction mixture was brought to room temperature and stirred for two hours. The reaction mixture was again cooled to 0° C. and acidified to pH 4 by using 1N aqueous HCL. Ethyl alcohol was evaporated under reduced pressure and the residue was taken up in dichloromethane (600 ml). The organic layer was washed with water (100 ml), dried over anhydrous sodium sulphate and filtered. The solvent was evaporated to give a crude product, which was purified by column chromatography over silica gel (100-200 mesh) using 1% methanol in dichloromethane as an eluent to yield the title compound (11.6 g, 39%).

MS: m/z 304 (M+1)

¹H NMR (CDCl₃, 400 MHz): δ 1.18-1.9 (m, 10H), 1.91-2.14 (m, 1H), 2.28-2.72 (m, 5H), 4.1-4.25 (m, 2H), 4.3-4.51 (m, 1H), 4.6-4.83 (m, 2H), 7.1-7.4 (m, 5H)

Step 2: 9-(Ethoxy carbonyl)-3-exo-benzyl-9-aza-bicyclo[3.3.1]non-3-yl methyl oxalate

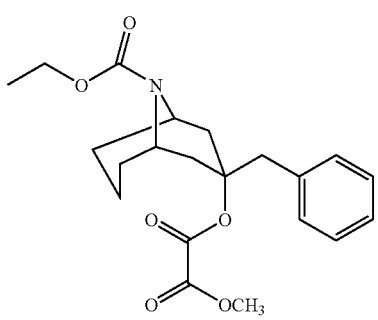

To a stirred solution of 3-benzyl-3-hydroxy-9-aza-bicyclo[3.3.1]nonane-9-carboxylic acid ethyl ester (13.5 g, 44.5 m mol) in dichloromethane (350 ml) was added pyridine (7 g, 89.1 m mol) and 4-dimethyl amino pyridine (0.54 g, 4.4m mol) at 0° C. A solution of mono methyl oxalyl chloride (6.0 g, 49 mmol) in dichloromethane (50 ml) was then added drop wise at 0° C. After the addition was completed, the reaction mixture was brought to room temperature and stirring was continued for 18 hours. The progress of reaction was monitored by TLC. After the completion of reaction, the reaction mixture was diluted with dichloromethane (200 ml) and washed with a saturated aqueous sodium bicarbonate solution (100 ml), water (100 ml), dried over anhydrous sodium sulphate and filtered. The solvent was removed under reduced pressure to get the crude product, which was purified by column chromatography over silica gel (100-200 mesh) using 7% ethyl acetate in hexane as an eluent to yield the title compound (13.6 g, 79%)

MS: m/z 390 (M+1)

$^1$HNMR (CDCl$_3$, 400 MHz): δ 1.29 (t, J=7.2 Hz, 3H), 1.43-1.6 (m, 3H), 1.63-1.8 (m, 2H), 2.09-2.2 (m, 3H), 2.26-2.35 (m, 2H), 3.14 (ABq, J=14.8 Hz, 2H), 3.87 (S, 3H), 4.14-4.25 (m, 2H), 4.42-4.50 (m, 1H), 4.52-4.59 (m, 1H), 7.13-7.17 (m, 2H), 7.22-7.32 (m, 3H)

Step 3: Ethyl-3-benzyl-9-aza-bicyclo[3.3.1]nonane-9-carboxylate

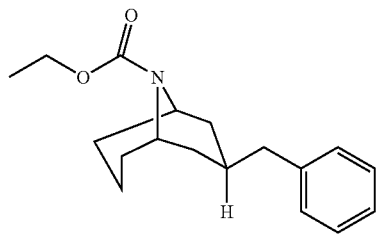

To a stirred solution of 9-(ethoxy carbonyl)-3-exo-benzyl-9-aza-bicyclo[3.3.1]non-3-yl methyl oxalate (13.5 g, 34.7 mmol) in toluene (350 ml) was added a solution of tri butyl tin hydride (15.15 g, 52 mmol) in toluene (55 ml) at room temperature. The reaction mixture was then heated at 110° C. and added a portion of 2,2'-azobis (2-methyl propionitrile) (AIBN, 0.57 g, 3.47m mol) under stirring. The progress of the reaction was monitored by TLC and more AIBN was added every one hour (9×0.57 g, 5.13 g, 31.2 m mol). The reaction was completed in 12 hours. The reaction mixture was cooled to room temperature and the solvent was removed under reduced pressure. The crude product so obtained was purified by column chromatography over silica gel (100-200 mesh) using 10% ethyl acetate in hexane as an eluent to yield the title compound (14.1 g)

MS: m/z 288 (M+1)

$^1$HNMR (CDCl$_3$, 400 MHz): δ 0.907 (t, J=7.6 Hz, 3H), 1.2-1.27 (m, 2H), 1.28-1.4 (m, 4H), 1.42-1.78 (m, 5H), 2.39-2.43 (m, 2H), 4.04-4.2 (m, 2H), 4.21-4.47 (m, 2H), 7.1-7.15 (m, 1H), 7:16-7.23 (m, 2H), 7.25-7.34 (m, 2H)

Step 4: [9-(Ethoxycarbonyl)-9-azabicyclo[3.3.1]-non-3yl]acetic acid

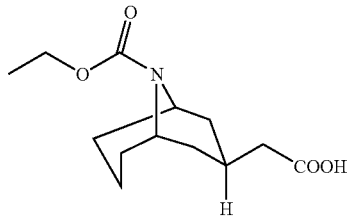

To a stirred solution of ethyl-3-benzyl-9-aza-bicyclo[3.3.1]nonane-9-carboxylate (14.0 g, 48.8 mmol) in mixture of carbon tetra chloride and acetonitrile (1:1, 280 ml) was added water (210 ml) followed by periodic acid (155 g, 683 mmol) at room temperature. The reaction was heated to 40-50° C. and RuCl$_3$ was added portion wise over the period of 20 mintues. Stirring was continued for 2.0 hours and the progress of the reaction was monitored by TLC. After the completion of reaction, the reaction mixture was cooled to room temperature and evaporated most of the organic solvents under reduced pressure. The aqueous layer was extracted with CCl$_4$ (3×200 ml). The combined organic layer was dried over anhydrous sodium sulphate and evaporated to yield the title compound (4.92 g, 40%), which was subjected to next reaction without further purification.

MS: m/z 254 (M−1)

$^1$HNMR (CDCl$_3$+D$_2$O, 200 MHz): δ 0.97 (t, J=7.4 Hz, 3H), 1.02-2.4 (m, 12H), 2.6-2.86 (m, 1H), 4.0-4.55 (m, 4H)

Step 5: 9-Azabicyclo[3.3.1]non-3-yl acetic acid hydrochloride

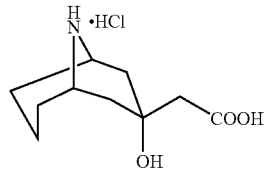

Concentrated HCl (36%, 73.5 ml) was added to [9-(ethoxy carbonyl)-9-azabicyclo[3.3.1]-non-3-yl]-acetic acid (4.9 g, 19.2 m mol) under stirring at room temperature. The reaction mixture was heated at 100° C. for 8 hours and progress of reaction was monitored by mass spectroscopy. After the completion of reaction, the reaction mixture was evaporated to dryness under reduced pressure and traces of water was removed by evaporating with dichloromethane (3×50 ml) the crude product was dried under high vacuum to yield the title compound (4.01 g, 95%) and subjected to further reaction without purification MS: m/z 184 (M+1)

Step 6:
Methyl-9-azabicyclo[3.3.1]-non-3-yl-exo-acetate

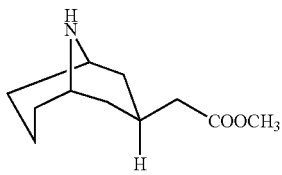

To a stirred solution of 9-azabicyclo[3.3.1]non-3-yl acetic acid hydrochloride (4.0 g, 18.2 mmol) in methanol (80 ml) was added concentrated sulfuric acid (1 ml) at 5° C. The reaction mixture was brought to room temperature and then refluxed at 65° C. for 15 hours under stirring. The progress of the reaction was monitored by mass spectroscopy. After the completion of reaction, the reaction mixture was cooled to room temperature and the solvent was evaporated under reduced pressure. The residue was diluted with chloroform (50 ml) and basified with ammonia in chloroform at 0° C. till pH turned to 10. The salt precipitated was filtered through a buchner funnel and the filtrate was concentrated to get a crude product, which was purified by column chromatography over silica gel (100-200 mesh) using (ammonia in chloroform: methanol:dichloromethane) in the ratio of 2:10:88 as an eluent to yield the title compound (1.07 g, 30%)

Exo isomer:
MS: m/z 198 (M+1)
$^1$HNMR (CDCl$_3$+D$_2$O, 400 MHz): δ 1.4-1.5 (m, 2H), 1.6-1.71 (m, 3H), 1.78-1.88 (m, 4H) 1.92-2.06 (m, 1H), 2.14 (d, J=6.8 Hz, 2H), 2.6-2.74 (m, 1H), 3.1-3.16 (m, 2H), 3.66 (S, 3H)

Endo isomer:
MS: m/z 198 (M+1)
$^1$HNMR (CDCl$_3$+D$_2$O, 400 MHz): δ 0.9-1.0 (m, 2H), 1.30-1.37 (m, 2H), 1.40-1.48 (m, 1H), 1.60-1.70 (m, 2H), 1.73-2.07 (m, 4H), 2.25 (d, J=6.8 Hz, 2H), 3.16-3.27 (m, 2H), 3.66 (S, 3H)

Step 7: Methyl {9-[4[trifluoromethyl]-9-azabicyclo [3.3.1]non-3-yl}-exo-acetate

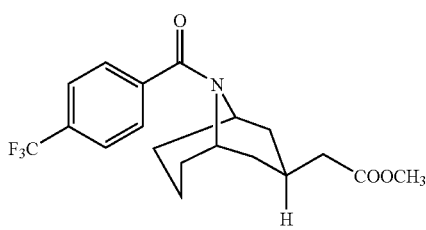

To a stirred solution of methyl-9-azabicyclo[3.3.1]-non-3-yl-exo-acetate (1.05 g, 5.3 m mol) in tetrahydrofuran (50 ml) was added 4-trifluoromethyl benzoic acid (1.01 g, 5.3 m mol) and 1-hydroxy benzotriazole (0.82 g, 5.3 m mol) at room temperature. The reaction mixture was cooled to 0° C. and 1-(3-dimethylaminopropyl)-3-ethylcarbodimide hydrochloride (1.12 g, 5.8 m mol) was added. The reaction mixture was then brought to room temperature and stirred for 18 hours at same temperature. The progress of the reaction was monitored by mass spectroscopy. The reaction mixture was concentrated under reduced pressure and the residue was taken up in dichloromethane (150 ml). The organic layer was washed with a saturated aqueous sodium bicarbonate solution (20 ml) and dried over anhydrous sodium sulphate. The solvent was evaporated to obtain a crude product, which was purified by column chromatography over silica gel (100-200 mesh) using 1.5% methanol in dichloromethane as an eluent to yield the title compound (1.22 g, 62%)

MS: m/z 370 (M+1)
$^1$HNMR (CDCl$_3$, 200 MHz): δ 1.3-1.5 (m, 1H), 1.51-2.3 (m, 11H), 2.68-2.93 (m, 1H) 3.67 S, 3H), 3.66-3.80 (m, 1H) 4.80-4.90 (m, 1H), 7.50 (d, J=8.1 Hz, 2H), 7.66 (d, J=8.1 Hz, 2H)

Step 8: Methyl-2-(1,2-di-tert-butyloxy carbonyl hydrazine)-2-[9-(4-trifluoromethyl benzoyl)-9-azabicyclo[3.3.1]-non-3-yl]-exo-acetate

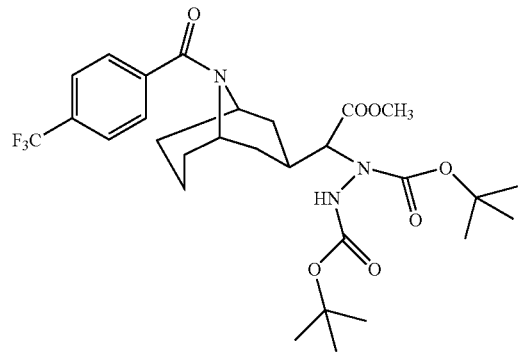

To a cold (−70° C.) and stirred solution of diisopropyl amine (0.49 g, 4.88 mmol) in THF (10 ml) was added n-butyl lithium (1.6 M, 0.31 g, 4.88 mmol) and stirred at the same temperature for one hour. A solution of methyl {9-[4-[trifluoro methyl]-9-azabicyclo[3.3.1]-non-3-yl}-exo-acetate (1.2 g, 3.25 mmol) in THF (40 ml) was added drop wise at −70° C. After 90 minutes, a solution of di-tert-butyl-diazene-1,2-dicarboxylate (3.0 g, 13 m mol) in THF (20 ml) was added to the reaction mixture at −70° C. After the addition, reaction mixture was allowed to come at room temperature and stirred for further 14 hours. The progress of the reaction was monitored by TLC. After the completion of reaction, the reaction mixture was cooled to 0° C. and the pH was adjusted to 7 with a saturated aqueous ammonium chloride solution. Tetra hydro furan was evaporated under reduced pressure and the aqueous layer was extracted with dichloromethane (4×100 ml). The combined organic layer was dried over anhydrous sodium sulphate and concentrated to obtain a crude product, which was purified by column chromatography over silica gel (100-200 mesh) using 1% methanol in dichloromethane as an eluent to yield the title compound (1.19 g, 61%)

MS: m/z 600 (M+1)

¹HNMR (CDCl₃, 200 MHz): δ 1.22-1.86 (m, 27H), 1.93-2.1 (m, 2H), 2.80-3.11 (m, 1H) 3.63-3.83 (m, 4H), 4.8-4.95 (m, 1H), 6.50-6.65 (m, 1H), 7.4-7.7 (m, 4H)

Step 9: Methyl-2-(hydrazino)-2-[9-(4-trifluoromethyl benzoyl)-9-azabicyclo[3.3.1]-non-3-yl]-exo-acetate di trifluoro acetic acid salt

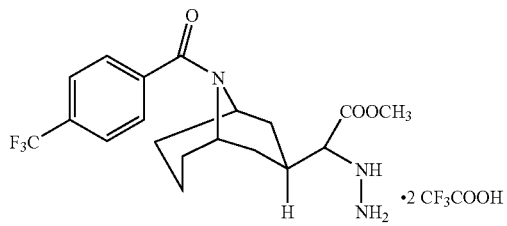

To a stirred solution of methyl-2-(1,2-di-tert-butyloxycarbonyl hydrazino)-2-[9-(4-trifluoromethyl benzoyl)-9-azabicyclo[3.3.1]-non-3-yl]-exo-acetate (1.15 g, 1.92 mmol) in dichloromethane (6 ml) was added a solution of tri fluoro acetic acid (11.5 ml, 11.7 g, 154.8 m mol) in dichloromethane (5.5 ml) at 0° C. The reaction mixture was allowed to come at room temperature and stirred for 4 hours. The progress of reaction was monitored by mass spectroscopy. After the completion of reaction, the solvent was evaporated to get a crude product (1.25 g) quantitatively, which was subjected to next step without purification MS: m/z 400 (M+1)

Step 10: Methyl amino {9-[4-(trifluoro methyl)benzoyl]-9-azabicyclo[3.3.1]non-3-yl}-exo-acetate

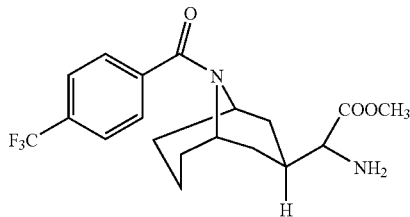

To a solution of methyl-2-(hydrazine)-2-[9-(4-trifluoro methyl benzoyl)-9-azabicyclo[3.3.1]-1-non-3-yl]-exo-acetate di trifluoro acetic acid salt (1.24 g, 1.98 mmol) in a mixture of methanol and water (1:1, 24.8 ml) was added Raney nickel (7.4 g) under a nitrogen atmosphere at room temperature. The reaction mixture was hydrogenated at 568 psi in an autoclave for 14.0 hours at room temperature. The progress of the reaction was monitored by mass spectroscopy. The catalyst was filtered through a Buchner funnel and the residue was washed with methanol (25 ml) and water (25 ml). The combined filtrates were evaporated to dryness under reduced pressure and the crude product was taken up in chloroform (20 ml). The reaction mixture was cooled to 0° C. and the pH was adjusted to 10 using ammonia in chloroform. The salt precipitated was filtered and the filtrate was concentrated to give a crude product (0.73 g, 96%), which was subjected to next step without purification MS: m/z 385 (M+1)

¹HNMR (CDCl₃+D₂O, 400 MHz): δ 1.18-1.40 (m, 2H), 1.5-1.87 (m, 6H), 1.88-2.10 (m, 2H), 2.70-2.82 (m, 1H), 3.2-3.3 (m, 1H), 3.79-3.85 (m, 4H), 4.85-4.94 (m, 1H), 7.51 (d, J=7.6 Hz, 2H), 7.66 (d, J=7.6 Hz, 2H)

Step 11: Methyl-2-(tert-butoxy carbonyl)amino-2-{9-[4-(trifluoromethyl)benzoyl]-9-azabicyclo[3.3.1]non-3-yl}-exo-acetate

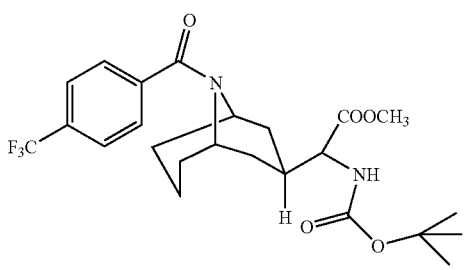

To a stirred solution of methyl amino {9-[4-(trifluoromethyl)-benzoyl]-9-azabicyclo[3.3.1]-non-3-yl}-exo-acetate (0.224 g, 2.22 mmol) in dichloromethane (35 ml) was added di-tert-butyl dicarbonate (0.71 g, 1.85 mmol) and triethyl amine (0.44 g, 2.03 mmol) at 0° C. The reaction mixture was allowed to come at room temperature and stirred for 15 hours. The progress of reaction was monitored by TLC. After the completion of reaction, the solvent was evaporated under reduced pressure to get the crude product, which was purified by column chromatography over silica gel (100-200 mesh) using 2% methanol in dichloromethane as an eluent to yield the title compound (0.67 g, 75%)

MS: m/z 485 (M+1)
¹HNMR (CDCl₃+D₂O, 200 MHz): δ 1.2-2.1 (m, 19H), 2.65-3.0 (m, 1H), 3.76 (S, 3H), 4.09-4.28 (m, 1H), 4.83-5.15 (m, 2H), 7.40-7.55 (m, 2H), 7.60-7.75 (m, 2H)

Step 12: 2-(tert-Butoxy carbonyl)amino-2-{9-(4-trifluoromethyl benzoyl)-9-azabicyclo[3.3.1]non-3-yl}-exo-ethanoic acid

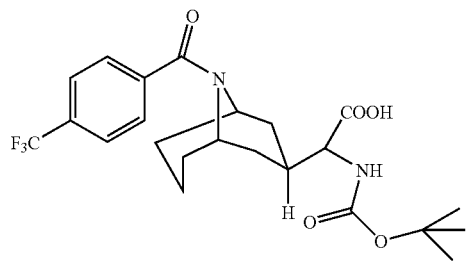

To a stirred solution of methyl-2-(tert-butoxy carbonyl)-amino-2-{9-[4-(trifluoromethyl)benzoyl]-9-azabicyclo [3.3.1]non-3-yl}-exo-acetate (0.645 g, 1.33 mmol) in methanol (39.0 ml) was added a solution of sodium carbonate (0.706 g, 6.66 mmol) in water (19.5 ml) at 0° C. The reaction mixture was allowed to come at room temperature and stirred for 20 hours. The progress of reaction was monitored by TLC. The reaction mixture was evaporated to dryness under reduced pressure and the residue was dissolved in water (20 ml). The aqueous solution was cooled to 0° C. and pH was adjusted to 6 by using 1N aqueous HCl. The reaction mixture was concentrated to dryness under reduced pressure and the residue was stirred with 10% methanol in dichloromethane (70 ml) at room temperature for 15 minutes. It was then filtered through a Buchner funnel and the residue was washed with 10% methanol in dichloromethane (2×70 ml). The combined filtrates were concentrated to yield the title compound (0.566 g, 90%)

MS: m/z 469 (M−1)

$^1$HNMR (CDCl$_3$, 400 MHz): δ 1.1-2.08 (m, 19H), 2.56-2.9 (m, 1H), 3.5-3.75 (m, 1H) 3.89-3.98 (m, 1H), 4.70-4.85 (m, 1H), 5.6-5.8 (m, 1H), 7.40-7.55 (m, 2H), 7.57-7.70 (m, 2H)

Intermediate 14

(1R,3R,5R)-2-aza-bicyclo[3.1.0]-hexane-3-carboxamide trifluoro acetic acid salt

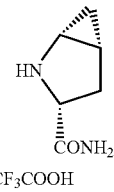

The title compound was prepared by following the procedure as described in WO 2004/052850 starting from (R)-(+)-2-pyrrolidinone-5-carboxylic acid MS: m/z 127 (M+1)

$^1$HNMR (D$_2$O, 400 MHz): δ 0.66-0.70 (m, 1H), 0.92-1.92 (m, 1H), 1.85-1.93 (m, 1H) 2.32 (dd, J=2.8, 14.0 Hz, 1H), 2.70-2.81 (m, 1H), 3.38-3.45 (m, 1H), 4.67 (dd, J=8.4, 11.2 Hz, 1H)

$[α]_D^{20}$ 30.59 (c 0.50, water)

Example 1

(2S)-1-{(2S)-2-Amino-2-[8-(2,4,5-trifluorobenzoyl)-8-aza-bicyclo[3.2.1]oct-3-yl]-exo-ethanoyl}-pyrrolidin-2-carbonitrile trifluoroacetic acid salt (Compound No. 1)

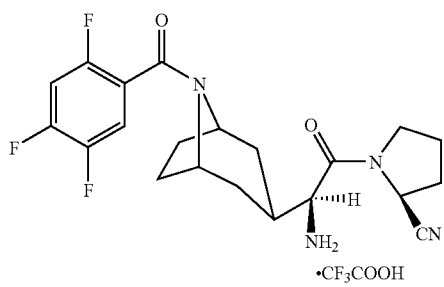

Step 1: (2S)-1-{(2S)-2-(tert-Butoxycarbonyl)amino-2-[8-(2,4,5-trifluorobenzoyl)-8-aza-bicyclo[3.2.1]oct-3-yl]-exo-ethanoyl}-pyrrolidin-2-carboxamide

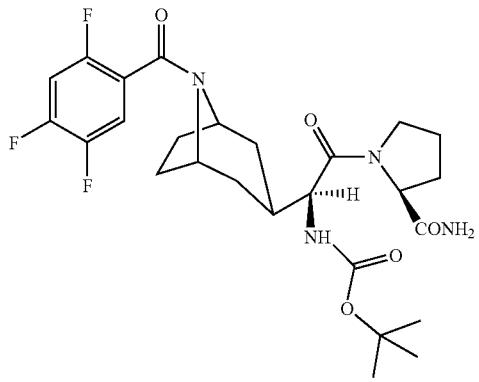

To a stirred solution of (2S)-2 (tert-butoxycarbony)lamino-2-[8-(2,4,5-trifluoro-benzoyl)-8-aza-bicyclo[3.2.1]oct-3-yl]-exo ethanoic acid (step 12 of intermediate 1, 0.35 g, 0.791 mmol) in dry DMF (10 ml) was added 1-hydroxy benzotriazole (HOBT, 0.321 g, 2.37 mmol) and L-prolinamide (0.0903 g, 0.791 mmol) at room temperature. The reaction mixture was cooled to 0° C. and added triethylamine (0.24 g, 0.31 ml, 2.37 mmol) and 1-(3-dimethyl amino propyl)-3-ethyl carbodiimide hydrochloride (0.303 g, 1.58 mmol). Ice bath was removed after 2 hours and the reaction mixture was stirred at room temperature for 24 hours. The solvent was removed under reduced pressure, added a saturated aqueous sodium bicarbonate solution (10 ml) and extracted with ethyl acetate (1×50 ml). The organic layer was dried over anhydrous Na$_2$SO$_4$ and the solvent was removed under reduced pressure to obtain a crude product, which was purified by column chromatography over silica gel (100-200 mesh) using methanol:NH$_3$ in chloroform:dichloromethane in the ratio of 2:10:88 as an eluent to yield the title compound (0.17 g, 40%).

MS: m/z 539 (M+1)

$^1$HNMR (CDCl$_3$, 200 MHz): δ 1.41 (s, 9H), 1.60-2.40 (m, 13H), 3.45-3.95 (m, 3H), 4.21-4.36 (m, 1H), 4.45-4.58 (m, 1H), 4.70-4.87 (m, 1H), 5.1-5.3 (m, 1H), 5.32-5.5 (m, 1H), 6.4-6.6 (m, 1H, exchangeable with D$_2$O), 6.85-7.02 (m, 1H), 7.07-7.35 (m, 1H).

Step 2: (2S)-1-{(2S)-2-(tert-butoxycarbonyl)-amino-2-[8-(2,4,5-trifluorobenzoyl)-8-aza-bicyclo[3.2.1]oct-3-yl]-exo-ethanoyl}-pyrrolidin-2-carbonitrile

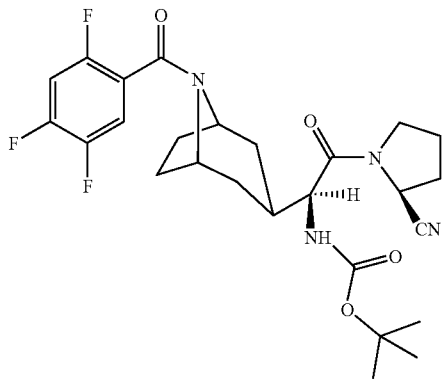

To a stirred solution of (2S)-1-{(2S)-2-(tert-butoxycarbonyl)amino-2-[8-(2,4,5-trifluorobenzoyl)-8-aza-bicyclo[3.2.1]oct-3-yl]-exo-ethanoyl}-pyrrolidin-2-carboxamide (0.08 g, 0.149 mmol) and imidazole (0.021 g, 0.312 mmol) in dry pyridine (2.8 ml) at –30° C. was added phosphorous oxy chloride (0.093 g, 0.057 ml, 0.609 mmol) dropwise. The reaction mixture was stirred at –30° C. for 2 hours. and completion of reaction was monitored by TLC. The reaction mixture was quenched with water (0.5 ml) at –30° C. and then it was allowed to come at room temperature. The solvent was removed under reduced pressure at room temperature. The crude product was dried under high vacuum. To this was added dichloromethane (20 ml), washed with water (2×5 ml) and dried over anhydrous Na$_2$SO$_4$. The solvent was evaporated to obtain a crude product, which was purified by column chromatography over silica gel (100-200 mesh) using 1.4% methanol in dichloromethane as an eluent to yield the title compound (0.06 g, 77%).

MS: m/z 521 (M+1)

$^1$HNMR (CDCl$_3$, 400 MHz): δ 1.35-1.45 (m, 9H), 1.65-1.85 (m, 6H), 1.95-2.08 (m, 2H), 2.12-2.34 (m, 5H), 3.57-3.95 (m, 3H), 4.15-4.25 (m, 1H), 4.74-4.88 (m, 2H), 5.05-5.15 (m, 1H), 6.92-7.02 (m, 1H), 7.26-7.33 (m, 1H).

Step 3: (2S)-1-{(2S)-2-Amino-2-[8-(2,4,5-trifluorobenzoyl)-8-aza-bicyclo[3.2.1]oct-3-yl]-exo-ethanoyl}-pyrrolidin-2-carbonitrile trifluoroacetic acid salt

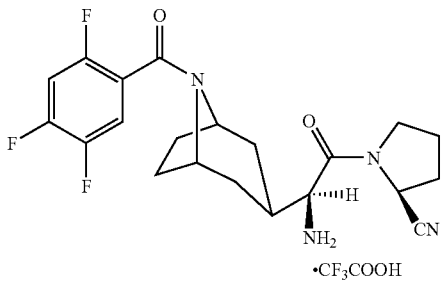

To a stirred solution of (2S)-1-{(2S)-2 (tert-butoxycarbonyl)amino-2-[8-(2,4,5-trifluorobenzoyl)-8-aza-bicyclo[3.2.1]oct-3-yl]-exo-ethanoyl}-pyrrolidin-2-carbonitrile. (0.10 g, 0.192 mmol) in dry dichloromethane (1.5 ml) at 0° C. was added a solution of trifluoroacetic acid (2.0 ml, 3.07 g, 26.9 mmol) in dry dichloromethane (1.5 ml) dropwise. The reaction mixture was sirred at 0° C. for 5 minutes, brought to room temperature and stirred for 25 minutes. The solvent was evaporated under reduced pressure at 30° C. and added dichloromethane (10 ml). The solvent was evaporated under reduced pressure and dried under high vacuum to remove trifluoroacetic acid. In order to remove traces of trifluoroacetic acid left and to solidify the product, petroleum ether (20 ml) was added to this mass, and evaporated under reduced pressure. The solid so obtained was stirred with ether (10 ml) at room temperature for 15 minutes. The solvent was decanted and dried the solid under high vacuum to yield the title compound (0.089 g, 87%).

MS: m/z 421 (M+1)

$^1$HNMR (CDCl$_3$+CD$_3$OD+D$_2$O): δ 1.4-1.85 (m, 4H), 1.95-2.06 (m, 2H), 2.07-2.34 (m, 4H), 2.43-2.56 (m, 1H), 3.42-3.52 (m, 1H), 3.54-3.83 (m, 3H), 3.84-3.94 (m, 1H), 3.98 (t, J=8 Hz, 1H), 4.67-4.8 (m, 2H), 6.92-7.04 (m, 1H), 7.28-7.37 (m, 1H).

The following compounds were prepared by procedure similar to those described for Compound No. 1 with appropriate variations of reactants, reaction conditions and quantities of reagents (2S)-1-{(2S)-2-Amino-2-[8-(4-trifluoromethylbenzoyl)-8-aza-bicyclo[3.2.1]oct-3-yl]-exo-ethanoyl}-pyrrolidin-2-carbonitrile trifluoroacetic acid salt (Compound No. 2).

mp: 162-164° C.

MS: m/z 435 (M+1)

$^1$HNMR (D$_2$O, 400 MHz): δ 1.51-1.95 (m, 6H), 1.97-2.22 (m, 4H), 2.23-2.4 (m, 2H), 2.55-2.68 (m, 1H), 3.63-3.74 (m, 2H), 4.05-4.13 (m, 1H), 4.26 (t, J=6.4 Hz, 1H), 4.7-4.85 (m, 2H) 7.6 (d, J=7.6 Hz, 2H), 7.79 (d, J=8 Hz, 2H)

$[α]_D^{21}$ –24.93 (c 1.07, water)

Yield: 99%

(2S)-1-{(2S)-2-Amino-2-[8-(adamantane-1-carbonyl)-8-aza-bicyclo[3.2.1]oct-3-yl]-exo-ethanoyl}-pyrrolidin-2-carbonitrile trifluoroacetic acid salt (Compound No. 3)

mp: 162-164° C.

MS: m/z 425 (M+1)

$^1$HNMR (D$_2$O, 400 MHz): δ 1.5-2.4 (m, 27H), 2.5-2.65 (m, 1H), 3.50-3.62 (m, 1H), 3.72-3.84 (m, 1H), 3.97-4.05 (m, 1H), 4.7-4.88 (m, 3H)

$[α]_D^{20}$ –18.23 (c 0.50, water)

Yield: 80%

(2S)-1-{(2S)-2-Amino-2-[8-(pyridine-4-carbonyl)-8-aza-bicyclo[3.2.1]oct-3-yl]-exo-ethanoyl}-pyrrolidin-2-carbonitrile trifluoroacetic acid salt (Compound No. 4)

mp: 125-127° C.

MS: m/z 368 (M+1)

$^1$HNMR (D$_2$O, 400 MHz): δ 1.52-2.0 (m, 6H), 2.02-2.22 (M, 4H), 2.25-2.40 (m, 2H), 2.60-2.72 (m, 1H), 3.65-3.75 (m, 2H), 4.03-4.10 (m, 1H), 4.30 (t, J=6.4 Hz, 1H), 4.75-4.85 (m, 2H), 8.13 (d, J=6.8 Hz, 2H), 8.93 (d, J=6.4 Hz, 2H).

Yield: 42%

(2S)-1-{(2S)-2-Amino-2-[8-(4-cyano-benzoyl)-8-aza-bicyclo[3.2.1]oct-3-yl]-exo-ethanoyl}-pyrrolidin-2-carbonitrile trifluoroacetic acid salt (Compound No. 5)

mp: 193-195° C.

MS: m/z 392 (M+1)

$^1$HNMR (D$_2$O, 200 MHz): δ 1.5-2.45 (m, 12H), 2.5-2.7 (m, 1H), 3.6-3.75 (m, 2H), 4.02-4.15 (m, 1H), 4.2-4.3 (m, 1H), 4.7-4.85 (m, 2H), 7.60 (d, J=8 Hz, 2H), 7.86 (d, J=8.0 Hz, 2H).

Yield: 98%

(2S)-1-{(2S)-2-Amino-2-[8-(2,5-difluorobenzoyl)-8-aza-bicyclo[3.2.1]oct-3-yl]-exo-ethanoyl}-pyrrolidin-2-carbonitrile trifluoroacetic acid salt (Compound No. 6)

mp: 170-172° C.

MS: m/z 403 (M+1)

$^1$HNMR (D$_2$O, 400 MHz): δ 1.52-1.63 (m, 2H), 1.67-1.95 (m, 4H), 2.02-2.22 (m, 4H), 2.25-2.40 (m, 2H), 2.52-2.68 (m, 1H), 3.65-3.75 (m, 2H), 4.02-4.12 (m, 1H), 4.21-4.26 (m, 1H), 4.75-4.84 (m, 2H), 7.16-7.23 (m, 1H), 7.26 (t, J=6.4 Hz, 2H).

Yield: 77%

(2S)-1-{(2S)-2-Amino-2-[8-(2-fluoro-pyridine-4-carbonyl)-8-aza-bicyclo[3.2.1]oct-3-yl]-exo-ethanoyl}-pyrrolidin-2-carbonitrile trifluoroacetic acid salt (Compound No. 7)

mp: 173-175° C.

MS: m/z 386 (M+1)

¹HNMR (D₂O, 400 MHz): δ 1.52-1.65 (m, 2H), 1.66-1.95 (m, 4H), 2.00-2.23 (m, 4H), 2.25-2.40 (m, 2H), 2.55-2.70 (m, 1H), 3.65-3.75 (m, 2H), 4.06-4.13 (m, 1H) 4.27 (t, J=7.2 Hz, 1H), 4.72-4.85 (m, 2H), 7.16-7.20 (m, 1H), 7.35-7.40 (m, 1H), 8.30 (d, J=4.8 Hz, 1H).

Yield: 87%

(2S)-1-{(2S)-2-Amino-2-[8-(4-trifluoromethyl phenyl carbamoyl)-8-aza-bicyclo[3.2.1]oct-3-yl]exo-ethanoyl}-pyrrolidin-2-carbonitrile trifluoroacetic acid salt (Compound No. 22)

mp: 196-198° C.

MS: m/z 450 (M+1)

¹HNMR (CDCl₃+CD₃OD, 400 MHz): δ 1.5-1.8 (m, 6H), 1.9-2.35 (m, 6H), 2.4-2.7 (m, 1H), 3.45-3.58 (m, 1H), 3.65-3.8 (m, 1H), 3.9-4.05 (m, 1H), 4.3-4.5 (m, 2H), 4.7-4.85 (m, 1H), 7.4-7.6 (m, 4H).

$[\alpha]_D^{20}$ −19.76 (c 0.50, water)

Yield: 90%

(2S)-1-{(2S)-2-Amino-2-[8-(2,4,5-trifluorobenzyl)-8-aza-bicyclo[3.2.1]oct-3-yl]-exo-ethanoyl}-pyrrolidin-2-carbonitrile trifluoroacetic acid salt (Compound No. 9)

mp: 132-134° C.

MS: m/z 407 (M+1)

¹HNMR (DMSO+D₂O, 200 MHz): δ 1.4-1.6 (m, 1H), 1.65-2.45 (m, 14H), 3.84-4.3 (m, 5H), 4.7-4.83 (m, 1H), 7.58-7.86 (m, 2H)

$[\alpha]_D^{24}$ −12.74 (c 1.00, water)

Yield: 45%

(2S)-{(2S)-1-[(2S)-2-Amino-2-(8-(benzo[1,3]dioxole-5-carbonyl)-8-aza-bicyclo[3.2.1]-oct-3-yl)-exo-acetyl]-pyrrolidin-2-yl}methanol trifluoroacetic acid salt (Compound No. 14)

mp: 193-195° C.

MS: m/z 416 (M+1)

¹HNMR (D₂O, 400 MHz): δ 1.45-2.05 (m, 12H), 2.4-2.6 (m, 1H), 3.4-3.68 (m, 4H), 2.88 4.11-4.31 (m, 3H), 4.62-4.72 (m, 1H), 5.99 (s, 2H), 6.9-7.0 (m, 3H)

$[\alpha]_D^{20}$ 3.80 (c 0.50, water)

Yield: 75%

Example 2

(2S)-1-{(2S)-2-Amino-2-[8-(4-trifluoromethyl-benzoyl)-8-aza-bicyclo[3.2.1]oct-3-yl]-exo-ethanoyl}-2-(2H-tetrazol-5-yl)pyrrolidine hydrochloride (Compound No. 13)

Step 1: (2S)-1-{(2S)-2-(tert-butoxycarbonyl)-amino-2-[8-(4-trifluoromethyl-benzoyl)-8-aza-bicyclo[3.2.1]-oct-3-yl]-exo-ethanoyl}-2-(2H-tetrazol-5-yl)pyrrolidine

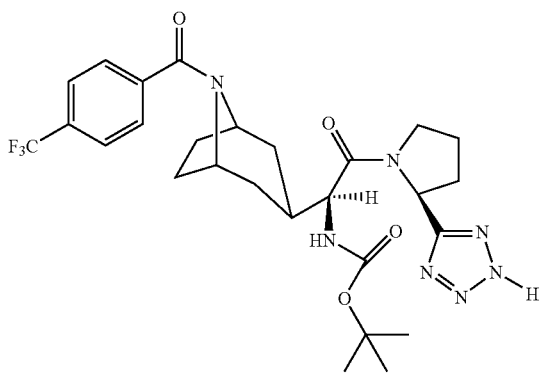

To a stirred solution of (2S)-1-{(2S)-2-(tert-butoxycarbonyl)-amino-2-[8-(4-trifluoromethyl-benzoyl)-8-aza-bicyclo[3.2.1]-oct-3-yl]-exo-ethanoyl}-pyrrolidin-2-carbonitrile (prepared by following the similar procedure as described in step 2 of Example 1, 0.17 g, 0.318 mmol) in isopropyl alcohol (4 ml) was added sodium azide (0.041 g, 0.636 mmol) and zinc bromide (0.035 g, 0.159 mmol). To make the solution clear, water (8 ml) was added to the reaction mixture and heated at reflux for 15 hours. The reaction mixture was allowed to come at room temperature. To this reaction mixture was added 3N HCl (1 ml) and stirred with ethyl acetate (25 ml) till the solid was dissoved. The organic layer was separated and the aqueous layer was extracted with ethyl acetate (20 ml). The combined organic layers were dried over anhydrous Na₂SO₄ and the solvent was evaporated under reduced pressure to yield a crude product, which was purified by column chromatography over silica gel (100-200 mesh) using 4% methanol in dichloromethane as an eluent to yield the title compound (0.095 g, 68%).

MS: m/z 576 (M−1)

¹HNMR (CDCl₃, 400 MHz): δ 1.32-1.42 (m, 9H), 1.44-2.53 (m, 13H), 2.65-2.85 (m, 1H), 3.62-3.82 (m, 1H), 3.87-4.03 (m, 2H), 4.26-4.4 (m, 1H), 4.65-4.84 (m, 1H), 5.34-5.48 (m, 1H), 5.6-5.8 (m, 1H), 7.46-7.61 (m, 2H), 7.62-7.73 (m, 2H).

Step 2: (2S)-1-{(2S)-2-Amino-2-[8-(4-trifluoromethyl-benzoyl)-8-aza-bicyclo[3.2.1]-oct-3-yl]-exo-ethanoyl}-2-(2H-tetrazol-5-yl)pyrrolidine hydrochloride

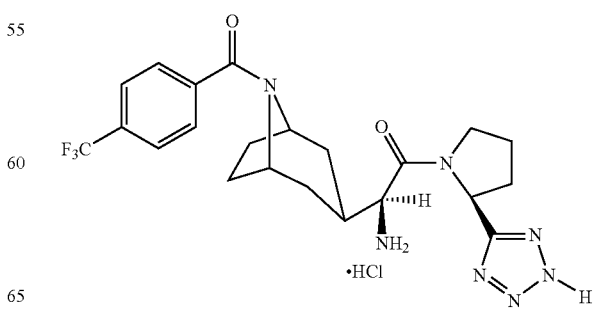

To a stirred a solution of (2S)-1-{(2S)-2-(tert-butoxycarbonyl)amino-2-[8-(4-trifluoromethyl-benzoyl)-8-aza-bicyclo[3.2.1]-oct-3-yl]-exo-ethanoyl}-2-(2H-tetrazol-5-yl) pyrrolidine (0.025, 0.043 mmol) in methanol (1.5 ml) was added 6N aqueous HCl (0.25 ml) at 0° C. and the reaction mixture was stirred at room temperature for 15 hours. The reaction mixture was concentrated under reduced pressure. Sticky oil so obtained was washed with dichloromethane (5 ml). The crude product was again stirred with 20% dichloromethane in diethyl ether (5 ml) for 15 minutes and decanted the organic layer. The solid so obtained was dried under high vacuum to yield the title compound (0.02 g, 90%).

mp: 244-246° C.
MS: m/z 478 (M+1)
$^1$HNMR (D$_2$O, 400 MHz): δ 1.43-1.56 (m, 2H), 1.6-1.85 (m, 4H), 1.95-2.27 (m, 5H), 2.4-2.56 (m, 2H), 3.75-3.9 (m, 2H), 4.0-4.07 (m, 1H), 4.26-4.3 (m, 1H), 4.7-4.85 (m, 1H), 5.43-5.49 (m, 1H), 7.5-7.6 (m, 2H) 7.75-7.81 (m, 2H)
$[α]_D^{20}$ 5.69 (c 0.50, water)

Example 3

Methyl (2S)-1-{(2S)-2-amino-2-[8-(4-trifluoromethyl-benzoyl)-8-aza-bicyclo[3.2.1]oct-3-yl]-exo-ethanoyl}-pyrrolidin-2-carboxylate trifluoro acetic acid (Compound No. 10)

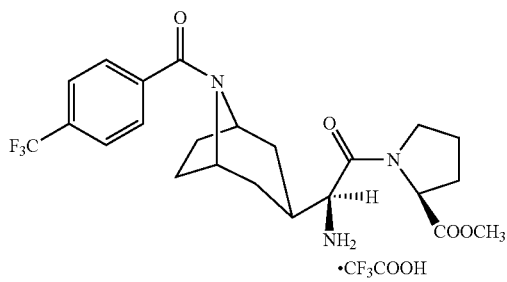

Step 1: Methyl (2S)-1-{(2S)-2-(tert-butoxycarbonyl)-amino-2-[8-(4-trifluoromethyl-benzoyl)-8-aza-bicyclo[3.2.1]-oct-3-yl]-exo-ethanoyl}-pyrrolidin-2-carboxylate

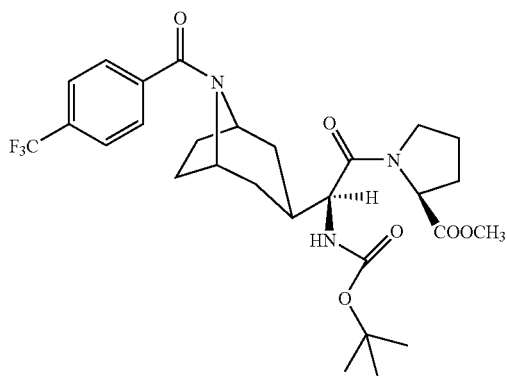

To a stirred solution of (2S)-2-(tert-butoxycarbonyl)-amino-2-[8-(4-trifluoro methyl-benzoyl)-8-aza-bicyclo[3.2.1]oct-3-yl]-exo-ethanoic acid (prepared by following the similar procedure as described in Intermediate 2, 1.5 g, 3.28 mmol) in DMF (20 ml) was added pyrrolidine-2-carboxylic acid methyl ester hydrochloride (0.544 g, 3.28 mmol) in water (5.0 ml), followed by the addition of 1-hydroxy benzotriazole (0.886 g, 6.56 mmol). The reaction mixture was cooled to 0° C. and added 1-(3-dimethyl amino propyl)-3-ethyl carbodiimide hydrochloride (1.25 g, 6.56 mmol) followed by triethylamine (1.36 ml, 0.993 g, 9.84 mmol). The reaction mixture was then stirred at room temperature for 18 hours. The solvent was evaporated under reduced pressure. To the residue was added ethyl acetate (50 ml) and the organic layer was washed with water (10 ml) and saturated solution of sodium bicarbonate (10 ml).

The organic layer was dried over anhydrous Na$_2$SO$_4$ and the solvent was removed under reduced pressure to obtain a crude product, which was purified by column chromatography over silica gel (100-200 mesh) using methanol:NH$_3$ in chloroform:dichloromethane in the ratio of 0.5:10:89.5 as an eluent to yield the title compound (0.79 g, 87%).

MS: m/z 568 (M+1)
$^1$HNMR (CDCl$_3$+D$_2$O, 200 MHz): δ 1.41 (s, 9H), 1.58-2.18 (m, 11H), 2.2-2.46 (m, 2H), 3.5-3.7 (m, 1H), 3.70 (s, 3H), 3.91-4.10 (m, 1H), 4.26-4.4 (m, 1H), 4.45-4.58 (m, 1H), 4.8-4.94 (m, 1H), 5.1-5.3 (m, 1H), 7.5-7.72 (m, 4H)

Step 2: Methyl-(2S)-1-{(2S)-2-amino-2-[8-(4-trifluoromethyl-benzoyl)-8-aza-bicyclo[3.2.1]-oct-3-yl]-exo-ethanoyl}-pyrrolidin-2-carboxylate trifluoroacetic acid

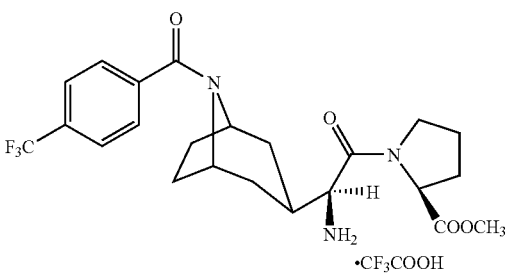

To a stirred solution of methyl-(2S)-1-{(2S)-2-(tert-butoxycarbonyl)-amino-2-[8-(4-trifluoromethyl-benzoyl)-8-aza-bicyclo[3.2.1]-oct-3-yl]-exo-ethanoyl}-pyrrolidin-2-carboxylate (0.13 g, 0.23 mmol) in dry dichloromethane (2.0 ml) was added a solution of trifluoro acetic acid (1.3 ml, 1.99 g, 17.5 mmol) in dry dichloromethane (1 ml) drop wise at 0° C. The reaction mixture was stirred at 0° C. for 5 minutes. The reaction mixture was allowed to come at room temperature and stirred for 40 minutes. The solvent was evaporated under reduced pressure and dried under high vacuum. The crude sticky product so obtained was stirred with 20% dichloromethane in diethyl ether (10 ml) for 15 minutes and filtered through a Buchner funnel. Solid so obtained was dried under high vacuum to yield the title compound (0.095 g, 71%).

mp: 173-175° C.
MS: m/z 468 (M+1)
$^1$HNMR (D$_2$O, 400 MHz): δ 1.58-1.9 (m, 6H), 1.92-2.1 (m, 5H), 2.14-2.24 (m, 1H), 2.5-2.62 (m, 1H), 3.58-3.77 (m, 6H), 4.05-4.11 (m, 1H), 4.25 (d, J=6.4 Hz, 1H) 4.47-4.52 (m, 1H), 7.57-7.63 (m, 2H) 7.76-7.82 (m, 2H)
$[α]_D^{20}$ −18.32 (c 0.50, water)

Example 4

(2S)-1-{(2S)-2-amino-2-[8-(4-trifluoromethyl-benzoyl)-8-aza-bicyclo[3.2.1]-oct-3-yl]-exo-ethanoyl}-pyrrolidin-2-carboxylic acid trifluoroacetic acid salt (Compound No. 11)

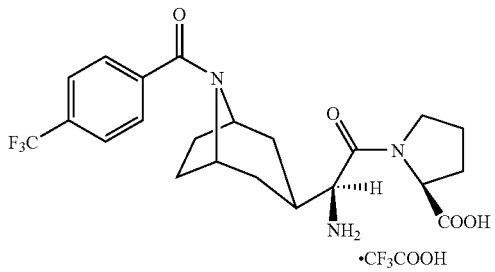

Step 1: (2S)-1-{(2S)-2-(tent-butoxycarbonyl)-amino-2-[8-(4-trifluoromethyl-benzoyl)-8-aza-bicyclo[3.2.1]-oct-3-yl]-exo-ethanoyl}-pyrrolidin-2-carboxylic acid

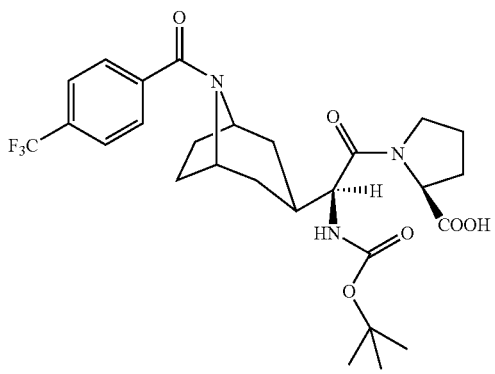

To a stirred solution of methyl (2S)-1-{(2S)-2-(tert-butoxycarbonyl)-amino-2-[8-(4-trifluoromethyl-benzoyl)-8-aza-bicyclo[3.2.1]oct-3-yl]-exo-ethanoyl}-pyrrolidin-2-carboxylate (step 1 of Example 3, 0.22 g, 0.388 mmol) in methanol (20 ml) was added a solution of sodium carbonate (0.205 g, 1.94 mmol) in water (10 ml) slowly at 0° C. The reaction mixture was allowed to come at room temperature and stirred for 16 hours. The solvent was removed under reduced pressure and the residue was diluted with water (10 ml). It was then cooled to 0° C. and pH was adjusted to 6.5 with 2N HCl. The aqueous layer was then extracted with dichloromethane (2×25 ml). The combined organic layers were dried over anhydrous sodium sulphate and the solvent was evaporated to yield a crude product. The crude was dissolved in diethyl ether (5 ml) and hexane was added till precipitation occurred. Solid was filtered through a Buchner funnel and dried under high vacuum to yield the title compound (0.121 g, 57%).

mp: 155-157° C.

MS: m/z 552 (M−1)

$^1$HNMR (CDCl$_3$, 400 MHz): δ 1.34-1.45 (m, 9H), 1.50-2.42 (m, 13H), 3.52-3.9 (m, 2H), 3.95-4.06 (m, 1H), 4.30-4.60 (m, 3H), 4.80-4.90 (m, 1H), 5.40-5.47 (m, 0.5H), 5.87-5.95 (m, 0.5H), 7.56-7.7 (m, 4H).

Step: 2 (2S)-1-{(2S)-2-amino-2-[8-(4-trifluoromethyl-benzoyl)-8-aza-bicyclo[3.2.1]-oct-3-yl]-exo-ethanoyl}-pyrrolidin-2-carboxylic acid trifluoroacetic acid salt

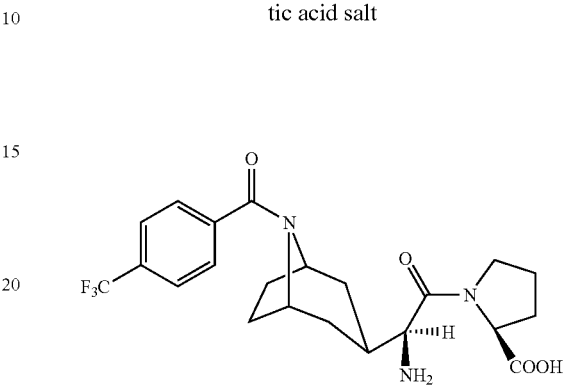

The title compound (0.095 g, 89%) was obtained from (2S)-1-{(2S)-2-(tert-butoxy carbonyl)-amino-2-[8-(4-trifluoromethyl-benzoyl)-8-aza-bicyclo[3.2.1]-oct-3-yl]-exo-ethanoyl}-pyrrolidin-2-carboxylic acid (0.105 g, 0.18 mmol), trifluoro acetic acid (1.0 ml., 1.53 g, 13.54 mmol) in dichloromethane by a similar procedure described in step 2 of Example 3 mp: 161-163° C.

MS: m/z 454 (M+1)

$^1$HNMR (D$_2$O, 400 MHz): δ 1.55-2.1 (m, 11H), 2.24-2.38 (m, 1H), 2.5-2.64 (m, 1H), 3.55-3.67 (m, 1H), 3.8-3.87 (m, 1H), 4.02-4.1 (m, 1H), 4.25 (t, J=6.8 Hz, 1H), 4.41-4.47 (m, 1H), 4.72-4.8 (m, 1H), 7.55-7.62 (m, 2H), 7.75-7.81 (m, 2H).

$[α]_D^{20}$ −17.92 (c 0.50, water)

Example 5

(2S,4S)-1-{(2S)-2-Amino-2-[8-(4-trifluoromethyl-benzoyl)-8-aza-bicyclo[3.2.1]oct-3-yl]-exo-ethanoyl}-4-fluoro-pyrrolidine-2-carbonitrile hydrochloride salt (Compound No. 15)

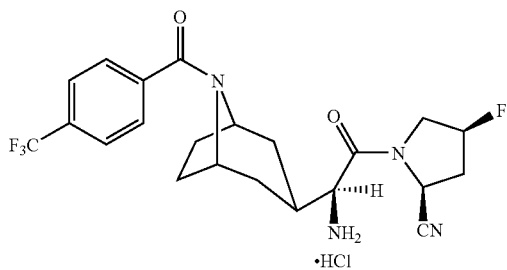

Step 1: (2S,4S)-1-{(2S)-2-(tert-butoxycarbonyl)-amino-2-[8-(4-trifluoromethyl-benzoyl)-8-aza-bicyclo[3.2.1]-oct-3-yl]-exo-ethanoyl}-4-fluoro-pyrrolidine-2-carboxylic acid amide

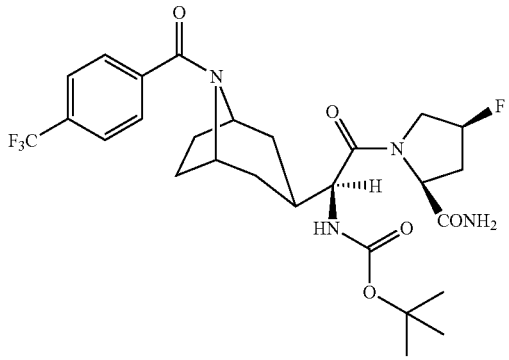

To a stirred solution of (2S)-2-(tert-butoxycarbonyl)-amino-2-[8-(4-trifluoromethyl-benzoyl)-8-aza-bicyclo[3.2.1]-oct-3-yl]-exo-ethanoic acid (prepared by following the similar procedure as described in Intermediate 2, 0.4 g, 0.877 mmol) in dry DMF (8.0 ml) was added 1-hydroxybenzotriazole (HOBT, 0.403 g, 2.63 mmol) and (2S,4S)-4-fluoro-pyrrolidine-2-carboxamide (which can be prepared by using method as provided in WO 03/002553, 0.116 g, 0.877 mmol) at room temperature. The reaction mixture was cooled to 0° C. To this was added triethylamine (0.266 g, 0.375 ml, 2.63 mmol) and 1-(3-dimethyl amino propyl-3-ethyl carbodimide hydrochloride (0.336 g, 1.75 mmol) under stirring. Ice Bath was removed after two hours and the reaction mixture was stirred at room temperature for 24 hours. The solvent was removed under reduced pressure and diluted with ethyl acetate (25.0 ml). The organic layer was washed with a saturated aqueous sodium bicarbonate solution (10 ml) and dried over anhydrous sodium sulphate. The solvent was removed to obtain a crude product, which was purified by column chromatography over silica gel (100-200 mesh) using methanol:NH$_3$ in chloroform:dichloromethane in the ratio of 3:10:87 as an eluent to get the title compound (0.27 g, 54%).

mp: 153-155° C.

MS: m/z 571 (M+1)

$^1$HNMR (CDCl$_3$+D$_2$O, 400 MHz): δ 1.35-1.52 (m, 10H), 1.53-1.83 (m, 5H), 1.9-2.1 (m, 2H), 2.13-2.42 (m, 2H), 2.73-2.87 (m, 1H), 3.81-4.16 (m, 2H), 4.2-4.29 (m, 1H), 4.73 (d, J=9.6 Hz, 1H), 4.77-4.93 (m, 2H), 5.23-5.27 (m, 0.5H), 5.36-5.42 (m, 0.5H), 7.51-7.62 (m, 2H), 7.63-7.7 (m, 2H).

Step 2: (2S,4S)-1-{(2S)-2-(tert-butoxycarbonyl)-amino-2-[8-(4-trifluoromethyl-benzoyl)-8-aza-bicyclo[3.2.1]oct-3-yl]-exo-ethanoyl}-4-fluoro-pyrrolidine-2-carbonitrile

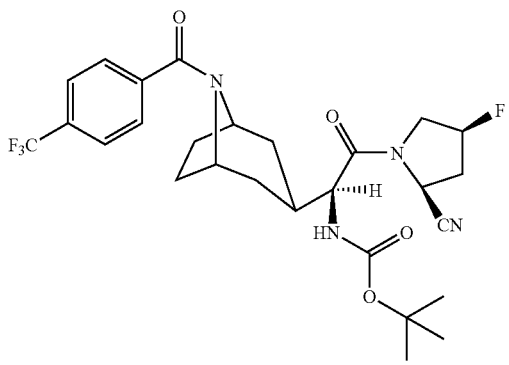

To a stirred solution of (2S,4S)-1-{(2S)-2-(tert-butoxycarbonyl)-amino-2-[8-(4-tri fluoromethyl-benzoyl)-8-aza-bicyclo[3.2.1]-oct-3-yl]-exo-ethanoyl}-4-fluoro-pyrrolidine-2-carboxylic acid amide (0.26 g, 0.456 mmol) and imidazole (0.065 g, 0.954 mmol) in dry pyridine (6.0 ml) was added phosphorous oxy chloride (0.279 g, 0.17 ml, 1.81 mmol) drop wise at −30° C. under nitrogen atmosphere. The reaction mixture was stirred at −30° C. for two hours. The completion of reaction was monitored by TLC. The reaction mixture was quenched with water (2.0 ml) at −30° C. Then reaction mixture was allowed to come at room temperature. The solvent was removed under reduced pressure and water (10 ml) was added to the residue. The aqueous layer was extracted with dichloromethane (4×10 ml) and the combined organic layer was dried over anhydrous sodium sulphate. The solvent was evaporated to obtain the crude product, which was purified by column chromatography over silica gel (100-200 mesh) using 1.2% methanol in dichloromethane as an eluent to yield the title compound (0.17 g, 68%).

mp: 155-157° C.

MS: m/z 553 (M+1)

$^1$HNMR (CDCl$_3$+D$_2$O, 400 MHz): δ 1.34-1.5 (m, 10H), 1.54-1.62 (m, 1H), 1.63-1.85 (m, 4H), 1.9-2.1 (m, 2H), 2.23-2.43 (m, 2H), 2.6-2.73 (m, 1H), 3.92-4.19 (m, 4H), 4.85-4.92 (m, 1H), 4.96-5.02 (m, 1H), 5.33-5.37 (m, 0.5H), 5.47-5.52 (m, 0.5H), 7.58-7.62 (m, 2H), 7.65-7.72 (m, 2H).

Step 3: (2S,4S)-1-{(2S)-2-Amino-2-[8-(4-trifluoromethyl-benzoyl)-8-aza-bicyclo[3.2.1]-oct-3-yl]-exo-ethanoyl}-4-fluoro-pyrrolidine-2-carbonitrile hydrochloride

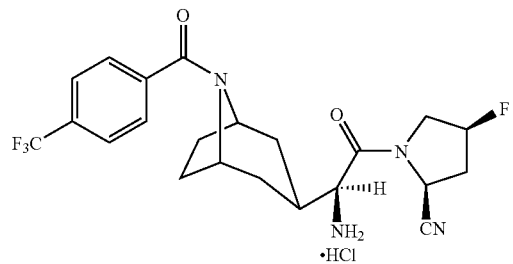

To a stirred solution of (2S,4S)-1-{(2S)-2-(tert-butoxycarbonyl)-amino-2-[8-(4-tri fluoromethyl-benzoyl)-8-aza-bicyclo[3.2.1]-oct-3-yl]-exo-ethanoyl}-4-fluoro-pyrrolidine-2-carbonitrile (0.16 g, 0.289 mmol) in dry dichloromethane (1.5 ml) at 0° C. was added a solution of trifluoroacetic acid (3.0 ml, 4.61 g, 40.4 mmol) in dry dichloromethane (1.5 ml) drop wise. First, the reaction mixture was stirred at 0° C. for 5 minutes and then stirred at room temperature for 25 minutes. The solvent was evaporated completely under reduced pressure at room temperature and dried under high vacuum. To this residue was added dichloromethane (15 ml), cooled to 0° C. and neutralized with NH$_3$ in chloroform. The solvent was evaporated and the crude was stirred with dichloromethane (30.0 ml) and then filtered through a Buchner funnel. The filtrate was concentrated at reduced pressure and the residue so obtained was taken in dry chloromethane (5.0 ml). To this mixture was added HCl in ether (0.8 ml, 0.85 N) under stirring at room temperature. Stirring was continued at room temperature for 45 minutes. The reaction mixture was diluted with diethyl ether (5 ml) and solvent was evaporated to yield the compound quantitatively (0.125 g)

mp: 168-170° C.
MS: m/z 453 (M+1)
$^1$HNMR (CDCl$_3$+CD$_3$OD, 200 MHz): δ 1.15-1.35 (m, 2H), 1.45-2.1 (m, 8H), 2.3-2.7 (m, 3H), 3.25-3.35 (m, 1H), 3.8-4.1 (m, 3H), 4.7-4.85 (m, 1H), 5.0-5.10 (m, 1H), 5.2-5.3 (m, 0.5H), 5.45-5.55 (m, 0.5H), 7.5-7.7 (m, 4H).

The following compounds were prepared by procedure similar to those described for Compound No. 15 with appropriate variations of reactants, reaction conditions and quantities of reagents (2S,4S)-1-{(2S)-2-Amino-2-[8-(2,4,5-trifluorobenzoyl)-8-aza-bicyclo[3.2.1]oct-3-yl]-exo-ethanoyl}-4-fluoro-pyrrolidin-2-carbonitrile trifluoroacetic acid salt (Compound No. 16)

mp: 163-165° C.
MS: m/z 439 (M+1)
$^1$HNMR (CDCl$_3$+D$_2$O, 400 MHz): δ 1.1-2.1 (m, 8H), 2.2-2.8 (m, 3H), 3.5-4.2 (m, 4H), 4.7-5.1 (m, 2H), 5.3-5.55 (m, 1H), 6.9-7.35 (m, 2H)
Yield: 92%

(2S,4S)-1-{(2S)-2-Amino-2-[8-(2,5-difluorobenzoyl)-8-aza-bicyclo[3.2.1]oct-3-yl]-exo-ethanoyl}-4-fluoro-pyrrolidin-2-carbonitrile trifluoroacetic acid salt (Compound No. 17)

mp: 198-200° C.
MS: m/z 421 (M+1)
$^1$HNMR (D$_2$O, 400 MHz): δ 1.52-1.63 (m, 2H), 1.68-1.96 (m, 4H), 2.0-2.13 (m, 2H), 2.43-2.8 (m, 3H), 3.76-3.95 (m, 1H), 4.02-4.16 (m, 2H), 4.2 (t, J=6 Hz, 1H), 4.75-4.8 (m, 1H), 5.06-5.12 (m, 1H), 5.45-5.5 (m, 0.5H), 5.56-5.62 (m, 0.5H), 7.15-7.22 (m, 1H), 7.24 (t, J=6.4 Hz, 2H)
Yield: 80%

(2S,4S)-1-{(2S)-2-Amino-2-[8-(2,4,5-trifluorobenzyl)-8-aza-bicyclo[3.2.1]oct-3-yl]-exo-ethanoyl}-4-fluoro-pyrrolidin-2-carbonitrile trifluoroacetic acid salt (Compound No. 19)

mp: 130-132° C.
MS: m/z 425 (M+1)
$^1$HNMR (DMSO+D$_2$O, 200 MHz): δ 1.4-1.6 (m, 1H), 1.65-2.05 (m, 6H), 2.1-2.5 (m, 4H), 3.75-4.35 (m, 7H), 5.0-5.12 (m, 1H), 5.35-5.45 (m, 0.5H), 5.6-5.7 (m, 0.5H), 7.55-7.85 (m, 2H)
Yield: 79%

Example 6

(4S)-3-{(2S)-2-Amino-2-[8-(4-trifluoromethyl-benzoyl)-8-aza-bicyclo[3.2.1]oct-3-yl]-exo-ethanoyl}-thiazolidin-4-carbonitrile trifluoroacetetic acid salt (Compound No. 20)

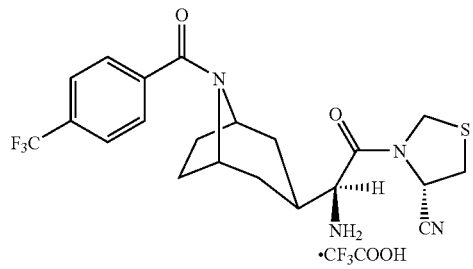

Step 1: (4S)-3-{(2S)-2-(tert-butoxycarbonyl)-amino-2-[8-(4-trifluoromethyl-benzoyl)-8-aza-bicyclo[3.2.1]-oct-3-yl]-exo-ethanoyl}-thizolidin-4-carboxylic acid amide

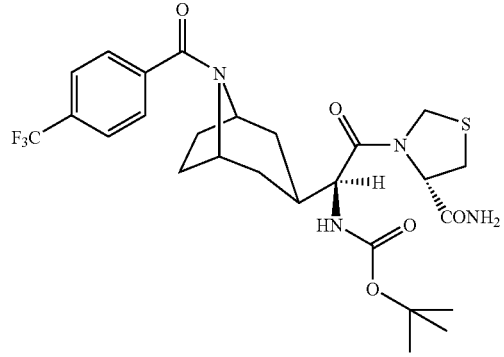

To a stirred solution of (2S)-2-(tert-butoxycarbonyl)amino-2-[8-(4-trifluoromethyl-benzoyl)-8-aza-bicyclo[3.2.1]-oct-3-yl]-exo-ethanoic acid (prepared by following the similar proceduras described in Intermediate 2, 0.47 g, 1.03 mmol) in dry DMF (8.0 ml) was added 1-hydroxybenzotriazole (0.473 g, 3.08 mmol) and (4S)-1,3-thizolidine-4-carboxamide (prepared by using method as provided in J. Am. Chem. Soc59, 200-206 (1937) and US 2005/0192324, 0.14 g, 1.06 mmol) at room temperature. The reaction mixture was cooled to 0° C. and added tri ethyl amine (0.45 ml, 0.31 g, 3.08 mmol) and 1-(3-dimethyl amino propyl-3-ethyl carbodimide hydrochloride (0.395 g, 2.06 mmol) under stirring. After 2 hours, ice bath was removed and the reaction mixture was stirred at room temperature for 24 hours. The solvent was removed under reduced pressure and the residue was diluted with ethyl acetate (25 ml). The organic layer was washed with a saturated aqueous sodium bicarbonate solution (20 ml) and dried over anhydrous Na$_2$SO$_4$. The solvent was removed under reduced pressure to yield a crude product, which was purified by column chromatography over silica gel (100-200 mesh) using methanol:NH$_3$ in chloroform:dichloromethane in the ratio of 3:10:87 as an eluent to yield the title compound (0.18 g, 31%).

MS: m/z 571 (M+1)
$^1$HNMR (CDCl$_3$+D$_2$O, 400 MHz): δ 1.36-1.5 (m, 9H), 1.53-1.8 (m, 6H), (m, 2H), 2.25-2.40 (m, 1H), 3.08-3.48 (m, 2H), 3.95-4.1 (m, 1H), 4.34-4.45 (m, 1H), 4.5-4.7 (m, 1H), 4.71-5.0 (m, 3H), 7.51-7.62 (m, 2H), 7.65-7.72 (m, 2H).

Step 2: (4S)-3-{(2S)-2-(tert-butoxycarbonyl)-amino-2-[8-(4-trifluoromethyl-benzoyl)-8-aza-bicyclo[3.2.1]-oct-3-yl]-exo-ethanoyl}-thiazolidine-4-carbonitrile

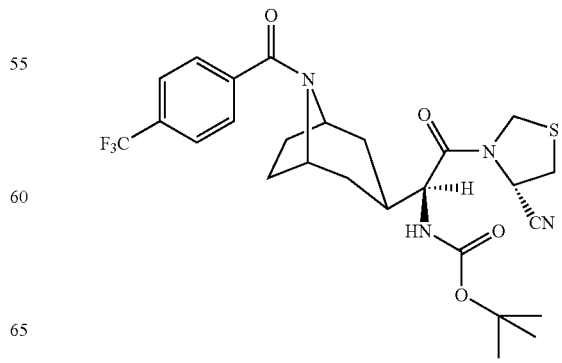

To a stirred solution of (4S)-3-{(2S)-2-(tert-butoxycarbonyl)-amino-2-[8-(4-tri fluoromethyl-benzoyl)-8-aza-bicyclo[3.2.1]-oct-3-yl]exo-ethanoyl}-thiazolidine-4-carboxylic acid amide (0.17 g, 0.298 mmol) and imidazole (0.043 g, 0.63 mmol) in dry pyridine (4.0 ml) at −30° C. was added phosphorous oxychloride (0.183 g, 0.11 ml, 1.19 mmol) drop wise under nitrogen atmosphere. The reaction mixture was stirred at −30° C. for two hours. The completion of reaction was monitored by TLC. The reaction mixture was quenched with water (3.0 ml) at −30° C. Then reaction mixture was allowed to come at room temperature. The solvent was removed under reduced pressure and water (10 ml) was added to the residue. The aqueous layer was extracted with dichloromethane (4×10 ml) and the combined organic layer was dried over anhydrous sodium sulphate. The solvent was evaporated at reduced pressure to get a crude product, which was purified by column chromatography over silica gel (100-200 mesh) using 1.2% methanol in dichloromethane as an eluent to yield the title compound (0.09 g, 55%).

MS: m/z 553 (M+1)

Step 3: (4S)-3-{(2S)-2-Amino-2-[8-(4-trifluoromethyl-benzoyl)-8-aza-bicyclo[3.2.1]oct-3-yl]-exo-ethanoyl}-thiazolidin-4-carbonitrile trifluoroacetetic acid salt

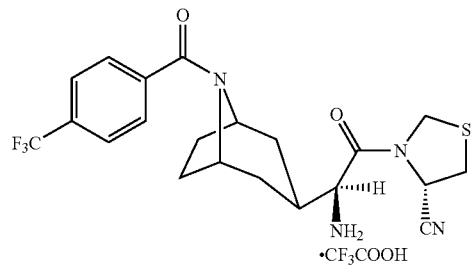

To a stirred solution of (4S)-3-{(2S)-2-(tert butoxycarbonyl)-amino-2-[8-(4-trifluoromethyl-benzoyl)-8-aza-bicyclo[3.2.1]-oct-3-yl]-exo-ethanoyl}-thiazolidine-4-carbonitrile (0.08 g, 0.144 mmol) in dry dichloromethane (1.0 ml) at 0° C. was added a solution of trifluoroacetic acid (1.5 ml, 2.3 g, 20.2 mmol) in dry dichloromethane (5 ml) drop wise. The reaction mixture was stirred at 0° C. for 5 minutes then brought to room temperature and stirred for further 25 minutes. The solvent was evaporated under reduced pressure at room temperature and dried under high vacuum. In order to solidify the product, petroleum ether (10 ml) was added and evaporated to get a solid, which was dried under high vacuum to yield the title compound (0.08 g, 98%).

mp: 159-161° C.

MS: m/z 453 (M+1)

¹HNMR (CDCl₃+D₂O, 400 MHz): δ 1.4-2.2 (m, 7H), 2.3-2.7 (m, 2H), 3.15-3.4 (m, 2H), 3.9-4.13 (m, 2H), 4.25-4.95 (m, 3H), 5.25-5.4 (m, 1H), 7.52-7.72 (m, 4H).

Example 7

3-{(2S)-2-Amino-2-[8-(4-trifluoromethyl-benzoyl)-8-aza-bicyclo[3.2.1]-oct-3-yl]-exo-ethanoyl}-1,3-thiazolidin trifluoroacetic acid salt (Compound No. 21)

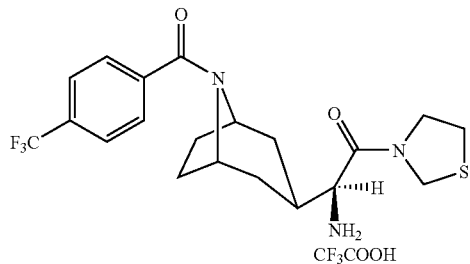

Step 1: 3 {(2S)-2-(tert-butoxycarbonyl)amino-2-[8-(4-trifluoromethyl-benzoyl)-8-aza-bicyclo[3.2.1]oct-3-yl]exo-ethanoyl}-1,3-thiazolidine

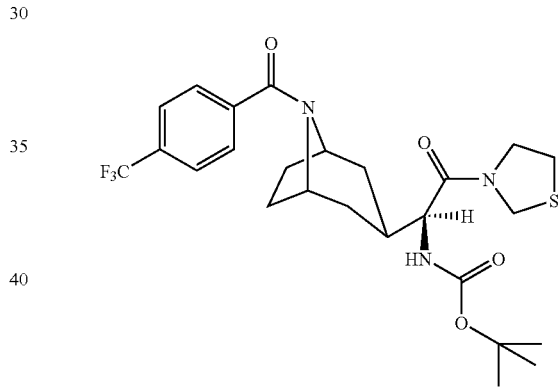

To a stirred solution of {(2S)-2-(tert-butoxycarbonyl)-amino-2-[8-(4-trifluoromethyl-benzoyl)-8-aza-bicyclo[3.2.1]-oct-3-yl]-exo-ethanoic acid (prepared by following the similar procedure as described in Intermediate 2, 150 mg, 0.328 mmol) in dry DMF (3.0 ml) was added 1-hydroxybenzotriazole (151 mg, 0.986 mmol) and 1,3-thizolidine (29 mg, 0.325 mmol) at room temperature. The reaction mixture was cooled to 0° C. and added triethyl amine (99 mg, 0.978 mmol) and 1-(3-dimethyl amino propyl-3-ethyl carbodiimide hydrochloride (126 mg, 0.83 mmol) under stirring. After 2 hours, ice bath was removed and the reaction mixture was stirred at room temperature for further 20 hours. The solvent was removed under reduced pressure and the residue so obtained was diluted with ethyl acetate (30 ml). The organic layer was washed with a saturated aqueous sodium bicarbonate solution (10 ml) and dried over anhydrous Na₂SO₄. The solvent was removed under reduced pressure to yield a crude product, which was purified by column chromatography over silica gel (100-200 mesh) using 1.2% methanol in dichloromethane as an eluent to yield the title compound (90 mg, 52%)

MS: m/z 528 (M+1)

¹HNMR (CDCl₃+D₂O, 400 MHz): δ 1.35-1.53 (m, 10H), 1.55-1.81 (m, 5H), 1.9-2.1 (m, 2H), 2.21-2.35 (m, 1H), 2.96-3.03 (m, 1H), 3.05-3.13 (m, 1H), 3.62-3.92 (m, 2H), 3.94-4.12 (m, 2H), 4.23-4.4 (m, 1H), 4.44-4.57 (m, 1H), 4.8-4.9 (m, 1H), 7.51-7.61 (m, 2H), 7.63-7.7 (m, 2H).

Step: 2 3-{(2S)-2-Amino-2-[8-(4-trifluoromethyl-benzoyl)-8-aza-bicyclo[3.2.1]-oct-3-yl]-exo-ethanoyl}-1,3-thiazolidine trifluoro acetic acid salt

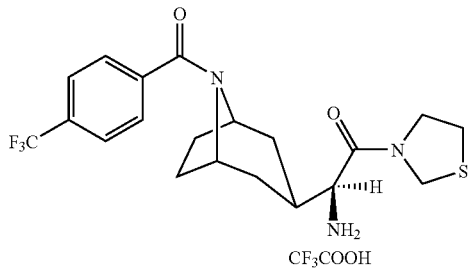

To a stirred solution of 3-{(2S)-2-(tert-butoxycarbonyl)-amino-2-[8-(4-trifluoromethyl-benzoyl)-8-aza-bicyclo[3.2.1]-oct-3-yl]-exo-ethanoyl}-1,3-thiazolidine (80 mg, 0.151 mmol) in dry dichloromethane (0.75 ml) at 0° C. was added a solution of trifluoroacetic acid (1.5 ml, 2.3 g 20.19 mmol) in dry dichloromethane (0.75 ml) and stirred at 0° C. for 5 minutes. The reaction mixture was then stirred at room temperature for 25 minutes. The solvent was evaporated under reduced pressure and dried under high vacuum. In order to remove traces of trifluoroacetic acid left and to solidify the product, petroleum ether (10 ml) was added and evaporated to obtain the title compound (80 mg, 98%).

mp: 123-125° C.

MS: m/z 428 (M+1)

¹HNMR (CDCl₃+D₂O, 400 MHz): δ 1.16-1.33 (m, 1H), 1.5-2.1 (m, 7H), 2.3-2.6 (m, 1H), 2.93-3.16 (m, 2H), 3.52-3.9 (m, 2H), 3.92-4.1 (m, 1H), 4.13-4.28 (m, 1H), 4.36-4.73 (m, 2H), 4.75-4.95 (m, 1H), 7.52-7.72 (m, 4H).

Example 8

(1S,3S,5S)-2-{(2S)-2-amino-2-[8-(2-fluoropyridine-4-carbonyl)-8-aza-bicyclo[3.2.1]-oct-3-yl]-exo-ethanoyl}-2-azabicyclo[3.1.0]-hexane-3-carbonitrile trifluoro acetic acid salt (Compound No. 28)

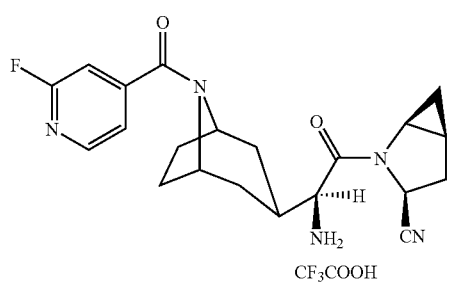

Step 1: 3S,5S)-2-{(2S)-2-(tert-butoxycarbonyl)-amino-2-[8-(2-fluoropyridine-4-carbonyl)-8-aza-bicyclo[3.2.1]-oct-3-yl]-exo-ethanoyl}-2-azabicyclo[3.1.0]-hexane-3-carboxamide

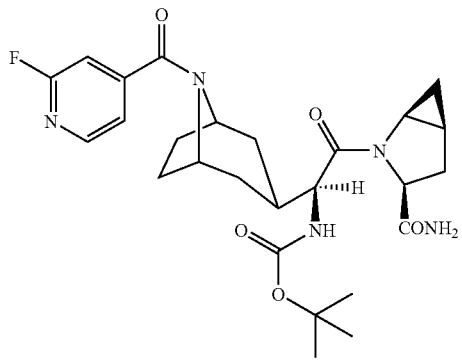

To a stirred solution of (2S)-2-(tert-butoxycarbonyl)-amino-2-[8-(2-fluoropyridine-4-carbonyl)-8-aza-bicyclo[3.2.1]-oct-3-yl]-exo-ethanoic acid (Intermediate 2, 7.6 g, 18.67 mmol) in DMF (120 ml) was added 1-hydroxybenzo-triazole (7.57 g, 56.02 mmol) and TFA salt of (1S,3S, 5S) 2-azabicyclo[3.1.0]-hexane-3-carboxamide (which can be prepared by using method as provided in WO 2004/052850, 4.48 g, 18.67 mmol) at room temperature. This reaction mixture was cooled to 0° C. and added triethyl amine (5.66 g, 7.8 ml, 56.02 mmol) and 1-(3-dimethyl amino propyl)-3-ethyl carbodiimide hydrochloride (7.16 g, 37.35 mmol) The reaction mixture was then brought to room temperature in 15 minutes and stirred at room temperature for 24 hours. The solvent was removed under reduced pressure, diluted with ethyl acetate (100 ml) washed with a saturated sodium bicarbonate solution (2×20 ml), water (20 ml) and brine (1×20 ml). The organic layer was dried over anhydrous Na₂SO₄ and the solvent was evaporated to get a crude product, which was purified by column chromatography over silica gel (200-400 mesh) using methanol:NH₃ in chloroform:dichloromethane in the ratio of 3:10:87 as an eluent to yield the title compound (3.61 g, 37%).

mp: 151-153° C.

MS: m/z 516 (M+1)

¹HNMR (CDCl₃+D₂O, 200 MHz): δ 0.80-0.98 (m, 1H), 1.02-1.18 (m, 1H), 1.3-2.1 (m, 16H), 2.27-2.7 (m, 3H), 3.5-3.7 (m, 1H), 3.9-4.04 (m, 1H), 4.5-4.68 (m, 1H) 4.73-4.9 (m, 2H), 5.20-5.45 (m, 2H), 6.97 (d, J=10.1 Hz, 1H), 7.15-7.3 (m, 1H), 8.22-8.32 (m, 1H).

Step 2: (1S,3S,5S)-2-{(2S)-2-(tert-butoxycarbonyl)-amino-2-[8-(2-fluoropyridine-4-carbonyl)-8-aza-bicyclo[3.2.1]-oct-3-yl]-exo-ethanoyl}-2-azabicyclo[3.1.0]-hexane-3-carbonitrile

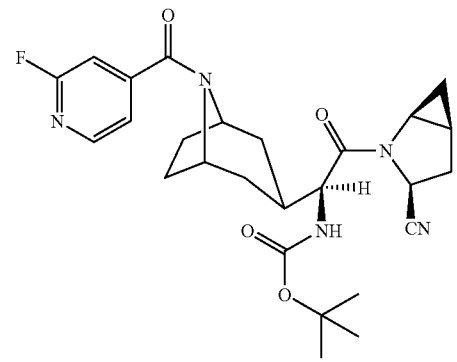

To a stirred solution of (1S,3S,5S)-2-{(2S)-2-(tert-butoxy-carbonyl)-amino-2-[8-(2-fluoropyridine-4-carbonyl)-8-aza-bicyclo[3.2.1]-oct-3-yl]-exo-ethanoyl}-2-azabicyclo[3.1.0]-hexane-3-carboxamide (3.6 g, 6.99 mmol) and imidazole (0.99 g, 14.68 mmol) in dry pyridine (80 ml) was added phosphorous oxy chloride (4.39 g, 2.67 ml, 28.66 mmol) drop wise at −30° C. under $N_2$ atmosphere. The reaction mixture was stirred at −30° C. for one hour and quenched with water (5 ml) at −30° C. It was allowed to come at room temperature and the solvent was removed under reduced pressure at same temperature. The crude product so obtained was dried under high vacuum and added dichloromethane (50 ml), washed with water (10 ml) dried over anhyd. $Na_2SO_4$. The solvent was evaporated to obtain a crude product, which was purified by column chromatography over silica gel (100-200 mesh) using 1.2% methanol in dichloromethane as an eluent to yield the title compound (2.9 g, 83%).

mp: 137-139° C.
MS: m/z 498 (M+1)
$^1$HNMR ($CDCl_3$+$D_2O$, 400 MHz): δ 0.98-1.16 (m, 2H), 1.35-1.85 (m, 13H), 1.9-2.1 (m, 3H), 2.36-2.65 (m, 3H), 3.76-3.86 (m, 1H), 3.95-4.04 (m, 1H), 4.48-4.56 (m, 1H), 4.7-4.76 (m, 1H), 4.84-4.9 (m, 1H), 4.99 (d, J=9.6 Hz, 1H), 5.2-5.3 (m, 1H), 6.94-7.03 (m, 1H), 7.18-7.28 (m, 1H), 8.27-8.32 (m, 1H).

Step 3: (1S,3S,5S)-2-{(2S)-2-Amino-2-[8-(2-fluoro-pyridine-4-carbonyl)-8-aza-bicyclo[3.2.1]-oct-3-yl]-exo-ethanoyl}-2-azabicyclo[3.1.0]-hexane-3-carbo-nitrile trifluoro acetic acid salt

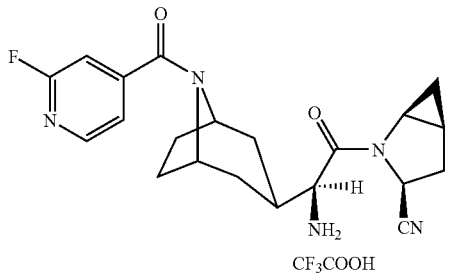

To a stirred solution of (1S,3S,5S)-2-{(2S)-2-(tert-butoxy-carbonyl)amino-2-[8-(2-fluoropyridine-4-carbonyl)-8-aza-bicyclo[3.2.1]-oct-3-yl]-exo-ethanoyl}-2-azabicyclo[3.1.0]-hexane-3-carbonitrile (3.0 g, 6.04 mmol) in dichloromethane (18 ml) was added a solution of trifluoro acetic acid (24.0 ml, 36.84 g, 323.15 mmol) in dichloromethane (18 ml) drop wise at 0° C. The reaction mixture was stirred at 0° C. for 5 minutes, brought to room temperature and stirred at room temperature for 20 min. The solvent was evaporated under reduced pressure at 30° C. and added dichloromethane (20 ml) The solvent was again evaporated and dried under high vacuum. In order to solidify the product, petroleum ether (20 ml) was added and evaporated. This process was repeated twice. In order to remove traces of trifluoroacetic acid, the reaction mixture was stirred at room temperature with 10% dichloromethane in ether (2×25 ml) and filtered to yield the title compound (2.6 g, 84%).

mp: 176-178° C.
MS: m/z 398 (M+1)
$^1$HNMR ($D_2O$, 400 MHz): δ 0.92-0.98 (m, 1H), 1.18-1.28 (m, 1H), 1.6-1.97 (m, 6H), 2.04-2.2 (m, 3H), 2.44 (d, J=14.0 Hz, 1H), 2.67-2.76 (m, 1H), 2.8-2.97 (m, 1H), 3.76-3.83 (m, 1H), 4.1-4.2 (m, 1H), 4.55-4.62 (m, 1H), 4.77-4.85 (m, 1H), 5.21 (d, J=10.8 Hz, 1H), 7.22 (s, 1H), 7.40-7.43 (m, 1H), 8.34 (d, J=5.2 Hz, 1H),
$[α]_D^{20}$ −14.37 (c 1.04, methanol)
Chiral Purity: 99.20%

The following compounds were prepared by procedure similar to those described for Compound No. 28 with appropriate variations of reactants, reaction conditions and quantities of reagents (1S,3S,5S)-2-{(2R)-2-Amino-2-[8-(2-fluoropyri-dine-4-carbonyl)-8-aza-bicyclo[3.2.1]oct-3-yl]-exo-ethanoyl}-2-azabicyclo[3.1.0]hexane-3-carbonitrile trifluoroacetic acid salt (Compound No. 31)

The intermediate (2R)-2-(tert-butoxycarbonyl)amino-2-[8-(2-fluoropyridine-4-carbonyl)-8-aza-bicyclo[3.2.1]-oct-3-yl]-exo-ethanoic-acid for the above title compound was prepared by using (S)-(+)-2-phenyl glycinol in place of (R)-(−)-2-phenyl glycinol as used in step 1 of Intermediate 1
mp: 196-199° C.
MS: m/z 398 (M+1)
$^1$HNMR ($D_2O$, 400 MHz): δ 0.94-1.08 (m, 2H), 1.55-1.88 (m, 6H), 1.92-2.10 (m, 3H), 2.35-2.42 (m, 1H), 2.51-2.70 (m, 2H), 3.62-3.71 (m, 1H), 4.03-4.11 (m, 1H), 4.46 (d, J=6.8 Hz, 1H), 4.75-4.81 (m, 1H), 5.0-5.08 (m, 1H), 7.13-7.17 (m, 1H), 7.33-7.37 (m, 1H), 8.27 (dd, J=2.8, 5.2 Hz, 1H)
$[α]_D^{20}$ −41.64 (c 1.0, methanol)
Yield: 58%

(1R,3R,5R)-2-{(2S)-2-Amino-2-[8-(2-fluoropyri-dine-4-carbonyl)-8-aza-bicyclo[3.2.1]oct-3-yl]-exo-ethanoyl}-2-azabicyclo[3.1.0]hexane-3-carbonitrile trifluoroacetic acid salt (Compound No. 29)

The above title compound was prepared by using Intermediate 14
mp: 215-218° C.
MS: m/z 398 (M+1)
$^1$HNMR ($D_2O$, 400 MHz): δ 0.94-1.08 (m, 2H), 1.55-1.88 (m, 6H), 1.92-2.10 (m, 3H), 2.35-2.42 (m, 1H), 2.51-2.70 (m, 2H), 3.62-3.71 (m, 1H), 4.03-4.11 (m, 1H), 4.46 (d, J=6.8 Hz, 1H), 4.75-4.81 (m, 1H), 5.0-5.08 (m, 1H), 7.13-7.17 (m, 1H), 7.33-7.37 (m, 1H), 8.27 (dd, J=2.8, 5.2 Hz, 1H)
$[α]_D^{20}$ +41.97 (c 1.0, methanol)
Yield: 82%

(1R,3R,5R)-2-{(2R)-2-Amino-2-[8-(2-fluoropyri-dine-4-carbonyl)-8-aza-bicyclo[3.2.1]oct-3-yl]-exo-ethanoyl}-2-azabicyclo[3.1.0]hexane-3-carbonitrile trifluoroacetic acid salt (Compound No. 30)

The above title compound was prepared by using the intermediate (2R)-2-(tert-butoxycarbonyl)amino-2-[8-(2-fluoro-pyridine-4-carbonyl)-8-aza-bicyclo[3.2.1]-oct-3-yl]-exo-ethanoic-acid (prepared by using (S)-(+)-2-phenyl glycinol in place of (R)-(−)-2-phenyl glycinol as used in step 1 of Intermediate 1) and intermediate 14
mp: 185-188° C.
MS: m/z 398 (M+1)
$^1$HNMR ($D_2O$, 400 MHz): δ 0.89-0.95 (m, 1H), 1.13-1.23 (m, 1H), 1.55-1.92 (m, 6H), 2.01-2.15 (m, 3H), 2.38-2.43 (m, 1H), 2.64-2.73 (m, 1H), 2.75-2.93 (m, 1H), 3.75-3.8 (m, 1H), 4.09-4.16 (m, 1H), 4.52-4.6 (m, 1H), 4.75-4.83 (m, 1H), 5.18 (d, J=10.8 Hz, 1H), 7.19 (s, 1H), 7.36-7.41 (m, 1H), 8.31 (d, J=5.2 Hz, 1H),
$[α]_D^{20}$ +14.71 (c 1.0, methanol)

Chiral Purity: 99.69%
Yield: 73%

(1S,3S,5S)-2-{(2S)-2-Amino-2-[8-(2,4,5-trifluorobenzoyl)-8-aza-bicyclo[3.2.1]oct-3-yl]-exo-ethanoyl}-2-azabicyclo[3.1.0]hexane-3-carbonitrile trifluoroacetic acid salt (Compound No. 23)

mp: 195-197° C.
MS: m/z 433 (M+1)
$^1$HNMR (D$_2$O, 400 MHz): δ 0.87-0.94 (m, 1H), 1.12-1.22 (m, 1H), 1.57-1.70 (m, 2H), 1.71-1.9 (m, 4H), 2.0-2.15 (m, 3H), 2.36-2.43 (m, 1H), 2.63-2.72 (m, 1H), 2.73-2.90 (m, 1H), 3.73-3.8 (m, 1H), 4.06-4.13 (m, 1H), 4.53 (dd, J=5.6, 13.6 Hz, 1H), 4.74-4.82 (m, 1H), 5.16 (dd, J=2.0, 10.8 Hz, 1H), 7.22-7.3 (m, 1H), 7.35-7.43 (m, 1H)
Yield: 71%

(1S,3S,5S)-2-{(2S)-2-Amino-2-[8-(4-cyanobenzoyl)-8-aza-bicyclo[3.2.1]oct-3-yl]-exo-ethanoyl}-2-azabicyclo[3.1.0]hexane-3-carbonitrile trifluoroacetic acid salt (Compound No. 24)

mp: 202-204° C.
MS: m/z 404 (M+1)
$^1$HNMR (D$_2$O, 400 MHz): δ 0.88-0.92 (m, 1H), 1.18-1.21 (m, 1H), 1.52-1.92 (m, 6H), 2.0-2.2 (m, 3H), 2.38-2.43 (m, 1H), 2.62-2.72 (m, 1H), 2.76-2.95 (m, 1H), 3.74-3.80 (m, 1H), 4.08-4.16 (m, 1H), 4.54 (dd, J=5.6, 12.8 Hz, 1H), 4.75-4.82 (m, 1H), 5.16 (dd, J=1.6, 10.4 Hz, 1H), 7.56-7.63 (m, 2H), 7.86 (d, J=8 Hz, 2H).
Yield: 94%

(1S,3S,5S)-2-{(2S)-2-Amino-2-[8-(pyridine-4-carbonyl)-8-aza-bicyclo[3.2.1]oct-3-yl]-exo-ethanoyl}-2-azabicyclo[3.1.0]hexane-3-carbonitrile trifluoroacetic acid salt (Compound No. 25)

mp: 138-140° C.
MS: m/z 380 (M+1)
$^1$HNMR (D$_2$O, 200 MHz): δ 0.8-1.0 (m, 1H), 1.1-1.3 (m, 1H), 1.5-2.25 (m, 9H), 2.33-2.50 (m, 1H), 2.60-3.05 (m, 2H), 3.7-3.85 (m, 1H), 4.0-4.12 (m, 1H), 4.5-4.63 (m, 1H), 4.7-4.85 (m, 1H), 5.1-5.25 (m, 1H), 8.06-8.18 (m, 2H), 8.93 (d, J=5.7 Hz, 2H)
Yield: 80%

(1S,3S,5S)-2-{(2S)-2-Amino-2-[8-(4-trifluoromethylbenzoyl)-8-aza-bicyclo[3.2.1]oct-3-yl]-exo-ethanoyl}-2-azabicyclo[3.1.0]hexane-3-carbonitrile trifluoroacetic acid salt (Compound No. 26)

mp: 183-185° C.
MS: m/z 447 (M+1)
$^1$HNMR (D$_2$O, 400 MHz): δ 0.88-0.94 (m, 1H), 1.13-1.23 (m, 1H), 1.55-1.92 (m, 6H), 2.01-2.15 (m, 3H), 2.37-2.45 (m, 1H), 2.64-2.75 (m, 1H), 2.76-2.94 (m, 1H), 3.5-3.81 (m, 1H), 4.08-4.18 (m, 1H), 4.52 (dd, J=5.2, 13.6 Hz, 1H), 4.75-4.83 (m, 1H), 5.18 (d, J=10.8 Hz, 1H), 7.63 (d, J=7.6 Hz, 2H), 7.83 (d, J=8 Hz, 2H)
$[α]_D^{20}$ −16.88 (c 0.50, water)
Yield: 80%

(1S,3S,5S)-2-{(2S)-2-Amino-2-[8-(2,5-difluorobenzoyl)-8-aza-bicyclo[3.2.1]oct-3-yl]-exo-ethanoyl}-2-azabicyclo[3.1.0]hexane-3-carbonitrile trifluoroacetic acid salt (Compound No. 27)

mp: 190-192° C.
MS: m/z 415 (M+1)
$^1$HNMR (D$_2$O, 400 MHz): δ 0.88-0.97 (m, 1H), 1.13-1.25 (m, 1H), 1.56-1.95 (m, 6H), 2.01-2.18 (m, 3H), 2.38-2.46 (m, 1H), 2.64-2.74 (m, 1H), 2.76-2.92 (m, 1H), 3.75-3.82 (m, 1H), 4.07-4.15 (m, 1H), 4.52 (dd, J=5.6, 14.8 Hz, 1H), 4.75-4.85 (m, 1H), 5.17 (d, J=10.4 Hz, 1H), 7.16-7.23 (m, 1H), 7.26 (t, J=6 Hz, 2H)
Yield: 83%

(1S,3S,5S)-2-{(2S)-2-Amino-2-[8-(2-fluoropyridine-3-carbonyl)-8-aza-bicyclo[3.2.1]oct-3-yl]-exo-ethanoyl}-2-azabicyclo[3.1.0]hexane-3-carbonitrile trifluoroacetic acid salt (Compound No. 32)

mp: 203-205° C.
MS: m/z 398 (M+1)
$^1$HNMR (D$_2$O, 400 MHz): δ 0.88-0.95 (m, 1H), 1.12-1.24 (m, 1H), 1.58-1.92 (m, 6H), 2.0-2.18 (m, 3H), 2.38-2.45 (m, 1H), 2.63-2.73 (m, 1H), 2.75-2.92 (m, 1H), 3.75-3.82 (m, 1H), 4.05-4.12 (m, 1H), 4.54 (dd, J=6, 11.6 Hz, 1H), 4.76-4.85 (m, 1H), 5.17 (dd, J=2.4, 10.8 Hz, 1H), 7.43-7.49 (m, 1H), 8.0-8.06 (m, 1H), 8.3-8.34 (m, 1H)
$[α]_D^{25}$ −10.24 (c 0.50, water)
Yield: 73%

(1S,3S,5S)-2-{(2S)-2-Amino-2-[8-(pyridine-3-carbonyl)-8-aza-bicyclo[3.2.1]oct-3-yl]-exo-ethanoyl}-2-azabicyclo[3.1.0]hexane-3-carbonitrile di trifluoroacetic acid salt (Compound No. 33)

mp: 146-148° C.
MS: m/z 380 (M+1)
$^1$HNMR (D$_2$O, 400 MHz): δ 0.88-0.98 (m, 1H), 1.12-1.23 (m, 1H), 1.56-1.97 (m, 6H), 2.0-2.2 (m, 3H), 2.40 (dd, J=2.0, 13.6 Hz, 1H), 2.62-2.73 (m, 1H), 2.8-2.98 (m, 1H), 3.75-3.82 (m, 1H), 4.17-4.23 (m, 1H), 4.55-4.62 (m, 1H), 4.74-4.86 (m, 1H), 5.13-5.22 (m, 1H), 8.1-8.15 (m, 1H), 8.62-8.67 (m, 1H), 8.91 (dd, J=4.8, 22.0 Hz, 2H)
$[α]_D^{26}$ −35.41 (c 0.50, water)
Yield: 95%

(1S,3S,5S)-2-{(2S)-2-Amino-2-[8-(thiophene-2-carbonyl)-8-aza-bicyclo[3.2.1]oct-3-yl]-exo-ethanoyl}-2-azabicyclo[3.1.0]hexane-3-carbonitrile trifluoroacetic acid salt (Compound No. 34)

mp: 197-199° C.
MS: m/z 385 (M+1)
$^1$HNMR (D$_2$O, 400 MHz): δ 0.89-0.95 (m, 1H), 1.12-1.23 (m, 1H), 1.68-1.92 (m, 6H), 1.95-2.15 (m, 3H), 2.35-2.43 (m, 1H), 2.62-2.71 (m, 1H), 2.76-2.95 (m, 1H), 3.72-3.79 (m, 1H), 4.52 (dd, J=5.2, 19.6 Hz, 1H), 4.7-4.82 (m, 2H), 5.14-5.18 (dd, J=2.4, 10.8 Hz, 1H), 7.13 (t, J=4.4 Hz, 1H), 7.48-7.52 (m, 1H), 7.65 (d, J=5.2 Hz, 1H)
$[α]_D^{25}$ −15.90 (c 0.50, water)
Yield: 77%

(1S,3S,5S)-2-{(2S)-2-Amino-2-[8-(pyrazine-2-carbonyl)-8-aza-bicyclo[3.2.1]oct-3-yl]-exo-ethanoyl}-2-azabicyclo[3.1.0]hexane-3-carbonitrile trifluoroacetic acid salt (Compound No. 35)

mp: 202-203° C.
MS: m/z 381 (M+1)
$^1$HNMR (D$_2$O, 400 MHz): δ 0.88-0.95 (m, 1H), 1.13-1.22 (m, 1H), 1.53-1.95 (m, 6H), 2.0-2.15 (m, 3H), 2.38 (dd, J=1.6, 13.6 Hz, 1H), 2.6-2.7 (m, 1H), 2.78-2.96 (m, 1H), 3.72-3.79 (m, 1H), 4.32-4.4 (m, 1H), 4.53 (dd, J=5.6, 17.2 Hz, 1H), 4.8-4.86 (m, 1H), 5.15 (d, J=10.8 Hz, 1H), 8.67-8.7 (m, 1H), 8.71-8.74 (m, 1H), 8.82-8.84 (m, 1H)

$[\alpha]_D^{20}$ −22.40 (c 0.50, water)

Chiral Purity: 99.10%

Yield: 95%

(1S,3S,5S)-2-{(2R)-2-Amino-2-[8-(pyrazine-2-carbonyl)-8-aza-bicyclo[3.2.1]oct-3-yl]-exo-ethanoyl}-2-azabicyclo[3.1.0]hexane-3-carbonitrile trifluoroacetic acid salt (Compound No. 36)

The intermediate (2R)-2-(tert-butoxycarbonyl)amino-2-[8-(pyrazine-2-carbonyl)-8-aza-bicyclo[3.2.1]-oct-3-yl]-exo-ethanoic-acid for the above title compound was prepared by using (S)-(+)-2-phenyl glycinol in place of (R)-(−)-2-phenyl glycinol as used in step 1 of Intermediate 1

MS: m/z 381 (M+1)

$^1$HNMR (D$_2$O, 400 MHz): δ 0.96-1.1 (m, 2H), 1.13-1.22 (m, 1H), 1.92-2.12 (m, 3H), 2.36-2.45 (m, 1H), 2.55-2.73 (m, 2H), 3.66-3.75 (m, 1H), 4.32-4.37 (m, 1H), 4.48 (dd, J=1.6, 7.2 Hz, 1H), 5.15 (d, J=10.8 Hz, 1H), 8.67-8.7 (m, 1H), 8.72-8.75 (m, 1H), 8.84 (S, 1H).

$[\alpha]_D^{20}$ −55.60 (c 0.50, Methanol)

Yield: 67%

(1R,3R,5R)-2-{(2S)-2-Amino-2-[8-(pyrazine-2-carbonyl)-8-aza-bicyclo[3.2.1]oct-3-yl]-exo-ethanoyl}-2-azabicyclo[3.1.0]hexane-3-carbonitrile trifluoroacetic acid salt (Compound No. 37)

The above title compound was prepared by using Intermediate 14

MS: m/z 381 (M+1)

$^1$HNMR (D$_2$O, 400 MHz): δ 0.96-1.1 (m, 2H), 1.65-1.91 (m, 6H), 1.92-2.12 (m, 3H), 2.36-2.45 (m, 1H), 2.55-2.73 (m, 2H), 3.66-3.75 (m, 1H), 4.32-4.37 (m, 1H), 4.48 (dd, J=1.6, 7.2 Hz, 1H), 4.77-4.83 (m, 1H), 5.05-5.08 (m, 1H), 8.67-8.7 (m, 1H), 8.72-8.75 (m, 1H), 8.84 (s, 1H)

mp: 157-159° C.

$[\alpha]_D^{20}$ +53.86 (c 0.50, Methanol)

Yield: 64%

(1R,3R,5R)-2-{(2R)-2-Amino-2-[8-(pyrazin-2-carbonyl)-8-aza-bicyclo[3.2.1]oct-3-yl]-exo-ethanoyl}-2-azabicyclo[3.1.0]hexane-3-carbonitrile trifluoroacetic acid salt (Compound No. 38)

The above title compound was prepared by using the intermediate (2R)-2-(tert-butoxycarbonyl)amino-2-[8-(pyrazin-2-carbonyl)-8-aza-bicyclo[3.2.1]-oct-3-yl]-exo-ethanoic-acid (prepared by using (S)-(+)-2-phenyl glycinol in place of (R)-(−)-2-phenyl glycinol as used in step 1 of Intermediate 1) and intermediate 14 mp: 112-115° C.

MS: m/z 381 (M+1)

$^1$HNMR (D$_2$O, 400 MHz): δ 0.88-0.95 (m, 1H), 1.13-1.22 (m, 1H), 1.53-1.95 (m, 6H), 2.0-2.15 (m, 3H), 2.38 (dd, J=1.6, 13.6 Hz, 1H), 2.6-2.7 (m, 1H), 2.78-2.96 (m, 1H), 3.72-3.79 (m, 1H), 4.32-4.4 (m, 1H), 4.53 (dd, J=5.6, 17.2 Hz, 1H), 4.8-4.86 (m, 1H), 5.15 (d, J=10.8 Hz, 1H), 8.67-8.7 (m, 1H), 8.71-8.74 (m, 1H), 8.82-8.84 (m, 1H)

$[\alpha]_D^{20}$ +22.40 (c 0.50, water)

Chiral Purity: 99.11%

Yield: 62%

(1S,3S,5S)-2-{(2S)-2-Amino-2-[8-(pyridine-2-carbonyl)-8-aza-bicyclo[3.2.1]oct-3-yl]-exo-ethanoyl}-2-azabicyclo[3.1.0]hexane-3-carbonitrile trifluoroacetic acid salt (Compound No. 39)

mp: 201-202° C.

MS: m/z 380 (M+1)

$^1$HNMR (D$_2$O, 400 MHz): δ 0.88-0.96 (m, 1H), 1.12-1.22 (m, 1H), 1.47-1.95 (m, 6H), 2.0-2.2 (m, 3H), 2.38 (d, J=14.04 Hz, 1H), 2.62-2.72 (m, 1H), 2.78-2.98 (m, 1H), 3.72-3.8 (m, 1H), 4.14-4.23 (m, 1H), 4.53 (dd, J=5.2, 18.8 Hz, 1H), 4.75-4.85 (m, 1H), 5.15 (d, J=10.4 Hz, 1H), 7.6-7.7 (m, 2H), 8.07 (t, J=7.6 Hz, 1H), 8.57-8.63 (m, 1H)

$[\alpha]_D^{25}$ −14.8 (c 0.56, water)

Yield: 60%

(1S,3S,5S)-2-{(2S)-2-Amino-2-[8-(furan-2-carbonyl)-8-aza-bicyclo[3.2.1]oct-3-yl]-exo-ethanoyl}-2-azabicyclo[3.1.0]hexane-3-carbonitrile trifluoroacetic acid salt (Compound No. 40)

mp: 197-199° C.

MS: m/z 369 (M+1)

$^1$HNMR (D$_2$O, 400 MHz): δ 0.9-0.98 (m, 1H), 1.1-1.28 (m, 1H), 1.74-1.93 (m, 6H), 1.98-2.2 (m, 3H), 2.38-2.44 (m, 1H), 2.62-2.72 (m, 1H), 2.8-3.0 (m, 1H), 3.73-3.8 (m, 1H), 4.53 (dd, J=5.6, 20.4 Hz, 1H), 4.78-4.83 (m, 1H), 5.04-5.10 (m, 1H), 5.16-5.19 (dd, J=2.4, 10.8 Hz, 1H), 6.6-6.64 (m, 1H), 7.13 (d, J=3.2 Hz, 1H), 7.67-7.70 (m, 1H)

$[\alpha]_D^{25}$ −21.07 (c 0.51, water)

Yield: 81%

(1S,3S,5S)-2-{(2S)-2-Amino-2-[8-(3-fluoropyridine-4-carbonyl)-8-aza-bicyclo[3.2.1]oct-3-yl]-exo-ethanoyl}-2-azabicyclo[3.1.0]hexane-3-carbonitrile trifluoroacetic acid salt (Compound No. 41)

mp: 202-204° C.

MS: m/z 398 (M+1)

$^1$HNMR (D$_2$O, 400 MHz): δ 0.88-0.96 (m, 1H), 1.16-1.25 (m, 1H), 1.6-1.94 (m, 6H), 2.02-2.18 (m, 3H), 2.38-2.45 (m, 1H), 2.65-2.74 (m, 1H), 2.77-2.92 (m, 1H), 3.75-3.83 (m, 1H), 4.02-4.08 (m, 1H), 4.52-4.58 (m, 1H), 4.83-4.9 (m, 1H), 5.15-5.22 (m, 1H), 7.54-7.6 (m, 1H), 8.51 (d, J=4.8 Hz, 1H), 8.62 (s, 1H)

$[\alpha]_D^{20}$ −9.75 (c 0.55, water)

Yield: 89%

(1S,3S,5S)-2-{(2S)-2-Amino-2-[8-(benzo[1,3]-dioxole-5-carbonyl)-8-aza-bicyclo[3.2.1]oct-3-yl]-exo-ethanoyl}-2-azabicyclo[3.1.0]-hexane-3-carbonitrile trifluoroacetic acid salt (Compound No. 44)

mp: 197-199° C.

MS: m/z 423 (M+1)

$^1$HNMR (D$_2$O, 400 MHz): δ 0.9-0.97 (m, 1H), 1.18-1.22 (m, 1H), 1.57-1.92 (m, 6H), 2.04-2.16 (m, 3H), 2.4-2.48 (m, 1H), 2.65-2.75 (m, 1H), 2.76-2.95 (m, 1H), 3.76-3.82 (m, 1H), 4.25-4.35 (m, 1H), 4.52-4.6 (dd, J=5.6, 16.8 Hz, 1H), 4.72-4.8 (m, 1H), 5.18-5.22 (dd, J=2.4, 10.8 Hz, 1H), 6.04 (s, 2H), 6.95-7.05 (m, 3H)

$[\alpha]_D^{22}$ −9.5 (c 0.50, water)

Yield: 59%

(1S,3S,5S)-2-{(2S)-2-Amino-2-[8-(3,5-difluorobenzene sulfonyl)-8-aza-bicyclo[3.2.1]oct-3-yl]-exo-ethanoyl}-2-azabicyclo[3.1.0]hexane-3-carbonitrile trifluoroacetic acid salt (Compound No. 42)

mp: 168-170° C.
MS: m/z 451 (M+1)
$^1$HNMR (D$_2$O, 400 MHz): δ 0.90-0.95 (m, 1H), 1.14-1.20 (m, 1H), 1.52-1.70 (m, 5H), 1.71-1.88 (m, 3H), 2.0-2.08 (m, 1H), 2.41 (dd, J=2.0, 14.0 Hz, 1H), 2.6-2.74 (m, 2H), 3.73-3.78 (m, 1H), 4.35-4.44 (m, 2H), 4.49 (d, J=6 Hz, 1H), 5.16 (dd, J=2.4, 10.84 Hz, 1H), 7.26-7.33 (m, 1H), 7.52-7.58 (m, 2H)
$[α]_D^{27}$ −16.98 (c 0.51, water)
Yield: 76%

(1S,3S,5S)-2-{(2S)-2-Amino-2-[8-(adamantane-1-carbonyl)-8-aza-bicyclo[3.2.1]oct-3-yl]-exo-ethanoyl}-2-azabicyclo[3.1.0]hexane-3-carbonitrile trifluoroacetic acid salt (Compound No. 43)

mp: 211-213° C.
MS: m/z 437 (M+1)
$^1$HNMR (D$_2$O, 400 MHz): δ 0.90-0.96 (m, 1H), 1.14-1.26 (m, 1H), 1.54-2.13 (m, 24H), 2.41 (dd, J=2.0, 14.0 Hz, 1H), 2.63-2.87 (m, 2H), 3.74-3.81 (m, 1H), 4.43-4.57 (m, 1H), 4.67-4.75 (m, 1H), 4.97-5.07 (m, 1H), 5.17 (dd, J=2.0, 10.8 Hz, 1H),
$[α]_D^{25}$ −17.13 (c 0.51, water)
Yield: 63%

(1S,3S,5S)-2-{(2S)-2-Amino-2-[8-(3,3,3-trifluoro propyl)-8-aza-bicyclo[3.2.1]oct-3-yl]-exo-ethanoyl}-2-azabicyclo[3.1.0]hexane-3-carbonitrile trifluoroacetic acid salt (Compound No. 47)

mp: 199-201° C.
MS: m/z 371 (M+1)
$^1$HNMR (D$_2$O, 400 MHz): δ 0.91-0.98 (m, 1H), 1.12-1.22 (m, 1H), 1.88-2.13 (m, 7H), 2.3-2.46 (m, 3H), 2.65-2.87 (m, 4H), 3.30-3.38 (m, 2H), 3.76-3.83 (m, 1H), 4.15-4.21 (m, 2H), 4.55 (d, J=6.8 Hz, 1H), 5.18 (d, J=8.4 Hz, 1H),
$[α]_D^{24}$ −12.31 (c 0.38, water)
Yield: 73%

(1S,3S,5S)-2-{(2S)-2-Amino-2-[8-(cyclohexyl methyl)-8-aza-bicyclo[3.2.1]oct-3-yl]-exo-ethanoyl}-2-azabicyclo-[3.1.0]hexane-3-carbonitrile trifluoroacetic acid salt (Compound No. 48)

mp: 188-189° C.
MS: m/z 371 (M+1)
$^1$HNMR (D$_2$O, 400 MHz): δ 0.93-1.09 (m, 3H), 1.13-1.33 (m, 4H), 1.61-2.18 (m, 13H), 2.23-2.36 (m, 2H), 2.4-2.47 (m, 1H), 2.66-2.77 (m, 2H), 2.88 (d, J=7.2 Hz, 2H), 3.78-3.85 (m, 1H), 4.1-4.15 (m, 2H), 4.55 (d, J=7.6 Hz, 1H), 5.19 (dd, J=2.4, 10.8 Hz, 1H)
$[α]_D^{20}$ −9.28 (c 0.50, water)
Yield: 79%

(1S,3S,5S)-2-{(2S)-2-Amino-2-[8-(benzyloxy-ethyl)-8-aza-bicyclo[3.2.1]oct-3-yl]-exo-ethanoyl}-2-azabicyclo[3.1.0]hexane-3-carbonitrile trifluoroacetic acid salt (Compound No. 50)

mp: 185-186° C.
MS: m/z 409 (M+1)
$^1$HNMR (D$_2$O, 200 MHz): δ 0.9-1.0 (m, 1H), 1.1-1.35 (m, 1H), 1.73-2.8 (m, 12H), 3.2-3.35 (m, 1H), 3.72-3.9 (m, 3H), 4.0-4.18 (m, 2H), 4.46-4.7 (m, 4H), 5.19 (d, J=10.1 Hz, 1H), 7.35-7.5 (m, 5H)
$[α]_D^{20}$ −9.464 (c 0.50, water)
Yield: 95%

(1S,3S,5S)-2-{(2S)-2-Amino-2-[8-(5-cyanopyridine-2-yl)-8-aza-bicyclo[3.2.1]oct-3-yl]-exo-ethanoyl}-2-azabicyclo[3.1.0]hexane-3-carbonitrile trifluoroacetic acid salt (Compound No. 51)

mp: 199-201° C.
MS: m/z 377 (M+1)
$^1$HNMR (D$_2$O, 400 MHz): δ 0.68-0.73 (m, 1H), 1.02-1.09 (m, 1H), 1.6-1.79 (m, 4H), 1.81-2.20 (m, 5H), 2.3-2.37 (m, 1H), 2.55-2.65 (m, 1H), 2.8-2.9 (m, 1H), 3.64-3.7 (m, 1H), 4.41 (d, J=4.8 Hz, 1H), 4.56-4.65 (m, 2H), 5.10 (d, J=10.8 Hz, 1H), 6.81 (d, J=9.2 Hz, 1H), 7.72-7.76 (m, 1H), 8.32 (s, 1H)
$[α]_D^{25}$ −10.84 (c 0.50, water)
Yield: 63%

(1S,3S,5S)-2-{(2S)-2-Amino-2-[8-(4-cyano-phenyl)-8-aza-bicyclo[3.2.1]oct-3-yl]-exo-ethanoyl}-2-azabicyclo[3.1.0]hexane-3-carbonitrile trifluoro acetic acid salt (Compound No. 52)

mp: 176-178° C.
MS: m/z 376 (M+1)
$^1$HNMR (D$_2$O, 400 MHz): δ 0.62-0.7 (m, 1H), 0.96-1.07 (m, 1H), 1.48-1.6 (m, 2H), 1.66-1.96 (m, 5H), 2.01-2.12 (m, 2H), 2.26-2.35 (m, 1H), 2.54-2.65 (m, 1H), 2.71-2.85 (m, 1H), 3.56-3.62 (m, 1H), 4.28-4.32 (m, 1H), 4.38-4.45 (m, 2H), 5.07 (d, J=10.4 Hz, 1H), 6.95 (d, J=8.4 Hz, 2H), 7.58 (d, J=8.4 Hz, 2H)
$[α]_D^{20}$ −4.43 (c 0.50, water)
Yield: 82%

(1S,3S,5S)-2-{(2S)-2-Amino-2-[8-(pyridin-4-yl-methyl)-8-aza-bicyclo[3.2.1]oct-3-yl]-exo-ethanoyl}-2-azabicyclo[3.1.0]hexane-3-carbonitrile trifluoroacetic acid salt (Compound No. 55)

mp: 136-138° C.
MS: m/z 366 (M+1)
$^1$HNMR (D$_2$O, 400 MHz): δ 0.86-0.93 (m, 1H), 1.10-1.19 (m, 1H), 1.82-2.20 (m, 7H), 2.35-2.53 (m, 3H), 2.62-2.78 (m, 2H), 3.72-3.8 (m, 1H), 4.14 (s, 2H), 4.47-4.6 (m, 3H), 5.15 (d, J=10.4 Hz, 1H), 8.20 (d, J=6.4 Hz, 2H), 8.88 (d, J=6.4 Hz, 2H)
$[α]_D^{28}$ −9.43 (c 0.51, water)
Yield: 80%

(1S,3S,5S)-2-{(2S)-2-Amino-2-[8-(2-pyridin-4-yl-acetyl)-8-aza-bicyclo[3.2.1]oct-3-yl]-exo-ethanoyl}-2-azabicyclo[3.1.0]hexane-3-carbonitrile di trifluoroacetic acid salt (Compound No. 54)

mp: 165-167° C.
MS: m/z 394 (M+1)
$^1$HNMR (D$_2$O, 400 MHz): δ 0.91-1.0 (m, 1H), 1.12-1.30 (m, 1H), 1.69-1.87 (m, 6H), 1.95-2.2 (m, 3H), 2.40-2.46 (m, 1H), 2.64-2.75 (m, 1H), 2.79-2.98 (m, 1H), 3.73-3.81 (m, 1H), 4.08 (dd, J=5.2, 16.4 Hz, 1H), 4.22-4.32 (m, 1H), 4.54-4.60 (m, 2H), 4.65-4.70 (m, 1H), 5.19 (dd, J=2.0, 10.8 Hz, 1H), 7.94 (d, J=6.0 Hz, 2H), 8.71 (d, J=6.4 Hz, 2H)

[α]$_D^{20}$ −9.73 (c 0.50, methanol)
Yield: 79%

(1S,3S,5S)-2-{(2S)-2-Amino-2-[8-(1-ethyl-propyl)-8-aza-bicyclo[3.2.1]oct-3-yl]-exo-ethanoyl}-2-azabicyclo[3.1.0]hexane-3-carbonitrile trifluoroacetic acid salt (Compound No. 59)

mp: 171-173° C.
MS: m/z 345 (M+1)
$^1$HNMR (D$_2$O, 400 MHz): δ 0.85-0.95 (m, 8H), 1.1-1.2 (m, 1H), 1.63-2.1 (m, 10H), 2.15-2.27 (m, 2H), 2.36-2.42 (m, 1H), 2.61-2.76 (m, 2H), 2.9-3.0 (m, 0.5H), 3.43-3.5 (m, 0.5H), 3.74-3.82 (m, 1H), 4.18-4.22 (m, 1H), 4.26-4.32 (m, 1H), 4.51 (d, J=7.6 Hz, 0.5H), 4.65 (d, J=6.4 Hz, 0.5H), 5.12-5.2 (m, 1H)
[α]$_D^{20}$ −10.0 (c 0.50, water)
Yield: 62%

(1S,3S,5S)-2-{(2S)-2-Amino-2-[8-(4-methanesulfonyl phenyl)-8-aza-bicyclo[3.2.1]oct-3-yl]-exo-ethanoyl}-2-azabicyclo[3.1.0]hexane-3-carbonitrile trifluoroacetic acid salt (Compound No. 53)

mp: 184-186° C.
MS: m/z 429 (M+1)
$^1$HNMR (D$_2$O, 400 MHz): δ 0.56-0.62 (m, 1H), 1.01-1.08 (m, 1H), 1.58-1.78 (m, 3H), 1.85-2.03 (m, 4H), 2.1-2.21 (m, 2H), 2.3-2.37 (m, 1H), 2.58-2.68 (m, 1H), 2.78-2.9 (m, 1H), 3.21 (s, 3H), 3.63-3.68 (m, 1H), 4.39 (d, J=4.8 Hz, 1H), 4.48-4.55 (m, 2H), 5.11 (dd, J=2.4, 10.8 Hz, 1H), 7.08 (d, J=8.8 Hz, 2H), 7.79 (d, J=8.8 Hz, 2H)
[α]$_D^{20}$ −6.98 (c 0.50, water)
Yield: 80%

(1S,3S,5S)-2-{(2S)-2-Amino-2-[8-(4-chlorophenyl-sulfonylcarbamoyl)-8-aza-bicyclo[3.2.1]oct-3-yl]-exo-ethanoyl}-2-azabicyclo[3.1.0]hexane-3-carbonitrile trifluoroacetic acid salt (Compound No. 61)

mp: 189-191° C.
MS: m/z 490 (M−1)
$^1$HNMR (D$_2$O, 400 MHz): δ 0.76-0.83 (m, 1H), 1.05 (m, 1H), 1.53-2.05 (m, 9H), 2.34-2.4 (m, 1H), 2.6-2.79 (m, 2H), 3.66-3.72 (m, 1H), 4.3-4.37 (M, 2H), 4.41 (d, J=5.6 Hz, 1H), 5.13 (dd, J=2.4, 10.8 Hz, 1H), 7.58-7.63 (m, 2H), 7.87-7.93 (m, 2H)
[α]$_D^{20}$ −10.37 (c 0.50, water)
Yield: 81%

(1S,3S,5S)-2-{(2S)-2-Amino-2-[8-(2-methoxyphenylthiocarbamoyl)-8-aza-bicyclo[3.2.1]oct-3-yl]-exo-ethanoyl}-2-azabicyclo[3.1.0]-hexane-3-carbonitrile trifluoroacetic acid salt (Compound No. 68)

mp: 125-127° C.
MS: m/z 440 (M+1)
$^1$HNMR (D$_2$O, 400 MHz): δ 0.94-1.0 (m, 1H), 1.16-1.25 (m, 1H), 1.65-1.98 (m, 6H), 2.0-2.27 (m, 3H), 2.38-2.45 (m, 1H), 2.63-2.72 (m, 1H), 2.80-3.0 (m, 1H), 3.80 (s, 3H), 4.48-4.57 (m, 1H), 4.65-4.82 (m, 2H), 5.04-5.12 (m, 1H), 5.17 (dd, J=2.0, 10.4 Hz, 1H), 6.98-7.3 (m, 1H)., 7.10 (d, J=8.4 Hz, 1H), 7.15-7.22 (m, 1H), 7.32-7.4 (m, 1H)
[α]$_D^{20}$ −4.49 (c 0.50, water)
Yield: 98%

(1S,3S,5S)-2-{(2S)-2-Amino-2-[8-(methanesulfonyl)-8-aza-bicyclo[3.2.1]oct-3-yl]-exo-ethanoyl}-2-azabicyclo[3.1.0]hexane-3-carbonitrile trifluoroacetic acid salt (Compound No. 56)

mp: 193-195° C.
MS: m/z 353 (M+1)
$^1$HNMR (D$_2$O, 400 MHz): δ 0.97-1.02 (m, 1H), 1.19-1.25 (m, 1H), 1.77-1.93 (m, 6H), 2.05-2.2 (m, 3H), 2.5 (dd, J=2.4, 14.0 Hz, 1H), 2.68-2.82 (m, 2H), 3.08 (s, 3H), 3.78-0.383 (m, 1H), 4.35-4.4 (m, 2H), 4.56 (d, J=6 Hz, 1H), 5.22 (dd, J=2.4, 10.8 Hz, 1H),
[α]$_D^{20}$ −20.57 (c 1.00, water)
Yield: 88%

(1S,3S,5S)-2-{(2S)-2-Amino-2-[8-(thiophene-2-sulfonyl)-8-aza-bicyclo[3.2.1]oct-3-yl]-exo-ethanoyl}-2-azabicyclo[3.1.0]hexane-3-carbonitrile trifluoroacetic acid salt (Compound No. 57)

mp: 190-192° C.
MS: m/z 421 (M+1)
$^1$HNMR (D$_2$O, 400 MHz): δ 0.86-0.92 (m, 1H), 1.09-1.17 (m, 1H), 1.5-1.65 (m, 5H), 1.67-1.88 (m, 3H), 1.95-2.05 (m, 1H), 2.33-2.40 (dd, J=14 Hz, 2.4 Hz, 1H), 2.55-2.7 (m, 2H), 3.67-3.74 (m, 1H), 4.33-4.39 (m, 2H), 4.44 (d, J=6 Hz, 1H), 5.10-5.15 (dd, J=10.8 Hz, 2.4 Hz, 1H), 7.16-7.19 (m, 1H), 7.68-7.72 (m, 1H), 7.82-7.85 (m, 1H).
[α]$_D^{20}$ −2.25 (c 0.50, water)
Yield: 95%

(1S,3S,5S)-2-{(2S)-2-Amino-2-[8-(cyclohexane-carbonyl)-8-aza-bicyclo[3.2.1]oct-3-yl]-exo-ethanoyl}-2-azabicyclo[3.1.0]hexane-3-carbonitrile trifluoroacetic acid salt (Compound No. 58)

mp: 184-186° C.
MS: m/z 385 (M+1)
$^1$HNMR (D$_2$O, 400 MHz): δ 0.88-0.96 (m, 1H), 1.09-1.43 (m, 6H), 1.52-1.85 (m, 11H), 1.86-1.98 (m, 1H), 2.0-2.11 (m, 2H), 2.36-2.43 (m, 1H), 2.53-2.70 (m, 2H), 2.71-2.9 (m, 1H), 3.71-3.77 (m, 1H), 4.47 (dd, J=5.6, 13.6 Hz, 1H), 4.53-4.65 (m, 2H), 5.15 (d, J=5.2 Hz, 1H)
[α]$_D^{20}$ −11.20 (c 1.07, water)
Yield: 76%

(1S,3S,5S)-2-{(2S)-2-Amino-2-[8-(1-acetyl-piperidin-4-carbonyl)-8-aza-bicyclo[3.2.1]oct-3-yl]-exo-ethanoyl}-2-azabicyclo[3.1.0]hexane-3-carbonitrile trifluoroacetic acid salt (Compound No. 69)

mp: 130-131° C.
MS: m/z 428 (M+1)
$^1$HNMR (D$_2$O, 200 MHz): δ 0.85-1.0 (m, 1H), 1.1-1.25 (m, 1H), 1.38-2.08 (m, 10H), 2.09 (s, 3H), 2.32-2.47 (m, 1H), 2.56-3.0 (m, 4H), 3.02-3.3 (m, 1H), 3.7-3.8 (m, 1H), 3.9-4.02 (m, 1H), 4.28-4.9 (m, 8H), 5.15 (d, J=10.3 Hz, 1H),
[α]$_D^{20}$ −10.664 (c 0.50, water)
Yield: 100%

(1S,3S,5S)-2-{(2S)-2-Amino-2-(8-cyclohexyl-8-aza-bicyclo[3.2.1]oct-3-yl)-exo-ethanoyl}-2-azabicyclo[3.1.0]hexane-3-carbonitrile trifluoroacetic acid salt (Compound No. 60)

mp: 162-164° C.
MS: m/z 357 (M+1)

¹HNMR (D₂O, 400 MHz): δ 0.88-0.95 (m, 1H), 1.2-1.4 (m, 6H), 1.58-2.25 (m, 14H), 2.37-2.45 (m, 1H), 2.61-2.8 (m, 2H), 2.85-2.95 (m, 0.5H), 3.35-3.45 (m, 0.5H), 3.75-3.83 (m, 1H), 4.20-4.26 (m, 1H), 4.35-4.4 (m, 1H), 4.52 (d, J=7.6 Hz, 0.5H), 4.66 (d, J=6.4 Hz, 0.5H), 5.13-5.21 (m, 1H)

$[\alpha]_D^{20}$ −7.6 (c 0.50, water)

Yield: 81%

(1S,3S,5S)-2-{(2S)-2-Amino-2-[8-(adamantan-1-yl methyl)-8-aza-bicyclo[3.2.1]oct-3-yl]-exo-ethanoyl}-2-azabicyclo[3.1.0]hexane-3-carbonitrile trifluoroacetic acid salt (Compound No. 49)

MS: m/z 423 (M+1)

¹HNMR (D₂O, 400 MHz): δ 0.91-0.97 (m, 1H), 1.15-1.25 (m, 1H), 1.6-1.88 (m, 14H), 1.92-2.17 (m, 8H), 2.24-2.38 (m, 3H), 2.41 (dd, J=2.4, 14 Hz, 1H), 2.64-2.74 (m, 2H), 2.77 (s, 1H), 3.75-3.82 (m, 1H), 4.10-4.15 (m, 2H), 4.55 (d, J=6.8 Hz, 1H), 4.18 (dd, J=2.4, 10.8 Hz, 1H).

Example 9

(1S,3S,5S)-2-{(2S)-2-Amino-2-[8-(benzo[1,3]-dioxole-5-carbonyl)-8-aza-bicyclo[3.2.1]-oct-3-yl]-exo-ethanoyl}-2-azabicyclo[3.1.0]hexane-3-carboxylic acid hydrochloride (Compound No. 46)

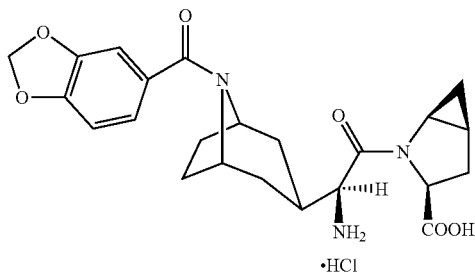

Concentrated HCl (10.0 ml) was added slowly to a round bottom flask containing (1S,3S,5S)-2-{(2S)-2-(tert-butoxycarbonyl)-amino-2-[8-(benzo[1,3]dioxole-5-carbonyl)-8-aza-bicyclo[3.2.1]oct-3-yl]-exo-ethanoyl}-2-azabicyclo [3.1.0]hexane-3-carbonitrile (prepared by following the similar procedure as described in step-2 of Example-8, 0.175 g, 0.33 mmol). The reaction mixture was brought to room temperature and stirred for 15 hours. The HCl was removed under reduced pressure and the residue was dried under high vacuum. The crude was stirred with dichloromethane (5 ml) and decanted. The solid so obtained was dried under high vacuum to yield the title compound (0.153 g, 96%).

mp: 280° C. [d]

MS: m/z 441 (M+1)

¹HNMR (D₂O, 400 MHz): δ 0.9-1.06 (m, 2H), 1.56-2.1 (m, 10H), 2.65-2.75 (m, 1H), 2.8-2.98 (m, 1H), 3.6-3.65 (m, 1H), 4.22-4.28 (m, 1H), 4.49 (dd, J=4.8, 20.8 Hz, 1H), 4.7-4.8 (m, 3H), 6.0 (s, 2H), 6.92 (dd, J=1.2, 8.0 Hz, 1H), 6.97-7.01 (m, 2H)

$[\alpha]_D^{20}$ 14.18 (c 0.50, water)

Example 10

(1S,3S,5S)-2-{(2S)-2-Amino-2-[8-(benzo-[1,3]dioxole-5-carbonyl)-8-aza-bicyclo[3.2.1]oct-3-yl]-exo-ethanoyl}-2-azabicyclo[3.1.0]-hexane-3-carboxamide trifluoro acetic acid salt (Compound No. 45)

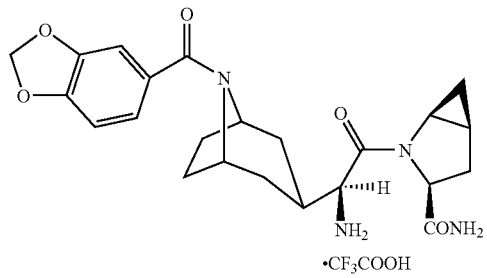

To a stirred solution of (1S,3S,5S)-2-{(2S)-2-(tert-butoxycarbonyl)-amino-2-[8-(benzo[1,3]dioxole-5-carbonyl)-8-aza-bicyclo[3.2.1]-oct-3-yl]-exo-ethanoyl}-2-azabicyclo [3.1.0]-hexane-3-carboxamide (prepared by following the similar procedure as described in step-1 of Example-8, 0.11 g, 0.2 mmol) in dichloromethane (2.0 ml) was added a solution of trifluoro acetic acid (1.0 ml, 1.54 g, 13.5 mmol) in dichloromethane (0.5 ml) drop wise at 0° C.

The reaction mixture was stirred at 0° C. for 5 minutes. Then it was brought to room temperature and stirred for 45 minutes. The solvent was evaporated under reduced pressure at room temperature and dried under high vacuum. In order to remove excess of trifluoro acetic acid, the crude product was stirred with diethyl ether (10.0 ml). The organic solvent was decanted and the solid product so obtained was stirred with 15% dichloromethane in diethyl ether (10 ml) at room temperature for 10 minutes The solvent was decanted and dried the solid under high vacuum to yield the title compound (0.095, 85%).

mp: 154-156° C.

MS: m/z 441 (M+1)

¹HNMR (D₂O, 400 MHz): δ 0.92-1.05 (m, 2H), 1.58-2.1 (m, 10H), 2.65-2.76 (m, 1H), 2.86-2.97 (m, 1H), 3.6-3.66 (m, 1H), 4.24-4.3 (m, 1H), 4.50 (dd, J=5.2, 21.2 Hz, 1H), 4.75-4.81 (m, 2H), 6.01 (s, 2H), 6.92-7.04 (m, 3H)

$[\alpha]_D^{20}$ 9.32 (c 0.50, water)

The following compound was prepared by procedure similar to those described for Compound No. 45 with appropriate variations of reactants, reaction conditions and quantities of reagents (2S)-1-{(2S)-2-amino-2-[8-(4-trifluoromethyl-benzoyl)-8-aza-bicyclo[3.2.1]-oct-3-yl]-exo-ethanoyl}-pyrrolidin-2-carboxamide trifluoroacetic acid salt (Compound No. 12)

mp: 156-158° C.

MS: m/z 453 (M+1)

¹HNMR (D₂O, 400 MHz): δ 1.55-1.66 (m, 2H), 1.68-2.12 (m, 9H), 2.28-2.38 (m, 1H), 2.5-2.63 (m, 1H), 3.55-3.66 (m, 1H), 3.73-3.82 (m, 1H), 4.05-4.12 (m, 1H), 4.2-4.27 (m, 1H), 4.4-4.47 (m, 1H), 4.7-4.9 (m, 1H), 7.80 (d, J=8.0 Hz, 2H), 7.77-7.82 (m, 2H)

$[\alpha]_D^{20}$ −12.10 (c 0.50, water)

Example 11

(2S,5R)-1-{(2S)-2-Amino-2-[8-(4-trifluoromethyl-benzoyl)-8-aza-bicyclo[3.2.1]oct-3-yl]-exo-ethanoyl}-5-ethynyl-pyrrolidin-2-carbonitrile trifluoro acetic acid salt (Compound No. 63)

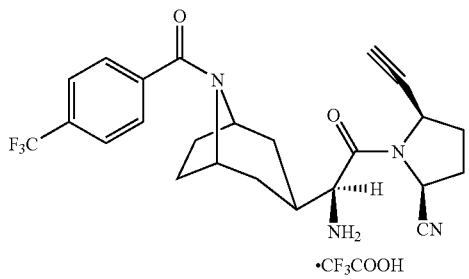

Step 1: Methyl-(2S,5R)-1-{(2S)-2-(tert-butoxy carbonyl)-amino-2-[8-(4-trifluoromethyl-benzoyl)-8-aza-bicyclo[3.2.1]-oct-3-yl]-exo-ethanoyl}-5-trimethyl silyl-ethynyl-pyrrolidin-2-carboxylate

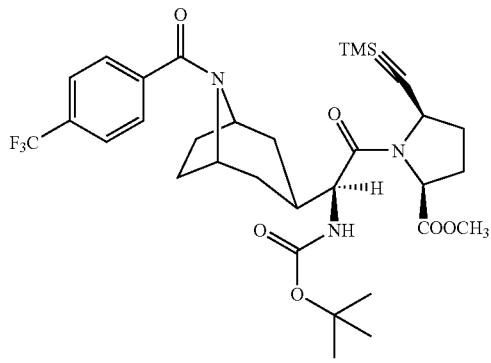

To a stirred solution of (2S)-2-(tert-butoxycarbonyl)-amino-2-[8-(4-trifluoromethyl benzoyl)-8-aza-bicyclo[3.2.1]-oct-3-yl]exo-ethanoic acid (prepared by following the similar procedure described in Intermediate 2, 2.0 g, 4.39 mmol) in dry DMF (20 ml) was added 1-hydroxybenzotriazole (1.77 g, 11.6 mmol) and methyl-(2S,5R)-5-(trimethyl silyl-ethynyl)pyrrolidine-2-carboxylate (which can be prepared by the procedure provided in J. Med. Chem. 49, 6416-6420 (2006), US 2006/0035954, US 2002/0019411, Synthesis, 1975, 391; 1.0 g, 4.82 mmol) at room temperature. The reaction mixture was cooled to 0° C. and added 1-(3-dimethyl amino propyl)-3-ethyl carbodiimide hydrochloride (1.85 g, 9.64 mmol) followed by tri ethyl amine (1.85 ml, 1.33 g, 13.16 mmol). The reaction mixture was stirred at 0° C. for 5 minutes and then at room temperature for 18 hours. The solvent was evaporated under reduced pressure at 35° C. To this residue was added water (30 ml) and extracted with ethyl acetate (3×100 ml). The combined organic layer was washed with 2% sodium bicarbonate solution in water (2×25 ml), water (100 ml) and dried over anhydrous $Na_2SO_4$. The solvent was evaporated under reduced pressure to get the crude product which was purified by column chromatography over silica gel (200-400 mesh) using ethyl acetate: $NH_3$ in chloroform:hexane in the ratio of 30:8:62 as an eluent to yield the title compound (1.6 g, 55%).

MS: m/z 664 (M+1)

$^1$HNMR ($CDCl_3+D_2O$, 400 MHz): δ 0.05-0.2 (m, 9H), 1.23-1.27 (m, 1H), 1.4-1.48 (m, 9H), 1.5-2.28 (m, 10H), 2.3-2.42 (m, 1H), 2.47-2.72 (m, 1H), 3.72 (s, 3H), 3.97-4.07 (m, 1H), 4.36-4.53 (m, 2H), 4.85-4.97 (m, 1H), 5.02-5.15 (m, 1H), 7.52-7.7 (m, 4H)

Step 2: (2S,5R)-1-{(2S)-2-(tert-Butoxycarbonyl)-amino-2-[8-(4-trifluoromethyl-benzoyl)-8-aza-bicyclo[3.2.1]oct-3-yl]-exo-ethanoyl}-5-ethynyl-pyrrolidin-2-carboxamide

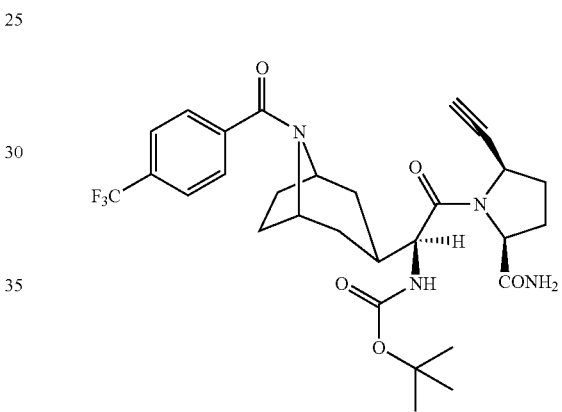

To a stirred solution of methyl-(2S,5R)-1-{(2S)-2-(tert-butoxy carbonyl)-amino-2-[8-(4-trifluoromethyl-benzoyl)-8-aza-bicyclo[3.2.1]-oct-3-yl]-exo-ethanoyl}-5-trimethyl silyl-ethynyl-pyrrolidin-2-carboxylate (1.5 g, 2.25 mmol) in methanol (10 ml) was added mixture of sodium methoxide (1.22 g, 22.62 mmol) and formamide (2.87 ml, 3.25 g, 72.32 mmol) drop wise at room temperature. After the addition was completed, reaction mixture was stirred for 4 hours. The reaction mixture was quenched at room temperature with a saturated aqueous ammonium chloride solution (15 ml) and the solvent was removed under reduced pressure. To this residue was added water (30 ml) and extracted with ethyl acetate (4×100 ml). The combined organic layers were washed with water (2×100 ml), brine (200 ml) and dried over anhydrous $Na_2SO_4$. The organic solvent was evaporated to get a crude product which was purified by column chromatography over silica gel (200-400 mesh) using methanol:$NH_3$ in chloroform:dichloromethane in the ratio of 0.2:10:89.8 as an eluent to yield the title compound (0.97 g, 75%).

MS: m/z 577 (M+1)

$^1$HNMR ($CDCl_3$, 200 MHz): δ 1.42 (s, 9H), 1.48-1.8 (m, 6H), 1.88-2.08 (m, 2H), 2.1-2.7 (m, 6H), 3.95-4.1 (m, 1H), 4.32-4.6 (m, 2H), 4.78-4.93 (m, 1H), 5-5.23 (m, 2H), 5.4-5.52 (m, 1H), 6.25-6.4 (m, 1H) 7.5-7.72 (m, 4H).

Step 3: (2S,5R)-1-{(2S)-2-(tert-Butoxycarbonyl)-amino-2-[8-(4-trifluoromethyl benzoyl)-8-aza-bicyclo[3.2.1]-oct-3-yl]-exo-ethanoyl}-5-ethynyl-pyrrolidin-2-carbonitrile

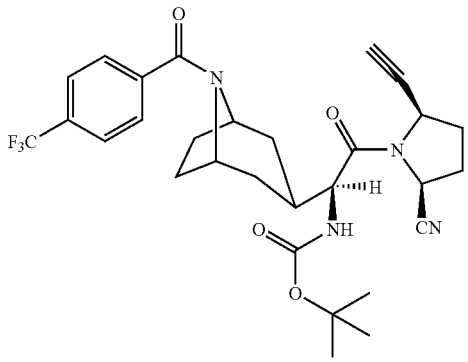

To a stirred solution of (2S,5R)-1-{(2S)-2-(tert-Butoxycarbonyl)-amino-2-[8-(4-trifluoromethyl-benzoyl)-8-aza-bicyclo[3.2.1]oct-3-yl]-exo-ethanoyl}-5-ethynyl-pyrrolidin-2-carboxamide (0.5 g, 0.86 mmol) and imidazole (0.059 g, 0.86 mmol) in dry pyridine (7.5 ml) was added phosphorous oxy chloride (0.16 ml, 0.266 g, 1.73 mmol) drop wise at −35° C. under nitrogen atmosphere. The reaction mixture was then stirred at −20° C. to −10° C. for 1.5 hours. The completion of reaction was monitored by TLC. After completion, the reaction mixture was quenched with water (1 ml) at −40° C. and then it was allowed to come at room temperature. The solvent was removed under reduced pressure. The crude product was taken in water (20 ml) and extracted with dichloromethane (3×50 ml). The combined organic layers were dried over anhydrous Na$_2$SO$_4$, filtered and concentrated at reduced pressure to yield a crude product; which was purified by column chromatography over silica gel (200-400 mesh) using ethyl acetate: NH$_3$ in chloroform:hexane in the ratio of 25:5:70 as an eluant to obtain the title compound (0.35 g, 72%).

MS: m/z 559 (M+1)

$^1$HNMR (CDCl$_3$, 400 MHz): δ 1.41 (s, 9H), 1.43-1.85 (m, 6H), 1.9-2.1 (m, 3H), 2.15-2.36 (m, 2H), 2.4-2.57 (m, 3H), 4.0-4.07 (m, 1H), 4.26-4.42 (m, 1H), 4.66 (t, J=8 Hz, 1H) 4.84-4.93 (m, 1H), 5.0-5.08 (m, 1H), 5.13-5.24 (m, 1H), 7.53-7.62 (m, 2H), 7.64-7.72 (m, 2H).

Step 4: (2S,5R)-1-{(2S)-2-Amino-2-[8-(4-trifluoromethyl-benzoyl)-8-aza-bicyclo[3.2.1]oct-3-yl]-exo-ethanoyl}-5-ethynyl-pyrrolidin-2-carbonitrile trifluoro acetic acid salt

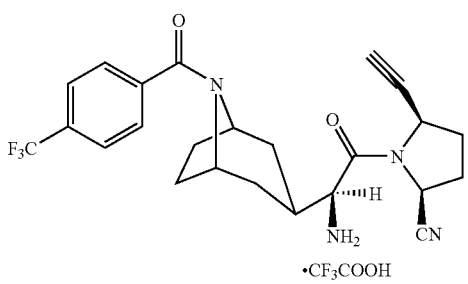

To a stirred solution of (2S,5R)-1-{(2S)-2-(tert-butoxycarbonyl)-amino-2-[8-(4-trifluoromethyl benzoyl)-8-aza-bicyclo[3.2.1]-oct-3-yl]-exo-ethanoyl}-5-ethynyl-pyrrolidin-2-carbonitrile (0.32 g, 0.573 mmol) in dry dichloromethane (5 ml) was added a solution trifluoroacetic acid (3.36 ml, 5.15 g, 45.2 mmol) in dry dichloromethane (5 ml) at 0° C. After the addition was completed, reaction mixture was stirred at room temperature for 40 minutes. The solvent was evaporated under reduced pressure at 30° C. and added dichloromethane (10 ml) The solvent was again evaporated and dried under high vacuum. In order to solidify the product, petroleum ether (10 ml) was added and evaporated. The solid product was then washed with mixture of 50% diethyl ether and 50% hexane (4×10 ml) and dried under high vacuum for four hours to yield the title compound (0.300 g, 91%).

mp: 160-163° C.

MS: m/z 459 (M+1)

$^1$HNMR (D$_2$O, 400 MHz): δ 1.5-2.12 (m, 8H), 2.15-2.35 (m, 2H), 2.5-2.63 (m, 2H), 2.83-3.04 (m, 1H), 3.08 (d, J=1.6 Hz, 0.5H), 3.13 (d, J=2.0 Hz, 0.5H), 4.08-4.14 (m, 1H), 4.39 (d, J=5.6 Hz, 0.5H), 4.46 (d, J=5.2 Hz, 0.5H), 4.77-4.84 (m, 2H), 5.0-5.06 (m, 1H), 7.62 (d, J=8 Hz, 2H), 7.81 (d, J=8.0 Hz, 2H)

[α]$_D^{20}$ −9.61 (c 1.09, Methanol)

The following compounds were prepared by procedure similar to those described for Compound No. 63 with appropriate variations of reactants, reaction conditions and quantities of reagents (2S,5R)-1-{(2S)-2-Amino-2-[8-(pyridin-4-carbonyl)-8-aza-bicyclo[3.2.1]oct-3-yl]-exo-ethanoyl}-5-ethynyl-pyrrolidin-2-carbonitrile di trifluoro acetic acid salt (Compound No. 64)

mp: 175-177° C.

MS: m/z 392 (M+1)

$^1$HNMR (D$_2$O, 400 MHz): δ 1.53-1.98 (m, 6H), 2.10-2.37 (m, 4H), 2.56-2.60 (m, 2H), 2.88-3.08 (m, 1H), 3.13-3.16 (m, 1H), 4.07-4.15 (m, 1H), 4.4-4.5 (m, 1H), 4.70-4.85 (m, 2H), 5.0-5.1 (m, 1H) 7.7-7.85 (m, 2H), 8.7-8.9 (m, 2H)

[α]$_D^{20}$ −8.38 (c 1.0, Methanol)

(2S,5R)-1-{(2S)-2-Amino-2-[8-(3-fluoropyridin-4-carbonyl)-8-aza-bicyclo[3.2.1]oct-3-yl]-exo-ethanoyl}-5-ethynyl-pyrrolidin-2-carbonitrile trifluoroacetic acid salt (Compound No. 65)

mp: 166-168° C.

MS: m/z 410 (M+1)

$^1$HNMR (D$_2$O, 400 MHz): δ 1.56-2.04 (m, 6H), 2.05-2.37 (m, 4H), 2.53-2.67 (m, 2H), 2.86-3.03 (m, 1H), 3.12-3.18 (dd, J=18.8 Hz, 2.0 Hz, 1H), 4.03-4.08 (m, 1H), 4.41-4.49 (dd, J=18.8 Hz, 5.64 Hz, 1H), 4.82-4.89 (m, 2H), 5.03-5.08 (m, 1H), 7.58-7.64 (m, 1H), 8.54 (d, J=5.2 Hz, 1H), 8.66 (s, 1H)

[α]$_D^{20}$ −2.35 (c 1.0, Methanol)

Yield: 80%

Example 12

(2S,5R)-1-{(2S)-2-Amino-2-[8-(2-fluoropyridin-4-carbonyl)-8-aza-bicyclo[3.2.1]-oct-3-yl]-exo-ethanoyl}-5-ethynyl-pyrrolidin-2-carbonitrile trifluoro acetic acid salt (Compound No. 66)

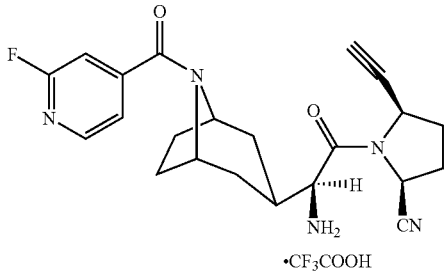

·CF₃COOH

Step 1: (2S,5R)-1-{(2S)-2-(tert-Butoxycarbonyl)-amino-2-[8-(2-fluoropyridin-4-carbonyl)-8-aza-bicyclo[3.2.1]-oct-3-yl]-exo-ethanoyl}-5-ethynyl-pyrrolidin-2-carboxamide

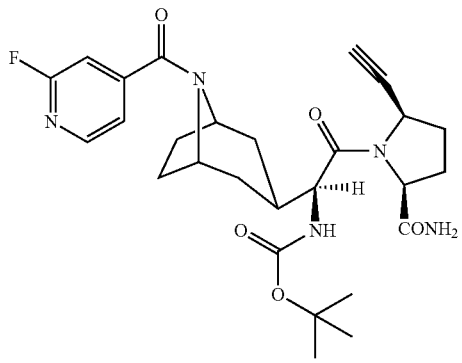

To a stirred solution of (2S)-2-(tert-butoxycarbonyl)-amino-2-[8-(2-fluoro pyridine-4-carbonyl)-8-aza-bicyclo [3.2.1]-oct-3-yl]-exo-ethanoic acid (Intermediate 2, 0.9 g, 2.21 mmol) in DMF (15 ml) was added 1-hydroxybenzotriazole (0.896 g, 6.63 mmol) and trifluoroacetic acid salt of (5R)-5-ethynyl-2-prolinamide (J. Med. chem. 49, 6416-6420 (2006), US 2002/0019411, Synthesis 391 (1975), 0.61 g, 2.42 mmol) at room temperature. The reaction mixture was cooled to 0° C., added 1-(3-dimethyl amino propyl)-3-ethyl carbodimide hydrochloride (0.847 g, 4.42 mmol) and triethyl amine (0.92 ml, 0.67 g, 6.63 mmol). The ice bath was removed and the reaction mixture was made clear by adding water (1 ml). The reaction mixture was stirred at room temperature for 12 hours. The solvent was evaporated under reduced pressure. The residue was taken in water (30 ml) and extracted with ethyl acetate (3×100 ml). The combined organic layers were washed with 5% NaHCO₃ solution (2×25 ml) and dried over anhydrous Na₂SO₄. The solvent was evaporated under reduced pressure to obtain the crude product; which was purified by column chromatography over silica gel (200-400 mesh) using methanol: NH₃ in chloroform: dichloromethane in the ratio of 1.5:3:95.5 as an eluent to yield the title compound (0.640 g, 55%).

MS: m/z 528 (M+1)

¹HNMR (CDCl₃, 400 MHz): δ 1.42 (s, 9H), 1.5-1.82 (m, 6H), 1.85-2.1 (m, 2H), 2.12-2.3 (m, 3H), 2.4-2.68 (m, 3H), 3.9-4.02 (m, 1H), 4.4-4.53 (m, 2H), 4.8-4.9 (m, 1H), 5.0-5.17 (m, 2H), 5.37-5.45 (m, 1H), 6.2-6.33 (m, 1H), 6.94-7.0 (m, 1H), 7.18-7.26 (m, 1H), 8.25-8.32 (m, 1H).

Step 2: (2S,5R)-1-{(2S)-2-(tert-Butoxycarbonyl)-amino-2-[8-(2-fluoropyridine-4-carbonyl)-8-aza-bicyclo[3.2.1]-oct-3-yl]exo-ethanoyl}-5-ethynyl-pyrrolidin-2-carbonitrile

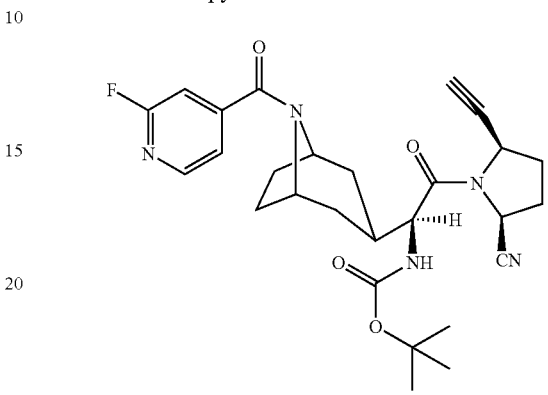

To the stirred solution of (2S,5R)-1-{(2S)-2-(tert-butoxycarbonyl)-amino-2-[8-(2-fluoropyridin-4-carbonyl)-8-aza-bicyclo[3.2.1]-oct-3-yl]-exo-ethanoyl}-5-ethynyl-pyrrolidin-2-carboxamide (0.62 g, 1.17 mmol) and imidazole (0.08 g, 1.17 mmol) in dry pyridine (9.3 ml) was added phosphorous oxy chloride (0.22 ml, 0.36 g, 2.35 mmol) drop wise at −35° C. under nitrogen atmosphere. The reaction mixture was then stirred at −20° C. to −10° C. for 1.5 hours. The completion of reaction was monitored by TLC. After completion, the reaction mixture was quenched with water (1 ml) at −40° C. and then it was allowed to come at room temperature. The solvent was removed under reduced pressure. The crude product was taken in water (20 ml) and extracted with dichloromethane (3×50 ml). The combined organic layer was dried over anhydrous Na₂SO₄. The organic solvent was evaporated to yield a crude product, which was purified by column chromatography over silica gel (200-400 mesh) using ethyl acetate: NH₃ in chloroform:hexane in the ratio of 45:05:50 as an eluent to yield the title compound (0.52 g, 86%).

MS: m/z 510 (M+1)

¹HNMR (CDCl₃, 400 MHz): δ 1.41 (s, 9H), 1.54-1.87 (m, 6H), 1.9-2.07 (m, 3H), 2.13-2.38 (m, 2H), 2.4-2.6 (m, 3H), 3.95-4.04 (m, 1H), 4.27-4.41 (m, 1H), 4.66 (t, J=8 Hz, 1H) 4.8-4.9 (m, 1H), 5.01-5.1 (m, 1H), 5.13-5.24 (m, 1H), 6.94-7.0 (m, 1H), 7.19-7.25 (m, 1H), 8.30 (t, J=5.6 Hz, 1H).

Step 3: (2S,5R)-1-{(2S)-2-Amino-2-[8-(2-fluoropyridin-4-carbonyl)-8-aza-bicyclo[3.2.1]oct-3-yl]-exo-ethanoyl}-5-ethynyl-pyrrolidin-2-carbonitrile trifluoro acetic acid salt

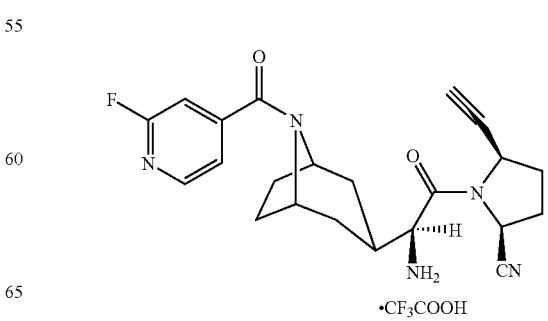

·CF₃COOH

To a stirred solution of (2S,5R)-1-{(2S)-2-(tett-butoxycarbonyl)-amino-2-[8-(2-fluoropyridine-4-carbonyl)-8-aza-bicyclo[3.2.1]-oct-3-yl]exo-ethanoyl}-5-ethynyl-pyrrolidin-2-carbonitrile (0.5 g, 0.98 mmol) in dichloromethane (10 ml) was added a solution of trifluoroacetic acid (5.25 ml, 8.06 g, 70.7 mmol) in dry dichloromethane (10.0 ml) at 0° C. After the addition was completed, the reaction mixture was stirred at room temperature for 1 hour. The solvent was evaporated under reduced pressure and added dichloromethane (10 ml). This process is repeated twice and residue was dried under high vacuum. In order to solidify the product, petroleum ether (10 ml) was added and evaporated. The solid product was then washed with diethyl ether (2×10 ml) and added dry dichloromethane (10 ml). It was again evaporated under reduced pressure and dried under high vacuum to yield the title compound (0.39 g, 76%)

mp: 199-200° C.

MS: m/z 410 (M+1)

$^1$HNMR (D$_2$O, 400 MHz): δ 1.5-1.96 (m, 6H), 2.0-2.1 (m, 2H), 2.12-2.32 (m, 2H), 2.49-2.62 (m, 2H), 2.82-3.04 (m, 1H), 3.09-3.14 (m, 1H), 4.07-4.13 (m, 1H), 4.37-4.48 (m, 1H), 4.76-4.85 (m, 2H), 5.0-5.05 (m, 1H), 7.18 (s, 1H), 7.38 (d, J=5.2 Hz, 1H), 8.30 (d, J=5.2 Hz, 1H)

$[α]_D^{20}$ −6.95 (c 0.50, Methanol)

The following compound was prepared by procedure similar to those described for Compound No. 66 with appropriate variations of reactants, reaction conditions and quantities of reagents (2S,5R)-1-{(2S)-2-Amino-2-[8-(benzo[1,3]dioxole-5-carbonyl)-8-aza-bicyclo[3.2.1]oct-3-yl]-exo-ethanoyl}-5-ethynyl-pyrrolidin-2-carbonitrile trifluoroacetic acid salt (Compound No. 67)

Yield: 87%
mp: 201-202° C.
MS: m/z 435 (M+1)

$^1$HNMR (D$_2$O, 400 MHz): δ 1.49-1.95 (m, 6H), 1.97-2.10 (m, 2H), 2.12-2.33 (m, 2H), 2.49-2.63 (m, 2H), 2.8-3.03 (m, 1H), 3.05-3.15 (m, 1H), 4.22-4.28 (m, 1H), 4.34-4.36 (m, 0.5H), 4.42-4.45 (m, 0.5H), 4.70-4.80 (m, 2H), 5.0-5.05 (m, 1H), 6.0 (s, 2H), 6.9-7.02 (m, 3H)

$[α]_D^{20}$ −7.66 (c 0.50, Methanol)

Example 13

{(2S)-2-Amino-2-[8-(3-fluoropyridine-4-carbonyl)-8-aza-bicyclo[3.2.1]-oct-3-yl]-exo-ethanoyl}-3-fluoroazetidine trifluoroacetic acid salt (Compound No. 62)

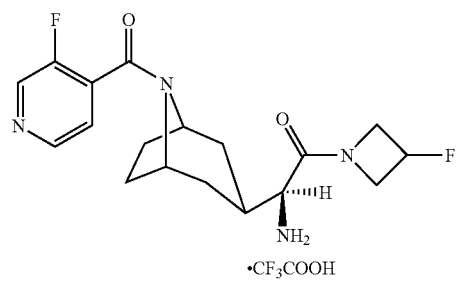

•CF$_3$COOH

Step 1: {(2S)-2-(tert-Butoxycarbonyl)-amino-2-[8-(3-fluoropyridine-4-carbonyl)-8-aza-bicyclo[3.2.1]-oct-3-yl]-exo-ethanoyl}-3-fluoroazetidine

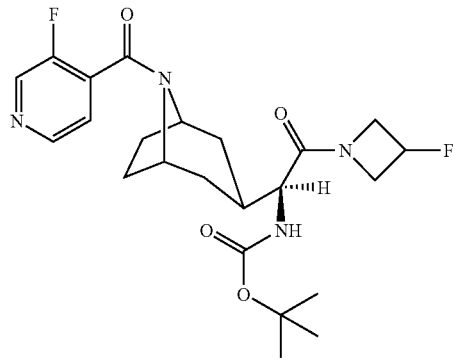

To a stirred solution of (2S)-2-(tert-butoxycarbonyl) amino-2-[8-(3-fluoropyridine -4-carbonyl)-8-aza-bicyclo [3.2.1]-oct-3-yl]-exo ethanoic acid (prepared by following the similar procedure described in Intermediate 2, 0.5 g, 1.22 mmol) in DMF (10 ml) was added 1-hydroxybenzotriazole (0.49 g, 3.68 mmol) and 3-fluoroazetidine hydrochloride (which can be prepared by following the procedures described in J. Org. Chem, 32, 2972 (1967) and Biorganic Med. Chem. Lett., 14, 1265, (2004), 0.15 g, 1.35 mmol) at room temperature. The reaction mixture was cooled to 0° C., added triethyl amine (0.37 g, 0.51 ml, 3.68 mmol) and 1-(3-dimethyl amino propyl)-3-ethyl carbodimide hydrochloride (0.47 g, 2.46 mmol). Ice bath was removed, added water (0.5 ml) and stirred at room temperature for 16 hours. The solvent was removed under reduced pressure, added water (20 ml) and extracted with ethyl acetate (3×100 ml). The combined organic layers were washed with 5% aqueous NaHCO$_3$ solution (2×25 ml) and dried over anhydrous Na$_2$SO$_4$. The solvent was evaporated to get a crude product, which was purified by column chromatography over silica gel (200-400 mesh) using ethyl acetate: ammonia in chloroform: hexane in ratio of 75:5:20 as an eluent to yield the title compound (0.3 g, 53%)

MS: m/z 465 (M+1)

$^1$HNMR (CDCl$_3$, 400 MHz): δ 1.35-1.47 (m, 9H), 1.48-1.8 (m, 6H), 1.93-2.08 (m, 2H), 2.13-2.3 (m, 1H), 3.7-3.83 (m, 1H), 3.85 -4.58 (m, 4H), 4.6-4.7 (m, 1H), 4.8-4.9 (m, 1H), 4.93-5.1 (m, 1H), 5.2-5.4 (m, 1H), 7.3-7.4 (m, 1H), 8.46-8.56 (m, 2H).

Step: 2 {(2S)-2-Amino-2-[8-(3-fluoropyridine-4-carbonyl)-8-aza-bicyclo[3.2.1]-oct-3-yl]-exo-ethanoyl}-3-fluoroazetidine trifluoroacetic acid salt

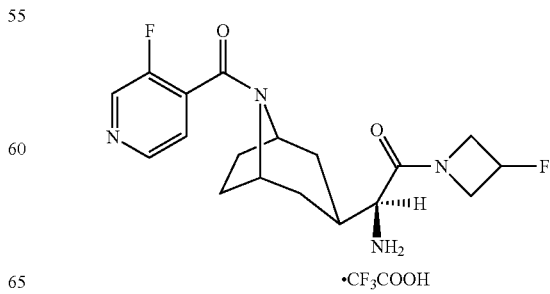

•CF$_3$COOH

To a stirred solution of {(2S)-2(tert-butoxycarbonyl)-amino-2-[8-(3-fluoropyridine-4-carbonyl)-8-aza-bicyclo[3.2.1]-oct-3-yl]-exo-ethanoyl}-3-fluoro-azetidine (0.22 g, 0.474 mmol) in dichloromethane (5 ml) was added a solution of trifluoroacetic acid (2.3 ml, 3.53 g, 30.9 mmol) in dry dichloromethane (5.0 ml) drop wise at 0° C. After the addition was completed, the ice bath was removed and the reaction mixture was stirred at room temperature for 1.5 hours. The solvent was evaporated under reduced pressure at room temperature and dried under high vacuum. In order to solidify the product, petroleum ether (10 ml) was added and evaporated to get a solid, which was washed with diethyl ether (2×10 ml) and dried under high vacuum to yield the title compound (0.24 g, 86%).

mp: 90-93° C.
MS: m/z 365 (M+1)
$^1$HNMR (D$_2$O, 400 MHz): δ 1.4-1.9 (m, 6H), 1.96-2.01 (m, 2H), 2.4-2.54 (m, 1H), 3.86-4.0 (m, 2H), 4.03-4.7 (m, 4H), 4.73-4.86 (m, 1H), 5.25-5.5 (m, 1H), 7.7-7.8 (m, 1H), 8.56-8.65 (m, 1H), 8.71-8.8 (m, 1H)

Example 14

Benzyl-(2S,5R)-1-{(2S)-2-amino-2-[8-(4-trifluoromethyl-benzoyl)-8-aza-bicyclo[3.2.1]-oct-3-yl]-exo-ethanoyl}-5-cyano pyrrolidin-2-carboxylate trifluoroacetic acid salt (Compound No. 18)

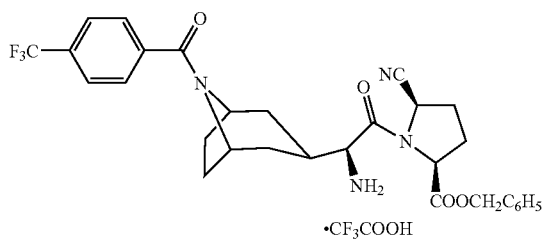

Step: 1 Benzyl-(2S,5R)-1-{(2S)-2-(tert-butoxy carbonyl)-amino-2-[8-(4-trifluoro methyl-benzoyl)-8-aza-bicyclo[3.2.1]oct-3-yl]-exo-ethanoyl}-5-cyano-pyrrolidin-2-carboxylate

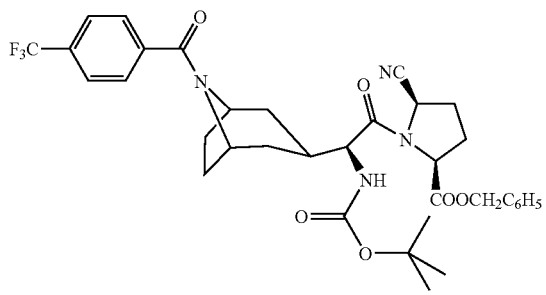

To a stirred solution of (2S)-2-(tert-butoxy carbonyl)-amino-2-[8-(4-trifluoro methyl-benzoyl)-8-aza-bicyclo[3.2.1]oct-3-yl]-exo-ethanoic acid (prepared by following the similar procedure described in Intermediate 2, 3.0 g, 6.6 mmol) in dichloromethane (90 ml) was added triethyl amine (1.4 ml, 1.0 g, 9.9 mmol) and the reaction mixture was cooled to −5° C. To this reaction mixture was added isobutyl chloro formate (0.95 ml, 0.992 g, 7.26 mmol) slowly under nitrogen atmosphere and stirred at −5° C. for 2.5 hours. More isobutyl chloro formate (0.175 ml, 0.18 g, 1.3 mmol) was added and the reaction mixture was brought to 0° C. and stirred for 1.0 hour. After 1 hour, benzyl (2S,5R)-5-cyanopyrrolidine-2-carboxylate (prepared by following the procedures described in Tetrahedron lett, 43, 3499-3501 (2002), Tetrahedron, 57, 6439-6446, (2001), J. Chem. Soc. Perkin Trans 1, 507-514, (1996), 1.51 g, 6.6 mmol) was added to the reaction mixture at 0° C. After the addition was completed, the reaction mixture was brought to room temperature and stirred for 15 hour's. The progress of the reaction was monitored by TLC. The reaction mixture was quenched with water (20 ml) and extracted with dichloromethane (3×250 ml). The combined organic layer was washed with 5% NaHCO$_3$ solution (5×200 ml) and dried over anhydrous sodium sulphate. The solvent was evaporated to obtain a crude product, which was purified by column chromatography over silica gel (100-200 mesh) using 50% ethyl acetate in hexane as an eluent to obtain the title compound (1.2 g, 28%).

MS: m/z 669 (M+1)
$^1$HNMR (CDCl$_3$+D$_2$O, 200 MHz): δ 1.3-2.01 (m, 15H), 2.05-2.55 (m, 7H), 3.55-3.70 (m, 1H), 4.03-4.20 (m, 1H), 4.48-4.61 (m, 1H), 4.62-4.88 (m, 1H), 5.0-5.32 (m, 2H), 5.48-5.58 (m, 1H), 7.1-7.4 (m, 5H), 7.5-7.71 (m, 4H)

Step 2: Benzyl-(2S,5R)-1-{(2S)-2-amino-2-[8-(4-trifluoromethyl-benzoyl)-8-aza-bicyclo[3.2.1]-oct-3-yl]-exo-ethanoyl}-5-cyano pyrrolidin-2-carboxylate trifluoroacetic acid salt

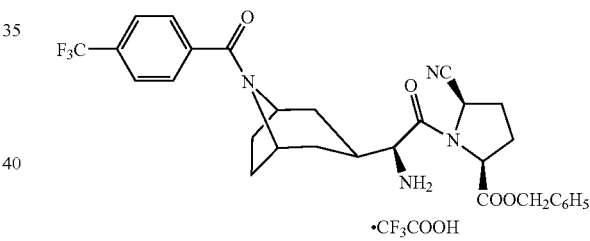

To a stirred solution of benzyl-(2S,5R)-1-{(2S)-2-(tert-butoxy carbonyl)-amino-2-[8-(4-trifluoro methyl-benzoyl)-8-aza-bicyclo[3.2.1]oct-3-yl]-exo-ethanoyl}-5-cyano-pyrrolidin-2-carboxylate (0.2 g, 0.3 mmol) in dry dichloromethane (5.0 ml) was added a solution of trifluoroacetic acid (1.37 ml, 2.1 g, 18.4 mmol) in dichloromethane (5.0 ml) at 0° C. under nitrogen atmosphere. After the addition, the ice bath was removed and the reaction mixture was monitored by TLC. After 1.0 hour, the reaction mixture was diluted with dichloromethane (10 ml) and evaporated to dryness under reduced pressure at room temperature. To remove traces of trifluoroacetic acid, the residue was taken with dichloromethane (25 ml) and evaporated. The solid so obtained was then washed with a 50% solution of diethyl ether in hexane (3×25 ml) and dried under high vacuum to obtain the title compound (0.18 g, 88%)

MS: m/z 569 (M+1)
$^1$HNMR (D$_2$O, 400 MHz): δ 0.9-1.09 (m, 1H), 1.15-1.43 (m, 2H), 1.5-1.93 (m, 5H), 2.1-2.22 (m, 1H), 2.26-2.50 (m, 2H), 2.55-2.84 (m, 2H), 4.03-4.11 (m, 1H), 4.45-4.70 (m, 2H), 4.86-5.12 (m, 3H), 5.28-5.36 (m, 1H), 6.7-7.01 (m, 3H), 7.06-7.3 (m, 2H), 7.36-7.52 (m, 2H), 7.6-7.8 (m, 2H)
$[α]_D^{20}$ −2.94 (c 0.80, Methanol)

Example 15

(2S)-1-{(2S)-2-Amino-2-[8-aza-bicyclo[3.2.1]oct-3-yl]-exo-ethanoyl}-pyrrolidin-2-carbonitrile trifluoro acetic acid salt (Compound No. 8)

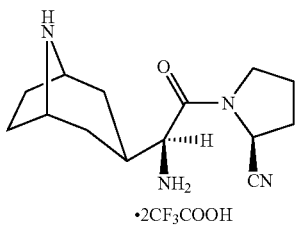

Step 1: (2S)-1-{(2S)-2-(tert-butoxy carbonyl)-amino-2-[8-(tert-butoxy carbonyl)-8-aza-bicyclo[3.2.1]oct-3-yl]-exo-ethanoyl}-pyrrolidin-2-carboxamide

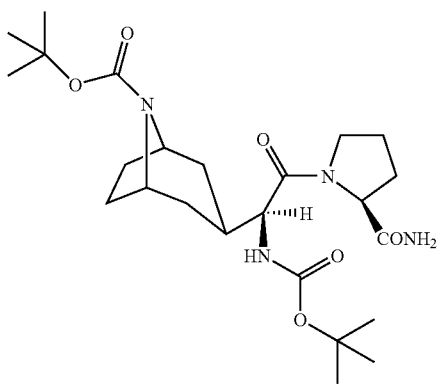

To a stirred solution of (2S)-2-(tert-butoxy carbonyl)-amino-2-{8-(tert-butoxy carbonyl)-8-aza-bicyclo[3.2.1]oct-3-yl}-exo-ethanoic acid (Intermediate 12, 0.88 g, 2.29 mmol) in dry DMF was added 1-hydroxy benzotriazole (0.92 g, 6.87 mmol) and L-prolinamide (0.26 g, 2.29 mmol) at room temperature. The reaction mixture was cooled to 0° C. and added triethyl amine (0.69 g, 0.96 ml, 6.87 mmol) and 1-(3-dimethyl amino propyl)-3-ethyl carbodimide hydrochloride (0.87 g, 4.58 mmol). Ice bath was removed after 2 hours and the reaction mixture was stirred at room temperature for 16 hours. The solvent was removed under reduced pressure, added a saturated aqueous sodium bicarbonate solution (25 ml) and extracted with ethyl acetate (1×50 ml). The organic layer was dried over anhydrous Na$_2$SO$_4$ and the solvent was removed under reduced pressure to obtain a crude product which was purified by column chromatography over silica gel (200-400 mesh) using methanol:NH$_3$ in chloroform:dichloromethane in the ratio 1.8:5:93.2 as an eluent to yield the title compound (0.46 g, 42%).

MS: m/z 481 (M+1)

$^1$HNMR (CDCl$_3$, 400 MHz): δ 1.41 (s, 9H), 1.42-1.68 (m, 15H), 1.83-2.06 (m, 4H), 2.08-2.10 (m, 2H), 2.12-2.20 (m, 1H) 3.5-3.62 (m, 1H), 3.65-3.8 (m, 1H), 4.03-4.40 (m, 3H), 4.52-4.62 (m, 1H), 5.12-5.21 (m, 1H) 5.33-5.45 (m, 1H) 6.55-6.80 (brs, 1H)

Step 2: (2S)-1-{(2S)-2-(tert-butoxy carbonyl)-amino-2-[8-(tert-butoxy carbonyl)-8-aza-bicyclo[3.2.1]oct-3-yl]-exo-ethanoyl}-pyrrolidin-2-carbonitrile

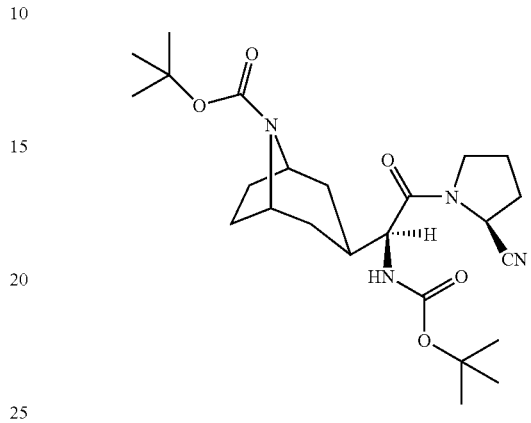

To a stirred solution of (2S)-1-{(2S)-2-(tert-butoxy carbonyl)-amino-2-[8-(tert-butoxy carbonyl)-8-aza-bicyclo[3.2.1]oct-3-yl]-exo-ethanoyl}-pyrrolidin-2-carboxamide (0.45 g, 0.94 mmol) and imidazole (0.134 g, 1.97 mmol) in dry pyridine (10 ml) at −30° C. was added phosphorous oxychloride (0.589 g, 0.33 ml, 3.84 mmol) drop wise. The reaction mixture was stirred at −30° C. for 1.5 hours and completion of reaction was monitored by TLC. The reaction mixture was quenched with water (0.5 ml) at −30° C. and then it was allowed to come at room temperature. The solvent was removed under reduced pressure at room temperature. The crude product was dried under high vacuum. To this was added dichloromethane (40 ml), washed with water (2×10 ml) and dried over anhydrous Na$_2$SO$_4$. The solvent was evaporated to obtain a crude product, which was purified by column chromatography over silica gel (100-200 mesh) using methanol in dichloromethane as an eluent to yield the title compound MS: m/z 461 (M−1)

$^1$HNMR (CDCl$_3$+D$_2$O, 400 MHz): δ 1.30-151 (m, 19H), 1.56-1.80 (m, 4H), 1.80-1.93 (m, 2H), 2.05-2.40 (m, 5H), 3.55-3.90 (m, 2H), 4.08-4.45 (m, 3H), 4.78 (s, 3H), 5.07 (d, J=9.2 Hz, 1H)

Step 3: (2S)-1-{(2S)-2-amino-2-[8-aza-bicyclo[3.2.1]oct-3-yl]-exo-ethanoyl}-pyrrolidin-2-carbonitrile trifluoro acetic acid salt

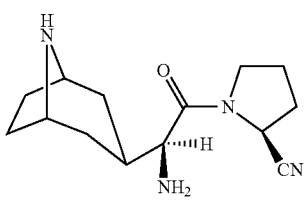

To a stirred solution of (2S)-1-{(2S)-2-(tert-butoxy carbonyl)-amino-2-[8-(tert-butoxy carbonyl)-8-aza-bicyclo[3.2.1]oct-3-yl]-exo-ethanoyl}-pyrrolidin-2-carbonitrile (0.34 g, 0.73 mmol) in dry dichloromethane (2.5 ml) at 0° C. was added a solution of trifluoroacetic acid (3.3 ml, 3.1 g, 27.19 mmol) in dry dichloromethane (2.5 ml) drop wise. The reaction mixture was stirred at 0° C. for 5 minutes. The reaction mixture was allowed to come at room temperature and stirred for 25 minutes. The solvent was evaporated under reduced pressure at 30° C. and to the residue was added dichloromethane (10 ml). The solvent was evaporated under reduced pressure and dried under high vacuum to remove trifluoroacetic acid. In order to remove trifluoroacetic acid left and to solidify the product, diethyl ether (20 ml) was added to this mass and the solid so obtained was stirred at room temperature for 15 minutes. The solvent was decanted and dried the solid under high vacuum to yield the title compound (0.34 g, 94%)

mp: 143-145° C.

MS: m/z 263 (M+1)

$^1$HNMR (D$_2$O, 400 MHz): δ 1.70-1.88 (m, 3H), 1.90-2.06 (m, 3H), 2.08-2.21 (m, 4H), 2.30-2.42 (m, 2H), 2.43-2.60 (m, 1H), 3.73 (t, J=6.8 Hz, 2H), 4.10-4.22 (m, 2H), 4.26 (d, J=7.6 Hz, 1H), 4.75-4.90 (m, 1H)

$[α]_D^{20}$ −39.11 (c 0.50, water)

Example 16

(2S)-1-{2-Amino-2-[9-(4-trifluoromethyl-benzoyl)-9-azabiacyclo[3.3.1]non-3-yl]-exo-ethanoyl}-pyrrolidin-2-carbonitrile trifluoro acetic acid' salt (Compound Nos. 70 A and 70 B)

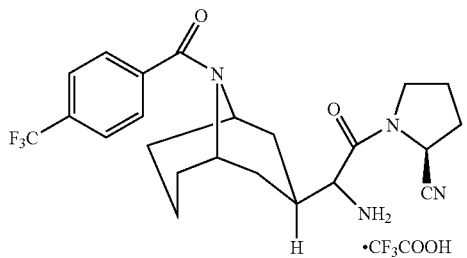

Step 1: (2S)-1-{2-(tert-Butoxycarbonyl)amino-2-[9-(4-trifluoromethyl-benzoyl)-9-azabiacyclo[3.3.1]non-3-yl]-exo-ethanoyl}-pyrrolidin-2-carboxamide

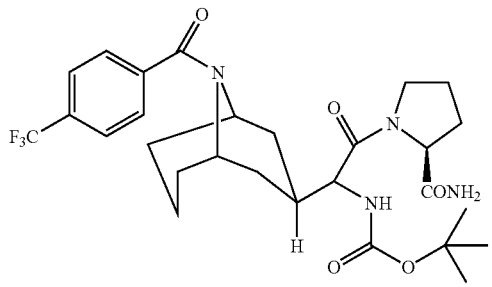

To a stirred solution of 2-(tert-butoxy carbonyl)amino-2-{9-(4-trifluoromethyl benzoyl)-9-azabicyclo[3.3.1]non-3-yl}-exo-ethanoic acid (Intermediate 13, 0.55 g, 1.17 mmol) in DMF (11 ml) at room temperature was added 1-hydroxy benzotriazole (0.537 g, 3.5 mmol) L-prolinamide (0.133 g, 1.17 mmol) and triethyl amine (0.354 g, 3.5 mmol). The reaction mixture was cooled to 0° C. and was added 1-(3-dimethyl amino propyl)-3-ethyl carbodimide hydrochloride (0.447 g, 2.34 mmol) portion wise. The reaction mixture was allowed to come at room temperature and stirred for 14 hours. The progress of reaction was monitored by TLC. After the completion of reaction, DMF was evaporated under reduced pressure and the residue was taken in ethyl acetate (100 ml). The organic layer was washed with a saturated sodium bicarbonate solution (10 ml) and aqueous layer was extracted with ethyl acetate (2×20 ml). The combined organic layers were dried with anhydrous sodium sulphate and the solvent was evaporated to obtain a crude product, which was purified by column chromatography over silica gel (200-400 mesh) using methanol:ammonia in chloroform:dichloromethane in the ratio of (1:10:89) as an eluent to yield polar diastereomer (0.25 g, 38%) and less polar diastereomer (0.17 g, 26%)

More polar diastereomer mp: 159-161° C.

MS: m/z 567 (M+1)

$^1$HNMR (CDCl$_3$+D$_2$O, 400 MHz): δ 1.36-1.58 (m, 10H), 1.59-1.88 (m, 7H), 1.9-2.2 (m, 5H), 2.22-2.34 (m, 1H), 2.70-2.81 (m, 1H), 3.54-3.57 (m, 1H), 3.73-3.84 (m, 2H), 4.20-4.27 (m, 1H), 4.50-4.55 (m, 1H), 4.87-4.95 (m, 1H), 7.46-7.54 (m, 2H), 7.64-7.70 (m, 2H)

Less polar diastereomer mp: 173-175° C.

MS: m/z 567 (M+1)

$^1$HNMR (CDCl$_3$+CD$_3$OD+D$_2$O, 400 MHz): δ 1.35-1.54 (m, 10H), 1.55-2.18 (m, 12H), 2.22-2.35 (m, 1H), 2.66-2.83 (m, 1H), 3.4-3.65 (m, 1H), 3.75-3.85 (m, 1H), 3.88-4.05 (m, 2H), 4.47-4.56 (m, 1H), 4.85-4.94 (m, 1H) 7.46-7.54 (m, 2H), 7.66 (d, J=8 Hz, 2H)

Step 2: (2S)-1-{2-(tert-Butoxycarbonyl)amino-2-[9-(4-trifluoromethyl-benzoyl)-9-azabiacyclo[3.3.1]non-3-yl]-exo-ethanoyl}-pyrrolidin-2-carbonitrile

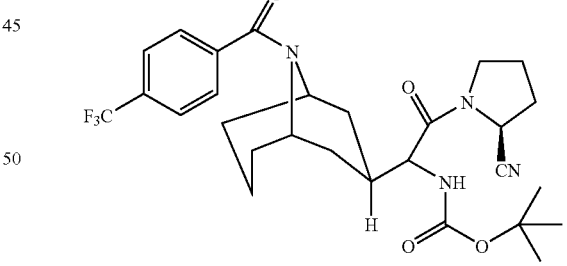

To a solution of (2S)-1-{2-(tent-butoxycarbonyl)amino-2-[9-(4-trifluoromethyl-benzoyl)-9-azabiacyclo[3.3.1]non-3-yl]exo-ethanoyl}-pyrrolidin-2-carboxamide (0.23 g, 0.41 mmol) and imidazole (0.058 g, 0.85 mmol) in dry pyridine (11.5 ml) under a nitrogen atmosphere at −30° C. was added phosphorous oxychloride (0.255 g, 1.66 mmol). The reaction mixture was stirred at −30° C. for 60 minutes and the progress of the reaction was monitored by TLC. It was then quenched with water (0.23 ml) at −30° C. and the reaction mixture was allowed to come at room temperature. The solvent was evaporated to dryness under reduced pressure and the residue was taken in dichloromethane (100 ml). After washing with water (10 ml), the organic layer was dried over anhydrous sodium sulphate. The solvent was evaporated to obtain a crude product, which was purified by column chromatography over silica gel (100-200 mesh) using 1% methanol in dichloromethane as an eluent to yield the title compound (0.136 g, 61%)

More polar diastereomer
mp: 146-148° C.
MS: m/z 549 (M+1)
$^1$HNMR (CDCl$_3$, 400 MHz): δ 1.38-1.55 (m, 10H), 1.6-1.86 (m, 6H), 1.88-2.06 (m, 3H), 2.10-2.35 (m, 4H), 2.67-2.83 (m, 1H), 3.61-3.87 (m, 3H), 4.06-4.15 (m, 1H), 4.75-4.80 (m, 1H), 4.9-4.98 (m, 1H), 5.11 (t, J=9.6 Hz, 1H), 7.47-7.54 (m, 2H), 7.67 (d, J=8.0 Hz, 2H)

Less polar diastereomer: It was also obtained by following the same procedure applied for more polar diastereomer as described above
(MS: m/z 549 (M+1)
$^1$HNMR (CDCl$_3$+D$_2$O, 400 MHz): δ 1.33-1.89 (m, 16H), 1.90-2.42 (m, 6H), 2.63-2.92 (m, 1H); 3.41-3.62 (m, 1H), 3.71-3.86 (m, 1H), 3.90-4.2 (m, 2H), 4.61-5.12 (m, 2H), 7.45-7.55 (m, 2H), 7.61-7.70 (m, 2H)

Step 3: (2S)-1-{2-Amino-2-[9-(4-trifluoromethyl-benzoyl)-9-azabiacyclo[3.3.1]non-3-yl]-exo-ethanoyl}-pyrrolidin-2-carbonitrile trifluoro acetic acid salt

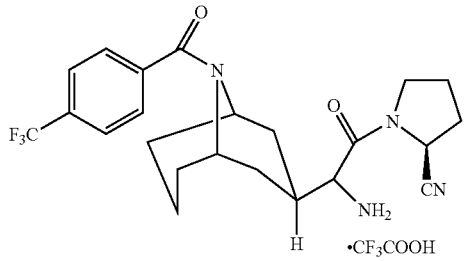

To a stirred solution of (2S)-1-{2-(tert-butoxycarbonyl)amino-2-[9-(4-trifluoromethyl-benzoyl)-9-azabiacyclo[3.3.1]non-3-yl]-ethanoyl}-pyrrolidin-2-carbonitrile (0.12 g, 0.22 mmol) in dichloromethane (1.2 ml) was added trifluoro acetic acid (1.2 ml) at 0° C. The reaction mixture was brought to room temperature in 10 minutes and stirred for 30 minutes. The progress of the reaction was monitored by TLC. After the completion of reaction, the solvent was evaporated under reduced pressure and the residue was taken in dichloromethane (20 ml) and evaporated to remove traces of trifluoro acetic acid. The residue so obtained was taken in diethyl ether (15 ml) and evaporated to obtain a solid, which was washed with 20% dichloromethane in diethyl ether (20 ml). To remove the traces of ether, the solid was taken in dichloromethane (10 ml) and evaporated to dryness twice. The crude product thus obtained was dried under high vacuum to yield the title compound (0.087 g, 71%)

More Polar Diastereomer (Compound No. 70 A)
mp: 172-174° C.
MS: m/z 449 (M+1)
$^1$HNMR (CDCl$_3$+D$_2$O, 400 MHz): δ 1.6-1.73 (m, 3H), 1.74-2.22 (m, 9H), 2.23-2.45 (m, 2H), 3.05-3.2 (m, 1H), 3.72 (t, J=6.8 Hz, 2H), 3.83-3.92 (m, 1H), 4.14 (dd, J=2.4, 6.8 Hz, 1H), 4.78-4.86 (m, 2H), 7.54-7.6 (m, 2H), 7.81 (d, J=7.8 Hz, 2H)
$[α]_D^{20}$ −16.45 (c 0.50, water)

Less polar diastereomer (Compound No. 70 B): It was also obtained by following the same procedure applied for more polar diastereomer as described above
mp: 168-170° C.
MS: m/z 449 (M+1)
$^1$HNMR (D$_2$O, 400 MHz): δ 1.21-1.34 (m, 1H), 1.6-2.06 (m, 10H), 2.10-2.41 (m, 4H), 2.98-3.12 (m, 1H), 3.5-3.68 (m, 1H), 3.8-3.91 (m, 2H), 4.08 (t, J=7.2 Hz, 1H), 4.73-4.9 (m, 1H), 7.57 (d, J=6.4 Hz, 2H), 7.81 (d, J=7.6 Hz, 2H)
$[α]_D^{20}$ −71.58 (c 0.50, water)

Demonstration of In Vitro Efficacy of Test Compounds
Inhibition of Human Recombinant DPP-IV The proteolytic activity of human recombinant DPP-IV was determined by following the hydrolysis of Gly-Pro-7-amino-4-methylcoumarin (Gly-Pro-AMC) and the fluorometric quantitation of the liberated AMC. Assays were routinely carried out in 96-well flat-bottom black microwell plates. The reaction mixture (100 µl) contained 10 ng of human recombinant DPP-IV enzyme (produced in-house or procured from R&D Systems, USA) in the assay buffer (25 mM Tris-HCl, pH 7.4, 140 mM NaCl, 10 mM KCl and 0.1 mg/ml BSA) and 50 µM Gly-Pro-AMC. After incubation of assay plates at 30° C. for 30 min, the hydrolysis of Gly-Pro-AMC was monitored in a fluorescence microplate reader (Molecular Devices SpectraMax M5), with excitation and emission wavelengths set at 360 nm and 460 nm, respectively.

The inhibition of DPP-IV activity by test compounds was routinely performed by preincubating the enzyme with test compound (10 and 100 nM for primary screening and 8 concentrations from 0.1 to 1000 nM for the dose-response study) or vehicle (0.01% DMSO) for 15 min at 30° C., in a total volume of 90 µl. Test compounds were dissolved in DMSO at a concentration of 10 mM and serially diluted further in assay buffer. The enzyme reaction was initiated by the addition of Gly-Pro-AMC, followed by incubation of assay plates for 30 min at 30° C. and the liberated AMC was measured as described above. A known inhibitor of DPP-IV (positive control) was always included in the assay. Test compounds at various concentrations were always evaluated in duplicate, along with substrate blanks, vehicle controls and positive controls.

The results are expressed as percent inhibition of the enzyme activity relative to vehicle controls. Dose-response studies were conducted for those compounds exerting ≧50% inhibition of activity at 10 nM in primary screening. IC$_{50}$, defined as the inhibitor concentration which caused a 50% decrease of the activity under assay conditions, was computed using GraphPad Prism software, version 5.0.

The DPP-IV inhibition data (expressed either as IC$_{50}$ in nanomolar or percent inhibition at a particular compound concentration) is presented in Table 1.

TABLE 1

Inhibition of human recombinant DPP-IV

| Compound No. | IC$_{50}$, nM |
|---|---|
| 1 | 2.20 |
| 2 | 1.30 |
| 3 | 6.67 |
| 4 | 1.03 |
| 5 | 1.52 |
| 6 | 2.30 |
| 7 | 1.90 |
| 8 | 6.84 |
| 9 | 3.13 |

TABLE 1-continued

Inhibition of human recombinant DPP-IV

| Compound No. | IC$_{50}$, nM |
|---|---|
| 10 | 41% inhibition at 1000 nM |
| 11 | 29% inhibition at 1000 nM |
| 12 | 30% inhibition at 1000 nM |
| 13 | 21% inhibition at 1000 nM |
| 14 | 12% inhibition at 10 nM |
| 15 | 1.72 |
| 16 | 2.90 |
| 17 | 2.40 |
| 18 | 1.11% inhibition at 10 nM |
| 19 | 6.25 |
| 20 | 2.80 |
| 21 | 17.90 |
| 22 | 2.83 |
| 23 | 9.75 |
| 24 | 3.52 |
| 25 | 3.61 |
| 26 | 8.90 |
| 27 | 17.20 |
| 28 | 4.70 |
| 29 | 0% inhibition at 10 nM |
| 30 | 0% inhibition at 10 nM |
| 31 | 6% inhibition at 10 nM |
| 32 | 6.84 |
| 33 | 9.43 |
| 34 | 12.90 |
| 35 | 4.20 |
| 36 | 17% inhibition at 10 nM |
| 37 | 7% inhibition at 10 nM |
| 38 | 16% inhibition at 100 nM |
| 39 | 11.70 |
| 40 | 44% inhibition at 10 nM |
| 41 | 4.92 |
| 42 | 9.00 |
| 43 | 49% inhibition at 100 nM |
| 44 | 2.40 |
| 45 | 12% inhibition at 1000 nM |
| 46 | 13% inhibition at 1000 nM |
| 47 | 29% inhibition at 10 nM |
| 48 | 22% inhibition at 10 nM |
| 49 | 60% inhibition at 100 nM |
| 50 | 21% inhibition at 10 nM |
| 51 | 9.60 |
| 52 | 25% inhibition at 10 nM |
| 53 | 19.70 |
| 54 | 3.30 |
| 55 | 45% inhibition at 10 nM |
| 56 | 4.14 |
| 57 | 8.00 |
| 58 | 31% inhibition at 10 nM |
| 59 | 34% inhibition at 10 nM |
| 60 | 10% inhibition at 10 nM |
| 61 | 9% inhibition at 10 nM |
| 62 | 12% inhibition at 10 nM |
| 63 | 15.50 |
| 64 | 11.01 |
| 65 | 7.10 |
| 66 | 8.24 |
| 67 | 7.68 |
| 68 | 16% inhibition at 10 nM |
| 69 | 13.00 |
| 70 A | 5.34 |
| 70 B | 0% inhibition at 10 nM |

Demonstration of In Vivo Efficacy of Test Compounds
A. Measurement of Plasma DPP-IV Activity in Male Wistar Rats Overnight-fasted male animals were administered either vehicle or single oral doses of compounds. Blood samples were withdrawn from retro-bulbar venous plexus under anesthesia at several time points up to 24 h post-dose. EDTA-plasma was separated and DPP-IV activity was measured using a fluorometric assay. Assays were carried out in 96-well flat-bottom black microwell plates. A typical reaction contained 25 µl plasma, 50 µl of 50 µM substrate (Gly-Pro-AMC) and 25 µl assay buffer (25 mM Tris-HCl, pH 7.4, 140 mM NaCl, 10 mM KCl and 1% BSA) in a total reaction volume of 100 µl. Plasma samples were incubated with the substrate for 30 min at 30° C., following which the fluorescence was measured in a microplate fluorescence redaer (POLARstar Galaxy), with excitation and emission wavelengths set at 360 nm and 460 nm, respectively. Percent inhibition in plasma DPP-IV activity due to compounds was calculated by comparing with plasma from vehicle-treated animals.

Table 2 shows the ability of selected test compounds to produce inhibition of plasma DPP-IV in Wistar rats.

TABLE 2

Inhibition of plasma DPP-IV activity in Wistar rats

| Compound No | Dose (mg/kg, p.o.) | Plasma DPP-IV Inhibition (%) | | |
|---|---|---|---|---|
| | | 4 h | 6 h | 8 h |
| 1 | 10 | 85 | 56 | 44 |
| 2 | 10 | 82 | 52 | 45 |
| 25 | 10 | 68 | 49 | 51 |
| 28 | 3 | 51 | 35 | 28 |
| 28 | 10 | 77 | 65 | 53 |
| 35 | 3 | 54 | 42 | 33 |
| 66 | 3 | 56 | 38 | 38 |
| 67 | 3 | 64 | 36 | 23 |

B. Oral Glucose Tolerance Test in Male C57BU6J Mice

Overnight-fasted male C67BL/6J mice were challenged 1 h, 4 h and 8 h after either vehicle or compound administration with an oral glucose load of 5 g/kg in three different groups of animals. Blood samples for glucose measurement were obtained by tail bleed at predose, before glucose load and at serial time points after the glucose load, to evaluate the efficacy and duration of effect on glucose tolerance test. Glucose excursion profile from t=0 to t=120 minutes was used to integrate an area under the curve (AUC) for each treatment. Improvement in glucose tolerance in compound-treated animals was estimated by comparing with vehicle-treated animals.

Table 3 provides data for the antihyperglycemic activity of selected compounds in C57BL/6J mice, as determined by oral glucose tolerance test.

TABLE 3

Effect of DPP-IV inhibitors on OGTT in C57BL/6J mice

| Compound No. | Dose (mg/kg, p.o.) | Improvement in Glucose Tolerance (%) 1 h |
|---|---|---|
| 28 | 3 | 54 |
| 35 | 3 | 46 |
| 66 | 3 | 48 |
| 67 | 3 | 50 |

The invention claimed is:
1. Compounds of the general formula A in exo configuration,

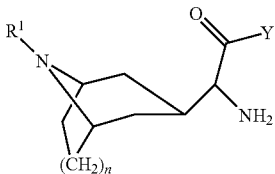

(A)

their optical isomers and pharmaceutically acceptable salts thereof, wherein,
n=1, 2
Y is selected from the groups

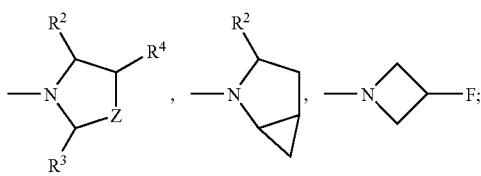

wherein, Z represents $CH_2$, —S—, CHF;
$R^1$ is selected from groups consisting of
i) Hydrogen;
ii) $C_1$-$C_8$alkyl (straight or branched) substituted with 1 to 3 substituents selected from halogens, such as pentyl, trifluoropropyl;
iii) cycloalkyl or cycloalkenyl having 3-10 carbon atoms such as cyclohexyl or cyclohex-2-enyl;
iv) cycloalkylmethyl having 4-10 carbon atoms such as cyclohexyl methyl;
v) Bridged polycycloalkyl methyl having 5 to 12 carbon atoms such as adamantyl methyl;
vi) phenyl which is unsubstituted or substituted with 1-3 substituents each independently selected from cyano or methanesulfonyl;
vii) aralkyl group such as benzyl which is unsubstituted or substituted with 1 to 3 substituents selected from halogens;
viii) heteroaryl group such as pyridyl substituted with cyano;
ix) heteroaralkyl group such as pyridyl methyl;
x) aralkoxyalkyl group such as benzyloxy ethyl;
xi) $SO_2R^5$; where $R^5$ is methyl, thiophenyl, or phenyl unsubstituted or substituted with 1 to 3 fluoro;
xii) —$CONHR^6$ or —$CSNHR^6$ or —$CONHSO_2R^6$; where $R^6$ is phenyl unsubstituted or substituted with chloro, fluoro, trifluoromethyl or methoxy;
xiii) $R^7CO$—, wherein $R^7$ is selected from
a. unsubstituted phenyl or substituted with 1 to 3 substituents selected from halogen, trifluoromethyl, cyano;
b. benzo[1,3]dioxolyl;
c. adamantyl;
d. heteroaryl such as thiophenyl; furyl; pyrazinyl; pyridyl unsubstituted or substituted with a substituent selected from halogen, cyano, methyl, benzyloxy;
e. N-acetylpiperidinyl;
f. Cyclohexyl;
g. Pyridine methyl;

$R^2$ is selected from hydrogen, CN, COOH, or isosteres of COOH, wherein said isosteres of COOH are selected from the groups consisting of esters, tetrazole, acid anhydrides, $CH_2OH$, $CH_2OBn$, CONHOH, $CONH_2$;
$R^3$ is selected from hydrogen, —CN, $C_2$-$C_5$ alkynyl;
$R^4$ is selected from hydrogen or fluoro.

2. A compound its stereoisomers, racemates, pharmaceutically acceptable salts thereof as claimed in claim 1 wherein the compound of the general formula (A) is selected from
(2S)-1-{(2S)-2-Amino-2-[8-(2,4,5-trifluorobenzoyl)-8-aza-bicyclo[3.2.1]oct-3-yl]-exo-ethanoyl}-pyrrolidin-2-carbonitrile trifluoroacetic acid salt;
(2S)-1-{(2S)-2-Amino-2-[8-(4-trifluoromethylbenzoyl)-8-aza-bicyclo[3.2.1]oct-3-yl]-exo-ethanoyl}-pyrrolidin-2-carbonitrile trifluoroacetic acid salt;
(2S)-1-{(2S)-2-Amino-2-[8-(adamantane-1-carbonyl)-8-aza-bicyclo[3.2.1]oct-3-yl]-exo-ethanoyl}-pyrrolidin-2-carbonitrile trifluoroacetic acid salt;
(2S)-1-{(2S)-2-Amino-2-[8-(pyridine-4-carbonyl)-8-aza-bicyclo[3.2.1]oct-3-yl]-exo-ethanoyl}-pyrrolidin-2-carbonitrile trifluoroacetic acid salt;
(2S)-1-{(2S)-2-Amino-2-[8-(4-cyano-benzoyl)-8-aza-bicyclo[3.2.1]oct-3-yl]-exo-ethanoyl}-pyrrolidin-2-carbonitrile trifluoroacetic acid salt;
(2S)-1-{(2S)-2-Amino-2-[8-(2,5-difluorobenzoyl)-8-aza-bicyclo[3.2.1]oct-3-yl]-exo-ethanoyl}-pyrrolidin-2-carbonitrile trifluoroacetic acid salt;
(2S)-1-{(2S)-2-Amino-2-[8-(2-fluoro-pyridine-4-carbonyl)-8-aza-bicyclo[3.2.1]oct-3-yl]-exo-ethanoyl}-pyrrolidin-2-carbonitrile trifluoroacetic acid salt;
(2S)-1-[(2S)-2-Amino-2-(8-aza-bicyclo[3.2.1]oct-3-yl)-exo-ethanoyl]-pyrrolidin-2-carbonitrile trifluoroacetic acid salt;
(2S)-1-{(2S)-2-Amino-2-[8-(2,4,5-trifluorobenzyl)-8-aza-bicyclo[3.2.1]oct-3-yl]-exo-ethanoyl}-pyrrolidin-2-carbonitrile trifluoroacetic acid salt;
Methyl-(2S)-1-{(2S)-2-amino-2-[8-(4-trifluoromethyl-benzoyl)-8-aza-bicyclo[3.2.1]-oct-3-yl]-exo-ethanoyl}-pyrrolidin-2-carboxylate trifluoroacetic acid salt;
(2S)-1-{(2S)-2-amino-2-[8-(4-trifluoromethyl-benzoyl)-8-aza-bicyclo[3.2.1]-oct-3-yl]-exo-ethanoyl}-pyrrolidin-2-carboxylic acid trifluoroacetic acid salt;
(2S)-1-{(2S)-2-amino-2-[8-(4-trifluoromethyl-benzoyl)-8-aza-bicyclo[3.2.1]-oct-3-yl]-exo-ethanoyl}-pyrrolidin-2-carboxamide trifluoroacetic acid salt;
(2S)-1-{(2S)-2-Amino-2-[8-(4-trifluoromethyl-benzoyl)-8-aza-bicyclo[3.2.1]-oct-3-yl]-exo-ethanoyl}-2-(2H-tetrazol-5-yl)pyrrolidine hydrochloride;
(2S)-{(2S)-1-[(2S)-2-Amino-2-(8-(benzo[1,3]dioxole-5-carbonyl)-8-aza-bicyclo [3.2.1]-oct-3-yl)-exo-acetyl]-pyrrolidin-2-yl}methanol trifluoroacetic acid salt;
(2S,4S)-1-{(2S)-2-Amino-2-[8-(4-trifluoromethylbenzoyl)-8-aza-bicyclo[3.2.1]oct-3-yl]-exo-ethanoyl}-4-fluoro-pyrrolidin-2-carbonitrile hydrochloride salt;
(2S,4S)-1-{(2S)-2-Amino-2-[8-(2,4,5-trifluorobenzoyl)-8-aza-bicyclo[3.2.1]oct-3-yl]-exo-ethanoyl}-4-fluoro-pyrrolidin-2-carbonitrile trifluoroacetic acid salt;
(2S,4S)-1-{(2S)-2-Amino-2-[8-(2,5-difluorobenzoyl)-8-aza-bicyclo[3.2.1]oct-3-yl]-exo-ethanoyl}-4-fluoro-pyrrolidin-2-carbonitrile trifluoroacetic acid salt;
Benzyl-(2S,5R)-1-{(2S)-2-amino-2-[8-(4-trifluoromethyl-benzoyl)-8-aza-bicyclo[3.2.1]-oct-3-yl]-exo-ethanoyl}-5-cyano pyrrolidin-2-carboxylate trifluoroacetic acid salt;
(2S,4S)-1-{(2S)-2-Amino-2-[8-(2,4,5-trifluorobenzyl)-8-aza-bicyclo[3.2.1]oct-3-yl]-exo-ethanoyl}-4-fluoro-pyrrolidin-2-carbonitrile trifluoroacetic acid salt;

(4S)-3-{(2S)-2-Amino-2-[8-(4-trifluoromethylbenzoyl)-8-aza-bicyclo[3.2.1]oct-3-yl]-exo-ethanoyl}-thiazolidine-4-carbonitrile trifluoroacetic acid salt;

3-{(2S)-2-Amino-2-[8-(4-trifluoromethylbenzoyl)-8-aza-bicyclo[3.2.1]oct-3-yl]-exo-ethanoyl}-1,3-thiazolidine trifluoroacetic acid salt;

(2S)-1-{(2S)-2-Amino-2-[8-(4-trifluoromethyl phenyl carbamoyl)-8-aza-bicyclo[3.2.1]oct-3-yl]-exo-ethanoyl}-pyrrolidin-2-carbonitrile trifluoroacetic acid salt;

(1S,3S,5S)-2-{(2S)-2-Amino-2-[8-(2,4,5-tiifluorobenzoyl)-8-aza-bicyclo[3.2.1]oct-3-yl]-exo-ethanoyl}-2-azabicyclo[3.1.0]hexane-3-carbonitrile trifluoroacetic acid salt;

(1S,3S,5S)-2-{(2S)-2-Amino-2-[8-(4-cyanobenzoyl)-8-aza-bicyclo[3.2.1]oct-3-yl]-exo-ethanoyl}-2-azabicyclo[3.1.0]hexane-3-carbonitrile trifluoroacetic acid salt;

(1S,3S,5S)-2-{(2S)-2-Amino-2-[8-(pyridine-4-carbonyl)-8-aza-bicyclo[3.2.1]oct-3-yl]-exo-ethanoyl}-2-azabicyclo[3.1.0]hexane-3-carbonitrile trifluoroacetic acid salt;

(1S,3S,5S)-2-{(2S)-2-Amino-2-[8-(4-trifluoromethylbenzoyl)-8-aza-bicyclo[3.2.1]oct-3-yl]-exo-ethanoyl}-2-azabicyclo[3.1.0]hexane-3-carbonitrile trifluoroacetic acid salt;

(1S,3S,5S)-2-{(2S)-2-Amino-2-[8-(2,5-difluorobenzoyl)-8-aza-bicyclo[3.2.1]oct-3-yl]-exo-ethanoyl}-2-azabicyclo[3.1.0]hexane-3-carbonitrile trifluoroacetic acid salt;

(1S,3S,5S)-2-{(2S)-2-Amino-2-[8-(2-fluoropyridine-4-carbonyl)-8-aza-bicyclo[3.2.1]oct-3-yl]-exo-ethanoyl}-2-azabicyclo[3.1.0]hexane-3-carbonitrile trifluoroacetic acid salt;

(1R,3R,5R)-2-{(2S)-2-Amino-2-[8-(2-fluoropyridine-4-carbonyl)-8-aza-bicyclo[3.2.1]oct-3-yl]-exo-ethanoyl}-2-azabicyclo[3.1.0]hexane-3-carbonitrile trifluoroacetic acid salt;

(1R,3R,5R)-2-{(2R)-2-Amino-2-[8-(2-fluoropyridine-4-carbonyl)-8-aza-bicyclo[3.2.1]oct-3-yl]-exo-ethanoyl}-2-azabicyclo[3.1.0]hexane-3-carbonitrile trifluoroacetic acid salt;

(1S,3S,5S)-2-{(2R)-2-Amino-2-[8-(2-fluoropyridine-4-carbonyl)-8-aza-bicyclo[3.2.1]oct-3-yl]exo-ethanoyl}-2-azabicyclo[3.1.0]hexane-3-carbonitrile trifluoroacetic acid salt;

(1S,3S,5S)-2-{(2S)-2-Amino-2-[8-(2-fluoropyridine-3-carbonyl)-8-aza-bicyclo[3.2.1]oct-3yl]-exo-ethanoyl}-2-azabicyclo[3.1.0]hexane-3-carbonitrile trifluoroacetic acid salt;

(1S,3S,5S)-2-{(2S)-2-Amino-2-[8-(pyridine-3-carbonyl)-8-aza-bicyclo[3.2.1]oct-3-yl]-exo-ethanoyl}-2-azabicyclo[3.1.0]hexane-3-carbonitrile trifluoroacetic acid salt;

(1S,3S,5S)-2-{(2S)-2-Amino-2-[8-(thiophene-2-carbonyl)-8-aza-bicyclo[3.2.1]oct-3yl]-exo-ethanoyl}-2-azabicyclo[3.1.0]hexane-3-carbonitrile trifluoroacetic acid salt;

(1S,3S,5S)-2-{(2S)-2-Amino-2-[8-(pyrazine-2-carbonyl)-8-aza-bicyclo[3.2.1]oct-3-yl]-exo-ethanoyl}-2-azabicyclo[3.1.0]hexane-3-carbonitrile trifluoroacetic acid salt;

(1S,3S,5S)-2-{(2R)-2-Amino-2-[8-(pyrazine-2-carbonyl)-8-aza-bicyclo[3.2.1]oct-3-yl]-exo-ethanoyl}-2-azabicyclo[3.1.0]hexane-3-carbonitrile trifluoroacetic acid salt;

(1R,3R,5R)-2-{(2S)-2-Amino-2-[8-(pyrazine-2-carbonyl)-8-aza-bicyclo[3.2.1]oct-3-yl]-exo-ethanoyl}-2-azabicyclo[3.1.0]hexane-3-carbonitrile trifluoroacetic acid salt;

(1R,3R,5R)-2-{(2R)-2-Amino-2-[8-(pyrazine-2-carbonyl)-8-aza-bicyclo[3.2.1]oct-3-yl]-exo-ethanoyl}-2-azabicyclo[3.1.0]hexane-3-carbonitrile trifluoroacetic acid salt;

(1S,3S,5S)-2-{(2S)-2-Amino-2-[8-(pyridine-2-carbonyl)-8-aza-bicyclo[3.2.1]oct-3-yl]-exo-ethanoyl}-2-azabicyclo[3.1.0]hexane-3-carbonitrile trifluoroacetic acid salt;

(1S,3S,5S)-2-{(2S)-2-Amino-2-[8-(furan-2-carbonyl)-8-aza-bicyclo[3.2.1]oct-3-yl]-exo-ethanoyl}-2-azabicyclo[3.1.0]hexane-3-carbonitrile trifluoroacetic acid salt;

(1S,3S,5S)-2-{(2S)-2-Amino-2-[8-(3-fluoropyridine-4-carbonyl)-8-aza-bicyclo[3.2.1]oct-3-yl]-exo-ethanoyl}-2-azabicyclo[3.1.0]hexane-3-carbonitrile trifluoroacetic acid salt;

(1S,3S,5S)-2-{(2S)-2-Amino-2-[8-(3,5-difluorobenzene sulfonyl)-8-aza-bicyclo[3.2.1]oct-3-yl]-exo-ethanoyl}-2-azabicyclo[3.1.0]hexane-3-carbonitrile trifluoroacetic acid salt;

(1S,3S,5S)-2-{(2S)-2-Amino-2-[8-(adamantane-1-carbonyl)-8-aza-bicyclo[3.2.1]oct-3-yl]-exo-ethanoyl}-2-azabicyclo[3.1.0]hexane-3-carbonitrile trifluoroacetic acid salt;

(1S,3S,5S)-2-{(2S)-2-Amino-2-[8-(benzo[1,3]dioxole-5-carbonyl)-8-aza-bicyclo[3.2.1]oct-3-yl]-exo-ethanoyl}-2-azabicyclo[3.1.0]-hexane-3-carbonitrile trifluoroacetic acid salt;

(1S,3S,5S)-2-{(2S)-2-Amino-2-[8-(benzo[1,3]-dioxole-5-carbonyl)-8-aza-bicyclo [3.2.1]oct-3-yl]-exo-ethanoyl}-2-azabicyclo[3.1.0]hexane-3-carboxamide trifluoroacetic acid salt;

(1S,3S,5S)-2-{(2S)-2-Amino-2-[8-(benzo[1,3]-dioxole-5-carbonyl)-8-aza-bicyclo [3.2.1]oct-3-yl]-exo-ethanoyl}-2-azabicyclo[3.1.0]hexane-3-carboxylic acid hydrochloride;

(1S,3S,5S)-2-{(2S )-2-Amino-2-[8-(3,3,3-trifluoro propyl)-8-aza-bicyclo[3.2.1]oct-3-yl]-exo-ethanoyl}-2-azabicyclo[3.1.0]hexane-3-carbonitrile trifluoroacetic acid salt;

(1S,3S,5S)-2-{(2S)-2-Amino-2-[8-(cyclohexyl methyl)-8-aza-bicyclo[3.2.1]oct-3-yl]-exo-ethanoyl}-2-azabicyclo[3.1.0]hexane-3-carbonitrile trifluoroacetic acid salt;

(1S,3S,5S)-2-{(2S)-2-Amino-2-[8-(adamantan-1-yl methyl)-8-aza-bicyclo[3.2.1]oct-3-yl]-exo-ethanoyl}-2-azabicyclo[3.1.0]hexane-3-carbonitrile trifluoroacetic acid salt;

(1S,3S,5S)-2-{(2S)-2-Amino-2-[8-(benzyloxy-ethyl)-8-aza-bicyclo[3.2.1]oct-3-yl]-exo-ethanoyl}-2-azabicyclo[3.1.0]hexane-3-carbonitrile trifluoroacetic acid salt;

(1S,3S,5S)-2-{(2S)-2-Amino-2-[8-(5-cyanopyridine-2-yl)-8-aza-bicyclo[3.2.1]oct-3-yl]-exo-ethanoyl}-2-azabicyclo[3.1.0]hexane-3-carbonitrile trifluoroacetic acid salt;

(1S,3S,5S)-2-{(2S)-2-Amino-2-[8-(4-cyano-phenyl)-8-aza-bicyclo[3.2.1]oct-3-yl]-exo-ethanoyl}-2-azabicyclo[3.1.0]hexane-3-carbonitrile trifluoro acetic acid salt;

(1S,3S,5S)-2-{(2S)-2-Amino-2-[8-(4-methanesulfonyl phenyl)-8-aza-bicyclo[3.2.1]oct-3-yl]-exo-ethanoyl}-2-azabicyclo[3.1.0]hexane-3-carbonitrile trifluoroacetic acid salt;

(1S,3S,5S)-2-{(2S)-2-Amino-2-[8-(2-pyridin-4-yl-acetyl)-8-aza-bicyclo[3.2.1]oct-3-yl]-exo-ethanoyl}-2-azabicyclo[3.1.0]hexane-3-carbonitrile trifluoroacetic acid salt;

(1S,3S,5S)-2-{(2S)-2-Amino-2-[8-(pyridine-4ylmethyl)-8-aza-bicyclo[3.2.1]oct-3-yl]-exo-ethanoyl}-2-azabicyclo[3.1.0]hexane-3-carbonitrile trifluoroacetic acid salt;

(1S,3S,5S)-2-{(2S)-2-Amino-2-[8-(methanesulfonyl)-8-aza-bicyclo[3.2.1]oct-3-yl]-exo-ethanoyl}-2-azabicyclo[3.1.0]hexane-3-carbonitrile trifluoroacetic acid salt;

(1S,3S,5S)-2-{(2S)-2-Amino-2-[8-(thiophene-2-sulfonyl)-8-aza-bicyclo[3.2.1]oct-3-yl]-exo-ethanoyl}-2-azabicyclo[3.1.0]hexane-3-carbonitrile trifluoroacetic acid salt;

(1S,3S,5S)-2-{(2S)-2-Amino-2-[8-(cyclohexane-carbonyl)-8-aza-bicyclo[3.2.1]oct-3-yl]-exo-ethanoyl}-2-azabicyclo[3.1.0]hexane-3-carbonitrile trifluoroacetic acid salt;

(1S,3S,5S)-2-{(2S)-2-Amino-2-[8-(1-ethyl-propyl)-8-aza-bicyclo[3.2.1]oct-3-3-yl]-exo-ethanoyl}-2-azabicyclo[3.1.0]hexane-3-carbonitrile trifluoroacetic acid salt;

(1S,3S,5S)-2-{(2S)-2-Amino-2-(8-cyclohexyl-8-aza-bicyclo[3.2.1]oct-3-yl)-exo-ethanoyl}-2-azabicyclo[3.1.0]hexane-3-carbonitrile trifluoroacetic acid salt;

(1S,3S,5S)-2-{(2S)-2-Amino-2-[8-(4-chlorophenylsulfonylcarbamoyl)-8-aza-bicyclo[3.2.1]oct-3-yl]-exo-ethanoyl}-2-azabicyclo[3.1.0]hexane-3-carbonitrile trifluoroacetic acid salt;

{(2S)-2-Amino-2-[8-(3-fluoro-pyridine-4-carbonyl)-8-aza-bicyclo[3.2.1]oct-3-yl]-exo-ethanoyl}-3-fluoro-azetidine trifluoroacetic acid salt;

(2S,5R)-1-{(2S)-2-Amino-2-[8-(4-trifluoromethyl-benzoyl)-8-aza-bicyclo[3.2.1]oct-3-yl]-exo-ethanoyl}-5-ethynyl-pyrrolidin-2-carbonitrile trifluoro acetic acid salt;

(2S,5R)-1-{(2S)-2-Amino-2-[8-(pyridin-4-carbonyl)-8-aza-bicyclo[3.2.1]oct-3-yl]-exo-ethanoyl}-5-ethynyl-pyrrolidin-2-carbonitrile trifluoroacetic acid salt;

(2S,5R)-1-{(2S)-2-Amino-2-[8-(3-fluoropyridin-4-carbonyl)-8-aza-bicyclo[3.2.1]oct-3-yl]-exo-ethanoyl}-5-ethynyl-pyrrolidin-2-carbonitrile trifluoroacetic acid salt;

(2S,5R)-1-{(2S)-2-Amino-2-[8-(2-fluoropyridin-4-carbonyl)-8-aza-bicyclo[3.2.1]-oct-3-yl]-exo-ethanoyl}-5-ethynyl-pyrrolidin-2-carbonitrile trifluoroacetic acid salt;

(2S,5R)-1-{(2S)-2-Amino-2-[8-(benzo[1,3]dioxole-5-carbonyl)-8-aza-bicyclo[3.2.1]oct-3-yl]exo-ethanoyl}-5-ethynyl-pyrrolidin-2-carbonitrile trifluoroacetic acid salt;

(1S,3S,5S)-2-{(2S)-2-Amino-2-[8-(2-methoxyphenylthiocarbamoyl)-8-aza-bicyclo [3.2.1]oct-3-yl]-exo-ethanoyl}-2-azabicyclo[3.1.0]hexane-3-carbonitrile trifluoroacetic acid salt;

(1S,3S,5S)-2-{(2S)-2-Amino-2-[8-(1-acetyl-piperidine-4-carbonyl)-8-aza-bicyclo [3.2.1]oct-3-yl]-exo-ethanoyl}-2-azabicyclo[3.1.0]hexane-3-carbonitrile trifluoroacetic acid salt;

(2S)-1-{2-Amino-2-[9-(4-trifluoromethyl-benzoyl)-9-azabiacyclo[3.3.1]non-3-yl]-exo-ethanoyl}-pyrrolidin-2-carbonitrile trifluoro acetic acid salt and its diastereomers.

3. A process for preparation of a compound of formula (A),

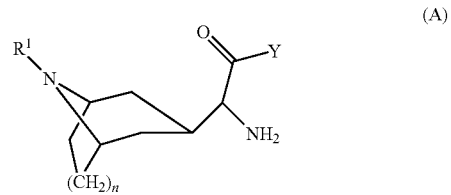

their optical isomers and pharmaceutically acceptable salts thereof, wherein, n=1, 2

Y is selected from the groups

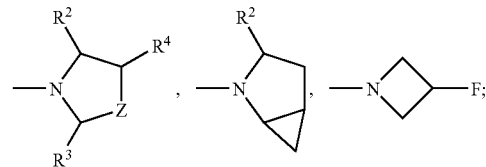

wherein, Z represents $CH_2$, —S—, CHF;

$R^1$ is selected from groups consisting of i) Hydrogen;

ii) $C_1$-$C_8$alkyl (straight or branched) substituted with 1 to 3 substituents selected from halogens, such as pentyl, trifluoropropyl;

iii) cycloalkyl or cycloalkenyl having 3-10 carbon atoms such as cyclohexyl or cyclohex-2-enyl;

iv) cycloalkylmethyl having 4-10 carbon atoms such as cyclohexyl methyl;

v) Bridged polycycloalkyl methyl having 5 to 12 carbon atoms such as adamantyl methyl;

vi) phenyl which is unsubstituted or substituted with 1-3 substituents each independently selected from cyano or methanesulfonyl;

vii) aralkyl group such as benzyl which is unsubstituted or substituted with 1 to 3 substituents selected from halogens;

viii) heteroaryl group such as pyridyl substituted with cyano;

ix) heteroaralkyl group such as pyridyl methyl;

x) aralkoxyalkyl group such as benzyloxy ethyl;

xi) $SO_2R^5$; where $R^5$ is methyl, thiophenyl, or phenyl unsubstituted or substituted with 1 to 3 fluoro;

xii) —$CONHR^6$ or —$CSNHR^6$ or —$CONHSO_2R^6$; where $R^6$ is phenyl unsubstituted or substituted with chloro, fluoro, trifluoromethyl or methoxy;

xiii) $R^7CO$—, wherein $R^7$ is selected from a. unsubstituted phenyl or substituted with 1 to 3 substituents selected from halogen, trifluoromethyl, cyano;

b. benzo[1,3]dioxolyl;

c. adamantyl;

d. heteroaryl such as thiophenyl; furyl; pyrazinyl; pyridyl unsubstituted or substituted with a substituent selected from halogen, cyano, methyl, benzyloxy;

e. N-acetylpiperidinyl;

f. Cyclohexyl;

g. Pyridine methyl;

$R^2$ is selected from hydrogen, CN, COOH, or isosteres of COOH, wherein said isosteres of COOH are selected from the groups consisting of esters, tetrazole, acid anhydrides, $CH_2OH$, $CH_2OBn$, CONHOH, $CONH_2$;

$R^3$ is selected from hydrogen, —CN, $C_2$-$C_5$ alkynyl;

$R^4$ is selected from hydrogen or fluoro;
which comprises the steps of:
(a) reaction of a compound of formula (VIII) or (XIX) or optical isomers thereof,

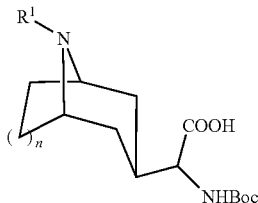

(n=1: compound VIII, n=2: compound XIX)
$R^1$ is selected from groups consisting of
i) $C_1$-$C_8$alkyl (straight or branched) substituted with 1 to 3 substituents selected from halogens, such as pentyl, trifluoropropyl;
ii) Cycloalkyl or cycloalkenyl having 3-10 carbon atoms such as cyclohexyl or cyclohex-2-enyl;
iii) cycloalkylmethyl having 4-10 carbon atoms such as cyclohexyl methyl;
iv) Bridged polycycloalkyl methyl having 5 to 12 carbon atoms such as adamantyl methyl;
v) phenyl which is unsubstituted or substituted with 1-3 substituents each independently selected from cyano or methanesulfonyl;
vi) aralkyl group such as benzyl which is unsubstituted or substituted with 1 to 3 substituents selected from halogens;
vii) heteroaryl group such as pyridyl substituted with cyano;
viii) heteroaralkyl group such as pyridyl methyl;
ix) aralkoxyalkyl group such as benzyloxy ethyl;
x) $SO_2R^5$; where $R^5$ is methyl, thiophenyl, or phenyl unsubstituted or substituted with 1 to 3 fluoro;
xi) —$CONHR^6$ or —$CSNHR^6$ or —$CONHSO_2R^6$; where $R^6$ is phenyl unsubstituted or substituted with chloro, fluoro, trifluoromethyl or methoxy;
xii) $R^7CO$—, wherein $R^7$ is selected from
a. unsubstituted phenyl or substituted with 1 to 3 substituents selected from halogen, trifluoromethyl, cyano;
b. benzo[1,3]dioxolyl;
c. adamantyl;
d. heteroaryl such as thiophenyl; furyl; pyrazinyl; pyridyl unsubstituted or substituted with a substituent selected from halogen, cyano, methyl, benzyloxy;
e. N-acetylpiperidinyl;
f. Cyclohexyl;
g. Pyridine methyl;
n is 1 or 2;
with a compound of formula Y—H or optical isomers thereof, wherein Y is selected from the fragments of formula

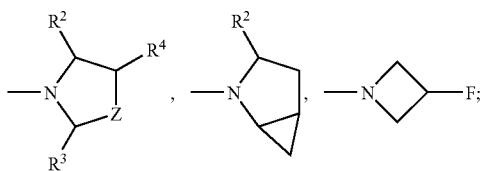

wherein, Z represents $CH_2$, —S—, CHF;

$R^2$ is selected from hydrogen, CN, COOH, or isosteres of COOH, wherein said isosteres of COOH are selected from the groups consisting of esters, tetrazole, acid anhydrides, $CH_2OH$, $CH_2OBn$, $CONHOH$, $CONH_2$;
$R^3$ is selected from hydrogen, —CN, $C_2$-$C_5$ alkynyl;
$R^4$ is selected from hydrogen or fluoro;
under standard peptide coupling conditions using EDCI, dicyclohexyl carbodiimide, HOBT and base such as triethyl amine or diisopropylethyl amine in a solvent such as N,N-dimethylformamide at the temperature ranging between about 0 and 35° C.; isolation of the product formed using standard techniques; and purification using suitable organic solvent;
wherein,
if $R^2$ is —$CONH_2$, then —$CONH_2$ group is converted to —CN by treatment of dehydrating agent such as $POCl_3$;
if $R^2$ is —COOH, then such group is converted to —CN by converting it to —$CONH_2$ and then treating the said amide with dehydrating agent such as $POCl_3$;
if $R^2$ is —CN, then —CN group is converted to tetrazole by treatment with sodium azide or organic azides;
(b) deprotection using suitable reagent such as trifluoroacetic acid in suitable solvent such as dichloromethane at a temperature between 0 and 30°C.
wherein,
if $R^1$ is tert-butyl carbonyl group, the said group is converted to —H by hydrolysis using agent such as trifluoroacetic acid;
if any of the reactants is in racemic form, the resultant product can be enriched to required stereoisomer by suitable method like column chromatography, fractional crystallization or salt formation at suitable step (a) or (b).

4. A process as claimed in claim 3, wherein 2S isomer of compound of formula VIII, is prepared from 3-Hydroxymethyl-8-methyl-8-aza-bicyclo[3.2.1]octane-3-ol (I) comprising steps of
(a) conversion of 3-Hydroxymethyl-8-methyl-8-aza-bicyclo[3.2.1]octane-3-ol (I) to 1-(2-Hydroxy-1-(1R)-phenylethyl amino)-1-(8-methyl-8-aza-bicyclo[3.2.1]-oct-3-yl)-exo-methane-1-(1S)-carbonitrile (II) comprising treatment of sulphuric acid followed by reaction with (R) phenyl glycinol and potassium cyanide followed by diastereomer separation;

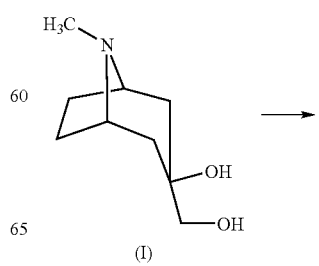

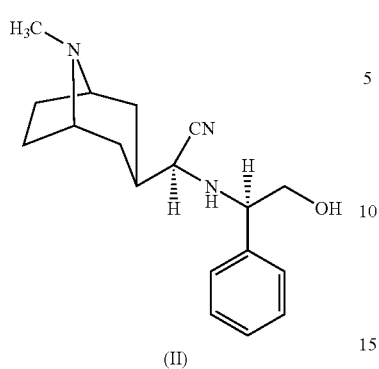

(II)

(b) conversion of compound of formula II to (2S)-2-Amino-(8-methyl-8-aza-bicyclo[3.2.1]oct-3-yl)-exo-acetic acid dihydrochloride (III) comprising first hydrolyzing cyano group to carboxylic acid using hydrochloric acid and then hydrogenating it in presence of palladium hydroxide at suitable pressure of hydrogen such as 80 to 100 psi;

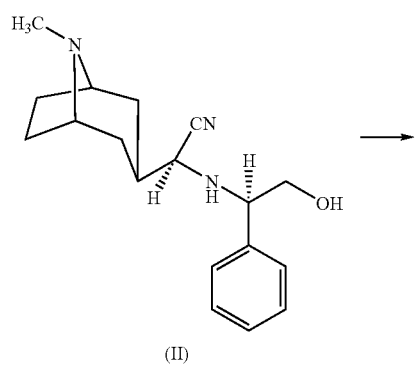

(II)

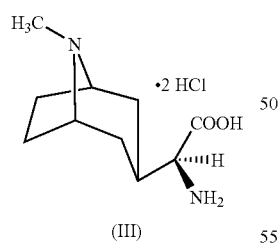

(III)

(c) conversion of compound of formula III to Methyl (2S)-2-(1,3-dioxo-1,3-dihydroisoindol-2-yl)-2-(8-methyl-8-aza-bicyclo[3.2.1]oct-3-yl)-exo-acetate (IV) comprising refluxing compound III in methanol with continuous purging of hydrogen chloride gas to yield Methyl (2S)-2-amino-2-(8-methyl-8-aza-bicyclo[3.2.1]oct-3-yl)-exo-acetate, followed by protection of amino group with phthalimido group in presence of base such as triethylamine;

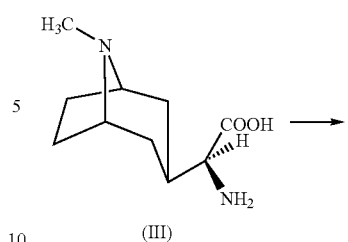

(III)

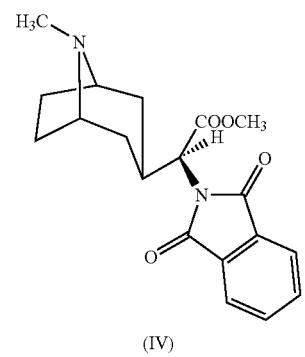

(IV)

(d) conversion of compound of formula IV to Methyl-(2S)-2-(1-hydroxy-3-oxo-1,3-dihydroisoindol-2-yl)-2-[8-aza-bicyclo[3.2.1]-oct-3-yl]-exo-acetate (V) comprising treatment with trichloroethyl chloroformate to yield Methyl-(2S)-2-(1,3-dioxo-1,3-dihydroisoindol-2-yl)-2-[8-(2,2,2-trichloro-ethyloxy carbonyl)-8-aza-bicyclo[3.2.1]-oct-3-yl]-exo-acetate, followed by treatment of zinc metal in acetic acid;

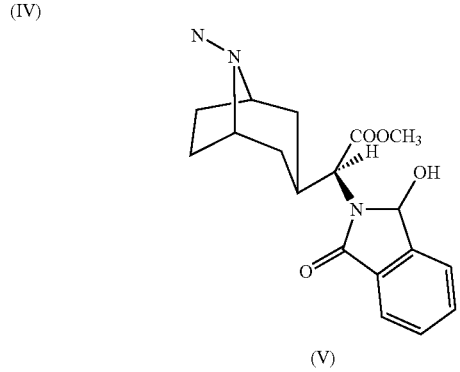

(IV)

(V)

(e) conversion of compound of formula V to Methyl (2S)-2-(1,3-dioxo-1,3-dihydroisoindol-2-yl)-2-[8-(carbobenzyloxy)-8-aza-bicyclo[3.2.1]-oct-3-yl]-exo-acetate (VI) comprising treatment with benzyl chloroformate in presence of a base such as sodium bicarbonate to yield Methyl-(2S)-2-(1-hydroxy-3-oxo-1,3-dihydroisoindol-2-yl)-2-[8-(carbobenzyl oxy)-8-aza-bicyclo[3.2.1]-oct-3-yl]-exo-acetate, followed by Jones oxidation;

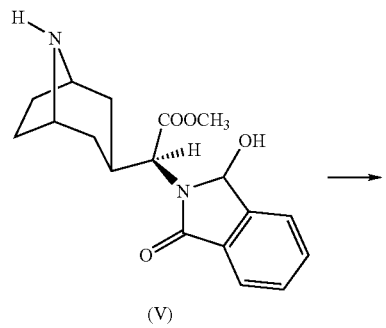

(V)

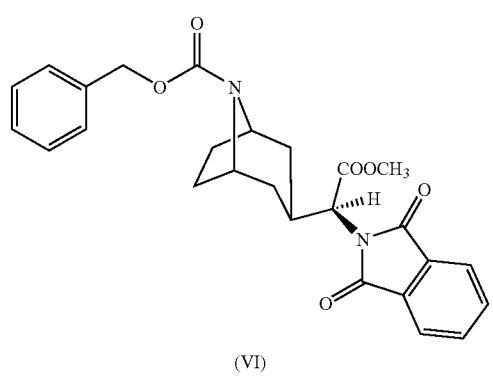

(VI)

(f) conversion of compound of formula VI to Methyl-(2S)-2-(tert-butoxycarbonyl)-amino-2-[8-(carbobenzyloxy)-8-aza-bicyclo[3.2.1]-oct-3-yl]-exo-acetate (VII) comprising deprotection with hydrazine hydrate to yield Methyl-(2S)-2-amino-2-[8-(carbobenzyloxy)-8-aza-bicyclo[3.2.1]-oct-3-yl]-exo-acetate, followed by protection with tert-butoxy carbonyl;

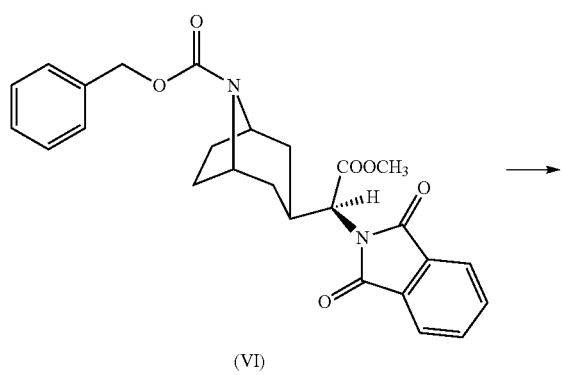

(VI)

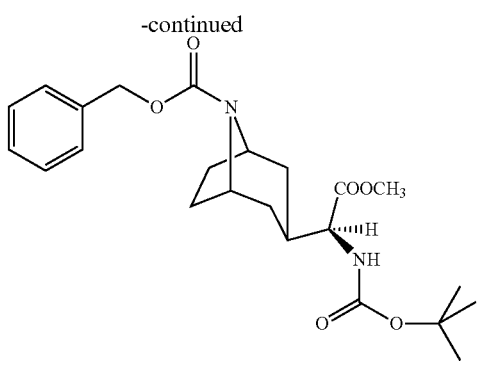

(VII)

(g) conversion of compound of formula VII to VIII comprising deprotection followed by condensation with either R¹L, wherein L is a leaving group such as halogen or hydroxy, R¹ is selected from it's definitions 'ii' to 'xi' and 'xiii' for compound of formula 'A'; or with R⁶N=C=O or R⁶N=C=S or R⁶SO₂N=C=O in case of R¹ is selected from definition 'xii' for compound of formula 'A', wherein R⁶ is selected from phenyl unsubstituted or substituted with chloro, fluoro, trifluoromethyl or methoxy;

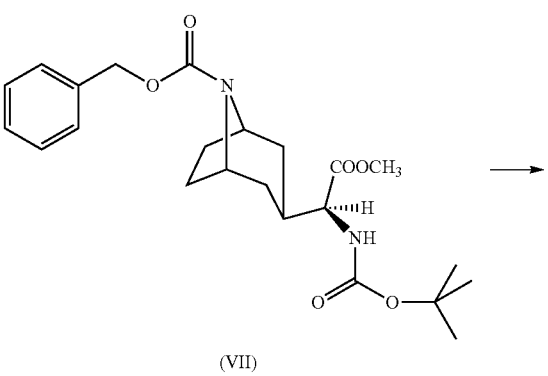

(VII)

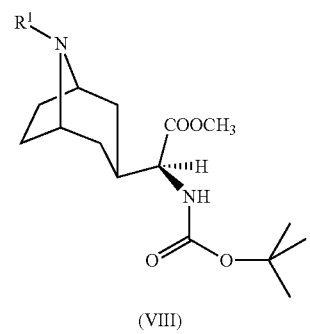

(VIII)

wherein,
if R¹ is cyclohex-2-enyl group, then such group is converted to cyclohexyl by catalytic hydrogenation;
If R¹ is adamantane carbonyl, then such group is converted to adamantane methyl by suitable reduction method;
such that,
at each step the product is optionally isolated and purified by standard techniques.

5. A process as claimed in claim 4, wherein 2R isomer of compound of formula VIII, wherein, n=1, is prepared from 3-Hydroxymethyl-8-methyl-8-aza-bicyclo[3.2.1]octane-3-ol (I) by replacing (R) phenyl glycinol with (S)-phenyl glycinol.

6. A process as claimed in claim 4, wherein racemate (2RS) of compound of formula VIII, wherein, n=1, is prepared from 3-Hydroxymethyl-8-methyl-8-aza-bicyclo[3.2.1]octane-3-ol (I) by replacing (R) phenyl glycinol with (RS)-phenyl glycinol and skipping the step of diastereomer separation.

7. A process as claimed in claim 3, wherein compound of formula VIII or its optical isomers, wherein, n=1, is prepared from compound of formula V comprising steps of
   (a) conversion of compound of formula V to IX comprising condensation with either $R^1L$, wherein L is a leaving group such as halogen or hydroxy, $R^1$ is selected from it's definitions (v), (vi), (viii), (xi) and (xiii) for compound of formula 'A', or with $R^6N{=}C{=}O$ or $R^6N{=}C{=}S$ or $R^6SO_2N{=}C{=}O$ in case of $R^1$ is selected from definition 'xii' for compound of formula 'A', wherein $R^6$ is selected from phenyl unsubstituted or substituted with chloro, fluoro, trifluoromethyl or methoxy; followed by Jones oxidation;

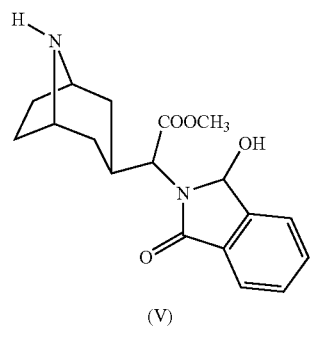

(V)

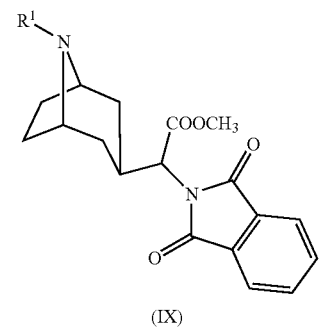

(IX)

(b) conversion of compound of formula IX to X comprising treatment with hydrazine hydrate in methanol followed by hydrolysis in presence of sodiumcarbonate in methanol and water;

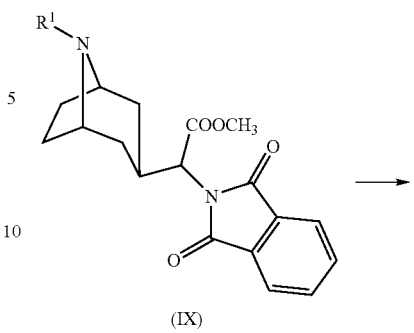

(IX)

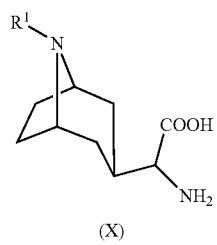

(X)

(c) conversion of compound of formula X to VIII comprising protection with tert-butyloxy carbonyl in presence of inorganic base such as potassiumcarbonate in aprotic polar solvent like N,N-dimethylformamide;

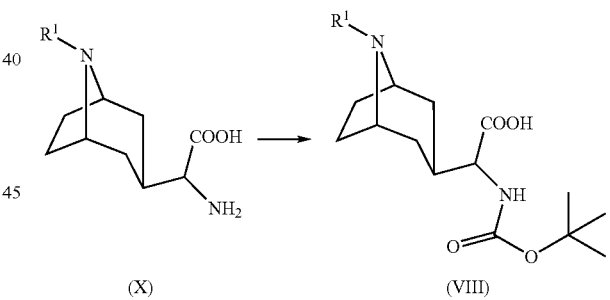

such that,
at each step the product was optionally isolated and purified by standard techniques.

8. A process as claimed in claim 3, wherein compound of formula XIX, is prepared from 3-oxo-9-aza-bicyclo[3.3.1]nonane-9-carboxylic acid ethyl ester (XIII) comprising steps of
   (a) conversion of 3-oxo-9-aza-bicyclo[3.3.1]nonane-9-carboxylic acid ethyl ester (XIII) to 9-(Ethoxy carbonyl)-3-exo-benzyl-9-aza-bicyclo[3.3.1]non-3-yl methyl oxalate (XIV) comprising treatment with benzyl magnesium halide under Grignard condition and reaction of the product formed with methyl oxalate in a solvent such as dichloromethane in presence of bases such as pyridine,2,6-lutidine or 4-dimethylaminopyridine;

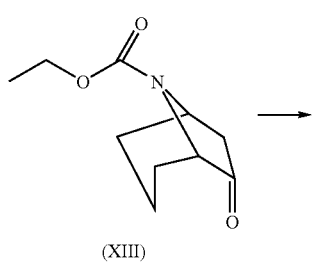

(XIII)

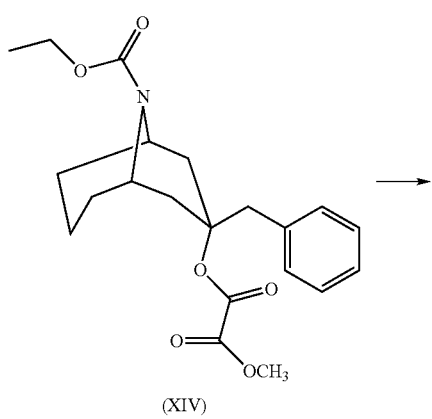

(XIV)

(b) conversion of compound of formula XIV to [9-(Ethoxycarbonyl)-9-azabicyclo [3.3.1]-non-3y1]acetic acid (XV) comprising first treatment with tributyl tin hydride or tris (trimethyl silyl) silane and 2,2'-azobis (2-methyl propionitrile) in a solvent such as toluene, or refluxing compound of formula XIV with dialkyl phosphite and a radical initiator such as benzoyl peroxide in toluene, and further treatment of the resultant product with ruthenium trichloride and periodic acid in a solvent such as carbon tetrachloride, acetonitrile or mixture thereof;

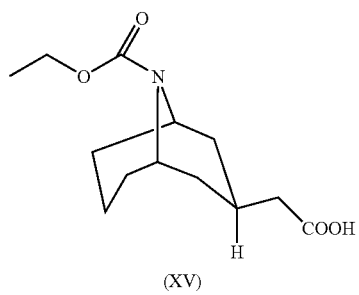

(XV)

(c) conversion of compound of formula XV to Methyl-9-azabicyclo[3.3.1]-non-3-yl-acetate (XVI) comprising hydrolysis using hydrochloric acid and further treatment of the resultant product with methanol and sulfuric acid;

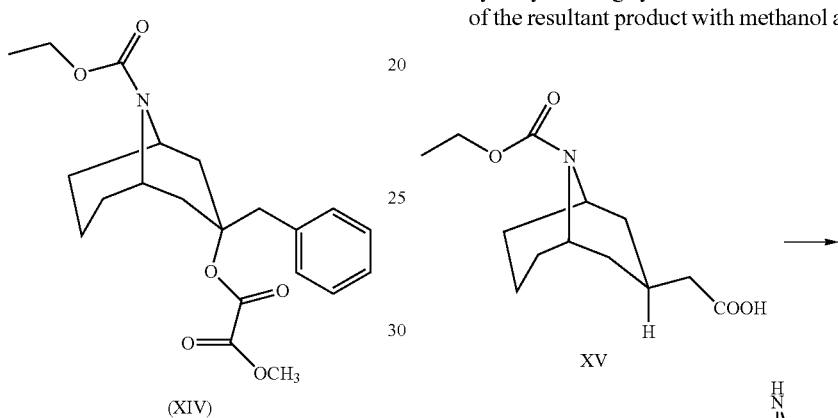

(d) conversion of compound of formula XVI to compound of formula XVII comprising condensation with either $R^1L$, wherein L is a leaving group such as halogen or hydroxy, $R^1$ is selected from definitions 'ii' to 'vi', viii, x and 'xiii' for compound of formula 'A'; or with $R^6N=C=O$ or $R^6SO_2N=C=O$ in case of $R^1$ is selected from definition 'xii' for compound of formula 'A', wherein $R^6$ is selected from phenyl unsubstituted or substituted with chloro, fluoro, trifluoromethyl or methoxy; and further treatment of the resultant product with lithium diisopropylamide and di-tert-butyl-diazine-1,2-dicarboxylate in solvent such as tetrahydrofuran;

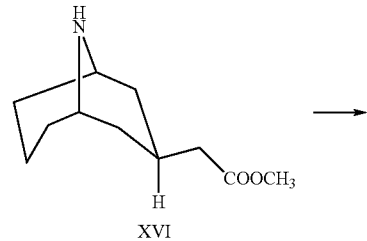

XVI

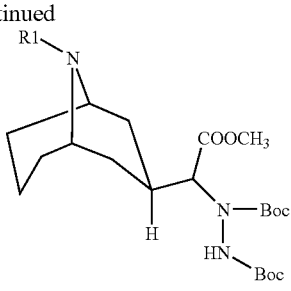

XVII (e) conversion of compound of formula XVII to compound of formula XVIII comprising treatment with trifluoro acetic acid in a suitable solvent such as dichloromethane, and further hydrogenation of the resultant product using suitable catalyst such as Raney Nickel;

XVII

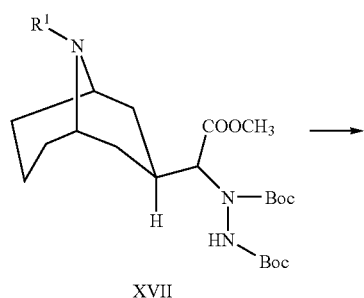

XVIII (f) conversion of compound of formula XVIII to compound of formula XIX comprising treatment of compound of formula XVIII with di-tert-butyl dicarbonate in presence of base such as triethyl amine in solvent such as dichloromethane followed by ester hydrolysis of the resultant product using suitable reagent;

XVIII

XIX wherein,
if $R^1$ is cyclohex-2-enyl group, then such group is converted to cyclohexyl by catalytic hydrogenation;
If $R^1$ is adamantane carbonyl, then such group is converted to adamantane methyl by suitable reduction method;
such that,
at each step the product is optionally isolated and purified by standard techniques.

9. A process as claimed in claim 8, wherein compound of formula XIX is prepared in exo configuration by isolating the exo conformer of compound of formula XVI of step (c) and proceeding ahead for steps (d), (e) and (f) with the pure exo confirmer.

10. A process as claimed in claim 8, wherein compound of formula XIX is prepared in endo configuration by isolating the endo conformer of compound of formula XVI of step (c) and proceeding ahead for steps (d), (e) and (f) with the pure endo confirmer.

11. Compounds of the general formula

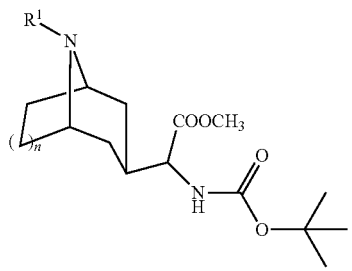

in exo configuration, their methyl esters and optical isomers thereof, wherein,
n=1 (compound VIII), 2 (compound XIX)
$R^1$ is selected from groups consisting of
i) $C_1$-$C_8$alkyl (straight or branched) substituted with 1 to 3 substituents selected from halogens, such as pentyl, trifluoropropyl;
ii) cycloalkyl having 3-10 carbon atoms such as cyclohexyl;
iii) cycloalkylmethyl having 4-10 carbon atoms such as cyclohexyl methyl;
iv) Bridged polycycloalkyl methyl having 5 to 12 carbon atoms such as adamantyl methyl;
v) phenyl which is unsubstituted or substituted with 1-3 substituents each independently selected from cyano or methanesulfonyl;
vi) aralkyl group such as benzyl which is unsubstituted or substituted with 1 to 3 substituents selected from halogens;
vii) heteroaryl group such as pyridyl substituted with cyano;

viii) heteroaralkyl group such as pyridyl methyl;
ix) aralkoxyalkyl group such as benzyloxy ethyl;
x) $SO_2R^5$; where $R^5$ is methyl, thiophenyl, or phenyl unsubstituted or substituted with 1 to 3 fluoro;
xi) —$CONHR^6$ or —$CSNHR^6$ or —$CONHSO_2R^6$; where $R^6$ is phenyl unsubstituted or substituted with chloro, fluoro, trifluoromethyl or methoxy;
xii) $R^7CO$—, wherein $R^7$ is selected from
  a. unsubstituted phenyl or substituted with 1 to 3 substituents selected from halogen, trifluoromethyl, cyano;
  b. benzo[1,3]dioxolyl;
  c. adamantyl;
  d. heteroaryl such as thiophenyl; furyl; pyrazinyl; pyridyl unsubstituted or substituted with a substituent selected from halogen, cyano, methyl, benzyloxy;
  e. N-acetylpiperidinyl;
  f. Cyclohexyl;
  g. Pyridine methyl.

12. A compound its stereoisomers, racemates, methylesters thereof as claimed in claim 11, wherein, the compound of the general formula VIII is selected from (2S)-2-(tert-Butoxycarbonyl)-amino-2-[8-(2,4,5-trifluorobenzoyl)-8-aza-bicyclo[3.2.1]-oct-3-yl]-exo-ethanoic acid;
(2S)-2-(tert-Butoxycarbonyl)-amino-2-[8-(4-trifluoromethylbenzoyl)-8-aza-bicyclo [3.2.1]-oct-3-yl]-exo-ethanoic acid;
(2S)-2-(tert-Butoxycarbonyl)-amino-2-[8-(adamantane-1-carbonyl)-8-aza-bicyclo [3.2.1]-oct-3-yl]-exo-ethanoic acid;
(2S)-2-(tert-Butoxycarbonyl)-amino-2-[8-(pyridine-4-carbonyl)-8-aza-bicyclo[3.2.1]-oct-3-yl]-exo-ethanoic acid;
(2S)-2-(tert-Butoxycarbonyl)-amino-2-[8-(4-cyano-benzoyl)-8-aza-bicyclo[3.2.1]-oct-3-yl]-exo-ethanoic acid;
(2S)-2-(tert-Butoxycarbonyl)-amino-2-[8-(2,5-difluorobenzoyl)-8-aza-bicyclo[3.2.1]-oct-3-yl]-exo-ethanoic acid;
(2S)-2-(tert-Butoxycarbonyl)-amino-2-[8-(2-fluoropyridine-4-carbonyl)-8-aza-bicyclo [3.2.1]-oct-3-yl]-exo-ethanoic acid;
(2R)-2-(tert-Butoxycarbonyl)-amino-2-[8-(2-fluoropyridin-4-carbonyl)-8-aza-bicyclo [3.2.1]-oct-3-yl]-exo-ethanoic acid;
(2S)-2-(tert-Butoxycarbonyl)-amino-2-[8-(2,4,5-trifluorobenzyl)-8-aza-bicyclo [3.2.1]-oct-3-yl]-exo-ethanoic acid;
(2S)-2-(tert-Butoxycarbonyl)-amino-2-[8-(cyclohexylmethyl)-8-aza-bicyclo[3.2.1]-oct-3-yl]-exo-ethanoic acid;
(2S)-2-(tert-Butoxycarbonyl)-amino-2-[8-(4-trifluoromethyl-phenyl carbamoyl)-8-aza-bicyclo [3.2.1]-oct-3-yl]-exo-ethanoic acid;
(2S)-2-(tert-Butoxycarbonyl)-amino-2-[8-(2-fluoropyridine-3-carbonyl)-8-aza-bicyclo [3.2.1]-oct-3-yl]-exo-ethanoic acid;
(2S)-2-(tert-Butoxycarbonyl)-amino-2-[8-(pyridine-3-carbonyl)-8-aza-bicyclo[3.2.1]-oct-3-yl]-exo-ethanoic acid;
(2S)-2-(tert-Butoxycarbonyl)-amino-2-[8-(thiophene-2-carbonyl)-8-aza-bicyclo[3.2.1]-oct-3-yl]exo-ethanoic acid;
(2S)-2-(tert-Butoxycarbonyl)-amino-2-[8-(pyrazine-2-carbonyl)-8-aza-bicyclo[3.2.1]-oct-3-yl]-exo-ethanoic acid;
(2R)-2-(tert-Butoxycarbonyl)-amino-2-[8-(pyrazine-2-carbonyl)-8-aza-bicyclo[3.2.1]-oct-3-yl]-exo-ethanoic acid;
(2S)-2-(tert-Butoxycarbonyl)-amino-2-[8-(pyridine-2-carbonyl)-8-aza-bicyclo[3.2.1]-oct-3-yl]-exo-ethanoic acid;
(2S)-2-(tert-Butoxycarbonyl)-amino-2-[8-(furan-2-carbonyl)-8-aza-bicyclo[3.2.1]-oct-3-yl]-exo-ethanoic acid;
(2S)-2-(tert-Butoxycarbonyl)-amino-2-[8-(3-fluoropyridine-4-carbonyl)-8-aza-bicyclo [3.2.1]-oct-3-yl]-exo-ethanoic acid;
(2S)-2-(tert-Butoxycarbonyl)-amino-2-[8-(3,5-difluorobenzene sulfonyl)-8-aza-bicyclo [3.2.1]-oct-3-yl]-exo-ethanoic acid;
(2S)-2-(tert-Butoxycarbonyl)-amino-2-[8-(benzo[1,3]dioxole-5-carbonyl)-8-aza-bicyclo [3.2.1]-oct-3-yl]-exo-ethanoic acid;
(2S)-2-(tert-Butoxycarbonyl)-amino-2-[8-(3,3,3-trifluoro propyl)-8-aza-bicyclo[3.2.1]-oct-3-yl]-exo-ethanoic acid;
(2S)-2-(tert-Butoxycarbonyl)-amino-2-[8-(benzyloxy-ethyl)-8-aza-bicyclo[3.2.1]-oct-3-yl]-exo-ethanoic acid;
(2S)-2-(tert-Butoxycarbonyl)-amino-2-[8-(5-cyanopyridin-2-yl)-8-aza-bicyclo[3.2.1]-oct-3-yl]-exo-ethanoic acid;
(2S)-2-(tert-Butoxycarbonyl)-amino-2-[8-(4-cyano-phenyl)-8-aza-bicyclo[3.2.1]-oct-3-yl]-exo-ethanoic acid;
(2S)-2-(tert-Butoxycarbonyl)-amino-2-[8-(4-methanesulfonyl phenyl)-8-aza-bicyclo [3.2.1]-oct-3-yl]-exo-ethanoic acid;
(2S)-2-(tert-Butoxycarbonyl)-amino-2-[8-(2-pyridin-4-yl-acetyl)-8-aza-bicyclo[3.2.1]-oct-3-yl]-exo-ethanoic acid;
(2S)-2-(tert-Butoxycarbonyl)-amino-2-[8-(pyridin-4-yl-methyl)-8-aza-bicyclo[3.2.1]-oct-3-yl]-exo-ethanoic acid;
(2S)-2-(tert-Butoxycarbonyl)-amino-2-[8-(methanesulfonyl)-8-aza-bicyclo[3.2.1]-oct-3-yl]-exo-ethanoic acid;
(2S)-2-(tert-Butoxycarbonyl)-amino-2-[8-(thiophene-2-sulfonyl)-8-aza-bicyclo[3.2.1]-oct-3-yl]-exo-ethanoic acid;
(2S)-2-(tert-Butoxycarbonyl)-amino-2-[8-(cyclohexane-carbonyl)-8-aza-bicyclo[3.2.1]-oct-3-yl]-exo-ethanoic acid;
(2S)-2-(tert-Butoxycarbonyl)-amino-2-[8-(1-ethyl-propyl)-8-aza-bicyclo[3.2.1]-oct-3-yl]-exo-ethanoic acid;
(2S)-2-(tert-Butoxycarbonyl)-amino-2-[8-(cyclohexyl)-8-aza-bicyclo[3.2.1]-oct-3-yl]-exo-ethanoic acid;
(2S)-2-(tert-Butoxycarbonyl)-amino-2-[8-(4-chlorophenylsulfonyl-carbamoyl)-8-aza-bicyclo[3.2.1]-oct-3-yl]-exo-ethanoic acid;
(2S)-2-(tert-Butoxycarbonyl)-amino-2-[8-(2-methoxyphenyl-thio-carbamoyl)-8-aza-bicyclo[3.2.1]-oct-3-yl]-exo-ethanoic acid;
(2S)-2-(tert-Butoxycarbonyl)-amino-2-[8-(1-acetyl-piperidine-4-carbonyl)-8-aza-bicyclo [3.2.1]-oct-3-yl]-exo-ethanoic acid;
(2S)-2-(tert-Butoxycarbonyl)-amino-2-[8-(adamantan-1-yl-methyl)-8-aza-bicyclo [3.2.1]-oct-3-yl]-exo-ethanoic acid;
(2S)-2-(tert-Butoxycarbonyl)-amino-2-[8-(tert-butoxycarbonyl)-8-aza-bicyclo[3.2.1]-oct-3-yl]-exo-ethanoic acid;
2-(tert-Butoxy carbonyl)amino-2-{9-(4-trifluoromethyl benzoyl)-9-azabicyclo[3.3.1]non-3-yl}-exo-ethanoic acid.

13. Compounds of the general formula X in exo configuration,

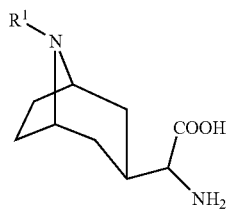

their methyl esters and optical isomers thereof, wherein,
R¹ is selected from groups consisting of
i) $C_1$-$C_8$alkyl (straight or branched) substituted with 1 to 3 substituents selected from halogens, such as pentyl, trifluoropropyl.
ii) cycloalkyl having 3-10 carbon atoms such as cyclohexyl;
iii) cycloalkylmethyl having 4-10 carbon atoms such as cyclohexyl methyl;
iv) Bridged polycycloalkyl methyl having 5 to 12 carbon atoms such as adamantyl methyl;
v) phenyl which is unsubstituted or substituted with 1-3 substituents each independently selected from cyano or methanesulfonyl;
vi) aralkyl group such as benzyl which is unsubstituted or substituted with 1 to 3 substituents selected from halogens;
vii) heteroaryl group such as pyridyl substituted with cyano;
viii) heteroaralkyl group such as pyridyl methyl;
ix) aralkoxyalkyl group such as benzyloxy ethyl;
x) $SO_2R^5$; where $R^5$ is methyl, thiophenyl, or phenyl unsubstituted or substituted with 1 to 3 fluoro;
xi) —$CONHR^6$ or —$CSNHR^6$ or —$CONHSO_2R^6$; where $R^6$ is phenyl unsubstituted or substituted with chloro, fluoro, trifluoromethyl or methoxy;
xii) $R^7CO$—, wherein $R^7$ is selected from
a. unsubstituted phenyl or substituted with 1 to 3 substituents selected from halogen, trifluoromethyl, cyano;
b. benzo[1,3]dioxolyl;
c. adamantyl;
d. heteroaryl such as thiophenyl; furyl; pyrazinyl; pyridyl unsubstituted or substituted with a substituent selected from halogen, cyano, methyl, benzyloxy;
e. N-acetylpiperidinyl;
f. Cyclohexyl;
g. Pyridine methyl.

14. A compound its stereoisomers, racemates, methylesters thereof as claimed in claim 13, wherein, the compound of the general formula X is selected from,
(2S)-2-Amino-2-[8-(2,4,5-trifluorobenzoyl)-8-aza-bicyclo[3.2.1]-oct-3-yl]-exo-ethanoic acid;
(2S)-2-Amino-2-[8-(4-trifluoromethylbenzoyl)-8-aza-bicyclo[3.2.1]-oct-3-yl]-exo-ethanoic acid;
(2S)-2-Amino-2-[8-(adamantane-1-carbonyl)-8-aza-bicyclo[3.2.1]-oct-3-yl]-exo-ethanoic acid;
(2S)-2-Amino-2-[8-(4-trifluoromethyl-phenyl carbamoyl)-8-aza-bicyclo[3.2.1]-oct-3-yl]-exo-ethanoic acid.

15. Compounds of the general, formula IX in exo configuration,

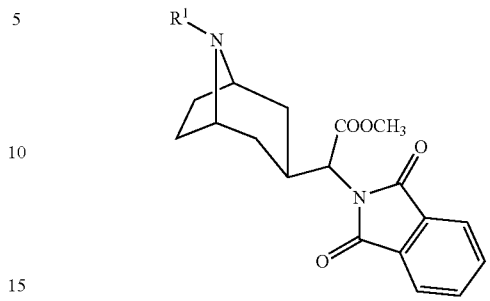

and optical isomers thereof, wherein,
R¹ is selected from groups consisting of
i) $C_1$-$C_8$alkyl (straight or branched) substituted with 1 to 3 substituents selected from halogens, such as pentyl, trifluoropropyl.
ii) cycloalkyl having 3-10 carbon atoms such as cyclohexyl;
iii) cycloalkylmethyl having 4-10 carbon atoms such as cyclohexyl methyl;
iv) Bridged polycycloalkyl methyl having 5 to 12 carbon atoms such as adamantyl methyl;
v) phenyl which is unsubstituted or substituted with 1-3 substituents each independently selected from cyano or methanesulfonyl;
vi) aralkyl group such as benzyl which is unsubstituted or substituted with 1 to 3 substituents selected from halogens;
vii) heteroaryl group such as pyridyl substituted with cyano;
viii) heteroaralkyl group such as pyridyl methyl;
ix) aralkoxyalkyl group such as benzyloxy ethyl;
x) $SO_2R^5$; where $R^5$ is methyl, thiophenyl, or phenyl unsubstituted or substituted with 1 to 3 fluoro;
xi) —$CONHR^6$ or —$CSNHR^6$ or —$CONHSO_2R^6$; where $R^6$ is phenyl unsubstituted or substituted with chloro, fluoro, trifluoromethyl or methoxy;
xii) $R^7CO$—, wherein $R^7$ is selected from
a. unsubstituted phenyl or substituted with 1 to 3 substituents selected from halogen, trifluoromethyl, cyano;
b. benzo[1,3]dioxolyl;
c. adamantyl;
d. heteroaryl such as thiophenyl; furyl; pyrazinyl; pyridyl unsubstituted or substituted with a substituent selected from halogen, cyano, methyl, benzyloxy;
e. N-acetylpiperidinyl;
f. Cyclohexyl;
g. Pyridine methyl.

16. A compound its stereoisomers, and racemates thereof as claimed in claim 15, wherein, the compound of the general formula IX is selected from,
Methyl-(2S)-2-(1,3-dioxo-1,3-dihydroisoindol-2-yl)-2-[8-(2,4,5-trifluorobenzoyl)-8-aza-bicyclo[3.2.1]-oct-3-yl]-exo-acetate;
Methyl-(2S)-2-(1,3-dioxo-1,3-dihydroisoindol-2-yl)-2-[8-(4-trifluoromethylbenzoyl)-8-aza-bicyclo[3.2.1]-oct-3-yl]-exo-acetate;
Methyl-(2S)-2-(1,3-dioxo-1,3-dihydroisoindol-2-yl)-2-[8-(adamantane-1-carbonyl)-8-aza-bicyclo[3.2.1]-oct-3-yl]-exo-acetate;
Methyl-(2S)-2-(1,3-dioxo-1,3-dihydroisoindol-2-yl)-2-[8-(4-trifluoromethyl-phenyl carbamoyl)-8-aza-bicyclo[3.2.1]-oct-3-yl]-exo-acetate.

17. Compounds, their stereoisomers, their racemates and salts thereof useful for the synthesis of compound of formula 'A' as listed below,

- 1-(2-Hydroxy-1-phenylethyl amino)-1-(8-methyl-8-aza-bicyclo[3.2.1]-oct-3-yl)-exo-methane-1-carbonitrile;
- 1-(2-Hydroxy-1-phenylethyl amino)-1-(8-methyl-8-aza-bicyclo[3.2.1]-oct-3-yl)-exo-methane-1-carboxylic acid;
- 2-Amino-(8-methyl-8-aza-bicyclo[3.2.1]oct-3-yl)-exo-acetic acid;
- Methyl-2-amino-2-(8-methyl-8-aza-bicyclo[3.2.1]-oct-3-yl)-exo-acetate;
- Methyl-2-(1,3-dioxo-1,3-dihydroisoindol-2-yl)-2-(8-methyl-8-aza-bicyclo[3.2.1]oct-3-yl)-exo-acetate;
- Methyl-2-(1,3-dioxo-1,3-dihydroisoindol-2-yl)-2-[8-(2,2,2-trichloro-ethyloxy carbonyl)-8-aza-bicyclo[3.2.1]-oct-3-yl]-exo-acetate;
- Methyl-2-(1-hydroxy-3-oxo-1,3-dihydroisoindol-2-yl)-2-[8-aza-bicyclo[3.2.1]-oct-3-yl]-exo-acetate;
- Methyl-2-(1-hydroxy-3-oxo-1,3-dihydroisoindol-2-yl)-2-[8-(carbobenzyl oxy)-8-aza-bicyclo[3.2.1]-oct-3-yl]-exo-acetate;
- Methyl-2-(1,3-dioxo-1,3-dihydroisoindol-2-yl)-2-[8-(carbobenzyloxy)-8-aza-bicyclo [3.2.1]-oct-3-yl]-exo-acetate;
- Methyl-2-amino-2-[8-(carbobenzyloxy)-8-aza-bicyclo [3.2.1]-oct-3-yl]-exo-acetate;
- Methyl-2-(tert-butoxycarbonyl)-amino-2-[8-(carbobenzyloxy)-8-aza-bicyclo[3.2.1]-oct-3-yl]-exo-acetate;
- Methyl-2-(text-butoxycarbonyl)-amino-2-[-8-aza-bicyclo [3.2.1]-oct-3-yl]-exo-acetate;
- 3-Benzyl-3-hydroxy-9-aza-bicyclo[3.3.1]nonane-9-carboxylic acid ethyl ester;
- 9-(Ethoxy carbonyl)-3-exo-benzyl-9-aza-bicyclo[3.3.1] non-3-yl methyl oxalate;
- Ethyl-3-benzyl-9-aza-bicyclo[3.3.1]nonane-9-carboxylate;
- [9-(Ethoxycarbonyl)-9-azabicyclo[3.3.1]-non-3yl]acetic acid;
- 9-Azabicyclo[3.3.1]non-3-yl acetic acid hydrochloride;
- Methyl-9-azabicyclo[3.3.1]-non-3-yl-acetate and exo and endo conformer thereof;
- Methyl {9-[4[trifluoromethyl]-9-azabicyclo[3.3.1]non-3-yl}-acetate and exo and endo conformer thereof;
- Methyl-2-(1,2-di-tert-butyloxy carbonyl hydrazine)-2-[9-(4-trifluoromethyl benzoyl)-9-azabicyclo[3.3.1]-non-3-yl]-acetate and exo and endo conformer thereof;
- Methyl-2-(hydrazino)-2-[9-(4-trifluoromethyl benzoyl)-9-azabicyclo[3.3.1]-non-3-yl]-acetate di trifluoro acetic acid salt and exo and endo conformer thereof;
- Methyl amino {9-[4-(trifluoro methyl)benzoyl]-9-azabicyclo[3.3.1]non-3-yl}-acetate and exo and endo conformer thereof;
- Methyl-2-(tert-butoxy carbonyl)amino-2-{9-[4-(trifluoromethyl)benzoyl]-9-azabicyclo [3.3.1]non-3-yl}-acetate and exo and endo conformer thereof.

18. A pharmaceutical composition, which comprises a compound of formula (A) as defined in claim 1 and a pharmaceutically acceptable carrier, diluent, excipients

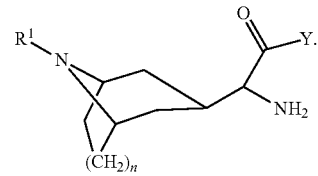

(A)

19. A pharmaceutical composition as claimed in claim 18, in the form of a tablet, capsule, suspension, powder, syrup, and solution.

20. A method of treating type-2 diabetes, comprising administering a compound of claim 1 or a pharmaceutical composition comprising the compound to a subject in need thereof.

21. A method according to claim 20, wherein the pharmaceutical composition comprises a compound of formula 1 and a pharmaceutically acceptable carrier, diluent, excipient, or mixture thereof.

22. A method of claim 21, wherein the pharmaceutical composition is in the form of a tablet, a capsule, a suspension, a powder, a syrup, or a solution.

23. The method of claim 20, wherein the compound is selected from:

- (2S)-1-{(2S)-2-Amino-2-[8-(2,4,5-trifluorobenzoyl)-8-aza-bicyclo[3.2.1]oct-3-yl]-exo-ethanoyl}-pyrrolidin-2-carbonitrile trifluoroacetic acid salt;
- (2S)-1-{(2S)-2-Amino-2-[8-(4-trifluoromethylbenzoyl)-8-aza-bicyclo[3.2.1]oct-3-yl]-exo-ethanoyl}-pyrrolidin-2-carbonitrile trifluoroacetic acid salt;
- (2S)-1-{(2S)-2-Amino-2-[8-(adamantane-1-carbonyl)-8-aza-bicyclo[3.2.1]oct-3-yl]-exo-ethanoyl}-pyrrolidin-2-carbonitrile trifluoroacetic acid salt;
- (2S)-1-{(2S)-2-Amino-2-[8-(pyridine-4-carbonyl)-8-aza-bicyclo[3.2.1]oct-3-yl]-exo-ethanoyl}-pyrrolidin-2-carbonitrile trifluoroacetic acid salt;
- (2S)-1-{(2S)-2-Amino-2-[8-(4-cyano-benzoyl)-8-aza-bicyclo[3.2.1]oct-3-yl]-exo-ethanoyl}-pyrrolidin-2-carbonitrile trifluoroacetic acid salt;
- (2S)-1-{(2S)-2-Amino-2-[8-(2,5-difluorobenzoyl)-8-aza-bicyclo[3.2.1]oct-3-yl]-exo-ethanoyl}-pyrrolidin-2-carbonitrile trifluoroacetic acid salt;
- (2S)-1-{(2S)-2-Amino-2-[8-(2-fluoro-pyridine-4-carbonyl)-8-aza-bicyclo[3.2.1]oct-3-yl]-exo-ethanoyl}-pyrrolidin-2-carbonitrile trifluoroacetic acid salt;
- (2S)-1-[(2S)-2-Amino-2-(8-aza-bicyclo[3.2.1]oct-3-yl)-exo-ethanoyl]-pyrrolidin-2-carbonitrile trifluoroacetic acid salt;
- (2S)-1-{(2S)-2-Amino-2-[8-(2,4,5-trifluorobenzyl)-8-aza-bicyclo[3.2.1]oct-3-yl]-exo-ethanoyl}-pyrrolidin-2-carbonitrile trifluoroacetic acid salt;
- Methyl-(2S)-1-{(2S)-2-amino-2[8-(4-trifluoromethyl-benzoyl)-8-aza-bicyclo[3.2.1]-oct-3-yl]-exo-ethanoyl}-pyrrolidin-2-carboxylate trifluoroacetic acid salt;
- (2S)-1-{(2S)-2-amino-2-[8-(4-trifluoromethyl-benzoyl)-8-aza-bicyclo[3.2.1]-oct-3-yl]-exo-ethanoyl}-pyrrolidin-2-carboxylic acid trifluoroacetic acid salt;
- (2S)-1-{(2S)-2-amino-2-[8-(4-trifluoromethyl-benzoyl)-8-aza-bicyclo[3.2.1]-oct-3-yl]-exo-ethanoyl}-pyrrolidin-2-carboxamide trifluoroacetic acid salt;
- (2S)-1-{(2S)-2-Amino-2-[8-(4-trifluromethyl-benzoyl)-8-aza-bicyclo[3.2.1]-oct-3-yl]-exo-ethanoyl}-2-(2H-tetrazol-5-yl) pyrrolidine hydrochloride;

(2S)-{(2S)-1-[(2S)-2-Amino-2-(8-(benzo [1,3]dioxole-5-carbonyl)-8-aza-bicyclo [3.2.1]-oct-3-yl)-exo-acetyl]-pyrrolidin-2-yl} methanol trifluoroacetic acid salt;

(2S,4S)-1-{(2S)-2-Amino-2-[8-(4-trifluoromethylbenzoyl)-8-aza-bicyclo[3.2.1]oct-3-yl]-exo-ethanoyl}-4-fluoro-pyrrolidin-2-carbonitrile hydrochloride salt;

(2S,4S)-1-{(2S)-2-Amino-2[8-(2,4,5-trifluorobenzoyl)-8-aza-bicyclo[3.2.1]oct-3-yl]-exo-ethanoyl}-4-fluoro-pyrrolidin-2-carbonitrile trifluoroacetic acid salt;

(2S,4S)-1-{(2S)-2-Amino-2-[8-(2,5-difluorobenzoyl)-8-aza-bicyclo[3.2.1]oct-3-yl]-exo-ethanoyl}-4-fluoro-pyrrolidin-2-carbonitrile trifluoroacetic acid salt;

Benzyl-(2S,5R)-1-{(2S)-2-amino-2-[8-(4-trifluoromethyl-benzoyl)-8-aza-bicyclo[3.2.1]-oct-3-yl]-exo-ethanoyl}-5-cyano pyrrolidin-2-carboxylate trifluoroacetic acid salt;

(2S,4S)-1-{(2S)-2-Amino-2-[8-(2,4,5-trifluorobenzyl)-8-aza-bicyclo[3.2.1]oct-3-yl]-exo-ethanoyl}-4-fluoro-pyrrolidin-2-carbonitrile trifluoroacetic acid salt;

(4S)-3-{(2S)-2-Amino-2-[8-(4-trifluoromethylbenzoyl)-8-aza-bicyclo[3.2.1]oct-3-yl]-exo-ethanoyl}-thiazolidine-4-carbonitrile trifluoroacetic acid salt;

3-{(2S)-2-Amino-2-[8-(4-trifluoromethylbenzoyl)-8-aza-bicyclo[3.2.1]oct-3-yl]-exo-ethanoyl}-1,3-thiazolidine trifluoroacetic acid salt;

(2S)-1-{(2S)-2-Amino-2-[8-(4-trifluoromethyl phenyl carbamoyl)-8-aza-bicyclo[3.2.1]oct-3-yl]-exo-ethanoyl}-pyrrolidin-2-carbonitrile trifluoroacetic acid salt;

(1S,3S,5S)-2-{(2S)-2-Amino-2-[8-(2,4,5-trifluorobenzoyl)-8-aza-bicyclo [3.2.1]oct-3-yl]-exo-ethanoyl}-2-azabicyclo[3.1.0]hexane-3-carbonitrile trifluoroacetic acid salt;

(1S,3S,5S)-2-{(2S)-2-Amino-2-[8-(4-cyanobenzoyl)-8-aza-bicyclo[3.2.1]oct-3-yl]-exo-ethanoyl}-2-azabicyclo[3.1.0]hexane-3-carbonitrile trifluoroacetic acid salt;

(1S,3S,5 S)-2-{(2S)-2-Amino-2-[8-(pyridine-4-carbonyl)-8-aza-bicyclo [3.2.1]oct-3-yl]-exo-ethanoyl}-2-azabicyclo[3.1.0]hexane-3-carbonitrile trifluoroacetic acid salt;

(1S,3S,5 S)-2-{(2S)-2-Amino-2-[8-(4-trifluoromethyl-benzoyl)-8-aza-bicyclo [3.2.1]oct-3-yl]-exo-ethanoyl}-2-azabicyclo[3.1.0]hexane-3-carbonitrile trifluoroacetic acid salt;

(1S,3S,5S)-2-{(2S)-2-Amino-2-[8-(2,5-difluorobenzoyl)-8-aza-bicyclo [3.2.1]oct-3-yl]-exo-ethanoyl}-2-azabicyclo[3.1.0]hexane-3-carbonitrile trifluoroacetic acid salt;

(1S,3S,5S)-2-{(2S)-2-Amino-2-[8-(2-fluoropyridine-4-carbonyl)-8-aza-bicyclo [3.2.1]oct-3-yl]-exo-ethanoyl}-2-azabicyclo[3.1.0]hexane-3-carbonitrile trifluoroacetic acid salt;

(1R,3R,5R)-2-{(2S)-2-Amino-2-[8-(2-fluoropyridine-4-carbonyl)-8-aza-bicyclo [3.2.1]oct-3-yl]-exo-ethanoyl}-2-azabicyclo[3.1.0]hexane-3-carbonitrile trifluoroacetic acid salt;

(1R,3R,5R)-2-{(2R)-2-Amino-2-[8-(2-fluoropyridine-4-carbonyl)-8-aza-bicyclo [3.2.1]oct-3-yl]-exo-ethanoyl}-2-azabicyclo[3.1.0]hexane-3-carbonitrile trifluoroacetic acid salt;

(1S,3 S,5S)-2-{(2R)-2-Amino-2-[8-(2-fluoropyridine-4-carbonyl)-8-aza-bicyclo[3.2.1]oct-3-yl]-exo-ethanoyl}-2-azabicyclo[3.1.0]hexane-3-carbonitrile trifluoroacetic acid salt;

(1S,3S,5S)-2-{(2S)-2-Amino-2-[8-(2-fluoropyridine-3-carbonyl)-8-aza-bicyclo[3.2.1]oct-3-yl]-exo-ethanoyl}-2-azabicyclo[3.1.0]hexane-3-carbonitrile trifluoroacetic acid salt;

(1S,3S,5S)-2-{(2S)-2-Amino-2-[8-(pyridine-3-carbonyl)-8-aza-bicyclo[3.2.1]oct-3-yl]-exo-ethanoyl}-2-azabicyclo[3.1.0]hexane-3-carbonitrile trifluoroacetic acid salt;

(1S,3S,5S)-2-{(2S)-2-Amino-2[8-(thiophene-2-carbonyl)-8-aza-bicyclo[3.2.1]oct-3-yl]-exo-ethanoyl}-2-azabicyclo[3.1.0]hexane-3-carbonitrile trifluoroacetic acid salt;

(1S,3S,5S)-2-{(2S)-2-Amino-2-[8-(pyrazine-2-carbonyl)-8-aza-bicyclo[3.2.1]oct-3-yl]-exo-ethanoyl}-2-azabicyclo[3.1.0]hexane-3-carbonitrile trifluoroacetic acid salt;

(1S,3S,5S)-2-{(2R)-2-Amino-2-[8-(pyrazine-2-carbonyl)-8-aza-bicyclo[3.2.1]oct-3-yl]-exo-ethanoyl}-2-azabicyclo[3.1.0]hexane-3-carbonitrile trifluoroacetic acid salt;

(1R,3R,5R)-2-{(2S)-2-Amino-2-[8-(pyrazine-2-carbonyl)-8-aza-bicyclo[3.2.1]oct-3-yl]-exo-ethanoyl}-2-azabicyclo[3.1.0]hexane-3-carbonitrile trifluoroacetic acid salt;

(1R,3R,5R)-2-{(2R)-2-Amino-2-[8-(pyrazine-2-carbonyl)-8-aza-bicyclo[3.2.1]oct-3-yl]-exo-ethanoyl}-2-azabicyclo[3.1.0]hexane-3-carbonitrile trifluoroacetic acid salt;

(1S,3S,5S)-2-{(2S)-2-Amino-2-[8-(pyridine-2-carbonyl)-8-aza-bicyclo[3.2.1]oct-3-yl]-exo-ethanoyl}-2-azabicyclo[3.1.0]hexane-3-carbonitrile trifluoroacetic acid salt;

(1S,3S,5S)-2-{(2S)-2-Amino-2-[8-(furan-2-carbonyl)-8-aza-bicyclo[3.2.1]oct-3-yl]-exo-ethanoyl}-2-azabicyclo[3.1.0]hexane-3-carbonitrile trifluoroacetic acid salt;

(1S,3S,5S)-2-{(2S)-2-Amino-2-[8-(3-fluoropyridine-4-carbonyl)-8-aza-bicyclo [3.2.1]oct-3-yl]-exo-ethanoyl}-2-azabicyclo[3.1.0]hexane-3-carbonitrile trifluoroacetic acid salt;

(1S,3S,5S)-2-{(2S)-2-Amino-2-[8-(3,5-difluorobenzene sulfonyl)-8-aza-bicyclo[3.2.1]oct-3-yl]-exo-ethanoyl}-2-azabicyclo[3.1.0]hexane-3-carbonitrile trifluoroacetic acid salt;

(1S,3S,5S)-2-{(2S)-2-Amino-2-[8-(adamantane-1-carbonyl)-8-aza-bicyclo [3.2.1]oct-3-yl]-exo-ethanoyl}-2-azabicyclo[3.1.0]hexane-3-carbonitrile trifluoroacetic acid salt;

(1S,3S,5S)-2-{(2S)-2-Amino-2-[8-(benzo[1,3]dioxole-5-carbonyl)-8-aza-bicyclo [3.2.1]oct-3-yl]-exo-ethanoyl}-2-azabicyclo[3.1.0]hexane-3-carbonitrile trifluoroacetic acid salt;

(1S,3S,5S)-2-{(2S)-2-Amino-2-[8-(benzo [1,3]-dioxole-5-carbonyl)-8-aza-bicyclo[3.2.1]oct-3-yl]-exo-ethanoyl}-2-azabicyclo[3.1.0]hexane-3-carboxamide trifluoroacetic acid salt;

(1S,3S,5S)-2-{(2S)-2-Amino-2-[8-(benzo [1,3]-dioxole-5-carbonyl)-8-aza-bicyclo[3.2.1]oct-3-yl]-exo-ethanoyl}-2-azabicyclo[3.1.0]-hexane-3-carboxylic acid hydrochloride;

(1S,3S,5S)-2-{(2S)-2-Amino-2-[8-(3,3,3-trifluoro propyl)-8-aza-bicyclo[3.2.1]oct-3-yl]-exo-ethanoyl}-2-azabicyclo[3.1.0]hexane-3-carbonitrile trifluoroacetic acid salt;

(1S,3S,5S)-2-{(2S)-2-Amino-2-[8-(cyclohexyl methyl)-8-aza-bicyclo[3.2.1]oct-3-yl]-exo-ethanoyl}-2-azabicyclo[3.1.0]hexane-3-carbonitrile trifluoroacetic acid salt;

(1S,3S,5S)-2-{(2S)-2-Amino-2-[8-(adamantan-1-yl methyl)-8-aza-bicyclo[3.2.1]oct-3-yl]-exo-ethanoyl}-2-azabicyclo[3.1.0]hexane-3-carbonitrile trifluoroacetic acid salt;

(1S,3S,5S)-2-{(2S)-2-Amino-2-[8-(benzyloxy-ethyl)-8-aza-bicyclo[3.2.1]oct-3-yl]-exo-ethanoyl}-2-azabicyclo[3.1.0]hexane-3-carbonitrile trifluoroacetic acid salt;

(1S,3S,5S)-2-{(2S)-2-Amino-2-[8-(5-cyanopyridine-2-yl)-8-aza-bicyclo[3.2.1]oct-3-yl]-exo-ethanoyl}-2-azabicyclo[3.1.0]hexane-3-carbonitrile trifluoroacetic acid salt;

(1S,3S,5S)-2-{(2S)-2-Amino-2-[8-(4-cyano-phenyl)-8-aza-bicyclo[3.2.1]oct-3-yl]-exo-ethanoyl}-2-azabicyclo[3.1.0]hexane-3-carbonitrile trifluoro acetic acid salt;

(1S,3S,5S)-2-{(2S)-2-Amino-2-[8-(4-methanesulfonyl phenyl)-8-aza-bicyclo[3.2.1]oct-3-yl]-exo-ethanoyl}-2-azabicyclo[3.1.0]hexane-3-carbonitrile trifluoroacetic acid salt;

(1S,3S,5S)-2-{(2S)-2-Amino-2-[8-(2-pyridin-4-yl-acetyl)-8-aza-bicyclo[3.2.1]oct-3-yl]-exo-ethanoyl}-2-azabicyclo[3.1.0]hexane-3-carbonitrile trifluoroacetic acid salt;

(1S,3S,5S)-2-{(2S)-2-Amino-2-[8-(pyridine-4ylmethyl)-8-aza-bicyclo[3.2.1]oct-3-yl]-exo-ethanoyl}-2-azabicyclo[3.1.0]hexane-3-carbonitrile trifluoroacetic acid salt;

(1S,3S,5S)-2-{(2S)-2-Amino-2-[8-(methanesulfonyl)-8-aza-bicyclo[3.2.1]oct-3-yl]-exo-ethanoyl}-2-azabicyclo[3.1.0]hexane-3-carbonitrile trifluoroacetic acid salt;

(1S,3S,5 S)-2-{(2S)-2-Amino-2-[8 -(thiophene-2-sulfonyl)-8-aza-bicyclo[3.2.1]oct-3-yl]-exo-ethanoyl}-2-azabicyclo[3.1.0]hexane-3-carbonitrile trifluoroacetic acid salt;

(1S,3S,5S)-2-{(2S)-2-Amino-2-[8-(cyclohexane-carbonyl)-8-aza-bicyclo[3.2.1]oct-3-yl]-exo-ethanoyl}-2-azabicyclo[3.1.0]hexane-3-carbonitrile trifluoroacetic acid salt;

(1S,3S,5S)-2-{(2S)-2-Amino-2-[8-(1-ethyl-propyl)-8-aza-bicyclo[3.2.1]oct-3-yl]-exo-ethanoyl}-2-azabicyclo[3.1.0]hexane-3-carbonitrile trifluoroacetic acid salt;

(1S,3S,5S)-2-{(2S)-2-Amino-2-(8-cyclohexyl-8-aza-bicyclo[3.2.1]oct-3-yl)-exo-ethanoyl}-2-azabicyclo[3.1.0]hexane-3-carbonitrile trifluoroacetic acid salt;

(1S,3S,5S)-2-{(2S)-2-Amino-2-[8-(4-chlorophenylsulfonylcarbamoyl)-8-aza-bicyclo [3.2.1]oct-3-yl]-exo-ethanoyl}-2-azabicyclo[3.1.0]hexane-3-carbonitrile trifluoroacetic acid salt;

{(2S)-2-Amino-2-[8-(3-fluoro-pyridine-4-carbonyl)-8-aza-bicyclo[3.2.1]oct-3-yl]-exo-ethanoyl}-3-fluoro-azetidine trifluoroacetic acid salt;

(2S,5R)-1-{(2S)-2-Amino-2-[8-(4-trifluoromethyl-benzoyl)-8-aza-bicyclo [3.2.1]oct-3-yl]-exo-ethanoyl}-5-ethynyl-pyrrolidin-2-carbonitrile trifluoro acetic acid salt;

(2S,5R)-1-{(2S)-2-Amino-2-[8-(pyridin-4-carbonyl)-8-aza-bicyclo[3.2.1]oct-3-yl]-exo-ethanoyl}-5-ethynyl-pyrrolidin-2-carbonitrile trifluoroacetic acid salt;

(2S,5R)-1-{(2S)-2-Amino-2-[8-(3-fluoropyridin-4-carbonyl)-8-aza-bicyclo[3.2.1]oct-3-yl]-exo-ethanoyl}-5-ethynyl-pyrrolidin-2-carbonitrile trifluoroacetic acid salt;

(2S,5R)-1-{(2S)-2-Amino-2-[8-(2-fluoropyridin-4-carbonyl)-8-aza-bicyclo[3.2.1]-oct-3-yl]-exo-ethanoyl}-5-ethynyl-pyrrolidin-2-carbonitrile trifluoroacetic acid salt;

(2S,5R)-1-{(2S)-2-Amino-2-[8-(benzo[1,3]dioxole-5-carbonyl)-8-aza-bicyclo[3.2.1]oct-3-yl]-exo-ethanoyl}-5-ethynyl-pyrrolidin-2-carbonitrile trifluoroacetic acid salt;

(1S,3S,5 S)-2-{(2S)-2-Amino-2-[8-(2-methoxyphenylthiocarbamoyl)-8-aza-bicyclo [3.2.1]oct-3-yl]-exo-ethanoyl}-2-azabicyclo[3.1.0]hexane-3-carbonitrile trifluoroacetic acid salt;

(1S,3S,5S)-2-{(2S)-2-Amino-2-[8-(1-acetyl-piperidine-4-carbonyl)-8-aza-bicyclo [3.2.1]oct-3-yl]-exo-ethanoyl}-2-azabicyclo[3.1.0]hexane-3-carbonitrile trifluoroacetic acid salt;

(2S)-1-{2-Amino-2-[9-(4-trifluoromethyl-benzoyl)-9-azabiacyclo[3.3.1]non-3-yl]-exo-ethanoyl}-pyrrolidin-2-carbonitrile trifluoro acetic acid salt and its diastereomers.

\* \* \* \* \*